(12) United States Patent
Hayashi et al.

(10) Patent No.: US 11,566,047 B2
(45) Date of Patent: Jan. 31, 2023

(54) PEPTIDE OR PHARMACEUTICALLY ACCEPTABLE SALT THEREOF, OR PRODRUG THEREOF

(71) Applicant: TOKYO UNIVERSITY OF PHARMACY & LIFE SCIENCES, Tokyo (JP)

(72) Inventors: Yoshio Hayashi, Tokyo (JP); Kentaro Takayama, Tokyo (JP); Yoichi Negishi, Tokyo (JP)

(73) Assignee: TOKYO UNIVERSITY OF PHARMACY & LIFE SCIENCES, Tokyo (JP)

( * ) Notice: Subject to any disclaimer, the term of this patent is extended or adjusted under 35 U.S.C. 154(b) by 582 days.

(21) Appl. No.: 16/324,495

(22) PCT Filed: Aug. 8, 2017

(86) PCT No.: PCT/JP2017/028834
§ 371 (c)(1),
(2) Date: Feb. 8, 2019

(87) PCT Pub. No.: WO2018/030432
PCT Pub. Date: Feb. 15, 2018

(65) Prior Publication Data
US 2019/0177370 A1 Jun. 13, 2019

(30) Foreign Application Priority Data
Aug. 10, 2016 (JP) .............................. JP2016-158123

(51) Int. Cl.
| C07K 7/08 | (2006.01) |
| A61P 21/02 | (2006.01) |
| A61P 21/04 | (2006.01) |
| A61K 47/66 | (2017.01) |
| A61K 38/00 | (2006.01) |

(52) U.S. Cl.
CPC ................ C07K 7/08 (2013.01); A61K 47/67 (2017.08); A61P 21/02 (2018.01); A61P 21/04 (2018.01); *A61K 38/00* (2013.01)

(58) Field of Classification Search
None
See application file for complete search history.

(56) References Cited

U.S. PATENT DOCUMENTS

| 2006/0073518 A1 | 4/2006 | Timmerman et al. |
| 2007/0014810 A1 | 1/2007 | Baker et al. |
| 2009/0324590 A1 | 12/2009 | Kambadur et al. |
| 2011/0318380 A1 | 12/2011 | Brix et al. |
| 2013/0065820 A1 | 3/2013 | Bower et al. |

FOREIGN PATENT DOCUMENTS

| EP | 1452868 A2 | 9/2004 |
| JP | 2009545313 A | 12/2009 |
| JP | 2013506660 A | 2/2013 |
| WO | 2005089164 A2 | 9/2005 |
| WO | 2010037395 A2 | 4/2010 |
| WO | 2014119753 A1 | 8/2014 |

OTHER PUBLICATIONS

Merck Manual (https://www.merckmanuals.com/professional/neurologic-disorders/peripheral-nervous-system-and-motor-unit-disorders/amyotrophic-lateral-sclerosis-als-and-other-motor-neuron-diseases-mnds accessed Apr. 3, 2022).*
Rybalka et al. (Cells Dec. 2020; 9(12): 2657).*
JPO, Office Action for the corresponding Japanese patent application No. 2018-533516, dated Aug. 24, 2021, with English translation.
K. Takayama, et al; Identification of the minimum peptide from mouse myostatin prodomain for human myostatin inhibition; Journal of Medicinal Chemistry; vol. 58; 2015; pp. 1544-1549.
International Search Report dated Dec. 5, 2017 for PCT/JP2017/028834 and English translation.

* cited by examiner

Primary Examiner — Julie Ha
Assistant Examiner — Tara L Martinez
(74) Attorney, Agent, or Firm — Lucas & Mercanti, LLP

(57) ABSTRACT

Provided is a peptide having a short chain length, for example, having the number of amino acid residues of 20 or less and having a high myostatin inhibitory activity. The present invention is a peptide comprising an amino acid sequence represented by Formula (1) in the specification and having the number of amino acid residues of 20 or less.

4 Claims, 13 Drawing Sheets

Specification includes a Sequence Listing.

[Fig. 1]
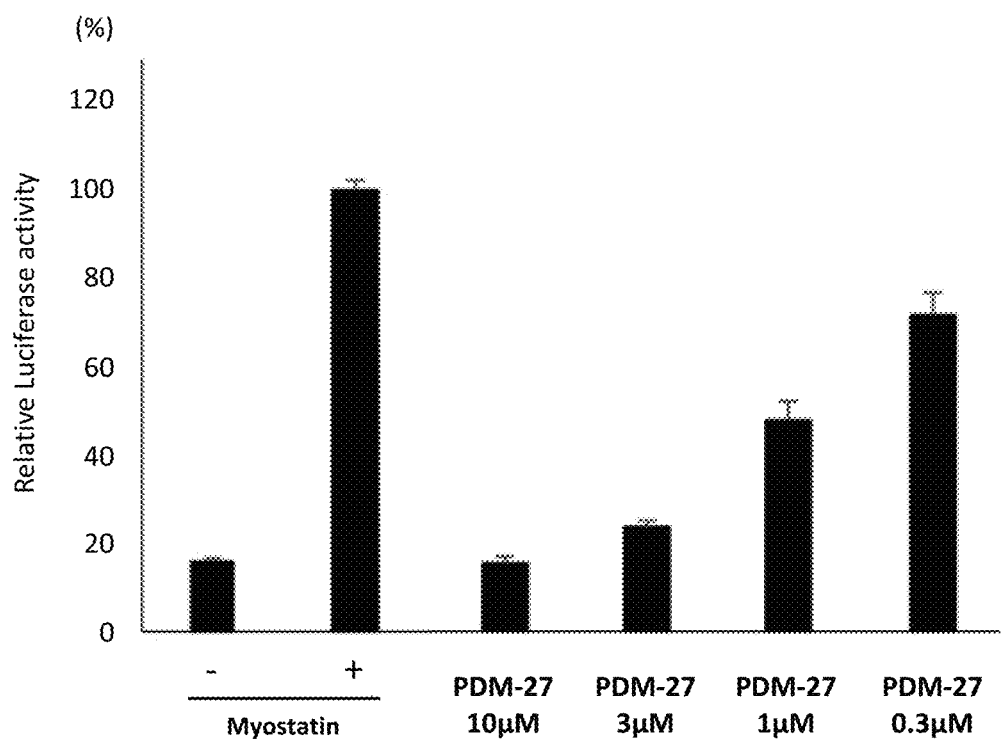

[Fig. 2]
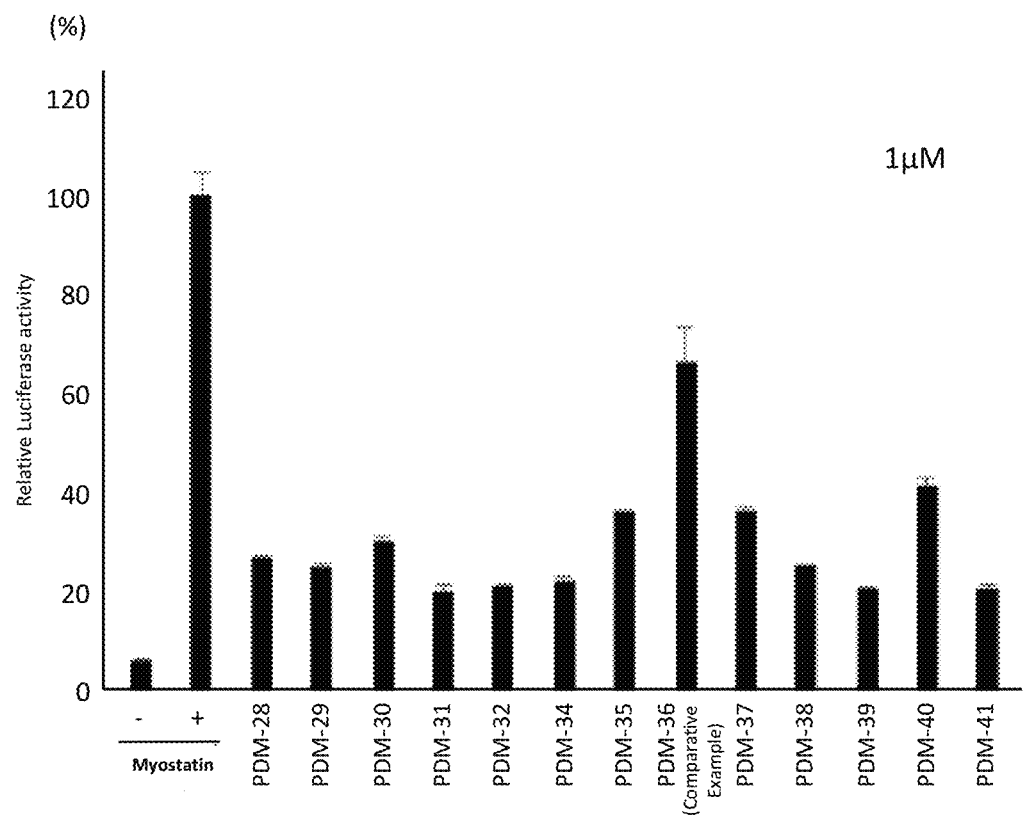

[Fig. 3]
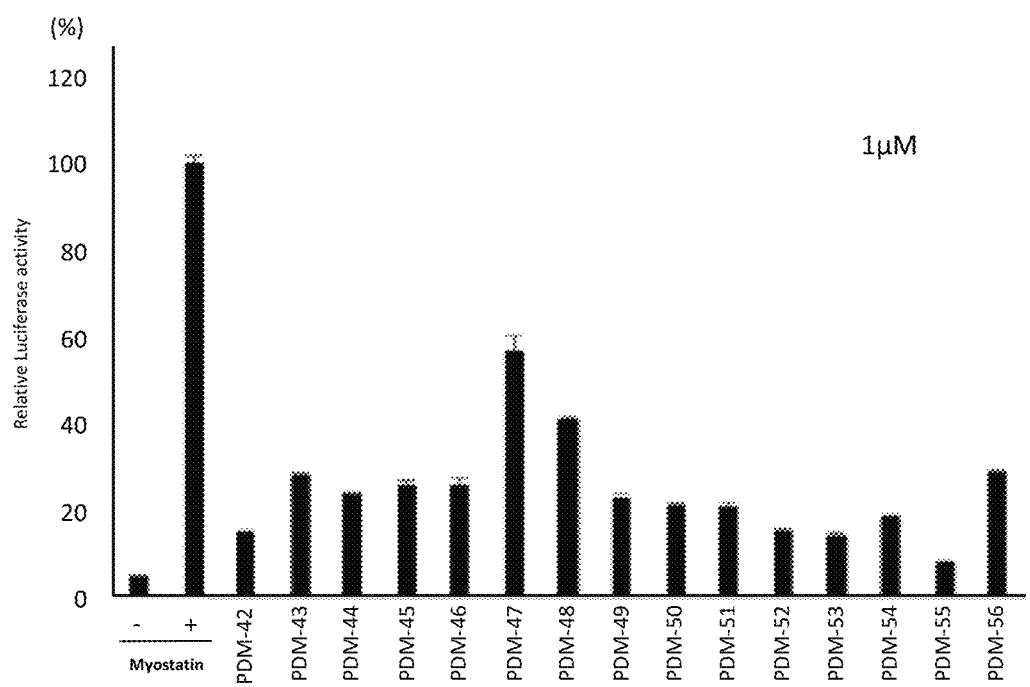

[Fig. 4]
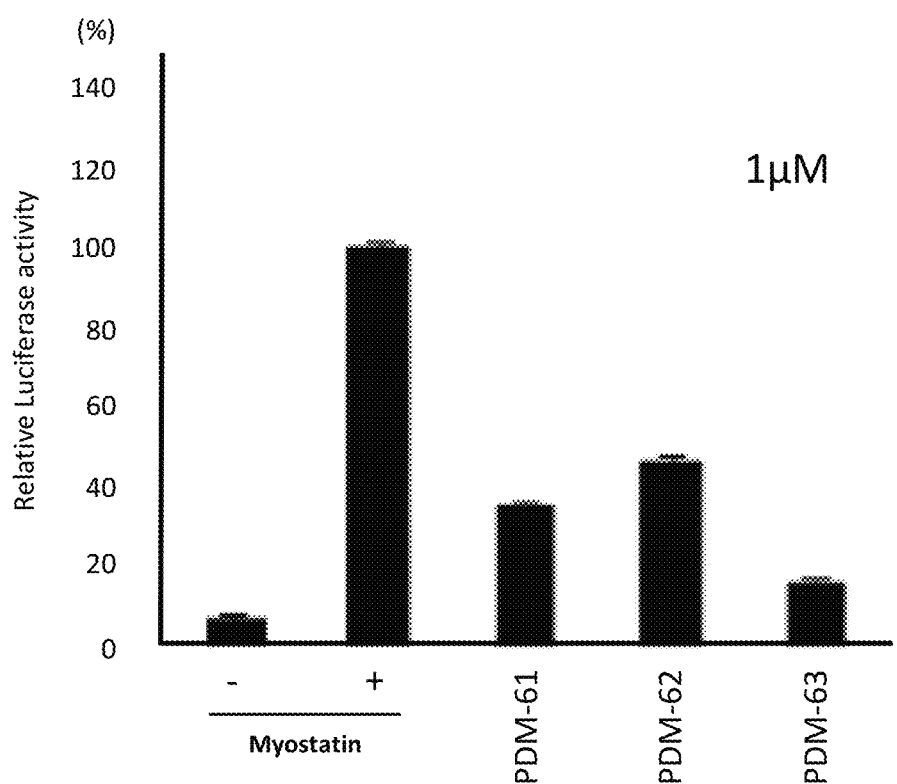

[Fig. 5]
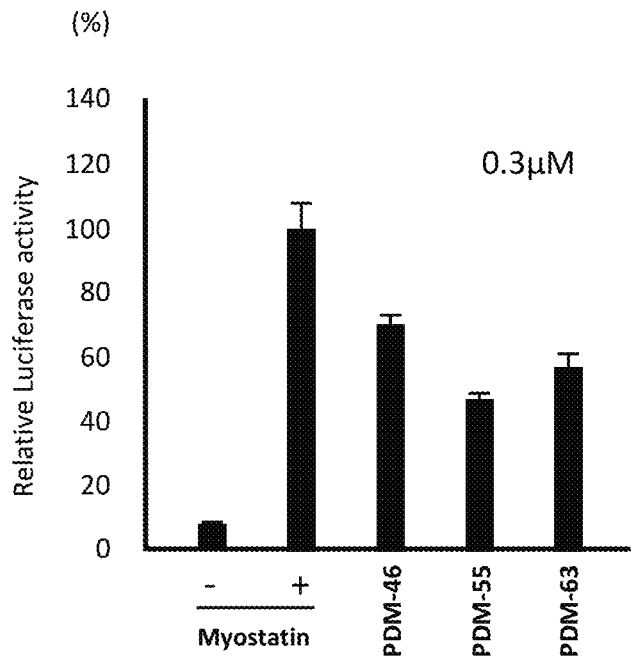
[Fig. 6]
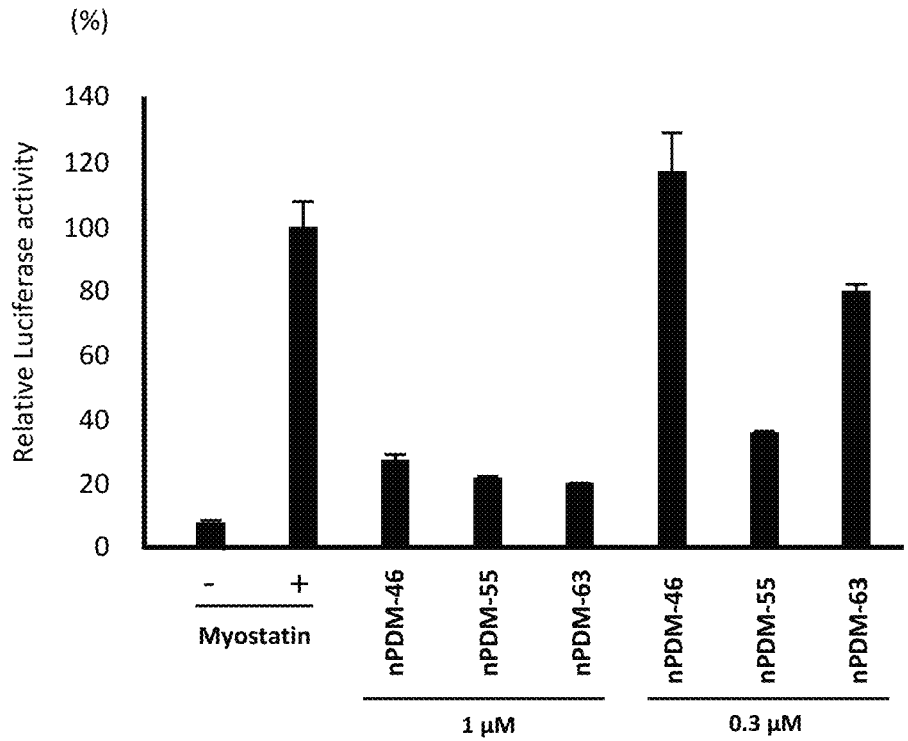

[Fig. 7]
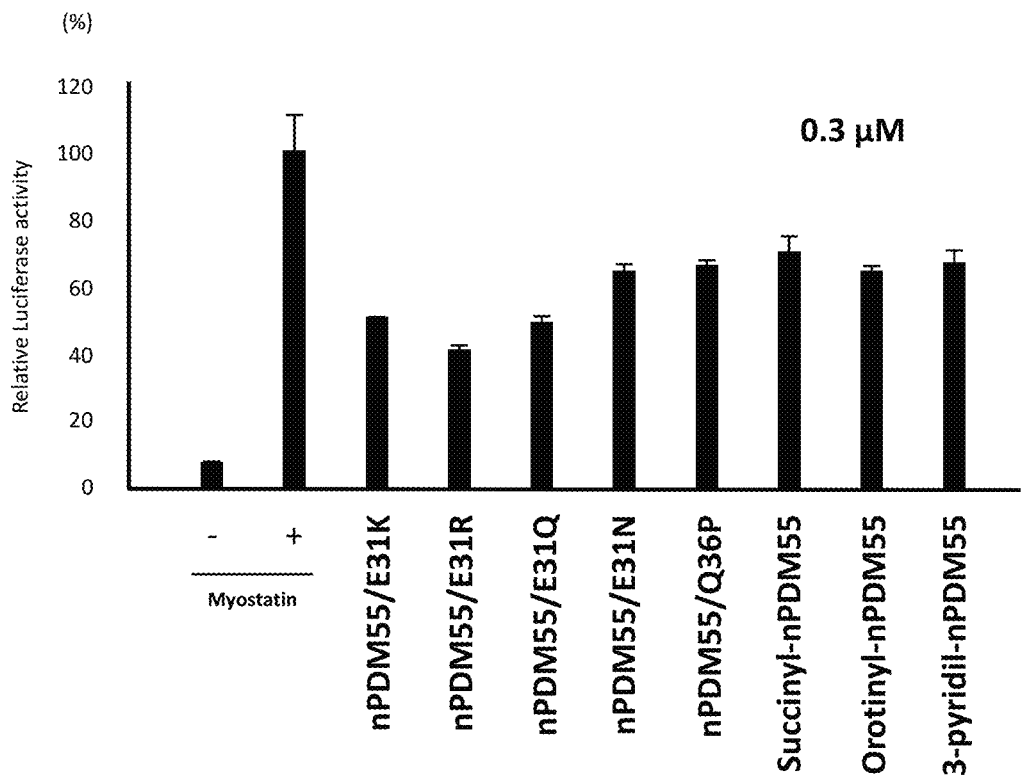
[Fig. 8]
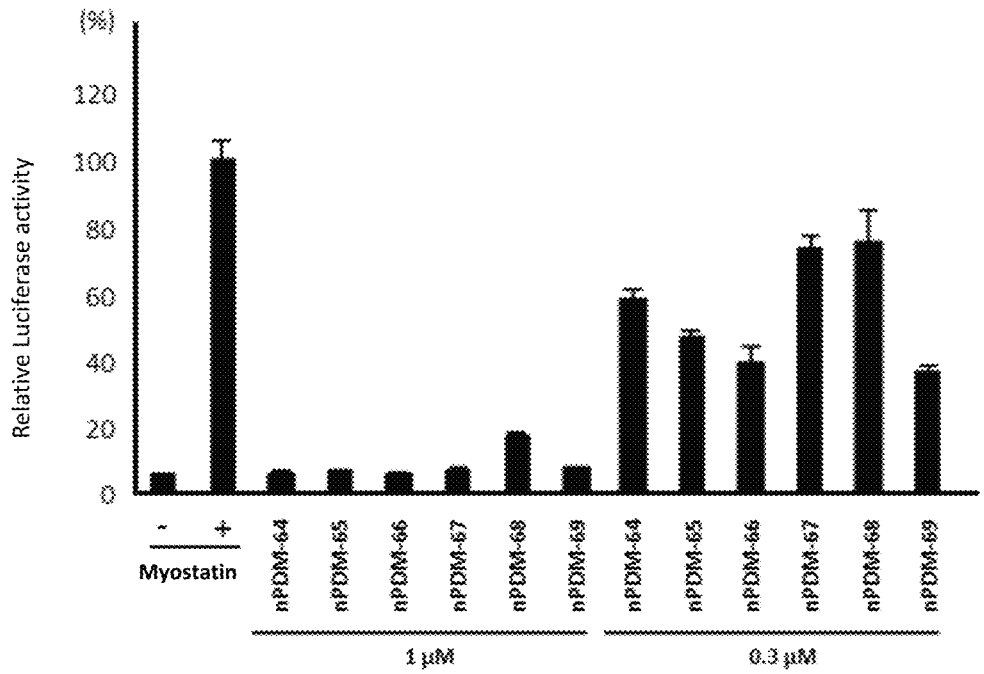

[Fig. 9]
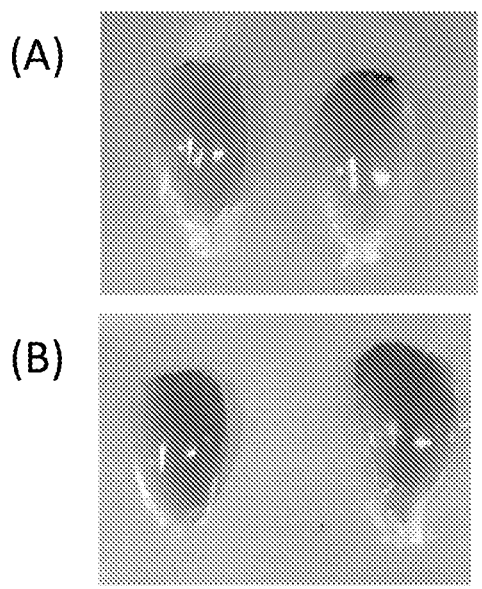
[Fig. 10]
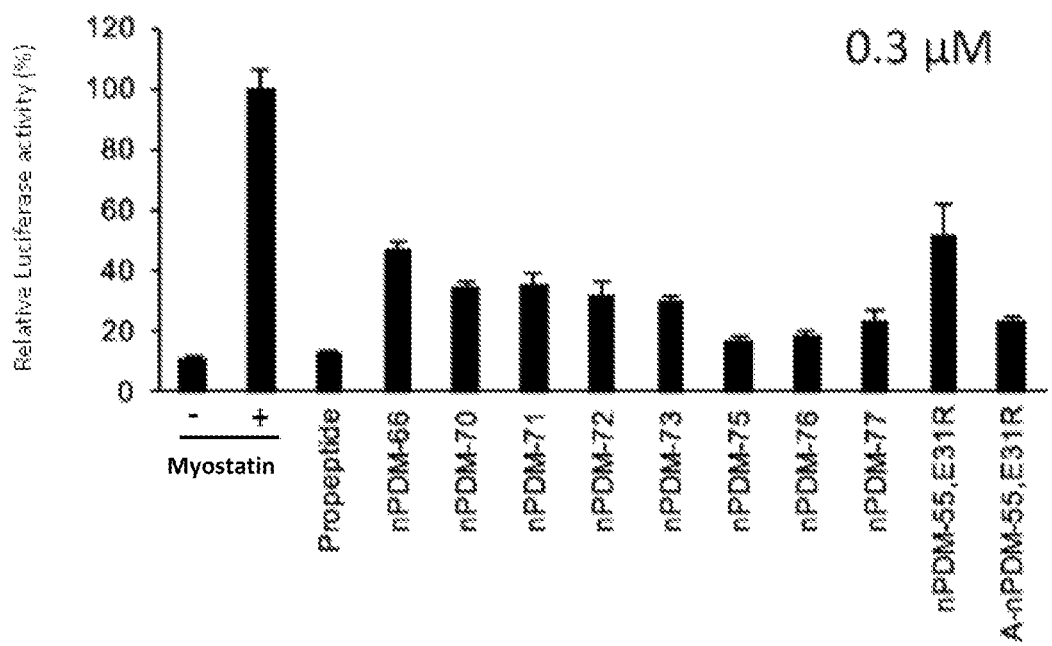

[Fig. 11]
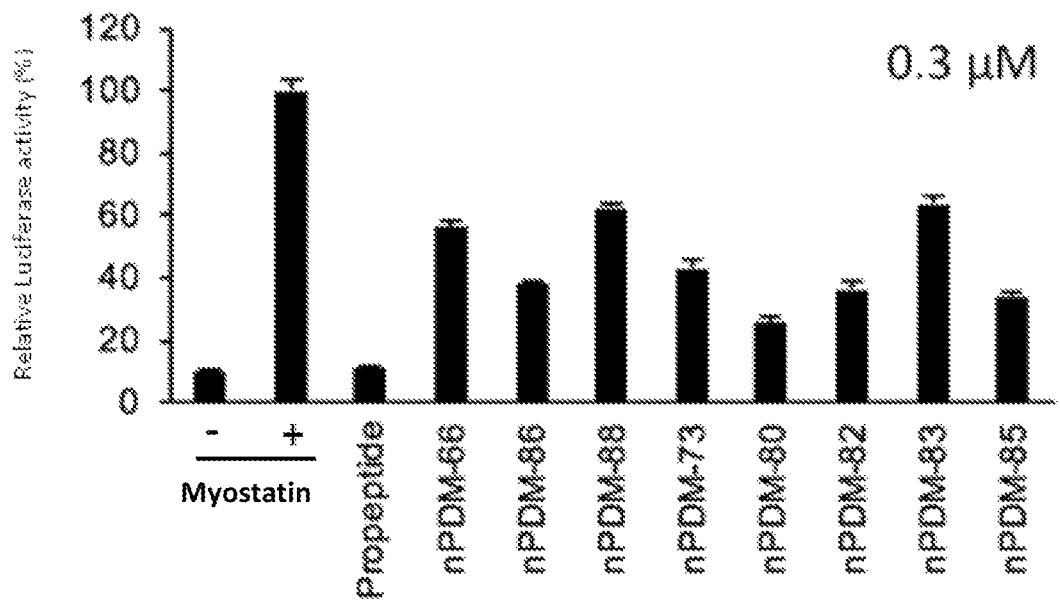
[Fig. 12]
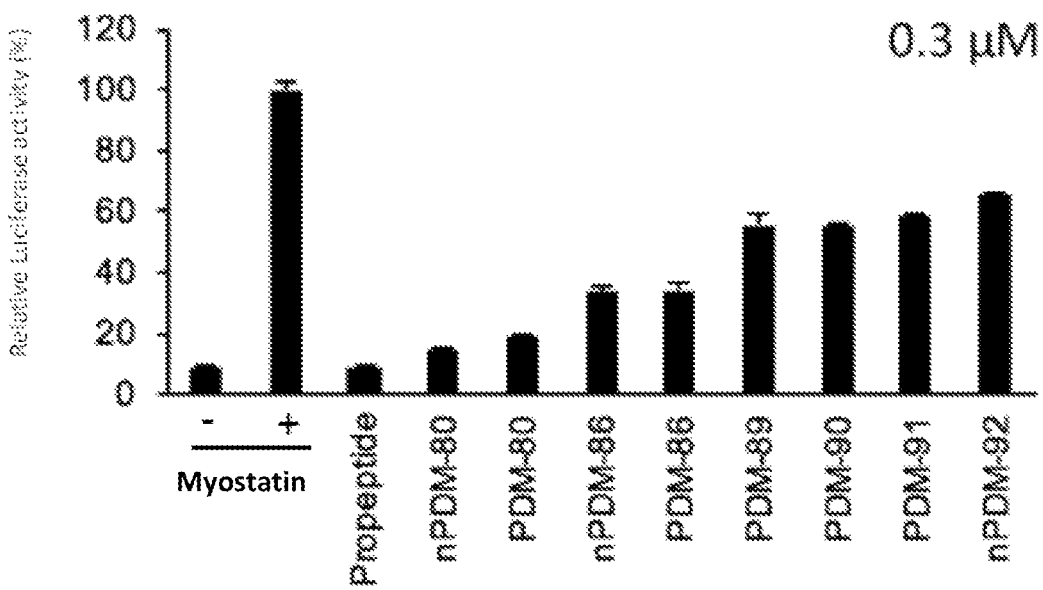

[Fig. 13]
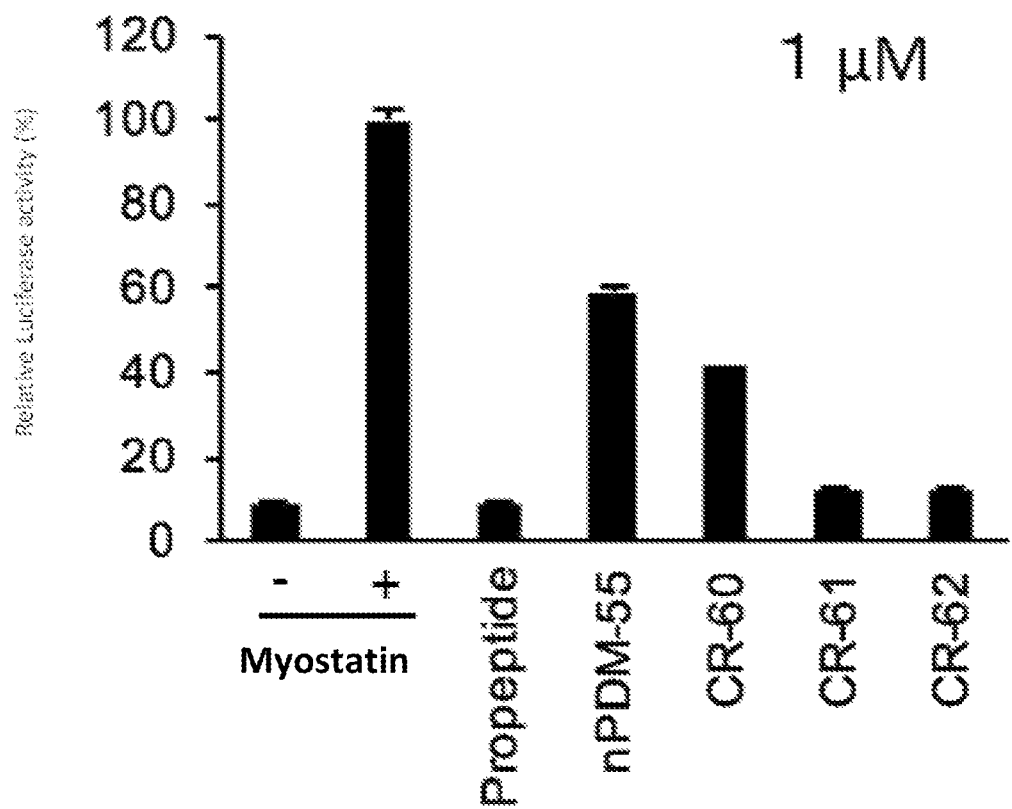

[Fig. 14A]
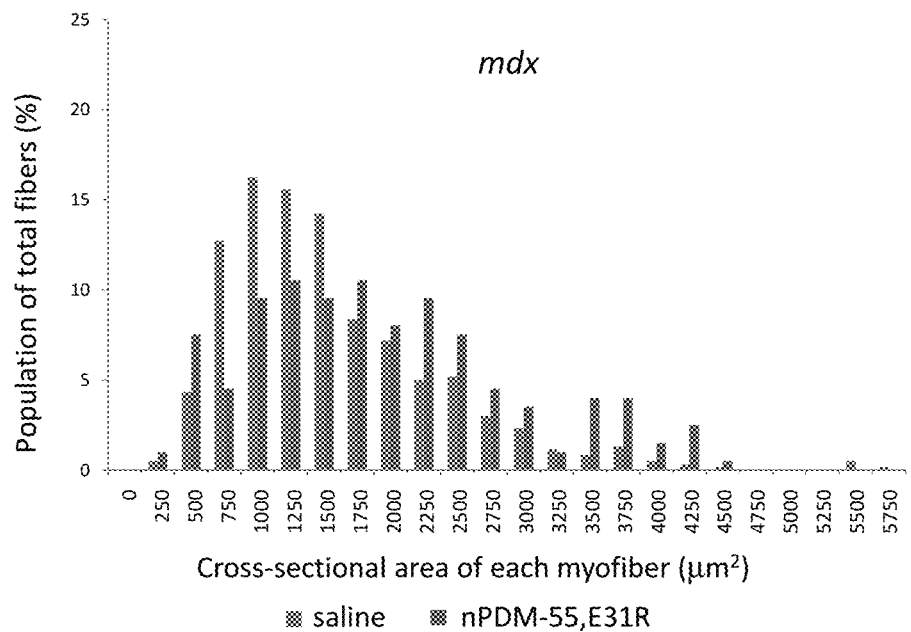
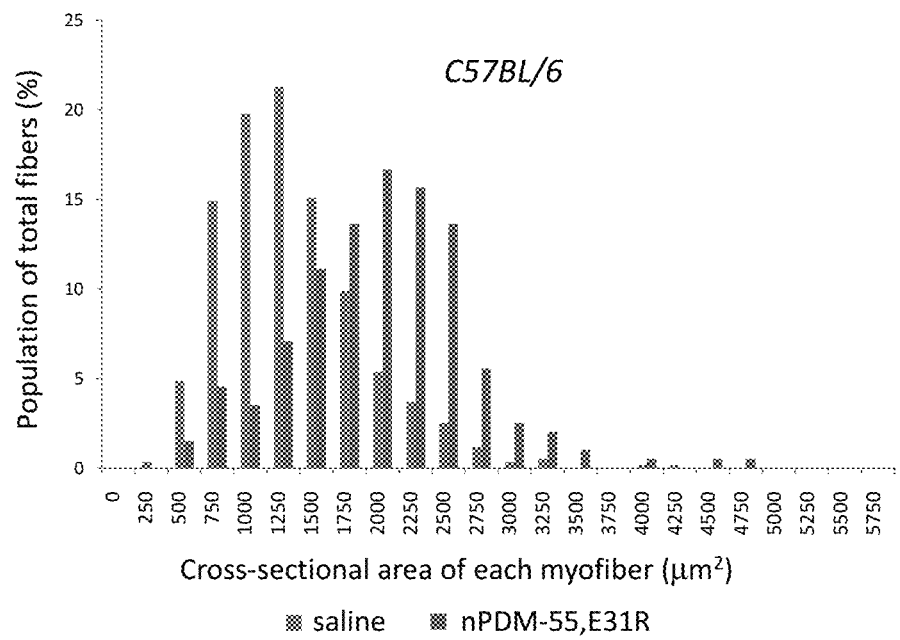

[Fig. 14B]
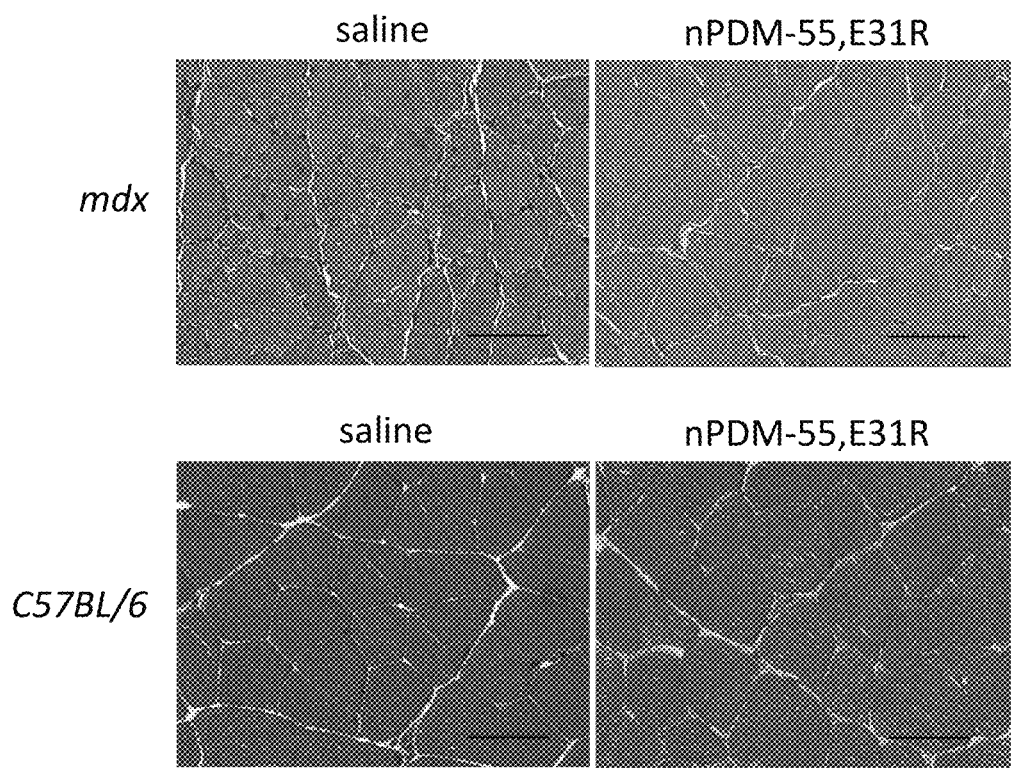

[Fig. 15]
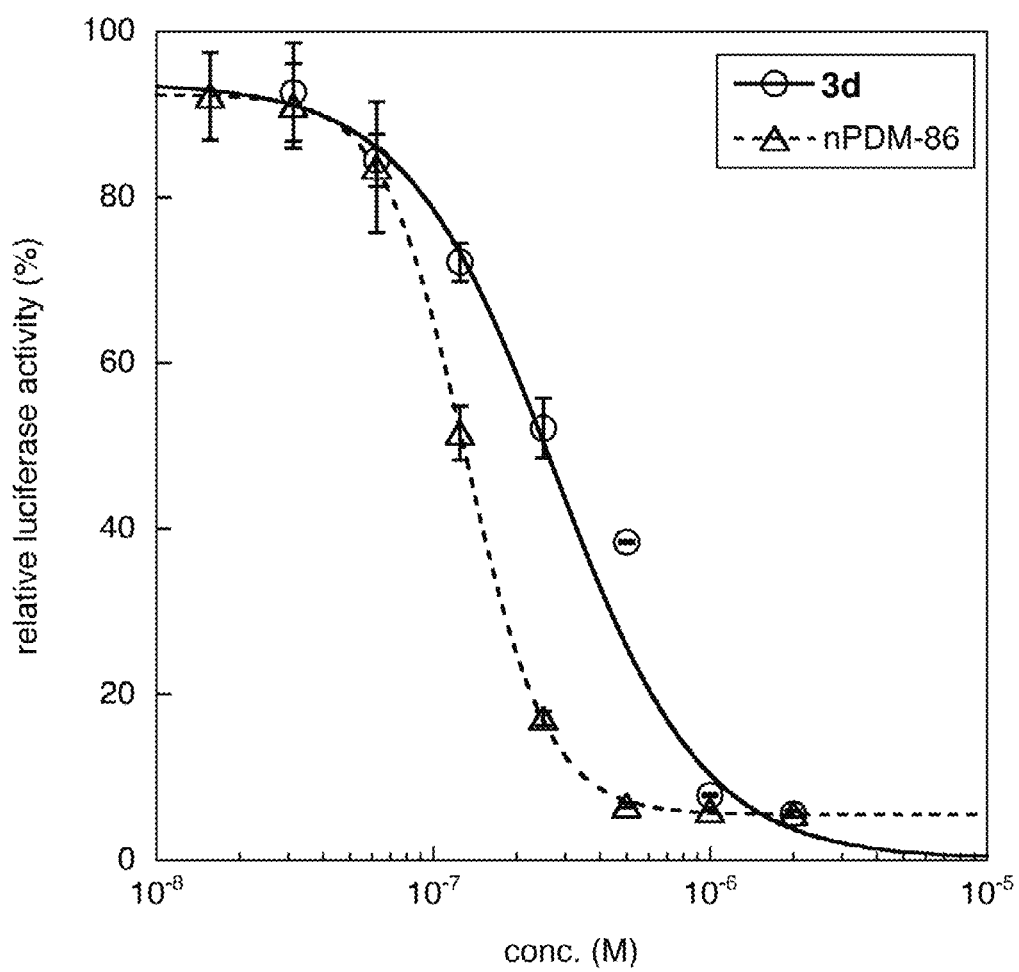

[Fig. 16]
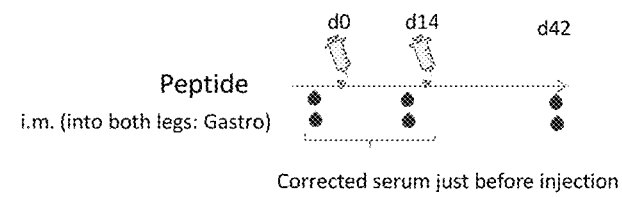
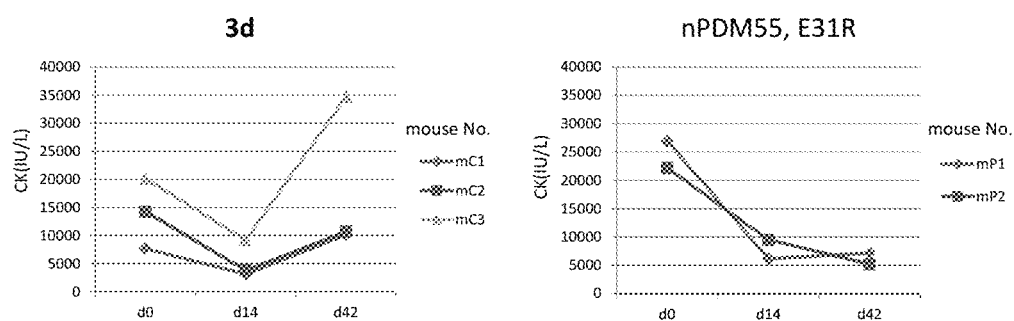

SEQUENCE LISTING

<160> NUMBER OF SEQ ID NOS: 595

<210> SEQ ID NO 1
<211> LENGTH: 16
<212> TYPE: PRT
<213> ORGANISM: Mus musculus

<400> SEQUENCE: 1

Ser Arg Ile Glu Ala Ile Lys Ile Gln Ile Leu Ser Lys Leu Arg Leu
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 2

Trp Tyr Ile Glu Trp Ile Lys Ile Gln Ile Ile Ser Lys Leu Arg Leu
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 3

Tyr Trp Ile Glu Trp Ile Lys Ile Gln Ile Ile Ser Lys Leu Arg Leu
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 4

Tyr Tyr Ile Glu Trp Ile Lys Ile Gln Ile Ile Ser Lys Leu Arg Leu
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 5

Trp Trp Ile Glu Trp Ile Lys Ile Gln Ile Ile Ser Lys Leu Arg Leu
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 6

```
Xaa Tyr Ile Glu Trp Ile Lys Ile Gln Ile Ile Ser Lys Leu Arg Leu
1               5                   10                  15
```

<210> SEQ ID NO 7
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 7

```
Phe Tyr Ile Glu Trp Ile Lys Ile Gln Ile Ile Ser Lys Leu Arg Leu
1               5                   10                  15
```

<210> SEQ ID NO 8
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 8

```
Leu Tyr Ile Glu Trp Ile Lys Ile Gln Ile Ile Ser Lys Leu Arg Leu
1               5                   10                  15
```

<210> SEQ ID NO 9
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 9

```
His Tyr Ile Glu Trp Ile Lys Ile Gln Ile Ile Ser Lys Leu Arg Leu
1               5                   10                  15
```

<210> SEQ ID NO 10
<211> LENGTH: 16
<212> TYPE: PRT
<213> ORGANISM: Artificial Sequence
<220> FEATURE:
<223> OTHER INFORMATION: Peptide

<400> SEQUENCE: 10

```
Ser Tyr Ile Glu Trp Ile Lys Ile Gln Ile Ile Ser Lys Leu Arg Leu
1               5                   10                  15
```

<210> SEQ ID NO 11
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 11

```
Trp Phe Ile Glu Trp Ile Lys Ile Gln Ile Ile Ser Lys Leu Arg Leu
1               5                   10                  15
```

<210> SEQ ID NO 12
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

```
<400> SEQUENCE: 12

Trp Xaa Ile Glu Trp Ile Lys Ile Gln Ile Ile Ser Lys Leu Arg Leu
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 13

Trp Xaa Ile Glu Trp Ile Lys Ile Gln Ile Ile Ser Lys Leu Arg Leu
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 14

Trp Leu Ile Glu Trp Ile Lys Ile Gln Ile Ile Ser Lys Leu Arg Leu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 15

Trp His Ile Glu Trp Ile Lys Ile Gln Ile Ile Ser Lys Leu Arg Leu
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 16

Trp Arg Ile Glu Trp Ile Lys Ile Gln Ile Ile Ser Lys Leu Arg Leu
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 17

Trp Ser Ile Glu Trp Ile Lys Ile Gln Ile Ile Ser Lys Leu Arg Leu
1               5                   10                  15

<210> SEQ ID NO 18
<211> LENGTH: 16
<212> TYPE: PRT
```

```
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 18

Trp Tyr Ile Glu Xaa Ile Lys Ile Gln Ile Ile Ser Lys Leu Arg Leu
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 19

Trp Tyr Ile Glu Leu Ile Lys Ile Gln Ile Ile Ser Lys Leu Arg Leu
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 20

Trp Tyr Ile Glu Ser Ile Lys Ile Gln Ile Ile Ser Lys Leu Arg Leu
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 21

Trp Tyr Ile Glu Arg Ile Lys Ile Gln Ile Ile Ser Lys Leu Arg Leu
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 22

Trp Tyr Ile Glu Glu Ile Lys Ile Gln Ile Ile Ser Lys Leu Arg Leu
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 23

Trp Tyr Ile Glu Phe Ile Lys Ile Gln Ile Ile Ser Lys Ile Arg Leu
1               5                   10                  15
```

```
<210> SEQ ID NO 24
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 24

Trp Tyr Ile Glu Tyr Ile Lys Ile Gln Ile Ile Ser Lys Ile Arg Leu
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 25

Trp Tyr Ile Glu His Ile Lys Ile Gln Ile Ile Ser Lys Ile Arg Leu
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 26

Trp Tyr Ile Glu Trp Ile Lys Ile Gln Ile Xaa Ser Lys Leu Arg Leu
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 27

Trp Tyr Ile Glu Trp Ile Lys Ile Gln Ile Xaa Ser Lys Leu Arg Leu
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 28

Trp Tyr Ile Glu Trp Ile Lys Ile Gln Ile Phe Ser Lys Leu Arg Leu
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Myostatin Inhibitory Peptide
```

```
<400> SEQUENCE: 29

Trp Tyr Ile Glu Trp Ile Lys Ile Gln Ile Trp Ser Lys Leu Arg Leu
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 30

Trp Tyr Ile Glu Trp Ile Lys Ile Gln Ile Tyr Ser Lys Leu Arg Leu
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 31

Tyr Tyr Ile Glu Ser Ile Lys Ile Gln Ile Ile Ser Lys Leu Arg Leu
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 32

Trp Arg Ile Glu Ser Ile Lys Ile Gln Ile Ile Ser Lys Leu Arg Leu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 33

Trp Tyr Ile Glu Ser Ile Lys Ile Gln Ile Trp Ser Lys Leu Arg Leu
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 34

Trp Tyr Ile Lys Trp Ile Lys Ile Gln Ile Trp Ser Lys Leu Arg Leu
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 35
```

```
Trp Tyr Ile Arg Trp Ile Lys Ile Gln Ile Trp Ser Lys Leu Arg Leu
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 36

Trp Tyr Ile Gln Trp Ile Lys Ile Gln Ile Trp Ser Lys Leu Arg Leu
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 37

Trp Tyr Ile Asn Trp Ile Lys Ile Gln Ile Trp Ser Lys Leu Arg Leu
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 38

Trp Tyr Ile Glu Trp Ile Lys Ile Pro Ile Trp Ser Lys Leu Arg Leu
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Peptide

<400> SEQUENCE: 39

Trp Tyr Ile Glu Ala Ile Lys Ile Gln Ile Leu Ser Lys Leu Arg Leu
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 40

Tyr Ser Ile Glu Trp Ile Lys Ile Gln Ile Ile Ser Lys Leu Arg Leu
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 41
```

```
Tyr Arg Ile Glu Trp Ile Lys Ile Gln Ile Ile Ser Lys Leu Arg Leu
1               5                   10                  15
```

<210> SEQ ID NO 42
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 42

```
Tyr Lys Ile Glu Trp Ile Lys Ile Gln Ile Ile Ser Lys Leu Arg Leu
1               5                   10                  15
```

<210> SEQ ID NO 43
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 43

```
Tyr His Ile Glu Trp Ile Lys Ile Gln Ile Ile Ser Lys Leu Arg Leu
1               5                   10                  15
```

<210> SEQ ID NO 44
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 44

```
Tyr Xaa Ile Glu Trp Ile Lys Ile Gln Ile Ile Ser Lys Leu Arg Leu
1               5                   10                  15
```

<210> SEQ ID NO 45
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 45

```
Tyr Xaa Ile Glu Trp Ile Lys Ile Gln Ile Ile Ser Lys Leu Arg Leu
1               5                   10                  15
```

<210> SEQ ID NO 46
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 46

```
Tyr Tyr Ile Arg Trp Ile Lys Ile Gln Ile Ile Ser Lys Leu Arg Leu
1               5                   10                  15
```

<210> SEQ ID NO 47
<211> LENGTH: 16

```
<212> TYPE: PRT
<213> ORGANISM: Artificial Sequence
<220> FEATURE:
<223> OTHER INFORMATION: Myostatin Inhibitory Peptide

<400> SEQUENCE: 47

Tyr Tyr Ile Lys Trp Ile Lys Ile Gln Ile Ile Ser Lys Leu Arg Leu
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 48

Tyr Tyr Ile Asn Trp Ile Lys Ile Gln Ile Ile Ser Lys Leu Arg Leu
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 49

Tyr Tyr Ile Gln Trp Ile Lys Ile Gln Ile Ile Ser Lys Leu Arg Leu
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 50

Tyr Tyr Ile Asp Trp Ile Lys Ile Gln Ile Ile Ser Lys Leu Arg Leu
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 51

Tyr Tyr Ile Glu Trp Ile Lys Ile Asn Ile Ile Ser Lys Leu Arg Leu
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 52

Tyr Tyr Ile Glu Trp Ile Lys Ile Pro Ile Ile Ser Lys Leu Arg Leu
1               5                   10                  15

<210> SEQ ID NO 53
<211> LENGTH: 16
<212> TYPE: PRT
```

```
<213> ORGANISM: Artificial Sequence
<220> FEATURE:
<223> OTHER INFORMATION: Myostatin Inhibitory Peptide

<400> SEQUENCE: 53

Tyr Tyr Ile Glu Trp Ile Lys Ile Gln Ile Val Ser Lys Leu Arg Leu
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 54

Tyr Tyr Ile Glu Trp Ile Lys Ile Gln Ile Leu Ser Lys Leu Arg Leu
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 55

Tyr Tyr Ile Glu Trp Ile Lys Ile Gln Ile Phe Ser Lys Leu Arg Leu
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 56

Tyr Tyr Ile Glu Trp Ile Lys Ile Gln Ile Trp Ser Lys Leu Arg Leu
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 57

Tyr Tyr Ile Glu Trp Ile Lys Ile Gln Ile Tyr Ser Lys Leu Arg Leu
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 58

Tyr Tyr Ile Glu Trp Ile Lys Ile Gln Ile Xaa Ser Lys Leu Arg Leu
1               5                   10                  15

<210> SEQ ID NO 59
```

```
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 59

Tyr Tyr Ile Glu Trp Ile Lys Ile Gln Ile Xaa Ser Lys Leu Arg Leu
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 60

Tyr Tyr Ile Glu Trp Ile Lys Ile Gln Ile Ile Ser Lys Ile Arg Leu
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 61

Xaa Ser Ile Glu Trp Ile Lys Ile Gln Ile Ile Ser Lys Leu Arg Leu
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 62

Xaa Trp Ile Glu Trp Ile Lys Ile Gln Ile Ile Ser Lys Leu Arg Leu
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 63

Xaa Arg Ile Glu Trp Ile Lys Ile Gln Ile Ile Ser Lys Leu Arg Leu
1               5                   10                  15
```

<210> SEQ ID NO 64
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 64

Xaa Lys Ile Glu Trp Ile Lys Ile Gln Ile Ile Ser Lys Leu Arg Leu
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 65

Xaa His Ile Glu Trp Ile Lys Ile Gln Ile Ile Ser Lys Leu Arg Leu
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine
<220> FEATURE:
<221> NAME/KEY: BINDING
<222> LOCATION: (2)..(2)
<223> OTHER INFORMATION: 3-Cyclohexyl alanine

<400> SEQUENCE: 66

Xaa Xaa Ile Glu Trp Ile Lys Ile Gln Ile Ile Ser Lys Leu Arg Leu
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(2)
<223> OTHER INFORMATION: 3-Naphtyl alanine

<400> SEQUENCE: 67

Xaa Xaa Ile Glu Trp Ile Lys Ile Gln Ile Ile Ser Lys Leu Arg Leu
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Myostatin Inhibitory Peptide

```
<220> FEATURE:
<221> NAME/KEY: BINDING
<222> LOCATION: (1)..(1)
<223> OTHER INFORMATION: 3-Naphtyl alanine

<400> SEQUENCE: 68

Xaa Tyr Ile Arg Trp Ile Lys Ile Gln Ile Ile Ser Lys Leu Arg Leu
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 69

Xaa Tyr Ile Lys Trp Ile Lys Ile Gln Ile Ile Ser Lys Leu Arg Leu
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 70

Xaa Tyr Ile Asn Trp Ile Lys Ile Gln Ile Ile Ser Lys Leu Arg Leu
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 71

Xaa Tyr Ile Gln Trp Ile Lys Ile Gln Ile Ile Ser Lys Leu Arg Leu
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 72

Xaa Tyr Ile Asp Trp Ile Lys Ile Gln Ile Ile Ser Lys Leu Arg Leu
1               5                   10                  15
```

```
<210> SEQ ID NO 73
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 73

Xaa Tyr Ile Glu Trp Ile Lys Ile Asn Ile Ile Ser Lys Leu Arg Leu
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 74

Xaa Tyr Ile Glu Trp Ile Lys Ile Pro Ile Ile Ser Lys Leu Arg Leu
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 75

Xaa Tyr Ile Glu Trp Ile Lys Ile Gln Ile Val Ser Lys Leu Arg Leu
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 76

Xaa Tyr Ile Glu Trp Ile Lys Ile Gln Ile Leu Ser Lys Leu Arg Leu
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine
```

```
<400> SEQUENCE: 77

Xaa Tyr Ile Glu Trp Ile Lys Ile Gln Ile Phe Ser Lys Leu Arg Leu
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 78

Xaa Tyr Ile Glu Trp Ile Lys Ile Gln Ile Trp Ser Lys Leu Arg Leu
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 79

Xaa Tyr Ile Glu Trp Ile Lys Ile Gln Ile Tyr Ser Lys Leu Arg Leu
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine
<220> FEATURE:
<221> NAME/KEY: Nva
<222> LOCATION: (11)..(11)

<400> SEQUENCE: 80

Xaa Tyr Ile Glu Trp Ile Lys Ile Gln Ile Xaa Ser Lys Leu Arg Leu
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine
<220> FEATURE:
<221> NAME/KEY: BINDING
<222> LOCATION: (11)..(11)
<223> OTHER INFORMATION: 2-Cyclohexyl glycine

<400> SEQUENCE: 81

Xaa Tyr Ile Glu Trp Ile Lys Ile Gln Ile Xaa Ser Lys Leu Arg Leu
1               5                   10                  15
```

<210> SEQ ID NO 82
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 82

Xaa Tyr Ile Glu Trp Ile Lys Ile Gln Ile Ile Ser Lys Ile Arg Leu
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 83

Phe Ser Ile Glu Trp Ile Lys Ile Gln Ile Ile Ser Lys Leu Arg Leu
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 84

Phe Trp Ile Glu Trp Ile Lys Ile Gln Ile Ile Ser Lys Leu Arg Leu
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 85

Phe Arg Ile Glu Trp Ile Lys Ile Gln Ile Ile Ser Lys Leu Arg Leu
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 86

Phe Lys Ile Glu Trp Ile Lys Ile Gln Ile Ile Ser Lys Leu Arg Leu
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 87

```
Phe His Ile Glu Trp Ile Lys Ile Gln Ile Ile Ser Lys Leu Arg Leu
1               5                   10                  15
```

<210> SEQ ID NO 88
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 88

```
Phe Xaa Ile Glu Trp Ile Lys Ile Gln Ile Ile Ser Lys Leu Arg Leu
1               5                   10                  15
```

<210> SEQ ID NO 89
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 89

```
Phe Xaa Ile Glu Trp Ile Lys Ile Gln Ile Ile Ser Lys Leu Arg Leu
1               5                   10                  15
```

<210> SEQ ID NO 90
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 90

```
Phe Tyr Ile Arg Trp Ile Lys Ile Gln Ile Ile Ser Lys Leu Arg Leu
1               5                   10                  15
```

<210> SEQ ID NO 91
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 91

```
Phe Tyr Ile Lys Trp Ile Lys Ile Gln Ile Ile Ser Lys Leu Arg Leu
1               5                   10                  15
```

<210> SEQ ID NO 92
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 92

```
Phe Tyr Ile Asn Trp Ile Lys Ile Gln Ile Ile Ser Lys Leu Arg Leu
1               5                   10                  15
```

<210> SEQ ID NO 93

```
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 93

Phe Tyr Ile Gln Trp Ile Lys Ile Gln Ile Ile Ser Lys Leu Arg Leu
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 94

Phe Tyr Ile Asp Trp Ile Lys Ile Gln Ile Ile Ser Lys Leu Arg Leu
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 95

Phe Tyr Ile Glu Trp Ile Lys Ile Asn Ile Ile Ser Lys Leu Arg Leu
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 96

Phe Tyr Ile Glu Trp Ile Lys Ile Pro Ile Ile Ser Lys Leu Arg Leu
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 97

Phe Tyr Ile Glu Trp Ile Lys Ile Gln Ile Val Ser Lys Leu Arg Leu
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 98

Phe Tyr Ile Glu Trp Ile Lys Ile Gln Ile Leu Ser Lys Leu Arg Leu
1               5                   10                  15

<210> SEQ ID NO 99
<211> LENGTH: 16
```

```
<212> TYPE: PRT
<213> ORGANISM: Artificial Sequence
<220> FEATURE:
<223> OTHER INFORMATION: Myostatin Inhibitory Peptide

<400> SEQUENCE: 99

Phe Tyr Ile Glu Trp Ile Lys Ile Gln Ile Phe Ser Lys Leu Arg Leu
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 100

Phe Tyr Ile Glu Trp Ile Lys Ile Gln Ile Trp Ser Lys Leu Arg Leu
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 101

Phe Tyr Ile Glu Trp Ile Lys Ile Gln Ile Tyr Ser Lys Leu Arg Leu
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 102

Phe Tyr Ile Glu Trp Ile Lys Ile Gln Ile Xaa Ser Lys Leu Arg Leu
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 103

Phe Tyr Ile Glu Trp Ile Lys Ile Gln Ile Xaa Ser Lys Leu Arg Leu
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 104
```

```
Phe Tyr Ile Glu Trp Ile Lys Ile Gln Ile Ile Ser Lys Ile Arg Leu
1               5                   10                  15
```

<210> SEQ ID NO 105
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 105

```
Leu Ser Ile Glu Trp Ile Lys Ile Gln Ile Ile Ser Lys Leu Arg Leu
1               5                   10                  15
```

<210> SEQ ID NO 106
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 106

```
Leu Trp Ile Glu Trp Ile Lys Ile Gln Ile Ile Ser Lys Leu Arg Leu
1               5                   10                  15
```

<210> SEQ ID NO 107
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 107

```
Leu Arg Ile Glu Trp Ile Lys Ile Gln Ile Ile Ser Lys Leu Arg Leu
1               5                   10                  15
```

<210> SEQ ID NO 108
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 108

```
Leu Lys Ile Glu Trp Ile Lys Ile Gln Ile Ile Ser Lys Leu Arg Leu
1               5                   10                  15
```

<210> SEQ ID NO 109
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 109

```
Leu His Ile Glu Trp Ile Lys Ile Gln Ile Ile Ser Lys Leu Arg Leu
1               5                   10                  15
```

<210> SEQ ID NO 110
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 110

Leu Xaa Ile Glu Trp Ile Lys Ile Gln Ile Ile Ser Lys Leu Arg Leu
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 111

Leu Xaa Ile Glu Trp Ile Lys Ile Gln Ile Ile Ser Lys Leu Arg Leu
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 112

Leu Tyr Ile Arg Trp Ile Lys Ile Gln Ile Ile Ser Lys Leu Arg Leu
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 113

Leu Tyr Ile Lys Trp Ile Lys Ile Gln Ile Ile Ser Lys Leu Arg Leu
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 114

Leu Tyr Ile Asn Trp Ile Lys Ile Gln Ile Ile Ser Lys Leu Arg Leu
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 115

Leu Tyr Ile Gln Trp Ile Lys Ile Gln Ile Ile Ser Lys Leu Arg Leu
1               5                   10                  15

<210> SEQ ID NO 116
<211> LENGTH: 16
<212> TYPE: PRT

-continued

```
<213> ORGANISM: Artificial Sequence
<220> FEATURE:
<223> OTHER INFORMATION: Myostatin Inhibitory Peptide

<400> SEQUENCE: 116

Leu Tyr Ile Asp Trp Ile Lys Ile Gln Ile Ile Ser Lys Leu Arg Leu
1 5 10 15

<210> SEQ ID NO 117
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 117

Leu Tyr Ile Glu Trp Ile Lys Ile Asn Ile Ile Ser Lys Leu Arg Leu
1 5 10 15

<210> SEQ ID NO 118
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 118

Leu Tyr Ile Glu Trp Ile Lys Ile Pro Ile Ile Ser Lys Leu Arg Leu
1 5 10 15

<210> SEQ ID NO 119
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 119

Leu Tyr Ile Glu Trp Ile Lys Ile Gln Ile Val Ser Lys Leu Arg Leu
1 5 10 15

<210> SEQ ID NO 120
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 120

Leu Tyr Ile Glu Trp Ile Lys Ile Gln Ile Leu Ser Lys Leu Arg Leu
1 5 10 15

<210> SEQ ID NO 121
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 121

Leu Tyr Ile Glu Trp Ile Lys Ile Gln Ile Phe Ser Lys Leu Arg Leu
1 5 10 15

<210> SEQ ID NO 122
<211> LENGTH: 16
<212> TYPE: PRT
<213> ORGANISM: Artificial Sequence

```
<220> FEATURE:
<223> OTHER INFORMATION: Myostatin Inhibitory Peptide

<400> SEQUENCE: 122

Leu Tyr Ile Glu Trp Ile Lys Ile Gln Ile Trp Ser Lys Leu Arg Leu
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 123

Leu Tyr Ile Glu Trp Ile Lys Ile Gln Ile Tyr Ser Lys Leu Arg Leu
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 124

Leu Tyr Ile Glu Trp Ile Lys Ile Gln Ile Xaa Ser Lys Leu Arg Leu
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 125

Leu Tyr Ile Glu Trp Ile Lys Ile Gln Ile Xaa Ser Lys Leu Arg Leu
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 126

Leu Tyr Ile Glu Trp Ile Lys Ile Gln Ile Ile Ser Lys Ile Arg Leu
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 127

Trp Lys Ile Glu Trp Ile Lys Ile Gln Ile Ile Ser Lys Leu Arg Leu
1               5                   10                  15
```

<210> SEQ ID NO 128
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 128

Trp Xaa Ile Arg Trp Ile Lys Ile Gln Ile Ile Ser Lys Leu Arg Leu
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 129

Trp Xaa Ile Lys Trp Ile Lys Ile Gln Ile Ile Ser Lys Leu Arg Leu
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 130

Trp Xaa Ile Asn Trp Ile Lys Ile Gln Ile Ile Ser Lys Leu Arg Leu
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 131

Trp Xaa Ile Gln Trp Ile Lys Ile Gln Ile Ile Ser Lys Leu Arg Leu
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)

```
<223> OTHER INFORMATION: 3-Naphtyl alanine

<400> SEQUENCE: 132

Trp Xaa Ile Asp Trp Ile Lys Ile Gln Ile Ile Ser Lys Leu Arg Leu
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 133

Trp Xaa Ile Glu Trp Ile Lys Ile Asn Ile Ile Ser Lys Leu Arg Leu
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 134

Trp Xaa Ile Glu Trp Ile Lys Ile Pro Ile Ile Ser Lys Leu Arg Leu
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 135

Trp Xaa Ile Glu Trp Ile Lys Ile Gln Ile Val Ser Lys Leu Arg Leu
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 136

Trp Xaa Ile Glu Trp Ile Lys Ile Gln Ile Leu Ser Lys Leu Arg Leu
1               5                   10                  15

<210> SEQ ID NO 137
<211> LENGTH: 16
<212> TYPE: PRT
```

```
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 137

Trp Xaa Ile Glu Trp Ile Lys Ile Gln Ile Phe Ser Lys Leu Arg Leu
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 138

Trp Xaa Ile Glu Trp Ile Lys Ile Gln Ile Trp Ser Lys Leu Arg Leu
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 139

Trp Xaa Ile Glu Trp Ile Lys Ile Gln Ile Tyr Ser Lys Leu Arg Leu
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine
<220> FEATURE:
<221> NAME/KEY: Nva
<222> LOCATION: (11)..(11)

<400> SEQUENCE: 140

Trp Xaa Ile Glu Trp Ile Lys Ile Gln Ile Xaa Ser Lys Leu Arg Leu
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine
<220> FEATURE:
```

```
<221> NAME/KEY: BINDING
<222> LOCATION: (11)..(11)
<223> OTHER INFORMATION: 2-Cyclohexyl glycine

<400> SEQUENCE: 141

Trp Xaa Ile Glu Trp Ile Lys Ile Gln Ile Xaa Ser Lys Leu Arg Leu
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 142

Trp Xaa Ile Glu Trp Ile Lys Ile Gln Ile Ile Ser Lys Ile Arg Leu
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 143

Trp Xaa Ile Arg Trp Ile Lys Ile Gln Ile Ile Ser Lys Leu Arg Leu
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 144

Trp Xaa Ile Lys Trp Ile Lys Ile Gln Ile Ile Ser Lys Leu Arg Leu
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 145

Trp Xaa Ile Asn Trp Ile Lys Ile Gln Ile Ile Ser Lys Leu Arg Leu
1               5                   10                  15

<210> SEQ ID NO 146
```

```
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 146

Trp Xaa Ile Gln Trp Ile Lys Ile Gln Ile Ile Ser Lys Leu Arg Leu
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 147

Trp Xaa Ile Asp Trp Ile Lys Ile Gln Ile Ile Ser Lys Leu Arg Leu
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 148

Trp Xaa Ile Glu Trp Ile Lys Ile Asn Ile Ile Ser Lys Leu Arg Leu
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 149

Trp Xaa Ile Glu Trp Ile Lys Ile Pro Ile Ile Ser Lys Leu Arg Leu
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 150
```

```
Trp Xaa Ile Glu Trp Ile Lys Ile Gln Ile Val Ser Lys Leu Arg Leu
1               5                   10                  15
```

<210> SEQ ID NO 151
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 151

```
Trp Xaa Ile Glu Trp Ile Lys Ile Gln Ile Leu Ser Lys Leu Arg Leu
1               5                   10                  15
```

<210> SEQ ID NO 152
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 152

```
Trp Xaa Ile Glu Trp Ile Lys Ile Gln Ile Phe Ser Lys Leu Arg Leu
1               5                   10                  15
```

<210> SEQ ID NO 153
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 153

```
Trp Xaa Ile Glu Trp Ile Lys Ile Gln Ile Trp Ser Lys Leu Arg Leu
1               5                   10                  15
```

<210> SEQ ID NO 154
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 154

```
Trp Xaa Ile Glu Trp Ile Lys Ile Gln Ile Tyr Ser Lys Leu Arg Leu
1               5                   10                  15
```

<210> SEQ ID NO 155
<211> LENGTH: 16
<212> TYPE: PRT
<213> ORGANISM: Artificial Sequence
<220> FEATURE:
<223> OTHER INFORMATION: Myostatin Inhibitory Peptide

```
<220> FEATURE:
<221> NAME/KEY: BINDING
<222> LOCATION: (2)..(2)
<223> OTHER INFORMATION: 3-Cyclohexyl alanine
<220> FEATURE:
<221> NAME/KEY: Nva
<222> LOCATION: (11)..(11)

<400> SEQUENCE: 155

Trp Xaa Ile Glu Trp Ile Lys Ile Gln Ile Xaa Ser Lys Leu Arg Leu
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine
<220> FEATURE:
<221> NAME/KEY: BINDING
<222> LOCATION: (11)..(11)
<223> OTHER INFORMATION: 2-Cyclohexyl glycine

<400> SEQUENCE: 156

Trp Xaa Ile Glu Trp Ile Lys Ile Gln Ile Xaa Ser Lys Leu Arg Leu
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 157

Trp Xaa Ile Glu Trp Ile Lys Ile Gln Ile Ile Ser Lys Ile Arg Leu
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 158

Trp His Ile Arg Trp Ile Lys Ile Gln Ile Ile Ser Lys Leu Arg Leu
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 159

Trp His Ile Lys Trp Ile Lys Ile Gln Ile Ile Ser Lys Leu Arg Leu
1               5                   10                  15

<210> SEQ ID NO 160
```

```
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 160

Trp His Ile Asn Trp Ile Lys Ile Gln Ile Ile Ser Lys Leu Arg Leu
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 161

Trp His Ile Gln Trp Ile Lys Ile Gln Ile Ile Ser Lys Leu Arg Leu
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 162

Trp His Ile Asp Trp Ile Lys Ile Gln Ile Ile Ser Lys Leu Arg Leu
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 163

Trp His Ile Glu Trp Ile Lys Ile Asn Ile Ile Ser Lys Leu Arg Leu
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 164

Trp His Ile Glu Trp Ile Lys Ile Pro Ile Ile Ser Lys Leu Arg Leu
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 165

Trp His Ile Glu Trp Ile Lys Ile Gln Ile Val Ser Lys Leu Arg Leu
1               5                   10                  15

<210> SEQ ID NO 166
<211> LENGTH: 16
```

```
<212> TYPE: PRT
<213> ORGANISM: Artificial Sequence
<220> FEATURE:
<223> OTHER INFORMATION: Myostatin Inhibitory Peptide

<400> SEQUENCE: 166

Trp His Ile Glu Trp Ile Lys Ile Gln Ile Leu Ser Lys Leu Arg Leu
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 167

Trp His Ile Glu Trp Ile Lys Ile Gln Ile Phe Ser Lys Leu Arg Leu
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 168

Trp His Ile Glu Trp Ile Lys Ile Gln Ile Trp Ser Lys Leu Arg Leu
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 169

Trp His Ile Glu Trp Ile Lys Ile Gln Ile Tyr Ser Lys Leu Arg Leu
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 170

Trp His Ile Glu Trp Ile Lys Ile Gln Ile Xaa Ser Lys Leu Arg Leu
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 171
```

Trp His Ile Glu Trp Ile Lys Ile Gln Ile Xaa Ser Lys Leu Arg Leu
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 172

Trp His Ile Glu Trp Ile Lys Ile Gln Ile Ile Ser Lys Ile Arg Leu
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 173

Trp Arg Ile Arg Trp Ile Lys Ile Gln Ile Ile Ser Lys Leu Arg Leu
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 174

Trp Arg Ile Lys Trp Ile Lys Ile Gln Ile Ile Ser Lys Leu Arg Leu
1               5                   10                  15

<210> SEQ ID NO 175
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 175

Trp Arg Ile Asn Trp Ile Lys Ile Gln Ile Ile Ser Lys Leu Arg Leu
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 176

Trp Arg Ile Gln Trp Ile Lys Ile Gln Ile Ile Ser Lys Leu Arg Leu
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 177

Trp Arg Ile Asp Trp Ile Lys Ile Gln Ile Ile Ser Lys Leu Arg Leu

-continued

```
1               5                  10                  15

<210> SEQ ID NO 178
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 178

Trp Arg Ile Glu Trp Ile Lys Ile Asn Ile Ile Ser Lys Leu Arg Leu
1               5                  10                  15

<210> SEQ ID NO 179
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 179

Trp Arg Ile Glu Trp Ile Lys Ile Pro Ile Ile Ser Lys Leu Arg Leu
1               5                  10                  15

<210> SEQ ID NO 180
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 180

Trp Arg Ile Glu Trp Ile Lys Ile Gln Ile Val Ser Lys Leu Arg Leu
1               5                  10                  15

<210> SEQ ID NO 181
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 181

Trp Arg Ile Glu Trp Ile Lys Ile Gln Ile Leu Ser Lys Leu Arg Leu
1               5                  10                  15

<210> SEQ ID NO 182
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 182

Trp Arg Ile Glu Trp Ile Lys Ile Gln Ile Phe Ser Lys Leu Arg Leu
1               5                  10                  15

<210> SEQ ID NO 183
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 183

Trp Arg Ile Glu Trp Ile Lys Ile Gln Ile Trp Ser Lys Leu Arg Leu
1               5                  10                  15
```

<210> SEQ ID NO 184
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 184

Trp Arg Ile Glu Trp Ile Lys Ile Gln Ile Tyr Ser Lys Leu Arg Leu
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 185

Trp Arg Ile Glu Trp Ile Lys Ile Gln Ile Xaa Ser Lys Leu Arg Leu
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 186

Trp Arg Ile Glu Trp Ile Lys Ile Gln Ile Xaa Ser Lys Leu Arg Leu
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 187

Trp Arg Ile Glu Trp Ile Lys Ile Gln Ile Ile Ser Lys Ile Arg Leu
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 188

Trp Ser Ile Glu Xaa Ile Lys Ile Gln Ile Ile Ser Lys Leu Arg Leu
1               5                   10                  15

<210> SEQ ID NO 189

```
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 189

Trp Trp Ile Glu Xaa Ile Lys Ile Gln Ile Ile Ser Lys Leu Arg Leu
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 190

Trp Arg Ile Glu Xaa Ile Lys Ile Gln Ile Ile Ser Lys Leu Arg Leu
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 191

Trp Lys Ile Glu Xaa Ile Lys Ile Gln Ile Ile Ser Lys Leu Arg Leu
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 192

Trp His Ile Glu Xaa Ile Lys Ile Gln Ile Ile Ser Lys Leu Arg Leu
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine
<220> FEATURE:
<221> NAME/KEY: BINDING
```

-continued

```
<222> LOCATION: (5)..(5)
<223> OTHER INFORMATION: 3-Naphtyl alanine

<400> SEQUENCE: 193

Trp Xaa Ile Glu Xaa Ile Lys Ile Gln Ile Ile Ser Lys Leu Arg Leu
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine
<220> FEATURE:
<221> NAME/KEY: BINDING
<222> LOCATION: (5)..(5)
<223> OTHER INFORMATION: 3-Naphtyl alanine

<400> SEQUENCE: 194

Trp Xaa Ile Glu Xaa Ile Lys Ile Gln Ile Ile Ser Lys Leu Arg Leu
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 195

Trp Tyr Ile Arg Xaa Ile Lys Ile Gln Ile Ile Ser Lys Leu Arg Leu
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 196

Trp Tyr Ile Lys Xaa Ile Lys Ile Gln Ile Ile Ser Lys Leu Arg Leu
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 197

Trp Tyr Ile Asn Xaa Ile Lys Ile Gln Ile Ile Ser Lys Leu Arg Leu
1               5                   10                  15
```

```
<210> SEQ ID NO 198
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 198

Trp Tyr Ile Gln Xaa Ile Lys Ile Gln Ile Ile Ser Lys Leu Arg Leu
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 199

Trp Tyr Ile Asp Xaa Ile Lys Ile Gln Ile Ile Ser Lys Leu Arg Leu
1               5                   10                  15

<210> SEQ ID NO 200
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 200

Trp Tyr Ile Glu Xaa Ile Lys Ile Asn Ile Ile Ser Lys Leu Arg Leu
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 201

Trp Tyr Ile Glu Xaa Ile Lys Ile Pro Ile Ile Ser Lys Leu Arg Leu
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
```

<223> OTHER INFORMATION: 3-Naphtyl alanine

<400> SEQUENCE: 202

Trp Tyr Ile Glu Xaa Ile Lys Ile Gln Ile Val Ser Lys Leu Arg Leu
1               5                   10                  15

<210> SEQ ID NO 203
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 203

Trp Tyr Ile Glu Xaa Ile Lys Ile Gln Ile Leu Ser Lys Leu Arg Leu
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 204

Trp Tyr Ile Glu Xaa Ile Lys Ile Gln Ile Phe Ser Lys Leu Arg Leu
1               5                   10                  15

<210> SEQ ID NO 205
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 205

Trp Tyr Ile Glu Xaa Ile Lys Ile Gln Ile Trp Ser Lys Leu Arg Leu
1               5                   10                  15

<210> SEQ ID NO 206
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 206

Trp Tyr Ile Glu Xaa Ile Lys Ile Gln Ile Tyr Ser Lys Leu Arg Leu
1               5                   10                  15

<210> SEQ ID NO 207
<211> LENGTH: 16
<212> TYPE: PRT

```
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine
<220> FEATURE:
<221> NAME/KEY: Nva
<222> LOCATION: (11)..(11)

<400> SEQUENCE: 207

Trp Tyr Ile Glu Xaa Ile Lys Ile Gln Ile Xaa Ser Lys Leu Arg Leu
1               5                   10                  15

<210> SEQ ID NO 208
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine
<220> FEATURE:
<221> NAME/KEY: BINDING
<222> LOCATION: (11)..(11)
<223> OTHER INFORMATION: 2-Cyclohexyl glycine

<400> SEQUENCE: 208

Trp Tyr Ile Glu Xaa Ile Lys Ile Gln Ile Xaa Ser Lys Leu Arg Leu
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 209

Trp Tyr Ile Glu Xaa Ile Lys Ile Gln Ile Ile Ser Lys Ile Arg Leu
1               5                   10                  15

<210> SEQ ID NO 210
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 210

Trp Ser Ile Glu Phe Ile Lys Ile Gln Ile Ile Ser Lys Ile Arg Leu
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 211

Trp Trp Ile Glu Phe Ile Lys Ile Gln Ile Ile Ser Lys Ile Arg Leu
1               5                   10                  15
```

-continued

```
<210> SEQ ID NO 212
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 212

Trp Arg Ile Glu Phe Ile Lys Ile Gln Ile Ile Ser Lys Ile Arg Leu
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 213

Trp Lys Ile Glu Phe Ile Lys Ile Gln Ile Ile Ser Lys Ile Arg Leu
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 214

Trp His Ile Glu Phe Ile Lys Ile Gln Ile Ile Ser Lys Ile Arg Leu
1               5                   10                  15

<210> SEQ ID NO 215
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 215

Trp Xaa Ile Glu Phe Ile Lys Ile Gln Ile Ile Ser Lys Ile Arg Leu
1               5                   10                  15

<210> SEQ ID NO 216
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 216

Trp Xaa Ile Glu Phe Ile Lys Ile Gln Ile Ile Ser Lys Ile Arg Leu
1               5                   10                  15

<210> SEQ ID NO 217
<211> LENGTH: 16
<212> TYPE: PRT
<213> ORGANISM: Artificial Sequence
```

```
<220> FEATURE:
<223> OTHER INFORMATION: Myostatin Inhibitory Peptide

<400> SEQUENCE: 217

Trp Tyr Ile Arg Phe Ile Lys Ile Gln Ile Ile Ser Lys Ile Arg Leu
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 218

Trp Tyr Ile Lys Phe Ile Lys Ile Gln Ile Ile Ser Lys Ile Arg Leu
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 219

Trp Tyr Ile Asn Phe Ile Lys Ile Gln Ile Ile Ser Lys Ile Arg Leu
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 220

Trp Tyr Ile Gln Phe Ile Lys Ile Gln Ile Ile Ser Lys Ile Arg Leu
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 221

Trp Tyr Ile Asp Phe Ile Lys Ile Gln Ile Ile Ser Lys Ile Arg Leu
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 222

Trp Tyr Ile Glu Phe Ile Lys Ile Asn Ile Ile Ser Lys Ile Arg Leu
1               5                   10                  15

<210> SEQ ID NO 223
<211> LENGTH: 16
<212> TYPE: PRT
<213> ORGANISM: Artificial Sequence
<220> FEATURE:
```

<223> OTHER INFORMATION: Myostatin Inhibitory Peptide

<400> SEQUENCE: 223

Trp Tyr Ile Glu Phe Ile Lys Ile Pro Ile Ile Ser Lys Ile Arg Leu
1 5 10 15

<210> SEQ ID NO 224
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 224

Trp Tyr Ile Glu Phe Ile Lys Ile Gln Ile Val Ser Lys Ile Arg Leu
1 5 10 15

<210> SEQ ID NO 225
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 225

Trp Tyr Ile Glu Phe Ile Lys Ile Gln Ile Leu Ser Lys Ile Arg Leu
1 5 10 15

<210> SEQ ID NO 226
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 226

Trp Tyr Ile Glu Phe Ile Lys Ile Gln Ile Phe Ser Lys Ile Arg Leu
1 5 10 15

<210> SEQ ID NO 227
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 227

Trp Tyr Ile Glu Phe Ile Lys Ile Gln Ile Trp Ser Lys Ile Arg Leu
1 5 10 15

<210> SEQ ID NO 228
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 228

Trp Tyr Ile Glu Phe Ile Lys Ile Gln Ile Tyr Ser Lys Ile Arg Leu
1 5 10 15

<210> SEQ ID NO 229
<211> LENGTH: 16
<212> TYPE: PRT
<213> ORGANISM: Artificial Sequence
<220> FEATURE:
<223> OTHER INFORMATION: Myostatin Inhibitory Peptide

```
<220> FEATURE:
<221> NAME/KEY: Nva
<222> LOCATION: (11)..(11)

<400> SEQUENCE: 229

Trp Tyr Ile Glu Phe Ile Lys Ile Gln Ile Xaa Ser Lys Ile Arg Leu
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 230

Trp Tyr Ile Glu Phe Ile Lys Ile Gln Ile Xaa Ser Lys Ile Arg Leu
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 231

Trp Tyr Ile Glu Phe Ile Lys Ile Gln Ile Ile Ser Lys Leu Arg Leu
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 232

Trp Ser Ile Glu Tyr Ile Lys Ile Gln Ile Ile Ser Lys Ile Arg Leu
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 233

Trp Trp Ile Glu Tyr Ile Lys Ile Gln Ile Ile Ser Lys Ile Arg Leu
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 234

Trp Arg Ile Glu Tyr Ile Lys Ile Gln Ile Ile Ser Lys Ile Arg Leu
1               5                   10                  15
```

```
<210> SEQ ID NO 235
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 235

Trp Lys Ile Glu Tyr Ile Lys Ile Gln Ile Ile Ser Lys Ile Arg Leu
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 236

Trp His Ile Glu Tyr Ile Lys Ile Gln Ile Ile Ser Lys Ile Arg Leu
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 237

Trp Xaa Ile Glu Tyr Ile Lys Ile Gln Ile Ile Ser Lys Ile Arg Leu
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 238

Trp Xaa Ile Glu Tyr Ile Lys Ile Gln Ile Ile Ser Lys Ile Arg Leu
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 239

Trp Tyr Ile Arg Tyr Ile Lys Ile Gln Ile Ile Ser Lys Ile Arg Leu
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: Myostatin Inhibitory Peptide
```

```
<400> SEQUENCE: 240

Trp Tyr Ile Lys Tyr Ile Lys Ile Gln Ile Ile Ser Lys Ile Arg Leu
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 241

Trp Tyr Ile Asn Tyr Ile Lys Ile Gln Ile Ile Ser Lys Ile Arg Leu
1               5                   10                  15

<210> SEQ ID NO 242
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 242

Trp Tyr Ile Gln Tyr Ile Lys Ile Gln Ile Ile Ser Lys Ile Arg Leu
1               5                   10                  15

<210> SEQ ID NO 243
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 243

Trp Tyr Ile Asp Tyr Ile Lys Ile Gln Ile Ile Ser Lys Ile Arg Leu
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 244

Trp Tyr Ile Glu Tyr Ile Lys Ile Asn Ile Ile Ser Lys Ile Arg Leu
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 245

Trp Tyr Ile Glu Tyr Ile Lys Ile Pro Ile Ile Ser Lys Ile Arg Leu
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: Myostatin Inhibitory Peptide
```

```
<400> SEQUENCE: 246

Trp Tyr Ile Glu Tyr Ile Lys Ile Gln Ile Val Ser Lys Ile Arg Leu
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 247

Trp Tyr Ile Glu Tyr Ile Lys Ile Gln Ile Leu Ser Lys Ile Arg Leu
1               5                   10                  15

<210> SEQ ID NO 248
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 248

Trp Tyr Ile Glu Tyr Ile Lys Ile Gln Ile Phe Ser Lys Ile Arg Leu
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 249

Trp Tyr Ile Glu Tyr Ile Lys Ile Gln Ile Trp Ser Lys Ile Arg Leu
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 250

Trp Tyr Ile Glu Tyr Ile Lys Ile Gln Ile Tyr Ser Lys Ile Arg Leu
1               5                   10                  15

<210> SEQ ID NO 251
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 251

Trp Tyr Ile Glu Tyr Ile Lys Ile Gln Ile Xaa Ser Lys Ile Arg Leu
1               5                   10                  15

<210> SEQ ID NO 252
<211> LENGTH: 16
<212> TYPE: PRT
<213> ORGANISM: Artificial Sequence
<220> FEATURE:
```

```
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 252

Trp Tyr Ile Glu Tyr Ile Lys Ile Gln Ile Xaa Ser Lys Ile Arg Leu
1               5                   10                  15

<210> SEQ ID NO 253
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 253

Trp Tyr Ile Glu Tyr Ile Lys Ile Gln Ile Ile Ser Lys Leu Arg Leu
1               5                   10                  15

<210> SEQ ID NO 254
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 254

Trp Ser Ile Glu His Ile Lys Ile Gln Ile Ile Ser Lys Ile Arg Leu
1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 255

Trp Trp Ile Glu His Ile Lys Ile Gln Ile Ile Ser Lys Ile Arg Leu
1               5                   10                  15

<210> SEQ ID NO 256
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 256

Trp Arg Ile Glu His Ile Lys Ile Gln Ile Ile Ser Lys Ile Arg Leu
1               5                   10                  15

<210> SEQ ID NO 257
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 257

Trp Lys Ile Glu His Ile Lys Ile Gln Ile Ile Ser Lys Ile Arg Leu
1               5                   10                  15

<210> SEQ ID NO 258
<211> LENGTH: 16
```

```
<212> TYPE: PRT
<213> ORGANISM: Artificial Sequence
<220> FEATURE:
<223> OTHER INFORMATION: Myostatin Inhibitory Peptide

<400> SEQUENCE: 258

Trp His Ile Glu His Ile Lys Ile Gln Ile Ile Ser Lys Ile Arg Leu
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 259

Trp Xaa Ile Glu His Ile Lys Ile Gln Ile Ile Ser Lys Ile Arg Leu
1               5                   10                  15

<210> SEQ ID NO 260
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 260

Trp Xaa Ile Glu His Ile Lys Ile Gln Ile Ile Ser Lys Ile Arg Leu
1               5                   10                  15

<210> SEQ ID NO 261
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 261

Trp Tyr Ile Arg His Ile Lys Ile Gln Ile Ile Ser Lys Ile Arg Leu
1               5                   10                  15

<210> SEQ ID NO 262
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 262

Trp Tyr Ile Lys His Ile Lys Ile Gln Ile Ile Ser Lys Ile Arg Leu
1               5                   10                  15

<210> SEQ ID NO 263
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 263
```

Trp Tyr Ile Asn His Ile Lys Ile Gln Ile Ile Ser Lys Ile Arg Leu
1               5                   10                  15

<210> SEQ ID NO 264
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 264

Trp Tyr Ile Gln His Ile Lys Ile Gln Ile Ile Ser Lys Ile Arg Leu
1               5                   10                  15

<210> SEQ ID NO 265
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 265

Trp Tyr Ile Asp His Ile Lys Ile Gln Ile Ile Ser Lys Ile Arg Leu
1               5                   10                  15

<210> SEQ ID NO 266
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 266

Trp Tyr Ile Glu His Ile Lys Ile Asn Ile Ile Ser Lys Ile Arg Leu
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 267

Trp Tyr Ile Glu His Ile Lys Ile Pro Ile Ile Ser Lys Ile Arg Leu
1               5                   10                  15

<210> SEQ ID NO 268
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 268

Trp Tyr Ile Glu His Ile Lys Ile Gln Ile Val Ser Lys Ile Arg Leu
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 269

```
Trp Tyr Ile Glu His Ile Lys Ile Gln Ile Leu Ser Lys Ile Arg Leu
1               5                   10                  15
```

<210> SEQ ID NO 270
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 270

```
Trp Tyr Ile Glu His Ile Lys Ile Gln Ile Phe Ser Lys Ile Arg Leu
1               5                   10                  15
```

<210> SEQ ID NO 271
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 271

```
Trp Tyr Ile Glu His Ile Lys Ile Gln Ile Trp Ser Lys Ile Arg Leu
1               5                   10                  15
```

<210> SEQ ID NO 272
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 272

```
Trp Tyr Ile Glu His Ile Lys Ile Gln Ile Tyr Ser Lys Ile Arg Leu
1               5                   10                  15
```

<210> SEQ ID NO 273
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 273

```
Trp Tyr Ile Glu His Ile Lys Ile Gln Ile Xaa Ser Lys Ile Arg Leu
1               5                   10                  15
```

<210> SEQ ID NO 274
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 274

```
Trp Tyr Ile Glu His Ile Lys Ile Gln Ile Xaa Ser Lys Ile Arg Leu
1               5                   10                  15
```

<210> SEQ ID NO 275
<211> LENGTH: 16
<212> TYPE: PRT

```
<213> ORGANISM: Artificial Sequence
<220> FEATURE:
<223> OTHER INFORMATION: Myostatin Inhibitory Peptide

<400> SEQUENCE: 275

Trp Tyr Ile Glu His Ile Lys Ile Gln Ile Ile Ser Lys Leu Arg Leu
1               5                   10                  15

<210> SEQ ID NO 276
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 276

Trp Ser Ile Glu Trp Ile Lys Ile Gln Ile Xaa Ser Lys Leu Arg Leu
1               5                   10                  15

<210> SEQ ID NO 277
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 277

Trp Trp Ile Glu Trp Ile Lys Ile Gln Ile Xaa Ser Lys Leu Arg Leu
1               5                   10                  15

<210> SEQ ID NO 278
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 278

Trp Lys Ile Glu Trp Ile Lys Ile Gln Ile Xaa Ser Lys Leu Arg Leu
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 279

Trp Tyr Ile Arg Trp Ile Lys Ile Gln Ile Xaa Ser Lys Leu Arg Leu
1               5                   10                  15

<210> SEQ ID NO 280
<211> LENGTH: 16
<212> TYPE: PRT
<213> ORGANISM: Artificial Sequence
<220> FEATURE:
```

<223> OTHER INFORMATION: Myostatin Inhibitory Peptide
<220> FEATURE:
<221> NAME/KEY: Nva
<222> LOCATION: (11)..(11)

<400> SEQUENCE: 280

Trp Tyr Ile Lys Trp Ile Lys Ile Gln Ile Xaa Ser Lys Leu Arg Leu
1               5                   10                  15

<210> SEQ ID NO 281
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 281

Trp Tyr Ile Asn Trp Ile Lys Ile Gln Ile Xaa Ser Lys Leu Arg Leu
1               5                   10                  15

<210> SEQ ID NO 282
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 282

Trp Tyr Ile Gln Trp Ile Lys Ile Gln Ile Xaa Ser Lys Leu Arg Leu
1               5                   10                  15

<210> SEQ ID NO 283
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 283

Trp Tyr Ile Asp Trp Ile Lys Ile Gln Ile Xaa Ser Lys Leu Arg Leu
1               5                   10                  15

<210> SEQ ID NO 284
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 284

Trp Tyr Ile Glu Trp Ile Lys Ile Asn Ile Xaa Ser Lys Leu Arg Leu
1               5                   10                  15

<210> SEQ ID NO 285
<211> LENGTH: 16
<212> TYPE: PRT
<213> ORGANISM: Artificial Sequence

```
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 285

Trp Tyr Ile Glu Trp Ile Lys Ile Pro Ile Xaa Ser Lys Leu Arg Leu
1               5                   10                  15

<210> SEQ ID NO 286
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 286

Trp Tyr Ile Glu Trp Ile Lys Ile Gln Ile Val Ser Lys Leu Arg Leu
1               5                   10                  15

<210> SEQ ID NO 287
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 287

Trp Tyr Ile Glu Trp Ile Lys Ile Gln Ile Leu Ser Lys Leu Arg Leu
1               5                   10                  15

<210> SEQ ID NO 288
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 288

Trp Tyr Ile Glu Trp Ile Lys Ile Gln Ile Xaa Ser Lys Ile Arg Leu
1               5                   10                  15

<210> SEQ ID NO 289
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 289

Trp Ser Ile Glu Trp Ile Lys Ile Gln Ile Xaa Ser Lys Leu Arg Leu
1               5                   10                  15

<210> SEQ ID NO 290
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
```

```
<222> LOCATION: (11)..(11)
<223> OTHER INFORMATION: 2-Cyclohexyl glycine

<400> SEQUENCE: 290

Trp Trp Ile Glu Trp Ile Lys Ile Gln Ile Xaa Ser Lys Leu Arg Leu
1               5                   10                  15

<210> SEQ ID NO 291
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 291

Trp Lys Ile Glu Trp Ile Lys Ile Gln Ile Xaa Ser Lys Leu Arg Leu
1               5                   10                  15

<210> SEQ ID NO 292
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 292

Trp Tyr Ile Arg Trp Ile Lys Ile Gln Ile Xaa Ser Lys Leu Arg Leu
1               5                   10                  15

<210> SEQ ID NO 293
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 293

Trp Tyr Ile Lys Trp Ile Lys Ile Gln Ile Xaa Ser Lys Leu Arg Leu
1               5                   10                  15

<210> SEQ ID NO 294
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 294

Trp Tyr Ile Asn Trp Ile Lys Ile Gln Ile Xaa Ser Lys Leu Arg Leu
1               5                   10                  15

<210> SEQ ID NO 295
<211> LENGTH: 16
```

-continued

```
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 295

Trp Tyr Ile Gln Trp Ile Lys Ile Gln Ile Xaa Ser Lys Leu Arg Leu
1               5                   10                  15

<210> SEQ ID NO 296
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 296

Trp Tyr Ile Asp Trp Ile Lys Ile Gln Ile Xaa Ser Lys Leu Arg Leu
1               5                   10                  15

<210> SEQ ID NO 297
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 297

Trp Tyr Ile Glu Trp Ile Lys Ile Asn Ile Xaa Ser Lys Leu Arg Leu
1               5                   10                  15

<210> SEQ ID NO 298
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 298

Trp Tyr Ile Glu Trp Ile Lys Ile Pro Ile Xaa Ser Lys Leu Arg Leu
1               5                   10                  15

<210> SEQ ID NO 299
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 299
```

```
Trp Tyr Ile Glu Trp Ile Lys Ile Gln Ile Xaa Ser Lys Ile Arg Leu
1               5                   10                  15
```

<210> SEQ ID NO 300
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 300

```
Trp Ser Ile Glu Trp Ile Lys Ile Gln Ile Phe Ser Lys Leu Arg Leu
1               5                   10                  15
```

<210> SEQ ID NO 301
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 301

```
Trp Trp Ile Glu Trp Ile Lys Ile Gln Ile Phe Ser Lys Leu Arg Leu
1               5                   10                  15
```

<210> SEQ ID NO 302
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 302

```
Trp Lys Ile Glu Trp Ile Lys Ile Gln Ile Phe Ser Lys Leu Arg Leu
1               5                   10                  15
```

<210> SEQ ID NO 303
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 303

```
Trp Tyr Ile Arg Trp Ile Lys Ile Gln Ile Phe Ser Lys Leu Arg Leu
1               5                   10                  15
```

<210> SEQ ID NO 304
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 304

```
Trp Tyr Ile Lys Trp Ile Lys Ile Gln Ile Phe Ser Lys Leu Arg Leu
1               5                   10                  15
```

<210> SEQ ID NO 305
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 305

```
Trp Tyr Ile Asn Trp Ile Lys Ile Gln Ile Phe Ser Lys Leu Arg Leu
```

```
<210> SEQ ID NO 306
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 306

Trp Tyr Ile Gln Trp Ile Lys Ile Gln Ile Phe Ser Lys Leu Arg Leu
1               5                   10                  15

<210> SEQ ID NO 307
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 307

Trp Tyr Ile Asp Trp Ile Lys Ile Gln Ile Phe Ser Lys Leu Arg Leu
1               5                   10                  15

<210> SEQ ID NO 308
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 308

Trp Tyr Ile Glu Trp Ile Lys Ile Asn Ile Phe Ser Lys Leu Arg Leu
1               5                   10                  15

<210> SEQ ID NO 309
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 309

Trp Tyr Ile Glu Trp Ile Lys Ile Pro Ile Phe Ser Lys Leu Arg Leu
1               5                   10                  15

<210> SEQ ID NO 310
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 310

Trp Tyr Ile Glu Trp Ile Lys Ile Gln Ile Phe Ser Lys Ile Arg Leu
1               5                   10                  15

<210> SEQ ID NO 311
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 311

Trp Ser Ile Glu Trp Ile Lys Ile Gln Ile Trp Ser Lys Leu Arg Leu
1               5                   10                  15
```

<210> SEQ ID NO 312
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 312

Trp Trp Ile Glu Trp Ile Lys Ile Gln Ile Trp Ser Lys Leu Arg Leu
1               5                   10                  15

<210> SEQ ID NO 313
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 313

Trp Lys Ile Glu Trp Ile Lys Ile Gln Ile Trp Ser Lys Leu Arg Leu
1               5                   10                  15

<210> SEQ ID NO 314
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 314

Trp Tyr Ile Asp Trp Ile Lys Ile Gln Ile Trp Ser Lys Leu Arg Leu
1               5                   10                  15

<210> SEQ ID NO 315
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 315

Trp Tyr Ile Glu Trp Ile Lys Ile Asn Ile Trp Ser Lys Leu Arg Leu
1               5                   10                  15

<210> SEQ ID NO 316
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 316

Trp Tyr Ile Glu Trp Ile Lys Ile Gln Ile Trp Ser Lys Ile Arg Leu
1               5                   10                  15

<210> SEQ ID NO 317
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 317

Trp Ser Ile Glu Ser Ile Lys Ile Gln Ile Trp Ser Lys Leu Arg Leu
1               5                   10                  15

<210> SEQ ID NO 318
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 318

Trp Trp Ile Glu Ser Ile Lys Ile Gln Ile Trp Ser Lys Leu Arg Leu
1               5                   10                  15

<210> SEQ ID NO 319
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 319

Trp Arg Ile Glu Ser Ile Lys Ile Gln Ile Trp Ser Lys Leu Arg Leu
1               5                   10                  15

<210> SEQ ID NO 320
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 320

Trp Lys Ile Glu Ser Ile Lys Ile Gln Ile Trp Ser Lys Leu Arg Leu
1               5                   10                  15

<210> SEQ ID NO 321
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 321

Trp His Ile Glu Ser Ile Lys Ile Gln Ile Trp Ser Lys Leu Arg Leu
1               5                   10                  15

<210> SEQ ID NO 322
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 322

Trp Xaa Ile Glu Ser Ile Lys Ile Gln Ile Trp Ser Lys Leu Arg Leu
1               5                   10                  15

<210> SEQ ID NO 323
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)

<223> OTHER INFORMATION: 3-Naphtyl alanine

<400> SEQUENCE: 323

Trp Xaa Ile Glu Ser Ile Lys Ile Gln Ile Trp Ser Lys Leu Arg Leu
1               5                   10                  15

<210> SEQ ID NO 324
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 324

Trp Tyr Ile Arg Ser Ile Lys Ile Gln Ile Trp Ser Lys Leu Arg Leu
1               5                   10                  15

<210> SEQ ID NO 325
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 325

Trp Tyr Ile Lys Ser Ile Lys Ile Gln Ile Trp Ser Lys Leu Arg Leu
1               5                   10                  15

<210> SEQ ID NO 326
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 326

Trp Tyr Ile Asn Ser Ile Lys Ile Gln Ile Trp Ser Lys Leu Arg Leu
1               5                   10                  15

<210> SEQ ID NO 327
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 327

Trp Tyr Ile Gln Ser Ile Lys Ile Gln Ile Trp Ser Lys Leu Arg Leu
1               5                   10                  15

<210> SEQ ID NO 328
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 328

Trp Tyr Ile Asp Ser Ile Lys Ile Gln Ile Trp Ser Lys Leu Arg Leu
1               5                   10                  15

<210> SEQ ID NO 329
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 329

Trp Tyr Ile Glu Ser Ile Lys Ile Asn Ile Trp Ser Lys Leu Arg Leu
1               5                   10                  15

<210> SEQ ID NO 330
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 330

Trp Tyr Ile Glu Ser Ile Lys Ile Pro Ile Trp Ser Lys Leu Arg Leu
1               5                   10                  15

<210> SEQ ID NO 331
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 331

Trp Tyr Ile Glu Ser Ile Lys Ile Gln Ile Val Ser Lys Leu Arg Leu
1               5                   10                  15

<210> SEQ ID NO 332
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 332

Trp Tyr Ile Glu Ser Ile Lys Ile Gln Ile Leu Ser Lys Leu Arg Leu
1               5                   10                  15

<210> SEQ ID NO 333
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 333

Trp Tyr Ile Glu Ser Ile Lys Ile Gln Ile Phe Ser Lys Leu Arg Leu
1               5                   10                  15

<210> SEQ ID NO 334
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 334

Trp Tyr Ile Glu Ser Ile Lys Ile Gln Ile Tyr Ser Lys Leu Arg Leu
1               5                   10                  15

<210> SEQ ID NO 335
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:

<221> NAME/KEY: Nva
<222> LOCATION: (11)..(11)

<400> SEQUENCE: 335

Trp Tyr Ile Glu Ser Ile Lys Ile Gln Ile Xaa Ser Lys Leu Arg Leu
1               5                   10                  15

<210> SEQ ID NO 336
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 336

Trp Tyr Ile Glu Ser Ile Lys Ile Gln Ile Xaa Ser Lys Leu Arg Leu
1               5                   10                  15

<210> SEQ ID NO 337
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 337

Trp Tyr Ile Glu Ser Ile Lys Ile Gln Ile Trp Ser Lys Ile Arg Leu
1               5                   10                  15

<210> SEQ ID NO 338
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 338

Trp Ser Ile Lys Trp Ile Lys Ile Gln Ile Trp Ser Lys Leu Arg Leu
1               5                   10                  15

<210> SEQ ID NO 339
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 339

Trp Trp Ile Lys Trp Ile Lys Ile Gln Ile Trp Ser Lys Leu Arg Leu
1               5                   10                  15

<210> SEQ ID NO 340
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 340

Trp Arg Ile Lys Trp Ile Lys Ile Gln Ile Trp Ser Lys Leu Arg Leu
1               5                   10                  15

<210> SEQ ID NO 341

```
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 341

Trp Lys Ile Lys Trp Ile Lys Ile Gln Ile Trp Ser Lys Leu Arg Leu
1               5                   10                  15

<210> SEQ ID NO 342
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 342

Trp His Ile Lys Trp Ile Lys Ile Gln Ile Trp Ser Lys Leu Arg Leu
1               5                   10                  15

<210> SEQ ID NO 343
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 343

Trp Xaa Ile Lys Trp Ile Lys Ile Gln Ile Trp Ser Lys Leu Arg Leu
1               5                   10                  15

<210> SEQ ID NO 344
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 344

Trp Xaa Ile Lys Trp Ile Lys Ile Gln Ile Trp Ser Lys Leu Arg Leu
1               5                   10                  15

<210> SEQ ID NO 345
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 345

Trp Tyr Ile Lys Trp Ile Lys Ile Asn Ile Trp Ser Lys Leu Arg Leu
1               5                   10                  15

<210> SEQ ID NO 346
<211> LENGTH: 16
<212> TYPE: PRT
<213> ORGANISM: Artificial Sequence
<220> FEATURE:
<223> OTHER INFORMATION: Myostatin Inhibitory Peptide
```

```
<400> SEQUENCE: 346

Trp Tyr Ile Lys Trp Ile Lys Ile Pro Ile Trp Ser Lys Leu Arg Leu
1               5                   10                  15

<210> SEQ ID NO 347
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 347

Trp Tyr Ile Lys Trp Ile Lys Ile Gln Ile Val Ser Lys Leu Arg Leu
1               5                   10                  15

<210> SEQ ID NO 348
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 348

Trp Tyr Ile Lys Trp Ile Lys Ile Gln Ile Leu Ser Lys Leu Arg Leu
1               5                   10                  15

<210> SEQ ID NO 349
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 349

Trp Tyr Ile Lys Trp Ile Lys Ile Gln Ile Ile Ser Lys Leu Arg Leu
1               5                   10                  15

<210> SEQ ID NO 350
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 350

Trp Tyr Ile Lys Trp Ile Lys Ile Gln Ile Tyr Ser Lys Leu Arg Leu
1               5                   10                  15

<210> SEQ ID NO 351
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 351

Trp Tyr Ile Lys Trp Ile Lys Ile Gln Ile Trp Ser Lys Ile Arg Leu
1               5                   10                  15

<210> SEQ ID NO 352
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 352
```

Trp Ser Ile Arg Trp Ile Lys Ile Gln Ile Trp Ser Lys Leu Arg Leu
1               5                   10                  15

<210> SEQ ID NO 353
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 353

Trp Trp Ile Arg Trp Ile Lys Ile Gln Ile Trp Ser Lys Leu Arg Leu
1               5                   10                  15

<210> SEQ ID NO 354
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 354

Trp Arg Ile Arg Trp Ile Lys Ile Gln Ile Trp Ser Lys Leu Arg Leu
1               5                   10                  15

<210> SEQ ID NO 355
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 355

Trp Lys Ile Arg Trp Ile Lys Ile Gln Ile Trp Ser Lys Leu Arg Leu
1               5                   10                  15

<210> SEQ ID NO 356
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 356

Trp His Ile Arg Trp Ile Lys Ile Gln Ile Trp Ser Lys Leu Arg Leu
1               5                   10                  15

<210> SEQ ID NO 357
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 357

Trp Xaa Ile Arg Trp Ile Lys Ile Gln Ile Trp Ser Lys Leu Arg Leu
1               5                   10                  15

<210> SEQ ID NO 358
<211> LENGTH: 16
<212> TYPE: PRT
<213> ORGANISM: Artificial Sequence
<220> FEATURE:

```
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 358

Trp Xaa Ile Arg Trp Ile Lys Ile Gln Ile Trp Ser Lys Leu Arg Leu
1               5                   10                  15

<210> SEQ ID NO 359
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 359

Trp Tyr Ile Arg Trp Ile Lys Ile Asn Ile Trp Ser Lys Leu Arg Leu
1               5                   10                  15

<210> SEQ ID NO 360
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 360

Trp Tyr Ile Arg Trp Ile Lys Ile Pro Ile Trp Ser Lys Leu Arg Leu
1               5                   10                  15

<210> SEQ ID NO 361
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 361

Trp Tyr Ile Arg Trp Ile Lys Ile Gln Ile Val Ser Lys Leu Arg Leu
1               5                   10                  15

<210> SEQ ID NO 362
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 362

Trp Tyr Ile Arg Trp Ile Lys Ile Gln Ile Leu Ser Lys Leu Arg Leu
1               5                   10                  15

<210> SEQ ID NO 363
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 363

Trp Tyr Ile Arg Trp Ile Lys Ile Gln Ile Ile Ser Lys Leu Arg Leu
1               5                   10                  15

<210> SEQ ID NO 364
<211> LENGTH: 16
```

```
<212> TYPE: PRT
<213> ORGANISM: Artificial Sequence
<220> FEATURE:
<223> OTHER INFORMATION: Myostatin Inhibitory Peptide

<400> SEQUENCE: 364

Trp Tyr Ile Arg Trp Ile Lys Ile Gln Ile Tyr Ser Lys Leu Arg Leu
1               5                   10                  15

<210> SEQ ID NO 365
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 365

Trp Tyr Ile Arg Trp Ile Lys Ile Gln Ile Trp Ser Lys Ile Arg Leu
1               5                   10                  15

<210> SEQ ID NO 366
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 366

Trp Ser Ile Gln Trp Ile Lys Ile Gln Ile Trp Ser Lys Leu Arg Leu
1               5                   10                  15

<210> SEQ ID NO 367
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 367

Trp Trp Ile Gln Trp Ile Lys Ile Gln Ile Trp Ser Lys Leu Arg Leu
1               5                   10                  15

<210> SEQ ID NO 368
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 368

Trp Arg Ile Gln Trp Ile Lys Ile Gln Ile Trp Ser Lys Leu Arg Leu
1               5                   10                  15

<210> SEQ ID NO 369
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 369

Trp Lys Ile Gln Trp Ile Lys Ile Gln Ile Trp Ser Lys Leu Arg Leu
1               5                   10                  15

<210> SEQ ID NO 370
<211> LENGTH: 16
<212> TYPE: PRT
```

<213> ORGANISM: Artificial Sequence
<220> FEATURE:
<223> OTHER INFORMATION: Myostatin Inhibitory Peptide

<400> SEQUENCE: 370

Trp His Ile Gln Trp Ile Lys Ile Gln Ile Trp Ser Lys Leu Arg Leu
1               5                   10                  15

<210> SEQ ID NO 371
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 371

Trp Xaa Ile Gln Trp Ile Lys Ile Gln Ile Trp Ser Lys Leu Arg Leu
1               5                   10                  15

<210> SEQ ID NO 372
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 372

Trp Xaa Ile Gln Trp Ile Lys Ile Gln Ile Trp Ser Lys Leu Arg Leu
1               5                   10                  15

<210> SEQ ID NO 373
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 373

Trp Tyr Ile Gln Trp Ile Lys Ile Asn Ile Trp Ser Lys Leu Arg Leu
1               5                   10                  15

<210> SEQ ID NO 374
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 374

Trp Tyr Ile Gln Trp Ile Lys Ile Pro Ile Trp Ser Lys Leu Arg Leu
1               5                   10                  15

<210> SEQ ID NO 375
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 375

```
Trp Tyr Ile Gln Trp Ile Lys Ile Gln Ile Val Ser Lys Leu Arg Leu
1               5                   10                  15
```

<210> SEQ ID NO 376
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 376

```
Trp Tyr Ile Gln Trp Ile Lys Ile Gln Ile Leu Ser Lys Leu Arg Leu
1               5                   10                  15
```

<210> SEQ ID NO 377
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 377

```
Trp Tyr Ile Gln Trp Ile Lys Ile Gln Ile Ile Ser Lys Leu Arg Leu
1               5                   10                  15
```

<210> SEQ ID NO 378
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 378

```
Trp Tyr Ile Gln Trp Ile Lys Ile Gln Ile Tyr Ser Lys Leu Arg Leu
1               5                   10                  15
```

<210> SEQ ID NO 379
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 379

```
Trp Tyr Ile Gln Trp Ile Lys Ile Gln Ile Trp Ser Lys Ile Arg Leu
1               5                   10                  15
```

<210> SEQ ID NO 380
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 380

```
Trp Tyr Ile Arg Trp Ile Lys Xaa Gln Ile Trp Ser Lys Leu Arg Leu
1               5                   10                  15
```

<210> SEQ ID NO 381
<211> LENGTH: 16
<212> TYPE: PRT
<213> ORGANISM: Artificial Sequence
<220> FEATURE:
<223> OTHER INFORMATION: Myostatin Inhibitory Peptide

```
<220> FEATURE:
<221> NAME/KEY: BINDING
<222> LOCATION: (14)..(14)
<223> OTHER INFORMATION: 2-Cyclohexyl glycine

<400> SEQUENCE: 381

Trp Tyr Ile Arg Trp Ile Lys Ile Gln Ile Trp Ser Lys Xaa Arg Leu
1               5                   10                  15

<210> SEQ ID NO 382
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 382

Trp Tyr Ile Arg Trp Ile Lys Xaa Gln Ile Trp Ser Lys Xaa Arg Leu
1               5                   10                  15

<210> SEQ ID NO 383
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 383

Trp Tyr Phe Arg Trp Ile Lys Ile Gln Ile Trp Ser Lys Leu Arg Leu
1               5                   10                  15

<210> SEQ ID NO 384
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 384

Trp Tyr Ile Arg Trp Ile Lys Ile Gln Phe Trp Ser Lys Leu Arg Leu
1               5                   10                  15

<210> SEQ ID NO 385
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 385

Tyr Tyr Ile Arg Xaa Ile Lys Ile Gln Ile Trp Ser Lys Leu Arg Leu
1               5                   10                  15

<210> SEQ ID NO 386
<211> LENGTH: 16
<212> TYPE: PRT
<213> ORGANISM: Artificial Sequence
```

```
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 386

Tyr Tyr Ile Glu Trp Ile Lys Ile Gln Ile Ile Ser Lys Xaa Arg Leu
1               5                   10                  15

<210> SEQ ID NO 387
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 387

Tyr Tyr Phe Glu Trp Ile Lys Ile Gln Ile Ile Ser Lys Leu Arg Leu
1               5                   10                  15

<210> SEQ ID NO 388
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 388

Tyr Tyr Ile Glu Trp Ile Lys Xaa Gln Ile Ile Ser Lys Leu Arg Leu
1               5                   10                  15

<210> SEQ ID NO 389
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine
<220> FEATURE:
<221> NAME/KEY: BINDING
<222> LOCATION: (14)..(14)
<223> OTHER INFORMATION: 2-Cyclohexyl glycine

<400> SEQUENCE: 389

Xaa Tyr Ile Glu Trp Ile Lys Ile Gln Ile Ile Ser Lys Xaa Arg Leu
1               5                   10                  15

<210> SEQ ID NO 390
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine

<400> SEQUENCE: 390

Xaa Tyr Phe Glu Trp Ile Lys Ile Gln Ile Ile Ser Lys Leu Arg Leu
1               5                   10                  15
```

```
<210> SEQ ID NO 391
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (1)..(1)
<223> OTHER INFORMATION: 3-Naphtyl alanine
<220> FEATURE:
<221> NAME/KEY: BINDING
<222> LOCATION: (8)..(8)
<223> OTHER INFORMATION: 2-Cyclohexyl glycine

<400> SEQUENCE: 391

Xaa Tyr Ile Glu Trp Ile Lys Xaa Gln Ile Ile Ser Lys Leu Arg Leu
1               5                   10                  15

<210> SEQ ID NO 392
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 392

Phe Tyr Ile Glu Trp Ile Lys Ile Gln Ile Ile Ser Lys Xaa Arg Leu
1               5                   10                  15

<210> SEQ ID NO 393
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 393

Phe Tyr Phe Glu Trp Ile Lys Ile Gln Ile Ile Ser Lys Leu Arg Leu
1               5                   10                  15

<210> SEQ ID NO 394
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 394

Phe Tyr Ile Glu Trp Ile Lys Xaa Gln Ile Ile Ser Lys Leu Arg Leu
1               5                   10                  15

<210> SEQ ID NO 395
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
```

```
<223> OTHER INFORMATION: 2-Cyclohexyl glycine

<400> SEQUENCE: 395

Leu Tyr Ile Glu Trp Ile Lys Ile Gln Ile Ile Ser Lys Xaa Arg Leu
1               5                   10                  15

<210> SEQ ID NO 396
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 396

Leu Tyr Phe Glu Trp Ile Lys Ile Gln Ile Ile Ser Lys Leu Arg Leu
1               5                   10                  15

<210> SEQ ID NO 397
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 397

Leu Tyr Ile Glu Trp Ile Lys Xaa Gln Ile Ile Ser Lys Leu Arg Leu
1               5                   10                  15

<210> SEQ ID NO 398
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine
<220> FEATURE:
<221> NAME/KEY: BINDING
<222> LOCATION: (14)..(14)
<223> OTHER INFORMATION: 2-Cyclohexyl glycine

<400> SEQUENCE: 398

Trp Xaa Ile Glu Trp Ile Lys Ile Gln Ile Ile Ser Lys Xaa Arg Leu
1               5                   10                  15

<210> SEQ ID NO 399
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 399

Trp Xaa Phe Glu Trp Ile Lys Ile Gln Ile Ile Ser Lys Leu Arg Leu
1               5                   10                  15

<210> SEQ ID NO 400
<211> LENGTH: 16
<212> TYPE: PRT
```

```
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine
<220> FEATURE:
<221> NAME/KEY: BINDING
<222> LOCATION: (8)..(8)
<223> OTHER INFORMATION: 2-Cyclohexyl glycine

<400> SEQUENCE: 400

Trp Xaa Ile Glu Trp Ile Lys Xaa Gln Ile Ile Ser Lys Leu Arg Leu
1               5                   10                  15

<210> SEQ ID NO 401
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine
<220> FEATURE:
<221> NAME/KEY: BINDING
<222> LOCATION: (14)..(14)
<223> OTHER INFORMATION: 2-Cyclohexyl glycine

<400> SEQUENCE: 401

Trp Xaa Ile Glu Trp Ile Lys Ile Gln Ile Ile Ser Lys Xaa Arg Leu
1               5                   10                  15

<210> SEQ ID NO 402
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 402

Trp Xaa Phe Glu Trp Ile Lys Ile Gln Ile Ile Ser Lys Leu Arg Leu
1               5                   10                  15

<210> SEQ ID NO 403
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine
<220> FEATURE:
<221> NAME/KEY: BINDING
<222> LOCATION: (8)..(8)
<223> OTHER INFORMATION: 2-Cyclohexyl glycine

<400> SEQUENCE: 403

Trp Xaa Ile Glu Trp Ile Lys Xaa Gln Ile Ile Ser Lys Leu Arg Leu
1               5                   10                  15

<210> SEQ ID NO 404
<211> LENGTH: 16
```

```
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 404

Trp His Ile Glu Trp Ile Lys Ile Gln Ile Ile Ser Lys Xaa Arg Leu
1               5                   10                  15

<210> SEQ ID NO 405
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 405

Trp His Phe Glu Trp Ile Lys Ile Gln Ile Ile Ser Lys Leu Arg Leu
1               5                   10                  15

<210> SEQ ID NO 406
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 406

Trp His Ile Glu Trp Ile Lys Xaa Gln Ile Ile Ser Lys Leu Arg Leu
1               5                   10                  15

<210> SEQ ID NO 407
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 407

Trp Arg Ile Glu Trp Ile Lys Ile Gln Ile Ile Ser Lys Xaa Arg Leu
1               5                   10                  15

<210> SEQ ID NO 408
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 408

Trp Arg Phe Glu Trp Ile Lys Ile Gln Ile Ile Ser Lys Leu Arg Leu
1               5                   10                  15

<210> SEQ ID NO 409
<211> LENGTH: 16
<212> TYPE: PRT
<213> ORGANISM: Artificial Sequence
```

```
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 409

Trp Arg Ile Glu Trp Ile Lys Xaa Gln Ile Ile Ser Lys Leu Arg Leu
1               5                   10                  15

<210> SEQ ID NO 410
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine
<220> FEATURE:
<221> NAME/KEY: BINDING
<222> LOCATION: (14)..(14)
<223> OTHER INFORMATION: 2-Cyclohexyl glycine

<400> SEQUENCE: 410

Trp Tyr Ile Glu Xaa Ile Lys Ile Gln Ile Ile Ser Lys Xaa Arg Leu
1               5                   10                  15

<210> SEQ ID NO 411
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 411

Trp Tyr Phe Glu Xaa Ile Lys Ile Gln Ile Ile Ser Lys Leu Arg Leu
1               5                   10                  15

<210> SEQ ID NO 412
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine
<220> FEATURE:
<221> NAME/KEY: BINDING
<222> LOCATION: (8)..(8)
<223> OTHER INFORMATION: 2-Cyclohexyl glycine

<400> SEQUENCE: 412

Trp Tyr Ile Glu Xaa Ile Lys Xaa Gln Ile Ile Ser Lys Leu Arg Leu
1               5                   10                  15

<210> SEQ ID NO 413
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
```

```
<221> NAME/KEY: BINDING
<222> LOCATION: (14)..(14)
<223> OTHER INFORMATION: 2-Cyclohexyl glycine

<400> SEQUENCE: 413

Trp Tyr Ile Glu Phe Ile Lys Ile Gln Ile Ile Ser Lys Xaa Arg Leu
1               5                   10                  15

<210> SEQ ID NO 414
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 414

Trp Tyr Phe Glu Phe Ile Lys Ile Gln Ile Ile Ser Lys Ile Arg Leu
1               5                   10                  15

<210> SEQ ID NO 415
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 415

Trp Tyr Ile Glu Phe Ile Lys Xaa Gln Ile Ile Ser Lys Ile Arg Leu
1               5                   10                  15

<210> SEQ ID NO 416
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 416

Trp Tyr Ile Glu Tyr Ile Lys Ile Gln Ile Ile Ser Lys Xaa Arg Leu
1               5                   10                  15

<210> SEQ ID NO 417
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 417

Trp Tyr Phe Glu Tyr Ile Lys Ile Gln Ile Ile Ser Lys Ile Arg Leu
1               5                   10                  15

<210> SEQ ID NO 418
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
```

<223> OTHER INFORMATION: 2-Cyclohexyl glycine

<400> SEQUENCE: 418

Trp Tyr Ile Glu Tyr Ile Lys Xaa Gln Ile Ile Ser Lys Ile Arg Leu
1               5                   10                  15

<210> SEQ ID NO 419
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 419

Trp Tyr Ile Glu His Ile Lys Ile Gln Ile Ile Ser Lys Xaa Arg Leu
1               5                   10                  15

<210> SEQ ID NO 420
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 420

Trp Tyr Phe Glu His Ile Lys Ile Gln Ile Ile Ser Lys Ile Arg Leu
1               5                   10                  15

<210> SEQ ID NO 421
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 421

Trp Tyr Ile Glu His Ile Lys Xaa Gln Ile Ile Ser Lys Ile Arg Leu
1               5                   10                  15

<210> SEQ ID NO 422
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)
<220> FEATURE:
<221> NAME/KEY: BINDING
<222> LOCATION: (14)..(14)
<223> OTHER INFORMATION: 2-Cyclohexyl glycine

<400> SEQUENCE: 422

Trp Tyr Ile Glu Trp Ile Lys Ile Gln Ile Xaa Ser Lys Xaa Arg Leu
1               5                   10                  15

<210> SEQ ID NO 423
<211> LENGTH: 16
<212> TYPE: PRT
<213> ORGANISM: Artificial Sequence

```
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 423

Trp Tyr Phe Glu Trp Ile Lys Ile Gln Ile Xaa Ser Lys Leu Arg Leu
1               5                   10                  15

<210> SEQ ID NO 424
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: Nva
<222> LOCATION: (11)..(11)

<400> SEQUENCE: 424

Trp Tyr Ile Glu Trp Ile Lys Xaa Gln Ile Xaa Ser Lys Leu Arg Leu
1               5                   10                  15

<210> SEQ ID NO 425
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 425

Trp Tyr Ile Glu Trp Ile Lys Ile Gln Ile Xaa Ser Lys Xaa Arg Leu
1               5                   10                  15

<210> SEQ ID NO 426
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 426

Trp Tyr Phe Glu Trp Ile Lys Ile Gln Ile Xaa Ser Lys Leu Arg Leu
1               5                   10                  15

<210> SEQ ID NO 427
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
```

```
<223> OTHER INFORMATION: 2-Cyclohexyl glycine
<220> FEATURE:
<221> NAME/KEY: BINDING
<222> LOCATION: (11)..(11)
<223> OTHER INFORMATION: 2-Cyclohexyl glycine

<400> SEQUENCE: 427

Trp Tyr Ile Glu Trp Ile Lys Xaa Gln Ile Xaa Ser Lys Leu Arg Leu
1               5                   10                  15

<210> SEQ ID NO 428
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 428

Trp Tyr Ile Glu Trp Ile Lys Ile Gln Ile Phe Ser Lys Xaa Arg Leu
1               5                   10                  15

<210> SEQ ID NO 429
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 429

Trp Tyr Phe Glu Trp Ile Lys Ile Gln Ile Phe Ser Lys Leu Arg Leu
1               5                   10                  15

<210> SEQ ID NO 430
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 430

Trp Tyr Ile Glu Trp Ile Lys Xaa Gln Ile Phe Ser Lys Leu Arg Leu
1               5                   10                  15

<210> SEQ ID NO 431
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 431

Trp Tyr Ile Glu Ser Ile Lys Ile Gln Ile Trp Ser Lys Xaa Arg Leu
1               5                   10                  15

<210> SEQ ID NO 432
<211> LENGTH: 16
<212> TYPE: PRT
```

-continued

```
<213> ORGANISM: Artificial Sequence
<220> FEATURE:
<223> OTHER INFORMATION: Myostatin Inhibitory Peptide

<400> SEQUENCE: 432

Trp Tyr Phe Glu Ser Ile Lys Ile Gln Ile Trp Ser Lys Leu Arg Leu
1               5                   10                  15

<210> SEQ ID NO 433
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 433

Trp Tyr Ile Glu Ser Ile Lys Xaa Gln Ile Trp Ser Lys Leu Arg Leu
1               5                   10                  15

<210> SEQ ID NO 434
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 434

Trp Ser Ile Arg Trp Ile Lys Xaa Gln Ile Trp Ser Lys Leu Arg Leu
1               5                   10                  15

<210> SEQ ID NO 435
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 435

Trp Trp Ile Arg Trp Ile Lys Xaa Gln Ile Trp Ser Lys Leu Arg Leu
1               5                   10                  15

<210> SEQ ID NO 436
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 436

Trp Arg Ile Arg Trp Ile Lys Xaa Gln Ile Trp Ser Lys Leu Arg Leu
1               5                   10                  15

<210> SEQ ID NO 437
```

```
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 437

Trp Lys Ile Arg Trp Ile Lys Xaa Gln Ile Trp Ser Lys Leu Arg Leu
1               5                   10                  15

<210> SEQ ID NO 438
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 438

Trp His Ile Arg Trp Ile Lys Xaa Gln Ile Trp Ser Lys Leu Arg Leu
1               5                   10                  15

<210> SEQ ID NO 439
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine
<220> FEATURE:
<221> NAME/KEY: BINDING
<222> LOCATION: (8)..(8)
<223> OTHER INFORMATION: 2-Cyclohexyl glycine

<400> SEQUENCE: 439

Trp Xaa Ile Arg Trp Ile Lys Xaa Gln Ile Trp Ser Lys Leu Arg Leu
1               5                   10                  15

<210> SEQ ID NO 440
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine
<220> FEATURE:
<221> NAME/KEY: BINDING
<222> LOCATION: (8)..(8)
<223> OTHER INFORMATION: 2-Cyclohexyl glycine

<400> SEQUENCE: 440

Trp Xaa Ile Arg Trp Ile Lys Xaa Gln Ile Trp Ser Lys Leu Arg Leu
1               5                   10                  15

<210> SEQ ID NO 441
<211> LENGTH: 16
<212> TYPE: PRT
<213> ORGANISM: Artificial Sequence
```

```
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 441

Trp Tyr Ile Lys Trp Ile Lys Xaa Gln Ile Trp Ser Lys Leu Arg Leu
1               5                   10                  15

<210> SEQ ID NO 442
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 442

Trp Tyr Ile Asn Trp Ile Lys Xaa Gln Ile Trp Ser Lys Leu Arg Leu
1               5                   10                  15

<210> SEQ ID NO 443
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 443

Trp Tyr Ile Gln Trp Ile Lys Xaa Gln Ile Trp Ser Lys Leu Arg Leu
1               5                   10                  15

<210> SEQ ID NO 444
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 444

Trp Tyr Ile Asp Trp Ile Lys Xaa Gln Ile Trp Ser Lys Leu Arg Leu
1               5                   10                  15

<210> SEQ ID NO 445
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 445

Trp Tyr Ile Glu Trp Ile Lys Xaa Gln Ile Trp Ser Lys Leu Arg Leu
1               5                   10                  15
```

<210> SEQ ID NO 446
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 446

Trp Tyr Ile Arg Trp Ile Lys Xaa Asn Ile Trp Ser Lys Leu Arg Leu
1               5                   10                  15

<210> SEQ ID NO 447
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 447

Trp Tyr Ile Arg Trp Ile Lys Xaa Pro Ile Trp Ser Lys Leu Arg Leu
1               5                   10                  15

<210> SEQ ID NO 448
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 448

Trp Tyr Ile Arg Trp Ile Lys Xaa Gln Ile Val Ser Lys Leu Arg Leu
1               5                   10                  15

<210> SEQ ID NO 449
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 449

Trp Tyr Ile Arg Trp Ile Lys Xaa Gln Ile Leu Ser Lys Leu Arg Leu
1               5                   10                  15

<210> SEQ ID NO 450
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)

-continued

<223> OTHER INFORMATION: 2-Cyclohexyl glycine

<400> SEQUENCE: 450

Trp Tyr Ile Arg Trp Ile Lys Xaa Gln Ile Ile Ser Lys Leu Arg Leu
1               5                   10                  15

<210> SEQ ID NO 451
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 451

Trp Tyr Ile Arg Trp Ile Lys Xaa Gln Ile Phe Ser Lys Leu Arg Leu
1               5                   10                  15

<210> SEQ ID NO 452
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 452

Trp Tyr Ile Arg Trp Ile Lys Xaa Gln Ile Tyr Ser Lys Leu Arg Leu
1               5                   10                  15

<210> SEQ ID NO 453
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: Nva
<222> LOCATION: (11)..(11)

<400> SEQUENCE: 453

Trp Tyr Ile Arg Trp Ile Lys Xaa Gln Ile Xaa Ser Lys Leu Arg Leu
1               5                   10                  15

<210> SEQ ID NO 454
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (11)..(11)
<223> OTHER INFORMATION: 2-Cyclohexyl glycine

<400> SEQUENCE: 454

```
Trp Tyr Ile Arg Trp Ile Lys Xaa Gln Ile Xaa Ser Lys Leu Arg Leu
1               5                   10                  15

<210> SEQ ID NO 455
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 455

Trp Ser Ile Arg Trp Ile Lys Ile Gln Ile Trp Ser Lys Xaa Arg Leu
1               5                   10                  15

<210> SEQ ID NO 456
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 456

Trp Trp Ile Arg Trp Ile Lys Ile Gln Ile Trp Ser Lys Xaa Arg Leu
1               5                   10                  15

<210> SEQ ID NO 457
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 457

Trp Arg Ile Arg Trp Ile Lys Ile Gln Ile Trp Ser Lys Xaa Arg Leu
1               5                   10                  15

<210> SEQ ID NO 458
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 458

Trp Lys Ile Arg Trp Ile Lys Ile Gln Ile Trp Ser Lys Xaa Arg Leu
1               5                   10                  15

<210> SEQ ID NO 459
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
```

```
<221> NAME/KEY: BINDING
<222> LOCATION: (14)..(14)
<223> OTHER INFORMATION: 2-Cyclohexyl glycine

<400> SEQUENCE: 459

Trp His Ile Arg Trp Ile Lys Ile Gln Ile Trp Ser Lys Xaa Arg Leu
1               5                   10                  15

<210> SEQ ID NO 460
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine
<220> FEATURE:
<221> NAME/KEY: BINDING
<222> LOCATION: (14)..(14)
<223> OTHER INFORMATION: 2-Cyclohexyl glycine

<400> SEQUENCE: 460

Trp Xaa Ile Arg Trp Ile Lys Ile Gln Ile Trp Ser Lys Xaa Arg Leu
1               5                   10                  15

<210> SEQ ID NO 461
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine
<220> FEATURE:
<221> NAME/KEY: BINDING
<222> LOCATION: (14)..(14)
<223> OTHER INFORMATION: 2-Cyclohexyl glycine

<400> SEQUENCE: 461

Trp Xaa Ile Arg Trp Ile Lys Ile Gln Ile Trp Ser Lys Xaa Arg Leu
1               5                   10                  15

<210> SEQ ID NO 462
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 462

Trp Tyr Ile Lys Trp Ile Lys Ile Gln Ile Trp Ser Lys Xaa Arg Leu
1               5                   10                  15

<210> SEQ ID NO 463
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine
```

<400> SEQUENCE: 463

Trp Tyr Ile Asn Trp Ile Lys Ile Gln Ile Trp Ser Lys Xaa Arg Leu
1               5                   10                  15

<210> SEQ ID NO 464
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 464

Trp Tyr Ile Gln Trp Ile Lys Ile Gln Ile Trp Ser Lys Xaa Arg Leu
1               5                   10                  15

<210> SEQ ID NO 465
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 465

Trp Tyr Ile Asp Trp Ile Lys Ile Gln Ile Trp Ser Lys Xaa Arg Leu
1               5                   10                  15

<210> SEQ ID NO 466
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 466

Trp Tyr Ile Glu Trp Ile Lys Ile Gln Ile Trp Ser Lys Xaa Arg Leu
1               5                   10                  15

<210> SEQ ID NO 467
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 467

Trp Tyr Ile Arg Trp Ile Lys Ile Asn Ile Trp Ser Lys Xaa Arg Leu
1               5                   10                  15

<210> SEQ ID NO 468
<211> LENGTH: 16
<212> TYPE: PRT
<213> ORGANISM: Artificial Sequence

```
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 468

Trp Tyr Ile Arg Trp Ile Lys Ile Pro Ile Trp Ser Lys Xaa Arg Leu
1               5                   10                  15

<210> SEQ ID NO 469
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 469

Trp Tyr Ile Arg Trp Ile Lys Ile Gln Ile Val Ser Lys Xaa Arg Leu
1               5                   10                  15

<210> SEQ ID NO 470
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 470

Trp Tyr Ile Arg Trp Ile Lys Ile Gln Ile Leu Ser Lys Xaa Arg Leu
1               5                   10                  15

<210> SEQ ID NO 471
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 471

Trp Tyr Ile Arg Trp Ile Lys Ile Gln Ile Ile Ser Lys Xaa Arg Leu
1               5                   10                  15

<210> SEQ ID NO 472
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 472

Trp Tyr Ile Arg Trp Ile Lys Ile Gln Ile Phe Ser Lys Xaa Arg Leu
1               5                   10                  15
```

```
<210> SEQ ID NO 473
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 473

Trp Tyr Ile Arg Trp Ile Lys Ile Gln Ile Tyr Ser Lys Xaa Arg Leu
1               5                   10                  15

<210> SEQ ID NO 474
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)
<220> FEATURE:
<221> NAME/KEY: BINDING
<222> LOCATION: (14)..(14)
<223> OTHER INFORMATION: 2-Cyclohexyl glycine

<400> SEQUENCE: 474

Trp Tyr Ile Arg Trp Ile Lys Ile Gln Ile Xaa Ser Lys Xaa Arg Leu
1               5                   10                  15

<210> SEQ ID NO 475
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 475

Trp Tyr Ile Arg Trp Ile Lys Ile Gln Ile Xaa Ser Lys Xaa Arg Leu
1               5                   10                  15

<210> SEQ ID NO 476
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 476

Trp Ser Ile Arg Trp Ile Lys Xaa Gln Ile Trp Ser Lys Xaa Arg Leu
1               5                   10                  15
```

<210> SEQ ID NO 477
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 477

Trp Trp Ile Arg Trp Ile Lys Xaa Gln Ile Trp Ser Lys Xaa Arg Leu
1               5                   10                  15

<210> SEQ ID NO 478
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 478

Trp Arg Ile Arg Trp Ile Lys Xaa Gln Ile Trp Ser Lys Xaa Arg Leu
1               5                   10                  15

<210> SEQ ID NO 479
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 479

Trp Lys Ile Arg Trp Ile Lys Xaa Gln Ile Trp Ser Lys Xaa Arg Leu
1               5                   10                  15

<210> SEQ ID NO 480
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

```
<400> SEQUENCE: 480

Trp His Ile Arg Trp Ile Lys Xaa Gln Ile Trp Ser Lys Xaa Arg Leu
1               5                   10                  15

<210> SEQ ID NO 481
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 481

Trp Xaa Ile Arg Trp Ile Lys Xaa Gln Ile Trp Ser Lys Xaa Arg Leu
1               5                   10                  15

<210> SEQ ID NO 482
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 482

Trp Xaa Ile Arg Trp Ile Lys Xaa Gln Ile Trp Ser Lys Xaa Arg Leu
1               5                   10                  15

<210> SEQ ID NO 483
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 483

Trp Tyr Ile Lys Trp Ile Lys Xaa Gln Ile Trp Ser Lys Xaa Arg Leu
1               5                   10                  15

<210> SEQ ID NO 484
```

```
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 484

Trp Tyr Ile Asn Trp Ile Lys Xaa Gln Ile Trp Ser Lys Xaa Arg Leu
1

-continued

Trp Tyr Ile Glu Trp Ile Lys Xaa Gln Ile Trp Ser Lys Xaa Arg Leu
1               5                   10                  15

<210> SEQ ID NO 488
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 488

Trp Tyr Ile Arg Trp Ile Lys Xaa Asn Ile Trp Ser Lys Xaa Arg Leu
1               5                   10                  15

<210> SEQ ID NO 489
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 489

Trp Tyr Ile Arg Trp Ile Lys Xaa Pro Ile Trp Ser Lys Xaa Arg Leu
1               5                   10                  15

<210> SEQ ID NO 490
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 490

Trp Tyr Ile Arg Trp Ile Lys Xaa Gln Ile Val Ser Lys Xaa Arg Leu
1               5                   10                  15

<210> SEQ ID NO 491
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 491

Trp Tyr Ile Arg Trp Ile Lys Xaa Gln Ile Leu Ser Lys Xaa Arg Leu
1               5                   10                  15

<210> SEQ ID NO 492
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 492

Trp Tyr Ile Arg Trp Ile Lys Xaa Gln Ile Ile Ser Lys Xaa Arg Leu
1               5                   10                  15

<210> SEQ ID NO 493
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 493

Trp Tyr Ile Arg Trp Ile Lys Xaa Gln Ile Phe Ser Lys Xaa Arg Leu
1               5                   10                  15

<210> SEQ ID NO 494
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 494

Trp Tyr Ile Arg Trp Ile Lys Xaa Gln Ile Tyr Ser Lys Xaa Arg Leu
1               5                   10                  15

<210> SEQ ID NO 495
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:

-continued

```
<221> NAME/KEY: BINDING
<222> LOCATION: (8)..(8)
<223> OTHER INFORMATION: 2-Cyclohexyl glycine
<220> FEATURE:
<221> NAME/KEY: Nva
<222> LOCATION: (11)..(11)
<220> FEATURE:
<221> NAME/KEY: BINDING
<222> LOCATION: (14)..(14)
<223> OTHER INFORMATION: 2-Cyclohexyl glycine

<400> SEQUENCE: 495

Trp Tyr Ile Arg Trp Ile Lys Xaa Gln Ile Xaa Ser Lys Xaa Arg Leu
1               5                   10                  15

<210> SEQ ID NO 496
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (11)..(11)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 496

Trp Tyr Ile Arg Trp Ile Lys Xaa Gln Ile Xaa Ser Lys Xaa Arg Leu
1               5                   10                  15

<210> SEQ ID NO 497
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 497

Trp Tyr Ile Arg Trp Ile Lys Xaa Gln Ile Trp Ser Lys Ile Arg Leu
1               5                   10                  15

<210> SEQ ID NO 498
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 498

Trp Tyr Phe Arg Trp Ile Lys Xaa Gln Ile Trp Ser Lys Xaa Arg Leu
1               5                   10                  15
```

<210> SEQ ID NO 499
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 499

Trp Ser Phe Arg Trp Ile Lys Ile Gln Ile Trp Ser Lys Leu Arg Leu
1               5                   10                  15

<210> SEQ ID NO 500
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 500

Trp Trp Phe Arg Trp Ile Lys Ile Gln Ile Trp Ser Lys Leu Arg Leu
1               5                   10                  15

<210> SEQ ID NO 501
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 501

Trp Arg Phe Arg Trp Ile Lys Ile Gln Ile Trp Ser Lys Leu Arg Leu
1               5                   10                  15

<210> SEQ ID NO 502
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 502

Trp Lys Phe Arg Trp Ile Lys Ile Gln Ile Trp Ser Lys Leu Arg Leu
1               5                   10                  15

<210> SEQ ID NO 503
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 503

Trp His Phe Arg Trp Ile Lys Ile Gln Ile Trp Ser Lys Leu Arg Leu
1               5                   10                  15

<210> SEQ ID NO 504
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 504

Trp Xaa Phe Arg Trp Ile Lys Ile Gln Ile Trp Ser Lys Leu Arg Leu
1               5                   10                  15

<210> SEQ ID NO 505
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 505

Trp Xaa Phe Arg Trp Ile Lys Ile Gln Ile Trp Ser Lys Leu Arg Leu
1               5                   10                  15

<210> SEQ ID NO 506
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 506

Trp Tyr Phe Lys Trp Ile Lys Ile Gln Ile Trp Ser Lys Leu Arg Leu
1               5                   10                  15

<210> SEQ ID NO 507
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 507

Trp Tyr Phe Asn Trp Ile Lys Ile Gln Ile Trp Ser Lys Leu Arg Leu
1               5                   10                  15

<210> SEQ ID NO 508
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 508

Trp Tyr Phe Gln Trp Ile Lys Ile Gln Ile Trp Ser Lys Leu Arg Leu
1               5                   10                  15

<210> SEQ ID NO 509
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 509

Trp Tyr Phe Asp Trp Ile Lys Ile Gln Ile Trp Ser Lys Leu Arg Leu
1               5                   10                  15

<210> SEQ ID NO 510
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 510

Trp Tyr Phe Glu Trp Ile Lys Ile Gln Ile Trp Ser Lys Leu Arg Leu
1               5                   10                  15

<210> SEQ ID NO 511
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 511

Trp Tyr Phe Arg Trp Ile Lys Ile Asn Ile Trp Ser Lys Leu Arg Leu
1               5                   10                  15

<210> SEQ ID NO 512
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 512

Trp Tyr Phe Arg Trp Ile Lys Ile Pro Ile Trp Ser Lys Leu Arg Leu
1               5                   10                  15

<210> SEQ ID NO 513
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 513

Trp Tyr Phe Arg Trp Ile Lys Ile Gln Ile Val Ser Lys Leu Arg Leu
1               5                   10                  15

<210> SEQ ID NO 514
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 514

Trp Tyr Phe Arg Trp Ile Lys Ile Gln Ile Leu Ser Lys Leu Arg Leu
1               5                   10                  15

<210> SEQ ID NO 515
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 515

Trp Tyr Phe Arg Trp Ile Lys Ile Gln Ile Ile Ser Lys Leu Arg Leu
1               5                   10                  15

<210> SEQ ID NO 516
<211> LENGTH: 16
<212> TYPE: PRT
<213> ORGANISM: Artificial Sequence
<220> FEATURE:
<223> OTHER INFORMATION: Myostatin Inhibitory Peptide

```
<400> SEQUENCE: 516

Trp Tyr Phe Arg Trp Ile Lys Ile Gln Ile Phe Ser Lys Leu Arg Leu
1               5                   10                  15

<210> SEQ ID NO 517
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 517

Trp Tyr Phe Arg Trp Ile Lys Ile Gln Ile Tyr Ser Lys Leu Arg Leu
1               5                   10                  15

<210> SEQ ID NO 518
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 518

Trp Tyr Phe Arg Trp Ile Lys Ile Gln Ile Xaa Ser Lys Leu Arg Leu
1               5                   10                  15

<210> SEQ ID NO 519
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 519

Trp Tyr Phe Arg Trp Ile Lys Ile Gln Ile Xaa Ser Lys Leu Arg Leu
1               5                   10                  15

<210> SEQ ID NO 520
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 520

Trp Tyr Phe Arg Trp Ile Lys Ile Gln Ile Trp Ser Lys Ile Arg Leu
1               5                   10                  15

<210> SEQ ID NO 521
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 521

Trp Tyr Phe Arg Trp Ile Lys Ile Gln Ile Trp Ser Lys Xaa Arg Leu
```

<210> SEQ ID NO 522
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 522

Trp Tyr Phe Arg Trp Ile Lys Xaa Gln Ile Trp Ser Lys Leu Arg Leu
1               5                   10                  15

<210> SEQ ID NO 523
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 523

Trp Ser Ile Arg Trp Ile Lys Ile Gln Phe Trp Ser Lys Leu Arg Leu
1               5                   10                  15

<210> SEQ ID NO 524
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 524

Trp Trp Ile Arg Trp Ile Lys Ile Gln Phe Trp Ser Lys Leu Arg Leu
1               5                   10                  15

<210> SEQ ID NO 525
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 525

Trp Arg Ile Arg Trp Ile Lys Ile Gln Phe Trp Ser Lys Leu Arg Leu
1               5                   10                  15

<210> SEQ ID NO 526
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 526

Trp Lys Ile Arg Trp Ile Lys Ile Gln Phe Trp Ser Lys Leu Arg Leu
1               5                   10                  15

<210> SEQ ID NO 527
<211> LENGTH: 16
<212> TYPE: PRT
<213> ORGANISM: Artificial Sequence
<220> FEATURE:
<223> OTHER INFORMATION: Myostatin Inhibitory Peptide

```
<400> SEQUENCE: 527

Trp His Ile Arg Trp Ile Lys Ile Gln Phe Trp Ser Lys Leu Arg Leu
1               5                   10                  15

<210> SEQ ID NO 528
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine

<400> SEQUENCE: 528

Trp Xaa Ile Arg Trp Ile Lys Ile Gln Phe Trp Ser Lys Leu Arg Leu
1               5                   10                  15

<210> SEQ ID NO 529
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine

<400> SEQUENCE: 529

Trp Xaa Ile Arg Trp Ile Lys Ile Gln Phe Trp Ser Lys Leu Arg Leu
1               5                   10                  15

<210> SEQ ID NO 530
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 530

Trp Tyr Ile Lys Trp Ile Lys Ile Gln Phe Trp Ser Lys Leu Arg Leu
1               5                   10                  15

<210> SEQ ID NO 531
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 531

Trp Tyr Ile Asn Trp Ile Lys Ile Gln Phe Trp Ser Lys Leu Arg Leu
1               5                   10                  15

<210> SEQ ID NO 532
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 532

Trp Tyr Ile Gln Trp Ile Lys Ile Gln Phe Trp Ser Lys Leu Arg Leu
1               5                   10                  15
```

```
<210> SEQ ID NO 533
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 533

Trp Tyr Ile Asp Trp Ile Lys Ile Gln Phe Trp Ser Lys Leu Arg Leu
1               5                   10                  15

<210> SEQ ID NO 534
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 534

Trp Tyr Ile Glu Trp Ile Lys Ile Gln Phe Trp Ser Lys Leu Arg Leu
1               5                   10                  15

<210> SEQ ID NO 535
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 535

Trp Tyr Ile Arg Trp Ile Lys Ile Asn Phe Trp Ser Lys Leu Arg Leu
1               5                   10                  15

<210> SEQ ID NO 536
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 536

Trp Tyr Ile Arg Trp Ile Lys Ile Pro Phe Trp Ser Lys Leu Arg Leu
1               5                   10                  15

<210> SEQ ID NO 537
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 537

Trp Tyr Ile Arg Trp Ile Lys Ile Gln Phe Val Ser Lys Leu Arg Leu
1               5                   10                  15

<210> SEQ ID NO 538
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 538

Trp Tyr Ile Arg Trp Ile Lys Ile Gln Phe Leu Ser Lys Leu Arg Leu
1               5                   10                  15

<210> SEQ ID NO 539
```

```
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 539

Trp Tyr Ile Arg Trp Ile Lys Ile Gln Phe Ile Ser Lys Leu Arg Leu
1               5                   10                  15

<210> SEQ ID NO 540
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 540

Trp Tyr Ile Arg Trp Ile Lys Ile Gln Phe Phe Ser Lys Leu Arg Leu
1               5                   10                  15

<210> SEQ ID NO 541
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 541

Trp Tyr Ile Arg Trp Ile Lys Ile Gln Phe Tyr Ser Lys Leu Arg Leu
1               5                   10                  15

<210> SEQ ID NO 542
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: Nva
<222> LOCATION: (11)..(11)

<400> SEQUENCE: 542

Trp Tyr Ile Arg Trp Ile Lys Ile Gln Phe Xaa Ser Lys Leu Arg Leu
1               5                   10                  15

<210> SEQ ID NO 543
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (11)..(11)
<223> OTHER INFORMATION: 2-Cyclohexyl glycine

<400> SEQUENCE: 543

Trp Tyr Ile Arg Trp Ile Lys Ile Gln Phe Xaa Ser Lys Leu Arg Leu
1               5                   10                  15

<210> SEQ ID NO 544
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 544
```

```
Trp Tyr Ile Arg Trp Ile Lys Ile Gln Phe Trp Ser Lys Ile Arg Leu
1               5                   10                  15

<210> SEQ ID NO 545
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (14)..(14)
<223> OTHER INFORMATION: 2-Cyclohexyl glycine

<400> SEQUENCE: 545

Trp Tyr Ile Arg Trp Ile Lys Ile Gln Phe Trp Ser Lys Xaa Arg Leu
1               5                   10                  15

<210> SEQ ID NO 546
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 546

Trp Tyr Phe Arg Trp Ile Lys Ile Gln Phe Trp Ser Lys Leu Arg Leu
1               5                   10                  15

<210> SEQ ID NO 547
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine

<400> SEQUENCE: 547

Trp Tyr Ile Arg Trp Ile Lys Xaa Gln Phe Trp Ser Lys Leu Arg Leu
1               5                   10                  15

<210> SEQ ID NO 548
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 548

Tyr Ser Ile Arg Xaa Ile Lys Ile Gln Ile Trp Ser Lys Leu Arg Leu
1               5                   10                  15

<210> SEQ ID NO 549
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine
```

```
<400> SEQUENCE: 549

Tyr Trp Ile Arg Xaa Ile Lys Ile Gln Ile Trp Ser Lys Leu Arg Leu
1               5                   10                  15

<210> SEQ ID NO 550
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 550

Tyr Arg Ile Arg Xaa Ile Lys Ile Gln Ile Trp Ser Lys Leu Arg Leu
1               5                   10                  15

<210> SEQ ID NO 551
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 551

Tyr Lys Ile Arg Xaa Ile Lys Ile Gln Ile Trp Ser Lys Leu Arg Leu
1               5                   10                  15

<210> SEQ ID NO 552
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 552

Tyr His Ile Arg Xaa Ile Lys Ile Gln Ile Trp Ser Lys Leu Arg Leu
1               5                   10                  15

<210> SEQ ID NO 553
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Cyclohexyl alanine
<220> FEATURE:
<221> NAME/KEY: BINDING
<222> LOCATION: (5)..(5)
<223> OTHER INFORMATION: 3-Naphtyl alanine

<400> SEQUENCE: 553

Tyr Xaa Ile Arg Xaa Ile Lys Ile Gln Ile Trp Ser Lys Leu Arg Leu
1               5                   10                  15
```

```
<210> SEQ ID NO 554
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (2)..(2)
<223> OTHER INFORMATION: 3-Naphtyl alanine
<220> FEATURE:
<221> NAME/KEY: BINDING
<222> LOCATION: (5)..(5)
<223> OTHER INFORMATION: 3-Naphtyl alanine

<400> SEQUENCE: 554

Tyr Xaa Ile Arg Xaa Ile Lys Ile Gln Ile Trp Ser Lys Leu Arg Leu
 1               5                  10                  15

<210> SEQ ID NO 555
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 555

Tyr Tyr Ile Lys Xaa Ile Lys Ile Gln Ile Trp Ser Lys Leu Arg Leu
 1               5                  10                  15

<210> SEQ ID NO 556
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 556

Tyr Tyr Ile Asn Xaa Ile Lys Ile Gln Ile Trp Ser Lys Leu Arg Leu
 1               5                  10                  15

<210> SEQ ID NO 557
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 557

Tyr Tyr Ile Gln Xaa Ile Lys Ile Gln Ile Trp Ser Lys Leu Arg Leu
 1               5                  10                  15

<210> SEQ ID NO 558
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
```

```
<221> NAME/KEY: BINDING
<222> LOCATION: (5)..(5)
<223> OTHER INFORMATION: 3-Naphtyl alanine

<400> SEQUENCE: 558

Tyr Tyr Ile Asp Xaa Ile Lys Ile Gln Ile Trp Ser Lys Leu Arg Leu
1               5                   10                  15

<210> SEQ ID NO 559
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 559

Tyr Tyr Ile Glu Xaa Ile Lys Ile Gln Ile Trp Ser Lys Leu Arg Leu
1               5                   10                  15

<210> SEQ ID NO 560
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 560

Tyr Tyr Ile Arg Xaa Ile Lys Ile Asn Ile Trp Ser Lys Leu Arg Leu
1               5                   10                  15

<210> SEQ ID NO 561
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 561

Tyr Tyr Ile Arg Xaa Ile Lys Ile Pro Ile Trp Ser Lys Leu Arg Leu
1               5                   10                  15

<210> SEQ ID NO 562
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 562

Tyr Tyr Ile Arg Xaa Ile Lys Ile Gln Ile Val Ser Lys Leu Arg Leu
1               5                   10                  15

<210> SEQ ID NO 563
```

```
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 563

Tyr Tyr Ile Arg Xaa Ile Lys Ile Gln Ile Leu Ser Lys Leu Arg Leu
1               5                   10                  15

<210> SEQ ID NO 564
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 564

Tyr Tyr Ile Arg Xaa Ile Lys Ile Gln Ile Ile Ser Lys Leu Arg Leu
1               5                   10                  15

<210> SEQ ID NO 565
<211> LENGTH: 16
<212> TYPE: PRT
<213> ORGANISM: Artificial Sequence
<220> FEATURE:
<223> OTHER INFORMATION: Myostatin Inhibtory Peptide
<220> FEATURE:
<221> NAME/KEY: BINDING
<222> LOCATION: (5)..(5)
<223> OTHER INFORMATION: 3-Naphtyl alanine

<400> SEQUENCE: 565

Tyr Tyr Ile Arg Xaa Ile Lys Ile Gln Ile Phe Ser Lys Leu Arg Leu
1               5                   10                  15

<210> SEQ ID NO 566
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 566

Tyr Tyr Ile Arg Xaa Ile Lys Ile Gln Ile Tyr Ser Lys Leu Arg Leu
1               5                   10                  15

<210> SEQ ID NO 567
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine
<220> FEATURE:
<221> NAME/KEY: Nva
```

<222> LOCATION: (11)..(11)

<400> SEQUENCE: 567

Tyr Tyr Ile Arg Xaa Ile Lys Ile Gln Ile Xaa Ser Lys Leu Arg Leu
1               5                   10                  15

<210> SEQ ID NO 568
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine
<220> FEATURE:
<221> NAME/KEY: BINDING
<222> LOCATION: (11)..(11)
<223> OTHER INFORMATION: 2-Cyclohexyl glycine

<400> SEQUENCE: 568

Tyr Tyr Ile Arg Xaa Ile Lys Ile Gln Ile Xaa Ser Lys Leu Arg Leu
1               5                   10                  15

<210> SEQ ID NO 569
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 569

Tyr Tyr Ile Arg Xaa Ile Lys Ile Gln Ile Trp Ser Lys Ile Arg Leu
1               5                   10                  15

<210> SEQ ID NO 570
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine
<220> FEATURE:
<221> NAME/KEY: BINDING
<222> LOCATION: (14)..(14)
<223> OTHER INFORMATION: 2-Cyclohexyl glycine

<400> SEQUENCE: 570

Tyr Tyr Ile Arg Xaa Ile Lys Ile Gln Ile Trp Ser Lys Xaa Arg Leu
1               5                   10                  15

<210> SEQ ID NO 571
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine

<400> SEQUENCE: 571

```
Tyr Tyr Phe Arg Xaa Ile Lys Ile Gln Ile Trp Ser Lys Leu Arg Leu
1               5                   10                  15

<210> SEQ ID NO 572
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: 3-Naphtyl alanine
<220> FEATURE:
<221> NAME/KEY: BINDING
<222> LOCATION: (8)..(8)
<223> OTHER INFORMATION: 2-Cyclohexyl glycine

<400> SEQUENCE: 572

Tyr Tyr Ile Arg Xaa Ile Lys Xaa Gln Ile Trp Ser Lys Leu Arg Leu
1               5                   10                  15

<210> SEQ ID NO 573
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 573

Trp Tyr Ile Arg Trp Ile Lys Xaa Gln Ile Trp Ser Arg Xaa Arg Leu
1               5                   10                  15

<210> SEQ ID NO 574
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 574

Trp Tyr Ile Arg Trp Ile Arg Xaa Gln Ile Trp Ser Lys Xaa Arg Leu
1               5                   10                  15

<210> SEQ ID NO 575
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
```

```
<221> NAME/KEY: BINDING
<222> LOCATION: (14)..(14)
<223> OTHER INFORMATION: 2-Cyclohexyl glycine

<400> SEQUENCE: 575

Trp Tyr Ile Arg Trp Ile Arg Xaa Gln Ile Trp Ser Arg Xaa Arg Leu
1               5                   10                  15

<210> SEQ ID NO 576
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 576

Trp Tyr Ile Arg Trp Ile Arg Xaa Gln Ile Trp Ser Arg Xaa Pro Leu
1               5                   10                  15

<210> SEQ ID NO 577
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 577

Trp Tyr Ile Arg Trp Ile Arg Xaa Gln Ile Trp Pro Arg Xaa Arg Leu
1               5                   10                  15

<210> SEQ ID NO 578
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 578

Trp Tyr Ile Arg Trp Ile Arg Xaa Pro Ile Trp Ser Arg Xaa Arg Leu
1               5                   10                  15

<210> SEQ ID NO 579
<211> LENGTH: 16
<212> TYPE: PRT
<213> ORGANISM: Artificial Sequence
<220> FEATURE:
<223> OTHER INFORMATION: Myostatin Inhibitory Peptide
```

```
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 579

Trp Tyr Ile Arg Trp Ile Pro Xaa Gln Ile Trp Ser Arg Xaa Arg Leu
1               5                   10                  15

<210> SEQ ID NO 580
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 580

Trp Tyr Ile Arg Trp Ile Arg Xaa Pro Ile Trp Ser Arg Xaa Pro Leu
1               5                   10                  15

<210> SEQ ID NO 581
<211> LENGTH: 15
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (7)..(7)
<223> OTHER INFORMATION: 2-Cyclohexyl glycine
<220> FEATURE:
<221> NAME/KEY: BINDING
<222> LOCATION: (13)..(13)
<223> OTHER INFORMATION: 2-Cyclohexyl glycine

<400> SEQUENCE: 581

Tyr Ile Arg Trp Ile Arg Xaa Gln Ile Trp Ser Arg Xaa Pro Leu
1               5                   10                  15

<210> SEQ ID NO 582
<211> LENGTH: 22
<212> TYPE: PRT
<213> ORGANISM: Artificial Sequence
<220> FEATURE:
<223> OTHER INFORMATION: Peptide

<400> SEQUENCE: 582

Arg Gln Asn Thr Arg Tyr Ser Arg Ile Glu Trp Ile Lys Ile Gln Ile
1               5                   10                  15

Ile Ser Lys Leu Arg Leu
            20

<210> SEQ ID NO 583
<211> LENGTH: 16
<212> TYPE: PRT
<213> ORGANISM: Artificial Sequence
<220> FEATURE:
<223> OTHER INFORMATION: Myostatin Inhibitory Peptide
```

```
<220> FEATURE:
<221> NAME/KEY: BINDING
<222> LOCATION: (7)..(7)
<223> OTHER INFORMATION: alpha-methyl Lys
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 583

Trp Tyr Ile Arg Trp Ile Xaa Xaa Gln Ile Trp Ser Lys Xaa Arg Leu
1               5                   10                  15

<210> SEQ ID NO 584
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 584

Trp Tyr Ile Arg Trp Ile Lys Xaa Gln Ile Trp Ser Lys Xaa Arg Leu
1               5                   10                  15

<210> SEQ ID NO 585
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 585

Trp Tyr Ile Cys Trp Ile Cys Ile Gln Ile Trp Ser Lys Leu Arg Leu
1               5                   10                  15

<210> SEQ ID NO 586
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 586

Trp Tyr Ile Glu Trp Ile Lys Ile Cys Ile Trp Cys Lys Leu Arg Leu
1               5                   10                  15

<210> SEQ ID NO 587
<211> LENGTH: 16
<212> TYPE: PRT
<213> ORGANISM: Artificial Sequence
<220> FEATURE:
<223> OTHER INFORMATION: Myostatin Inhibitory Peptide

<400> SEQUENCE: 587

Trp Tyr Ile Glu Trp Ile Lys Ile Gln Ile Trp Cys Lys Leu Cys Leu
1               5                   10                  15
```

-continued

```
<210> SEQ ID NO 588
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: D-Trp
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 588

Trp Tyr Ile Arg Xaa Ile Arg Xaa Gln Ile Trp Ser Arg Xaa Pro Leu
1               5                   10                  15

<210> SEQ ID NO 589
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: D-Trp
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (12)..(12)
<223> OTHER INFORMATION: D-Ser
<220> FEATURE:
<221> NAME/KEY: BINDING
<222> LOCATION: (14)..(14)
<223> OTHER INFORMATION: 2-Cyclohexyl glycine

<400> SEQUENCE: 589

Trp Tyr Ile Arg Xaa Ile Arg Xaa Gln Ile Trp Xaa Arg Xaa Pro Leu
1               5                   10                  15

<210> SEQ ID NO 590
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: D-Trp
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 590

Trp Tyr Ile Arg Xaa Ile Lys Xaa Gln Ile Trp Ser Lys Xaa Arg Leu
1               5                   10                  15
```

```
<210> SEQ ID NO 591
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: D-Trp
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (12)..(12)
<223> OTHER INFORMATION: D-Ser
<220> FEATURE:
<221> NAME/KEY: BINDING
<222> LOCATION: (14)..(14)
<223> OTHER INFORMATION: 2-Cyclohexyl glycine

<400> SEQUENCE: 591

Trp Tyr Ile Arg Xaa Ile Lys Xaa Gln Ile Trp Xaa Lys Xaa Arg Leu
1               5                   10                  15

<210> SEQ ID NO 592
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (5)..(5)
<223> OTHER INFORMATION: D-Trp
<220> FEATURE:
<221> NAME/KEY: BINDING
<222> LOCATION: (7)..(7)
<223> OTHER INFORMATION: alpha-methyl Lys
<220> FEATURE:
<221> NAME/KEY: BINDING
<222> LOCATION: (8)..(8)
<223> OTHER INFORMATION: 2-Cyclohexyl glycine
<220> FEATURE:
<221> NAME/KEY: BINDING
<222> LOCATION: (14)..(14)
<223> OTHER INFORMATION: 2-Cyclohexyl glycine

<400> SEQUENCE: 592

Trp Tyr Ile Arg Xaa Ile Xaa Xaa Gln Ile Trp Ser Lys Xaa Arg Leu
1               5                   10                  15

<210> SEQ ID NO 593
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (4)..(4)
<223> OTHER INFORMATION: D-Cys

<400> SEQUENCE: 593

Trp Tyr Ile Xaa Trp Ile Cys Ile Gln Ile Trp Ser Lys Leu Arg Leu
1               5                   10                  15

<210> SEQ ID NO 594
<211> LENGTH: 16
<212> TYPE: PRT
<213> ORGANISM: Artificial Sequence
```

```
<220> FEATURE:
<223> OTHER INFORMATION: Myostatin Inhibitory Peptide
<220> FEATURE:
<221> NAME/KEY: BINDING
<222> LOCATION: (9)..(9)
<223> OTHER INFORMATION: D-Cys

<400> SEQUENCE: 594

Trp Tyr Ile Glu Trp Ile Lys Ile Xaa Ile Trp Cys Lys Leu Arg Leu
1               5                   10                  15

<210> SEQ ID NO 595
<211> LENGTH: 16
<212> TYPE: PRT
<213> ORGANISM: Artificial Sequence
<220> FEATURE:
<223> OTHER INFORMATION: Myostatin Inhibitory Peptide
<220> FEATURE:
<221> NAME/KEY: BINDING
<222> LOCATION: (12)..(12)
<223> OTHER INFORMATION: D-Cys

<400> SEQUENCE: 595

Trp Tyr Ile Glu Trp Ile Lys Ile Gln Ile Trp Xaa Lys Leu Arg Leu
1               5                   10                  15
```

PEPTIDE OR PHARMACEUTICALLY ACCEPTABLE SALT THEREOF, OR PRODRUG THEREOF

CROSS REFERENCE TO RELATED APPLICATION

This Application is a 371 of PCT/JP2017/028834 filed on Aug. 8, 2017 which, in turn, claimed the priority of Japanese Patent Application No. 2016-158123 filed on Aug. 10, 2016, both applications are incorporated herein by reference.

TECHNICAL FIELD

The present invention relates to a peptide having a myostatin inhibitory activity or a pharmaceutically acceptable salt of the peptide, or a prodrug thereof. The present invention also relates to a myostatin inhibitory agent and a preventive and/or therapeutic agent of amyotrophic disorder which contain the peptide or the pharmaceutically acceptable salt of the peptide, or the prodrug thereof. The present invention also relates to a method for prevention and/or treatment of amyotrophic disorder, the method including administering the peptide or the pharmaceutically acceptable salt of the peptide, or the prodrug thereof to a patient.

BACKGROUND ART

Muscular dystrophy is a hereditary disorder in which a major lesion is denaturation or necrosis of skeletal muscles and a decrease in muscular power proceeds. In expression of the muscular power, a mechanism is necessary in which tension generated at myofibrils in cells is transferred to basement membranes outside the cells through a plurality of proteins. Defects of genes encoding a protein group involved in this mechanism cause muscular dystrophy to occur. For example, in the most critical Duchenne muscular dystrophy, main causes are said that dystrophin genes vary to cause deletion or malfunction of the protein. In this regard, as a means against denaturation or necrosis of skeletal muscles in muscular dystrophy, development of a treatment method to increase muscle mass by inhibiting the function of a myostatin (growth differentiation factor-8, GDF-8) that is a factor controlling a skeletal muscle mass to be negative is considered to be particularly effective.

The myostatin is a secretory protein that belongs to TGF-β Family and is expressed more on skeletal muscles and is produced as a precursor protein including an N-terminal side prodomain and a C-terminal side mature domain, in cells. The myostatin is secreted from cells, and the propeptide which is called a latency associated protein (LAP) and derived from prodomain, associates with an activated dimer and inactivates the activated dimer mainly controlling a skeletal muscle mass to be negative. The myostatin stocked in a living body as an inactivate state in this way is considered that the propeptide is decomposed by an enzyme as needed to be an active state. The myostatin becoming an active state functions as a signal molecule controlling a skeletal muscle mass to be negative through binding with a receptor typified by an activin type IIB receptor.

Therefore, when the myostatin in the living body is inhibited using a peptide derived from a myostatin propeptide, effects such as an increase in skeletal muscle mass and a medical treatment of amyotrophic disorder as typified by muscular dystrophy can be expected. For example, Patent Literature 1 and Non-Patent Literature 1 describe a myostatin inhibitory peptide derived from a myostatin propeptide.

CITATION LIST

Patent Literatures

Patent Literature 1: WO 2014/119753 A

Non-Patent Literatures

Non-Patent Literature 1: K. Takayama, et al., Journal of Medicinal Chemistry (2015) 58, 1544-1549

SUMMARY OF INVENTION

Herein, in the case of using the peptide as described above as a physiological activator of a medical drug or the like, it is advantageous to shorten a chain length (the number of residues of the peptide) in terms of a utilization rate both in synthesis and in the living body. That is, by shortening the chain length of the peptide to be synthesized, it is possible to simplify synthesis processes and reduce synthesis cost. Further, by shortening the chain length of the peptide, it is possible to expect an effect that sites to be decomposed by an enzyme or the like are reduced or incorporation to cells can be promoted.

However, conventionally, when the chain length of a peptide derived from a myostatin propeptide is reduced, there is a problem in that a myostatin inhibitory activity tends to be degraded. For example, as shown in FIG. 6 of Patent Literature 1, as compared to peptide 1 comprising SEQ ID NO: 2 having a long chain length of the peptide, the myostatin inhibitory activity is degraded in peptide 3 comprising SEQ ID NO: 4 having a short chain length in the same literature. Further, also in FIG. 2 of Non-Patent Literature 1, the myostatin inhibitory activity of peptide 11 having a short chain length is degraded as compared to other peptides.

Therefore, the present invention is made in view of the above-described circumstances, and an object thereof is to provide a peptide having a short chain length, for example, having the number of amino acid residues of 20 or less and having a high myostatin inhibitory activity.

The present inventors have conducted intensive studies in order to solve the above-described problems. As a result, the present inventors have found that the above-described problems are solved by a peptide comprising a predetermined amino acid sequence, thereby completing the present invention.

An aspect of the present invention relates to a peptide or a pharmaceutically acceptable salt of the peptide, or a prodrug thereof, the peptide comprising an amino acid sequence represented by the following Formula (1) and having the number of amino acid residues of 20 or less. Incidentally, the "peptide comprising an amino acid sequence represented by the following Formula (1) and having the number of amino acid residues of 20 or less or a pharmaceutically acceptable salt of the peptide" is also simply referred to as the "peptide according to a first aspect of the present invention."

[Chem. 1]

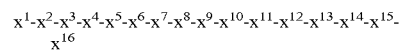

$$X^1\text{-}X^2\text{-}X^3\text{-}X^4\text{-}X^5\text{-}X^6\text{-}X^7\text{-}X^8\text{-}X^9\text{-}X^{10}\text{-}X^{11}\text{-}X^{12}\text{-}X^{13}\text{-}X^{14}\text{-}X^{15}\text{-}X^{16}$$

Formula (1)

In the above Formula (1), $X^1$ represents an amino acid residue selected from the group consisting of Trp, Gly, Ala, Val, Leu, Ile, Pro, Phe, His, Tyr, norleucine, norvaline, isovaline, 2-aminobutyric acid, 2-aminoisobutyric acid, 3,4-didehydroproline, homophenylalanine, and homomethionine, which may have a substituent selected from the group consisting of an alicyclic group, an aromatic hydrocarbon group, an aralkyl group, and a heterocyclic group in a side chain, or deletion;

$X^2$ represents an amino acid residue selected from the group consisting of Tyr, Ser, Thr, Trp, Phe, Ala, Leu, Ile, Val, Arg, Lys, His, 2-hydroxyglycine, homoserine, homophenylalanine, norleucine, norvaline, isovaline, 2-aminobutyric acid, and 2-aminoisobutyric acid, which may have a substituent selected from the group consisting of an alicyclic group, an aromatic hydrocarbon group, an aralkyl group, and a heterocyclic group in a side chain, or deletion;

$X^3$, $X^6$, $X^8$, $X^{10}$, $X^{14}$, and $X^{16}$ each independently represent an amino acid residue selected from the group consisting of Gly, Ala, Phe, Val, Leu, Ile, Met, norleucine, norvaline, isovaline, 2-aminobutyric acid, 2-aminoisobutyric acid, homophenylalanine, and homomethionine, which may have a substituent selected from the group consisting of an alicyclic group, an aromatic hydrocarbon group, an aralkyl group, and a heterocyclic group in a side chain;

$X^4$ represents a hydrophilic amino acid residue or Cys;

$X^5$ represents an amino acid residue selected from the group consisting of Trp, Ser, Tyr, Val, Leu, Ile, Arg, His, Glu, Asp, Phe, 2-hydroxyglycine, homoserine, norleucine, norvaline, isovaline, 2-aminobutyric acid, homophenylalanine, and Ala which has a substituent selected from the group consisting of an alicyclic group, an aromatic hydrocarbon group, an aralkyl group, and a heterocyclic group;

$X^7$ and $X^{13}$ each independently represent an amino acid residue selected from the group consisting of Arg, Lys, Pro, Cys, His, (α-methyl)lysine, 2,3-diaminopropionic acid, 2,4-diaminobutanoic acid, and ornithine;

$X^9$ represents an amino acid residue selected from the group consisting of Asn, Pro, Gln, Cys, and 3,4-didehydroproline;

$X^{11}$ represents an arbitrary amino acid residue which may have a substituent selected from the group consisting of an alicyclic group, an aromatic hydrocarbon group, an aralkyl group, and a heterocyclic group in a side chain;

$X^{12}$ represents an amino acid residue selected from the group consisting of Ser, Pro, Cys, Thr, Tyr, 2-hydroxyglycine, homoserine, and homocysteine; and $X^{15}$ represents an arbitrary amino acid residue, which may have a substituent selected from the group consisting of an alicyclic group, an aromatic hydrocarbon group, an aralkyl group, and a heterocyclic group in a side chain, or deletion.

Another aspect of the present invention relates to a peptide or a pharmaceutically acceptable salt of the peptide, or a prodrug thereof, the peptide satisfying the following (a) or (b) and having the number of amino acid residues of 20 or less. Incidentally, the "peptide satisfying the following (a) or (b) and having the number of amino acid residues of 20 or less or a pharmaceutically acceptable salt of the peptide" is also simply referred to as the "peptide according to a second aspect of the present invention."

(a) the peptide comprising any one of amino acid sequences represented by the following SEQ ID NOs: 2 to 9, SEQ ID NOs: 11 to 38, SEQ ID NOs: 380 to 385, SEQ ID NOs: 573 to 581, and SEQ ID NOs: 583 to 597; or (b) the peptide comprising one amino acid sequence in which one amino acid residue of $X^2$ to $X^4$ and $X^6$ to $X^{16}$ in the amino acid sequences of the above (a) is substituted or deleted and having a myostatin inhibitory activity.

TABLE 1-1

| | (Position) | | | | | | | | | | | | | | | |
|---|---|---|---|---|---|---|---|---|---|---|---|---|---|---|---|---|
| | $X^1$ | $X^2$ | $X^3$ | $X^4$ | $X^5$ | $X^6$ | $X^7$ | $X^8$ | $X^9$ | $X^{10}$ | $X^{11}$ | $X^{12}$ | $X^{13}$ | $X^{14}$ | $X^{15}$ | $X^{16}$ |
| SEQ ID NO: 2 | W | Y | I | E | W | I | K | I | Q | I | I | S | K | L | R | L |
| SEQ ID NO: 3 | Y | W | I | E | W | I | K | I | Q | I | I | S | K | L | R | L |
| SEQ ID NO: 4 | Y | Y | I | E | W | I | K | I | Q | I | I | S | K | L | R | L |
| SEQ ID NO: 5 | W | W | I | E | W | I | K | I | Q | I | I | S | K | L | R | L |
| SEQ ID NO: 6 | Naa | Y | I | E | W | I | K | I | Q | I | I | S | K | L | R | L |
| SEQ ID NO: 7 | F | Y | I | E | W | I | K | I | Q | I | I | S | K | L | R | L |
| SEQ ID NO: 8 | L | Y | I | E | W | I | K | I | Q | I | I | S | K | L | R | L |
| SEQ ID NO: 9 | H | Y | I | E | W | I | K | I | Q | I | I | S | K | L | R | L |
| SEQ ID NO: 11 | W | F | I | E | W | I | K | I | Q | I | I | S | K | L | R | L |
| SEQ ID NO: 12 | W | Naa | I | E | W | I | K | I | Q | I | I | S | K | L | R | L |
| SEQ ID NO: 13 | W | Cha | I | E | W | I | K | I | Q | I | I | S | K | L | R | L |
| SEQ ID NO: 14 | W | L | I | E | W | I | K | I | Q | I | I | S | K | L | R | L |
| SEQ ID NO: 15 | W | H | I | E | W | I | K | I | Q | I | I | S | K | L | R | L |
| SEQ ID NO: 16 | W | R | I | E | W | I | K | I | Q | I | I | S | K | L | R | L |
| SEQ ID NO: 17 | W | S | I | E | W | I | K | I | Q | I | I | S | K | L | R | L |
| SEQ ID NO: 18 | W | Y | I | E | Naa | I | K | I | Q | I | I | S | K | L | R | L |
| SEQ ID NO: 19 | W | Y | I | E | L | I | K | I | Q | I | I | S | K | L | R | L |
| SEQ ID NO: 20 | W | Y | I | E | S | I | K | I | Q | I | I | S | K | L | R | L |
| SEQ ID NO: 21 | W | Y | I | E | R | I | K | I | Q | I | I | S | K | L | R | L |
| SEQ ID NO: 22 | W | Y | I | E | E | I | K | I | Q | I | I | S | K | L | R | L |
| SEQ ID NO: 23 | W | Y | I | E | F | I | K | I | Q | I | I | S | K | I | R | L |
| SEQ ID NO: 24 | W | Y | I | E | Y | I | K | I | Q | I | I | S | K | I | R | L |
| SEQ ID NO: 25 | W | Y | I | E | H | I | K | I | Q | I | I | S | K | I | R | L |
| SEQ ID NO: 26 | W | Y | I | E | W | I | K | I | Q | I | Nva | S | K | L | R | L |
| SEQ ID NO: 27 | W | Y | I | E | W | I | K | I | Q | I | Chg | S | K | L | R | L |
| SEQ ID NO: 28 | W | Y | I | E | W | I | K | I | Q | I | F | S | K | L | R | L |
| SEQ ID NO: 29 | W | Y | I | E | W | I | K | I | Q | I | W | S | K | L | R | L |
| SEQ ID NO: 30 | W | Y | I | E | W | I | K | I | Q | I | Y | S | K | L | R | L |

TABLE 1-2

| | (Position) | | | | | | | | | | | | | | | |
|---|---|---|---|---|---|---|---|---|---|---|---|---|---|---|---|---|
| | $X^1$ | $X^2$ | $X^3$ | $X^4$ | $X^5$ | $X^6$ | $X^7$ | $X^8$ | $X^9$ | $X^{10}$ | $X^{11}$ | $X^{12}$ | $X^{13}$ | $X^{14}$ | $X^{15}$ | $X^{16}$ |
| SEQ ID NO: 31 | Y | Y | I | E | S | I | K | I | Q | I | I | S | K | L | R | L |
| SEQ ID NO: 32 | W | R | I | E | S | I | K | I | Q | I | I | S | K | L | R | L |
| SEQ ID NO: 33 | W | Y | I | E | S | I | K | I | Q | I | W | S | K | L | R | L |
| SEQ ID NO: 34 | W | Y | I | K | W | I | K | I | Q | I | W | S | K | L | R | L |
| SEQ ID NO: 35 | W | Y | I | R | W | I | K | I | Q | I | W | S | K | L | R | L |
| SEQ ID NO: 36 | W | Y | I | Q | W | I | K | I | Q | I | W | S | K | L | R | L |
| SEQ ID NO: 37 | W | Y | I | N | W | I | K | I | Q | I | W | S | K | L | R | L |
| SEQ ID NO: 38 | W | Y | I | E | W | I | K | I | P | I | W | S | K | L | R | L |
| SEQ ID NO: 380 | W | Y | I | R | W | I | K | Chg | Q | I | W | S | K | L | R | L |
| SEQ ID NO: 381 | W | Y | I | R | W | I | K | I | Q | I | W | S | K | Chg | R | L |
| SEQ ID NO: 382 | W | Y | I | R | W | I | K | Chg | Q | I | W | S | K | Chg | R | L |
| SEQ ID NO: 383 | W | Y | F | R | W | I | K | I | Q | I | W | S | K | L | R | L |
| SEQ ID NO: 384 | W | Y | I | R | W | I | K | I | Q | F | W | S | K | L | R | L |
| SEQ ID NO: 385 | Y | Y | I | R | Naa | I | K | I | Q | I | W | S | K | L | R | L |
| SEQ ID NO: 573 | W | Y | I | R | W | I | K | Chg | Q | I | W | S | R | Chg | R | L |
| SEQ ID NO: 574 | W | Y | I | R | W | I | R | Chg | Q | I | W | S | K | Chg | R | L |
| SEQ ID NO: 575 | W | Y | I | R | W | I | R | Chg | Q | I | W | S | R | Chg | R | L |
| SEQ ID NO: 576 | W | Y | I | R | W | I | R | Chg | Q | I | W | S | R | Chg | P | L |
| SEQ ID NO: 577 | W | Y | I | R | W | I | R | Chg | Q | I | W | P | R | Chg | R | L |
| SEQ ID NO: 578 | W | Y | I | R | W | I | R | Chg | P | I | W | S | R | Chg | R | L |
| SEQ ID NO: 579 | W | Y | I | R | W | I | P | Chg | Q | I | W | S | R | Chg | R | L |
| SEQ ID NO: 580 | W | Y | I | R | W | I | R | Chg | P | I | W | S | R | Chg | P | L |
| SEQ ID NO: 581 | Deletion | Y | I | R | W | I | R | Chg | Q | I | W | S | R | Chg | P | L |
| SEQ ID NO: 583 | W | Y | I | R | W | I | (α-Me)Lys | Chg | Q | I | W | S | K | Chg | R | L |
| SEQ ID NO: 584 | W | Y | I | R | W | I | K | Chg | Q | I | W | S | K | Chg | R | L |
| SEQ ID NO: 585 | W | Y | I | C | W | I | C | I | Q | I | W | S | K | L | R | L |
| SEQ ID NO: 586 | W | Y | I | E | W | I | K | I | C | I | W | C | K | L | R | L |
| SEQ ID NO: 587 | W | Y | I | E | W | I | K | I | Q | I | W | C | K | L | C | L |

TABLE 1-3

| | (Position) | | | | | | | | | | | | | | | |
|---|---|---|---|---|---|---|---|---|---|---|---|---|---|---|---|---|
| | $X^1$ | $X^2$ | $X^3$ | $X^4$ | $X^5$ | $X^6$ | $X^7$ | $X^8$ | $X^9$ | $X^{10}$ | $X^{11}$ | $X^{12}$ | $X^{13}$ | $X^{14}$ | $X^{15}$ | $X^{16}$ |
| SEQ ID NO: 588 | W | Y | I | R | w | I | R | Chg | Q | I | W | S | R | Chg | P | L |
| SEQ ID NO: 589 | W | Y | I | R | w | I | R | Chg | Q | I | W | s | R | Chg | P | L |
| SEQ ID NO: 590 | W | Y | I | R | w | I | K | Chg | Q | I | W | S | K | Chg | R | L |
| SEQ ID NO: 591 | W | Y | I | R | w | I | K | Chg | Q | I | W | s | K | Chg | R | L |
| SEQ ID NO: 592 | W | Y | I | R | w | I | (α-Me)Lys | Chg | Q | I | W | S | K | Chg | R | L |
| SEQ ID NO: 593 | W | Y | I | c | W | I | C | I | Q | I | W | S | K | L | R | L |
| SEQ ID NO: 594 | W | Y | I | E | W | I | K | I | c | I | W | C | K | L | R | L |
| SEQ ID NO: 595 | W | Y | I | E | W | I | K | I | Q | I | W | c | K | L | C | L |

Naa: 3-naphthylalanine
Cha: 3-cyclohexylalanine
Nva: norvaline
Chg: 2-cyclohexylglycine
(α-Me)Lys: (α-methyl)lysine
w and c represent D-Trp and D-Cys, respectively.
SEQ ID NOs: 585 to 587 and SEQ ID NOs: 593 to 595 may represent a cyclic peptide in which a disulfide bond is formed between side-chain SH groups of two Cys's.

An embodiment of the present invention relates to a method for inhibiting myostatin, the method including administering an effective dose of one or more kinds selected from the group consisting of the peptide according to the first aspect of the present invention, the peptide according to the second aspect of the present invention, and a prodrug thereof to a patient.

An embodiment of the present invention relates to use of one or more compounds selected from the group consisting of the peptide according to the first aspect of the present invention, the peptide according to the second aspect of the present invention, and a prodrug thereof for the production of a myostatin inhibitory agent.

An embodiment of the present invention relates to a method for prevention and/or treatment of amyotrophic disorder, the method including administering an effective dose of one or more kinds selected from the group consisting of the peptide according to the first aspect of the present invention, the peptide according to the second aspect of the present invention, and a prodrug thereof to a patient.

An embodiment of the present invention relates to use of one or more compounds selected from the group consisting of the peptide according to the first aspect of the present invention, the peptide according to the second aspect of the present invention, and a prodrug thereof for the production of a preventive and/or therapeutic agent of amyotrophic disorder.

BRIEF DESCRIPTION OF DRAWINGS

FIG. 1 shows a myostatin inhibitory activity by a peptide according to an embodiment of the present invention.

FIG. 2 shows a myostatin inhibitory activity by the peptide according to the embodiment of the present invention or a peptide of Comparative Example.

FIG. 3 shows a myostatin inhibitory activity by the peptide according to the embodiment of the present invention.

FIG. 4 shows a myostatin inhibitory activity by the peptide according to the embodiment of the present invention.

FIG. 5 shows a myostatin inhibitory activity by the peptide according to the embodiment of the present invention.

FIG. 6 shows a myostatin inhibitory activity by the peptide according to the embodiment of the present invention.

FIG. 7 shows a myostatin inhibitory activity by the peptide according to the embodiment of the present invention.

FIG. 8 shows a myostatin inhibitory activity by the peptide according to the embodiment of the present invention.

FIG. 9 shows photographs of anterior tibial muscles of legs of muscular dystrophy model mice fed for 6 weeks while the peptide according to the embodiment of the present invention was administered to the left leg and saline was administered to the right leg (FIG. 9(A): individual number 1, FIG. 9(B): individual number 2, the left side in each photograph is the leg administered with the peptide according to the embodiment of the present invention, and the right side is the leg administered with the saline).

FIG. 10 shows a myostatin inhibitory activity by the peptide according to the embodiment of the present invention.

FIG. 11 shows a myostatin inhibitory activity by the peptide according to the embodiment of the present invention.

FIG. 12 shows a myostatin inhibitory activity by the peptide according to the embodiment of the present invention.

FIG. 13 shows a myostatin inhibitory activity by the peptide according to the embodiment of the present invention.

FIG. 14A shows results obtained by analyzing cross-sectional areas of muscle fibers (200 fibers) of mdx mice and C57BL/6 mice fed for 6 weeks while the peptide according to the embodiment of the present invention or saline was administered into calf muscles of both legs.

FIG. 14B shows photographs of calf muscles of mdx mice and C57BL/6 mice fed for 6 weeks while the peptide according to the embodiment of the present invention or saline was administered into calf muscles of both legs.

FIG. 15 shows a myostatin inhibitory activity by the peptide according to the embodiment of the present invention and a peptide of Comparative Example.

FIG. 16 shows a variation in serum creatine kinase level of mdx mice caused by administration of the peptide according to the embodiment of the present invention and the peptide of Comparative Example into calf muscles of both legs (FIG. 16(A): a schematic view of a test, FIG. 16(B): a variation in serum creatine kinase level).

DESCRIPTION OF EMBODIMENTS

The following SEQ ID NO: 1 is, as also described in the above Non-Patent Literature 1, an amino acid sequence of a peptide derived from a myostatin propeptide in which the myostatin inhibitory activity has not been recognized.

[Chem. 2]

(SEQ ID NO: 1)
SRIEAIKIQILSKLRL

The present inventors have found that, surprisingly, a peptide in which Ser at the first position and Ala at the fifth position from the N-terminal side in the peptide of SEQ ID NO: 1 are substituted, that is, the peptide according to the first aspect of the present invention or the peptide according to the second aspect has a high myostatin inhibitory activity. With such a peptide, it is possible to provide a peptide having a short chain length and having a high myostatin inhibitory activity.

Hereinafter, embodiments of the present invention will be described. Incidentally, the present invention is not limited only to the following embodiments.

In the present specification, "X-Y" indicating a range means "X or more and Y or less." In addition, unless otherwise noted, the operations, physical properties, and the like are measured under the condition of room temperature (20-25° C.)/a relative humidity of 40-50% RH.

In the present specification, the "peptide comprising an amino acid sequence represented by the following Formula (1) and having the number of amino acid residues of 20 or less or a pharmaceutically acceptable salt of the peptide" and the "peptide satisfying the following (a) or (b) and having the number of amino acid residues of 20 or less or a pharmaceutically acceptable salt of the peptide" are also simply referred to as the "peptide according to the present invention" collectively.

The "amino acid residue" in the present invention means a single unit in the amino acids constituting a peptide or a protein, on a peptide or a protein molecule. More specifically, the "amino acid residue" means a bivalent group, which is as represented in the following Formula (2), derived from α-amino acid:

[Chem. 3]

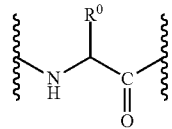

Formula (2)

Note that $R^0$ described above represents a side chain of amino acid, and for example, represents a hydrogen atom in the case of Gly and a methyl group in the case of Ala.

The "amino acid residue" may be derived from natural or non-natural α-amino acid and may be either an L form or a D form in a case where there may be an optical active material, but an L form is preferable. More specific examples of the "amino acid residue" may include Arg, Lys, Asp, Asn, Glu, Gln, His, Pro, Tyr, Trp, Ser, Thr, Gly, Ala, Met, Cys, Phe, Leu, Val, and Ile, and an analog thereof. As the above-described analog, for example, a derivative or the like in which side chains of 20 kinds of amino acid residues described above are substituted with an arbitrary substituent may be employed, and for example, amino acid residues derived from amino acids such as halogenated derivatives of 20 kinds of amino acid residues described above (for example, 3-chloroalanine), 2-aminobutyric acid, norleucine, norvaline, isovaline, 2-aminoisobutyric acid, homophenylalanine, 2,3-diaminopropionic acid, 2,4-diaminobutanoic acid, ornithine, 2-hydroxyglycine, homoserine, hydroxylysine, hydroxyproline, 3,4-didehydroproline, homocysteine, homomethionine, aspartate ester (for example, asparagic acid-methyl ester, asparagic acid-ethyl ester, asparagic acid-propyl ester, asparagic acid-cyclohexyl ester, asparagic acid-benzyl ester, or the like), glutamate ester (glutamic acid-cyclohexyl ester, glutamic acid-ethyl ester, glutamic acid-propyl ester, glutamic acid-methyl ester, glutamic acid-benzyl ester, or the like), formyltryptophan, 2-cyclopentylglycine, 2-cyclohexylglycine, 2-phenylglycine, 3-cyclopentylalanine, 3-cyclohexylalanine, 3-pyridylalanine, 3-pyrazolylalanine, 3-furanylalanine, 3-thienylalanine, methoxyphenylalanine, and 3-naphthylalanine can be exemplified, but the amino acid residue is not limited thereto. Further, in the case of those in which a diastereomer having an asymmetric carbon is present in a side chain, such as Ile and Thr, a natural type (for example, (2R*,3R*)-2-amino-3-methylpentanoic acid, and (2R*,3S*)-2-amino-3-hydroxybutanoic acid) and a non-natural type (for example, (2R*,3S*)-2-amino-3-methylpentanoic acid, and (2R*,3R*)-2-amino-3-hydroxybutanoic acid) can be used without particular discrimination. That is, "Ile" is used as meaning including both (2R*,3R*)-2-amino-3-methylpentanoic acid and (2R*,3S*)-2-amino-3-methylpentanoic acid, and "Thr" is used as meaning including both (2R*,3S*)-2-amino-3-hydroxybutanoic acid and (2R*,3R*)-2-amino-3-hydroxybutanoic acid. Preferably, a natural diastereomer (that is, in the case of Ile, (2R*,3R*)-2-amino-3-methylpentanoic acid, and in the case of Thr, (2R*,3S*)-2-amino-3-hydroxybutanoic acid) is used.

The amino acid sequences described in the present specification are described in accordance with the conventional denotation in a direction from the N-terminal (amino terminal) side to the C-terminal (carboxyl terminal) side unless otherwise noted.

It is known in the present technical field that respective amino acid residues may be substituted with amino acid residues having similar properties on the basis of a difference in side chains thereof (conservative substitution). For example, Val, Leu, Ile, 2-aminobutyric acid (Abu), norleucine (Nle), norvaline (Nva), and isovaline (Iva) that are aliphatic hydrophobic amino acids may be substituted with each other. Gly, Ala, and 2-aminoisobutyric acid (Aib) of which side chain is a hydrogen atom or a methyl group may be substituted with each other. Phe and homophenylalanine (Hph) of which side chain is a phenylalkyl group may be substituted with each other. Asn and Gln that are neutral polar amino acids may be substituted with each other. Arg, Lys, His, 2,3-diaminopropionic acid (Dpr), 2,4-diaminobutanoic acid (Dbu), and ornithine (Orn) that are basic amino acids may be substituted with each other. Asp and Glu that are acidic amino acids may be substituted with each other. Ser, 2-hydroxyglycine (Hyg), and homoserine (Hse) of which side chain is a hydroxy group or a short-chain hydroxyalkyl group may be substituted with each other. 3,4-didehydroproline (Dhp) having a side chain with a structure in which a pyrrolidyl group of the side chain is dehydrogenated, and Pro may be substituted with each other. Cys and homocysteine (Hcy) of which side chain is a short-chain thioalkyl group may be substituted with each other. Met and homomethionine (Hme) of which side chain has a short-chain sulfide structure may be substituted with each other.

The "pharmaceutically acceptable salt" in the present specification is a metallic salt, an ammonium salt, an organic acid salt, an inorganic acid salt, or a salt with an organic base or an inorganic base that does not cause undesirable physiological effects after administered to a patient or a subject. More specific examples thereof may include a sodium salt, a potassium salt, a calcium salt, a magnesium salt, a barium salt, an aluminum salt, a zinc salt, an ammonium salt, a methylamine salt, an ethylamine salt, an aniline salt, a dimethylamine salt, a diethylamine salt, a pyrrolidine salt, a piperidine salt, a morpholine salt, a piperazine salt, a trimethylamine salt, a triethylamine salt, an ethanolamine salt, a diethanolamine salt, a triethanolamine salt, a hydrochloride salt, a hydrobromic acid salt, a nitrate salt, a sulfate salt, a phosphoric salt, a formate salt, an acetate salt, a trifluoroacetate salt, a phthalate salt, a fumarate salt, an oxalate salt, a tartrate salt, a maleate salt, a citric salt, a succinate salt, a malate salt, a methanesulfonic acid salt, a benzene sulfonate salt, a p-toluenesulfonate salt, and the like, but the pharmaceutically acceptable salt is not limited thereto.

A prodrug of the peptides according to the first aspect and the second aspect of the present invention (hereinafter, the "prodrug of the peptide according to the first aspect of the present invention" and the "prodrug of the peptide according to the second aspect of the present invention" are collectively and simply also referred to as "prodrug") indicate peptide derivatives converted to the peptide according to the present invention, that is, peptide derivatives converted to the peptide according to the present invention by causing oxidation, reduction, hydrolysis, or the like by gastric acid, an enzyme, or the like. Those peptide derivatives can be produced from the peptide according to the present invention by a conventionally known method described in Bundgard, H., Design of Prodrugs, pp. 7-9, 21-24, Elsevier, Amsterdam 1985, or the like.

Examples of the prodrug in a case where the side chain of the peptide according to the present invention has a carboxyl group may include ester derivatives obtained by reacting the carboxyl group with alcohol or amide derivatives obtained by reacting the carboxyl group with amine. More specific examples thereof include peptides in which the carboxyl group in the side chain of the peptide is derivatized by am ester represented by —COOR (R represents an alkyl group having 1 to 20 carbon atoms) or an amide group represented by —CONHR or —CONRR' (R and R' each independently represent an alkyl group having 1 to 20 carbon atoms).

Examples of the prodrug in a case where the side chain of the peptide according to the present invention has a hydroxyl group may include acyloxy derivatives which are acylated by reacting the hydroxyl group with acid anhydride or the like. More specific examples thereof include peptides in which the hydroxyl group in the side chain of the peptide is derivatized by an acyloxy group represented by —OCOR (R represents an alkyl group having 1 to 20 carbon atoms).

Examples of the prodrug in a case where the side chain of the peptide according to the present invention has an amino group may include derivatives in which the amino group is acylated, N-oxidized, alkylated, or phosphorylated. More specific examples thereof include peptides in which the amino group in the side chain is derivatized by an amide group represented by —NHCOR (R represents an alkyl group having 1 to 20 carbon atoms) or —NHCOCH(NH$_2$)CH$_3$.

The structure of the N-terminal of the peptide according to the present invention is not particularly limited, and for example, may be a structure of a hydrogen atom (that is, unmodified) or a structure in which a modifying group is introduced by a conventionally known method. Examples of the modifying group of the N-terminal may include an alkyl group having 1 to 20 carbon atoms, an alkenyl group having 1 to 20 carbon atoms, an alkynyl group having 1 to 20 carbon atoms, an aromatic hydrocarbon group having 6 to carbon atoms, a heterocyclic group, a group represented by the following Formula (3), a sulfonyl group, a carboxyl group, a glyoxyl group, a formyl group; a polyethylene glycol group (PEGylated), a polyoxyethylene glycol group, a polypropylene glycol group; a protective group such as a tert-butoxycarbonyl group (Boc group), a benzyloxycarbonyl group (Z group), or a fluorenylmethoxycarbonyl group (Fmoc group); a cycloalkyloxycarbonyl group such as a cyclopentyloxycarbonyl group, a cyclohexyloxycarbonyl group, an adamantyloxycarbonyl group, a norbornyloxycarbonyl group, or an isobornyloxycarbonyl group; a protective group derived from an amino acid such as pyroglutamic acid or montanic acid; a carbamate-based protective group; and a protective group derived from phosphoric acid or sulfonic acid such as benzenesulfonic acid. Of them, from the viewpoint of the myostatin inhibitory activity, the N-terminal of the peptide is preferably a hydrogen atom, an alkyl group, an aromatic hydrocarbon group, a heterocyclic group, a group represented by the following Formula (3), a sulfonyl group, a carboxyl group, a glyoxyl group, a formyl group, or a polyethylene glycol group and more preferably a hydrogen atom, an acyl group, or a polyethylene glycol group.

The number of carbon atoms of the alkyl group which may be present at the N-terminal of the peptide is, for example, 1 to 20 and preferably 1 to 10. The alkyl group may have a saturated-chain, unsaturated-chain, or cyclic structure and may have a branched-chain structure. More specific examples of the alkyl group may include a methyl group, an ethyl group, a propyl group, an isopropyl group, a cyclopropyl group, a butyl group, an isobutyl group, a sec-butyl group, a tert-butyl group, an amyl group, an isoamyl group, a tert-amyl group, a hexyl group, a cyclohexyl group, a heptyl group, an octyl group, a 2-ethylhexyl group, a nonyl group, a decyl group, and the like.

The number of carbon atoms of the aromatic hydrocarbon group which may be present at the N-terminal of the peptide is, for example, 6 to 20, more specifically, a phenyl group, a naphthyl group, a tolyl group, a phenanthryl group, and the like can be exemplified. Examples of the heterocyclic group which may be present at the N-terminal of the peptide may include substituents having a monocyclic, fused bicyclic, or fused tricyclic structure including 1 to 3 hetero atoms selected from a nitrogen atom, an oxygen atom, and a sulfur atom in a ring, and more specific examples thereof may include a pyrrolidyl group, a pyrrole group, a piperidyl group, a pyridyl group, an imidazolyl group, a pyrazolyl group, an oxazolyl group, a thiazolyl group, a morpholyl group, an indolyl group, a benzimidazolyl group, a quinolyl group, a carbazolyl group, a tetrahydrofuranyl group, a tetrahydrothiophenyl group, a furanyl group, a thiophenyl group, a tetrahydropyranyl group, a tetrahydrothiopyranyl group, and the like. Those aromatic hydrocarbon groups and heterocyclic groups may be substituted with a further substituent such as a linear or branched-chain alkyl group having 1 to 6 carbon atoms, a linear or branched-chain alkoxy group having 1 to 6 carbon atoms, an amino group, a carboxyl group, an ester group, a carbamoyl group, an amide group, a nitro group, a sulfo group, a sulfonamide group, and/or a halogen.

The modifying group in the N-terminal may be, for example, a functional group represented by the following Formula (3).

[Chem. 4]

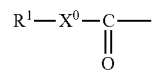

Formula (3)

Note that, in Formula (3), $X^0$ represents a single bond, an oxygen atom, or sulfur atom, or represents a bivalent linking group selected from the group consisting of alkylene groups having 1 to 3 carbon atoms (for example, a methylene group, an ethylene group, a trimethylene group, and a propylene group), oxyalkylene groups having 1 to 3 carbon atoms (for example, an oxymethylene group, an oxyethylene group, an oxytrimethylene group, and an oxypropylene group), and alkyleneoxy groups having 1 to carbon atoms (for example, a methyleneoxy group, an ethyleneoxy group, a trimethyleneoxy group, and a propyleneoxy group), which may have a substituent selected from the consisting of an amino group, an acetylamino group, and a propionylamino group;

$R^1$ is selected from the group consisting of an alkyl group having 1 to 20 which may have a substituent, and the following groups:

[Chem. 5]

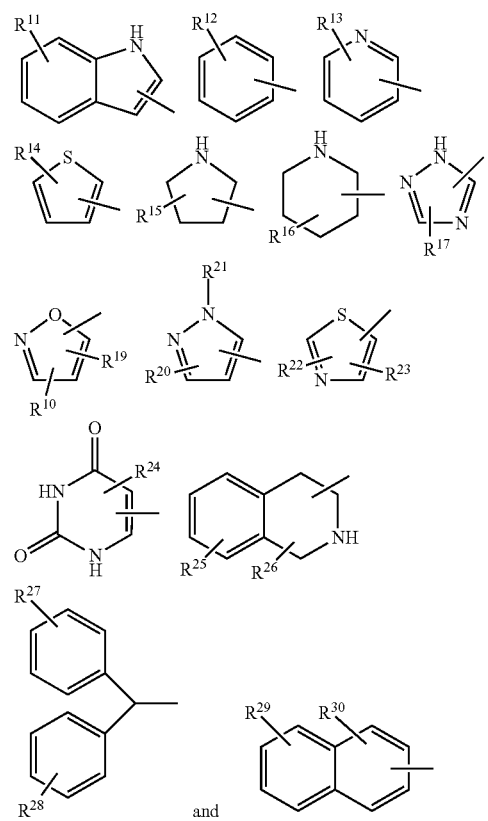

$R^{11}$ to $R^{30}$ are each independently selected from the group consisting of a hydrogen atom, a halogen atom (for example, a fluorine atom, a chlorine atom, a bromine atom, or an iodine atom), an alkyl group having 1 to 3 carbon atoms (that is, a methyl group, an ethyl group, or a propyl group), an alkoxy group having 1 to 3 carbon atoms (that is, a methoxy group, an ethoxy group, or a propoxy group), a hydroxyl group, and an amino group.

In the above Formula (3), in a case where $R^1$ represents an alkyl group having 1 to 20 carbon atoms which may have a substituent, the aliphatic chain thereof may have a saturated-chain, unsaturated-chain, or cyclic structure, or may have a branched-chain structure. The number of carbon atoms of the alkyl group as $R^1$ is preferably 2 to 12.

Examples of the substituent of $R^1$ may include a hydroxy group, an alkoxy group having 1 to 5 or less carbon atoms (for example, a methoxy group, an ethoxy group, or the like), an amino group, a carboxyl group, an ester group, a carbamoyl group, an amide group, a nitro group, a sulfo group, halogen (fluorine, chlorine, bromine, or iodine), and the like.

In the above Formula (3), preferably, $X^0$ represents a single bond, or a bivalent linking group selected from the group consisting of an alkylene group having 1 to 3 carbon atoms and an oxyalkylene group having 1 to 3 carbon atoms, which may have a substituent selected from the group consisting of an amino group and an acetylamino group.

In an embodiment, the group represented by the above Formula (3) is an acyl group. As the acyl group, various acyl groups derived from carboxylic acid are included. More specifically, the acyl group may be an acyl group having an aliphatic chain, an aromatic ring, or a hetero ring, or may be an acyl group derived from a compound selected from the group consisting of an amino acid, vitamin having an acyl group, and a nucleobase having an acyl group.

More specific examples of the acyl group that is an alkyl group having 1 to 20 carbon atoms in which $R^1$ in the above Formula (3) may have a substituent may include an acetyl group, a propionyl group, a butyryl group, an isobutyryl group, a valeryl group, an isovaleryl group, a pivaloyl group, a caproyl group, a caprinoyl group, a methylhexanoyl group, a cyclopropanecarbonyl group, an aminocyclopropanecarbonyl group, a cyclohexanecarbonyl group, a cyclohexylacetyl group, a cyclopentylpropionyl group, a cyclohexylpropionyl group, a cyclopentylbutanoyl group, a cyclohexylbutanoyl group, an adamantylacetyl group, a lauroyl group, a myristoyl group, a palmitoyl group, a stearoyl group, an oxalyl group, a malonyl group, a succinyl group, a glutaryl group, an adipoyl group, a glycol group, a lactoyl group, a glyceroyl group, a pyruvoyl group, an acetoacetyl group, and the like, but the acyl group is not limited thereto.

Examples of the vitamin having an acyl group include nicotinic acid, pantothenic acid, biotin, pteroylglutamic acid (folic acid), orotic acid, fluoroorotic acid, α-lipoic acid, pyridoxine acid, biocytin, pteroic acid, 10-formylpteroic acid, 7,8-dihydrofolic acid, homopteroic acid, pterin-6-carboxylic acid, dihydrolipoic acid, hydroorotic acid, and the like.

A nucleic acid base derivative having an acyl group refers to a base component and a derivative thereof that constitute a nucleotide, and preferably, a pyrimidine derivative and the like, for example, 5-carboxymethyluracil, 5-carboxythiouracil, and the like can be exemplified.

Examples of a sulfonyl group which may be present at the N-terminal of the peptide may include those having a structure in which a carbonyl structure in the above-described acyl group is converted to a sulfone structure.

A polyethylene glycol group which may be present at the N-terminal of the peptide has a structure in which polyethylene glycol or an analog thereof is linked through an ester bond, amine (—NH—), an acyl group (for example, an acyl group having 1 to 12 carbon atoms), or the like, or a combination thereof. The number of carbon atoms of the polyethylene glycol group is, for example, 2 to 20 (that is, has a structural unit represented by —$(C_2H_4O)_n$— and n is 1 to 10), and preferably 4 to 16 (that is, has a structural unit represented by —$(C_2H_4O)_n$— and n is 2 to 8). The terminal at the opposite side to the side, to which the N-terminal of the peptide is linked, in the polyethylene glycol group may be modified by a protective group, which is generally used for protection of a hydroxyl group, such as an alkyl group having 1 to carbon atoms (for example, a methyl group, an ethyl group, a propyl group, an isopropyl group, a cyclopropyl group, a butyl group, an isobutyl group, a sec-butyl group, a tert-butyl group, an amyl group, an isoamyl group, a tert-amyl group, or a hexyl group), or an amino group.

The structure of the C-terminal of the peptide according to the present invention is also not particularly limited, and may be a structure which is modified by a protective group generally used for protection of a carboxylic acid. More specifically, the structure of the C-terminal of the peptide according to the present invention may be a carboxyl group (—COOH), carboxylate (—COO$^-$), amide (—CONH$_2$), alkylamide (—CONHR$^{31}$, —CONR$^{31}$R$^{32}$), ester (—COOR$^{31}$), acyloxy alkyl (—R$^{33}$—OCOR$^{31}$) such as a pivaloyl oxymethyl group, a phthalidyl group which may be substituted with an alkyl group or alkoxy group having 1 to 4 carbon atoms (for example, a phthalidyl group, a dimethyl phthalidyl group, or a dimethoxyphthalidyl group), or a (5-methyl-2-oxo-1,3-dioxolen-4-yl)methyl group. Of them, the C-terminal of the peptide is preferably amide. Examples of $R^{31}$ and $R^{32}$ in alkylamide, ester, and acyloxy alkyl described above each independently include an alkyl group having 1 to 6 carbon atoms such as a methyl group, an ethyl group, a propyl group, an isopropyl group, a cyclopropyl group, a butyl group, an isobutyl group, a sec-butyl group, a tert-butyl group, an amyl group, an isoamyl group, a tert-amyl group, a hexyl group, or a cyclohexyl group; an aryl group having 6 to 10 carbon atoms such as a phenyl group or naphthyl; an aralkyl group having 7 to carbon atoms such as a benzyl group, a phenethyl group, or a benzhydryl group; sugar such as glucose; and a polyethylene glycol group which may be modified by an alkyl group having 1 to 6 carbon atoms (for example, a methyl group, an ethyl group, a propyl group, an isopropyl group, a cyclopropyl group, a butyl group, an isobutyl group, a sec-butyl group, a tert-butyl group, an amyl group, an isoamyl group, a tert-amyl group, or a hexyl group), and the like. $R^{33}$ in acyloxy alkyl represents an alkylene group having 1 to 4 carbon atoms such as a methylene group, an ethylene group, an n-propylene group, an isopropylene group, an n-butylene group, an isobutylene group, an s-butylene group, or a t-butylene group.

In the peptide according to the present invention, a peptide derivative chemically modified by a covalent bond with a polymer, lipid, or the like and a derivative in which α-helix content included in the peptide is further reinforced are also included. Examples of the derivative in which α-helix content is further reinforced may include a derivative in which a salt bridge is formed at the position of i, i+4, or the like as amino acid configuration and a derivative having a cross-linked structure formed by a disulfide bond, a carbon-carbon bond, or the like.

The number of amino acid residues of the peptide according to the present invention is 20 or less. When the number of amino acid residues is 20 or less, there is an advantage of utilization rate both in synthesis and in the living body. In the peptide according to the present invention, as long as the number of amino acid residues is 20 or less, a structure may be employed in which one to five amino acid residues are added to the N-terminal side or the C-terminal side of an amino acid sequence represented by Formula (1), amino acid sequences represented by SEQ ID NOs: 2 to 9, amino acid sequences in which one amino acid residue of $X^2$ to $X^4$ and $X^6$ to $X^{16}$ in amino acid sequences represented by SEQ ID NOs: 2 to 9 is substituted or deleted, amino acid sequences represented by SEQ ID NOs: 11 to 38, amino acid sequences in which one amino acid residue of $X^2$ to $X^4$ and $X^6$ to $X^{16}$ in amino acid sequences represented by SEQ ID NOs: 11 to 38 is substituted or deleted, amino acid sequences represented by SEQ ID NOs: 380 to 385, or amino acid sequences in which one amino acid residue of $X^2$ to $X^4$ and $X^6$ to $X^{16}$ in amino acid sequences represented by SEQ ID NOs: 380 to 385 is substituted or deleted. Alternatively, in the peptide according to the present invention, as long as the number of amino acid residues is 20 or less, a structure may be employed in which amino acid residues are added to the N-terminal side or the C-terminal side of an amino acid sequence represented by Formula (1), amino acid sequences represented by SEQ ID NOs: 2 to 9, amino acid sequences in which one amino acid residue of $X^2$ to $X^4$ and $X^6$ to $X^{16}$ in amino acid sequences represented by SEQ ID NOs: 2 to is substituted or deleted, amino acid sequences represented by SEQ ID NOs: 11 to 38, amino acid sequences in which one amino acid residue of $X^2$ to $X^4$ and $X^6$ to $X^{16}$ in amino acid sequences represented by SEQ ID NOs: 11 to 38 is substituted or deleted, amino acid sequences represented by SEQ ID NOs: 380 to 385, or amino acid sequences in which one amino acid residue of $X^2$ to $X^4$ and $X^6$ to $X^{16}$ in amino acid sequences represented by SEQ ID NOs: 380 to 385 is substituted or deleted, and the number of amino acid residues added may be 2 to 5 residues. The number of amino acid residues of the peptide according to the present invention is, for example, 15 to 20 residues, preferably 15 to 19 residues, more preferably 15 to 18 residues, still more preferably 15 to 17 residues, and particularly preferably 16 residues.

In the present specification, a "substituent selected from the group consisting of an alicyclic group, an aromatic hydrocarbon group, an aralkyl group, and a heterocyclic group" of the amino acid or the amino acid residue is a substituent of the side chain bonded to a carbon of the amino acid or the amino acid residue. The number of substituents is usually 0 to 3 per amino acid and preferably 0 or 1.

Examples of the alicyclic group may include alicyclic groups having 3 to 12 carbon atoms such as a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, and an adamantyl group, and the alicyclic group is preferably a cyclohexyl group.

The aromatic hydrocarbon group is a group derived from aromatic hydrocarbon of a monocyclic or fused-ring structure, more specific examples thereof may include aromatic hydrocarbon groups having 6 to 20 carbon atoms such as a phenyl group, a naphthyl group, a tolyl group, and a phenanthryl group, and the aromatic hydrocarbon group is preferably a phenyl group or a naphthyl group.

The aralkyl group is a group in which an alkyl group having 1 to 4 carbon atoms is substituted with the aromatic hydrocarbon group having 6 to 20 carbon atoms, and more specific examples thereof may include aralkyl groups having 7 to 24 carbon atoms such as a benzyl group, a phenethyl group, and a benzhydryl group.

Examples of the heterocyclic group may include substituents of a monocyclic, fused bicyclic, or fused tricyclic structure containing 1 to 3 hetero atoms selected from a nitrogen atom, an oxygen atom, and a sulfur atom in a ring, and more specific examples thereof may include a pyrrolidyl group, a pyrrole group, a piperidyl group, a pyridyl group, an imidazolyl group, a pyrazolyl group, an oxazolyl group, a thiazolyl group, a morpholyl group, an indolyl group, a benzimidazolyl group, a quinolyl group, a carbazolyl group, an oxetanyl group, a thietanyl group, a tetrahydrofuranyl group, a tetrahydrothienyl group, a furanyl group, a thienyl group, a tetrahydropyranyl group, a tetrahydrothiopyranyl group, and the like.

The substituent of the amino acid or the amino acid residue may be further substituted with a substituent such as a linear or branched-chain alkyl group having 1 to 6 carbon atoms, a branched-chain alkoxy group having 1 to 6 carbon atoms, a hydroxyl group, an amino group, a carboxyl group, an ester group, a carbamoyl group, an amide group, an acyl group, a nitro group, a sulfo group, a sulfonamide group, and/or halogen.

The amino acid or amino acid residue which is substituted with the substituent as described above is not particularly limited, but examples thereof may include 2-cyclopentylglycine, 2-cyclohexylglycine, 2-phenylglycine, 3-cyclopentylalanine, 3-cyclohexylalanine, 3-pyridylalanine, 3-pyrazolylalanine, 3-furanylalanine, 3-thienylalanine, methoxyphenylalanine, 3-biphenylalanine, 3-(3-benzothienyl)-alanine, 3-naphthylalanine (for example, 3-(1-naphthyl)-alanine, and 3-(2-naphthyl)-alanine), and the like.

The structure of the peptide of the present invention is not particularly limited, and may be linear or cyclic. As the cyclic peptide, for example, a peptide in which a ring is formed by a disulfide bond of two Cys's is exemplified.

<Peptide According to First Aspect>

In a peptide comprising an amino acid sequence represented by the above Formula (1) and having the number of amino acid residues of 20 or less or a pharmaceutically acceptable salt of the peptide (peptide according to the first aspect of the present invention), $X^1$ represents an amino acid residue selected from the group consisting of Trp, Gly, Ala, Val, Leu, Ile, Pro, Phe, His, Tyr, norleucine, norvaline, isovaline, 2-aminobutyric acid, 2-aminoisobutyric acid, 3,4-didehydroproline, homophenylalanine, and homomethionine, which may have a substituent selected from the group consisting of an alicyclic group, an aromatic hydrocarbon group, an aralkyl group, and a heterocyclic group in a side chain, or deletion. For a high myostatin inhibitory activity, it is necessary to substitute Ser at the first position from the N-terminal side in the peptide of SEQ ID NO: 1 with a predetermined amino acid.

For example, $X^1$ may be selected from the group consisting of Trp, Gly, Ala, Val, Leu, Ile, Pro, Phe, His, Tyr, 2-cyclopentylglycine, 2-cyclohexylglycine, 2-phenylglycine, 3-cyclopentylalanine, 3-cyclohexylalanine, 3-pyridylalanine, 3-pyrazolylalanine, 3-furanylalanine, 3-thienylalanine, methoxyphenylalanine, 3-naphthylalanine, norleucine, norvaline, isovaline, 2-aminobutyric acid, 2-aminoisobutyric acid, 3,4-didehydroproline, homophenylalanine, and homomethionine.

From the viewpoint of the myostatin inhibitory activity, preferably, $X^1$ represents an amino acid residue selected from the group consisting of Trp, Val, Leu, Ile, Phe, His, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, norleucine, norvaline, isovaline, 2-aminobutyric acid, and homophenylalanine, or deletion.

More preferably, $X^1$ represents an amino acid residue selected from the group consisting of Trp, Val, Leu, Ile, Phe, His, Tyr, 3-naphthylalanine, norleucine, norvaline, and isovaline, or deletion.

Still more preferably, $X^1$ represents an amino acid residue selected from the group consisting of Trp, Val, Leu, Ile, Phe, Tyr, 3-naphthylalanine, norleucine, norvaline, and isovaline, or deletion.

Particularly preferably, X' represents an amino acid residue selected from the group consisting of Trp, Leu, Phe, Tyr, and 3-naphthylalanine, or deletion.

In the peptide according to the first aspect of the present invention, $X^2$ represents an amino acid residue selected from the group consisting of Tyr, Ser, Thr, Trp, Phe, Ala, Leu, Ile, Val, Arg, Lys, His, 2-hydroxyglycine, homoserine, homophenylalanine, norleucine, norvaline, isovaline, 2-aminobutyric acid, and 2-aminoisobutyric acid, which may have a substituent selected from the group consisting of an alicyclic group, an aromatic hydrocarbon group, an aralkyl group, and a heterocyclic group in a side chain, or deletion. For example, $X^2$ may be selected from the group consisting of Tyr, Ser, Thr, Trp, Phe, Ala, Leu, Ile, Val, Arg, Lys, His, 2-hydroxyglycine, homoserine, homophenylalanine, norleucine, norvaline, isovaline, 2-aminobutyric acid, 2-aminoisobutyric acid, 3-cyclopentylalanine, 3-cyclohexylalanine, 3-pyridylalanine, 3-pyrazolylalanine, 3-furanylalanine, 3-thienylalanine, methoxyphenylalanine, and 3-naphthylalanine.

From the viewpoint of the myostatin inhibitory activity, preferably, $X^2$ represents an amino acid residue selected from the group consisting of Tyr, Ser, Thr, Trp, Phe, Leu, Ile, Val, Arg, Lys, His, 2-hydroxyglycine, homoserine, homophenylalanine, norleucine, norvaline, isovaline, 3-cyclopentylalanine, 3-cyclohexylalanine, 3-pyridylalanine, 3-pyrazolylalanine, 3-furanylalanine, 3-thienylalanine, methoxyphenylalanine, and 3-naphthylalanine, or deletion.

More preferably, $X^2$ represents an amino acid residue selected from the group consisting of Tyr, Ser, Trp, Phe, Arg, Lys, His, 2-hydroxyglycine, homoserine, homophenylalanine, 3-cyclohexylalanine, and 3-naphthylalanine, or deletion.

Still more preferably, $X^2$ represents an amino acid residue selected from the group consisting of Tyr, Ser, Trp, Arg, Lys, His, 2-hydroxyglycine, homoserine, 3-cyclohexylalanine, and 3-naphthylalanine, or deletion.

Particularly preferably, $X^2$ represents an amino acid residue selected from the group consisting of Tyr, Ser, Trp, Arg, Lys, His, 3-cyclohexylalanine, and 3-naphthylalanine, or deletion.

In $X^1$ and $X^2$ of the peptide according to the first aspect of the present invention, deletion is preferably only any one of $X^1$ and $X^2$.

In the peptide according to the first aspect of the present invention, in a case where $X^5$ represents Ser, 2-hydroxyglycine, or homoserine, $X^2$ preferably represents an amino acid residue selected from the group consisting of Tyr, Ser, Thr, Trp, Phe, Leu, Ile, Val, 2-hydroxyglycine, homoserine, homophenylalanine, norleucine, norvaline, isovaline, 3-cyclopentylalanine, 3-cyclohexylalanine, and 3-naphthylalanine. In particular, in a case where $X^5$ represents Ser, $X^2$ more preferably represents an amino acid residue selected from the group consisting of Tyr, Ser, Trp, 3-cyclohexylalanine, and 3-naphthylalanine.

In the peptide according to the first aspect of the present invention, $X^3$, $X^6$, $X^8$, $X^{10}$, $X^{14}$, and $X^{16}$ each independently represent an amino acid residue selected from the group consisting of Gly, Ala, Phe, Val, Leu, Ile, Met, norleucine, norvaline, isovaline, 2-aminobutyric acid, 2-aminoisobutyric acid, homophenylalanine, and homomethionine, which may have a substituent selected from the group consisting of an alicyclic group, an aromatic hydrocarbon group, an aralkyl group, and a heterocyclic group in a side chain. $X^3$, $X^6$, $X^8$, $X^{10}$, $X^{14}$, and $X^{16}$ may each independently represent, for example, an amino acid residue selected from the group consisting of Gly, Ala, Phe, Val, Leu, Ile, Met, norleucine, norvaline, isovaline, 2-aminobutyric acid, 2-aminoisobutyric acid, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, homophenylalanine, and homomethionine.

From the viewpoint of the myostatin inhibitory activity, preferably, $X^3$, $X^6$, $X^8$, $X^{10}$, $X^{14}$ and $X^{16}$ each independently represent an amino acid residue selected from the group consisting of Ala, Val, Leu, Ile, Phe, 2-cyclohexylglycine, norleucine, norvaline, isovaline, 2-aminobutyric acid, and 2-aminoisobutyric acid.

More preferably, $X^3$, $X^6$, $X^8$, $X^{10}$, $X^{14}$ and $X^{16}$ each independently represent an amino acid residue selected from the group consisting of Val, Leu, Ile, Phe, 2-cyclohexylglycine, norleucine, norvaline, and isovaline.

Still more preferably, $X^3$, $X^6$, $X^8$, $X^{10}$, $X^{14}$ and $X^{16}$ each independently represent an amino acid residue selected from the group consisting of Val, Leu, Ile, Phe, and 2-cyclohexylglycine.

Particularly preferably, $X^3$ and $X^{10}$ represent Ile or Phe, $X^6$ represents Ile, $X^8$ represents Ile or 2-cyclohexylglycine, $X^{14}$ represents Leu, Ile, or 2-cyclohexylglycine, and $X^{16}$ represents Leu. In particular, when $X^{14}$ represents 2-cyclohexylglycine, a particularly high myostatin activity may be exhibited.

In the peptide according to the first aspect of the present invention, $X^4$ represents a hydrophilic amino acid residue or Cys. In the present specification, the "hydrophilic amino acid" is an amino acid residue having a hydrophilic group such as a hydroxyl group, an amino group, a carboxyl group, a sulfo group, an imidazolyl group, or a guanidino group in a side chain, and examples thereof may include hydrophilic amino acids having a hydrophobic index of –0.1 or less in Wimley and White, Nat. Struct. Biol., 3, 842-848 (1996). The hydrophobic index (wwHydrophobicity) of Wimley and White is exemplified in the following table. More specific examples of the hydrophilic amino acid may include Arg, Lys, Asp, Asn, Glu, Gln, His, Pro, Ser, Thr, 2,3-diaminopropionic acid, 2,4-diaminobutanoic acid, ornithine, 2-hydroxyglycine, homoserine, hydroxylysine, and hydroxyproline.

TABLE 2

| Description with one letter | Description with three letters | wwHydrophobicity |
|---|---|---|
| Glutamic acid | E | Glu | –2.02 |
| Asparagic acid | D | Asp | –1.23 |
| Lysine | K | Lys | –0.99 |
| Histidine | H | His | –0.96 |
| Arginine | R | Arg | –0.81 |
| Glutamine | Q | Gln | –0.58 |
| Proline | P | Pro | –0.45 |
| Asparagine | N | Asn | –0.42 |
| Alanine | A | Ala | –0.17 |
| Threonine | T | Thr | –0.14 |
| Serine | S | Ser | –0.13 |
| Valine | V | Val | –0.07 |
| Glycine | G | Gly | –0.01 |
| Methionine | M | Met | 0.23 |
| Cysteine | C | Cys | 0.24 |
| Isoleucine | I | Ile | 0.31 |
| Leucine | L | Leu | 0.56 |
| Tyrosine | Y | Tyr | 0.94 |

TABLE 2-continued

| | Description with one letter | Description with three letters | wwHydrophobicity |
|---|---|---|---|
| Phenylalanine | F | Phe | 1.13 |
| Tryptophan | W | Trp | 1.85 |

From the viewpoint of the myostatin inhibitory activity, preferably, $X^4$ represents an amino acid residue selected from the group consisting of Arg, Lys, His, Asn, Gln, Asp, Glu, Cys, 2,3-diaminopropionic acid, 2,4-diaminobutanoic acid, and ornithine.

More preferably, $X^4$ represents an amino acid residue selected from the group consisting of Arg, Lys, Gln, Asp, Glu, Cys, and ornithine.

Still more preferably, $X^4$ represents an amino acid residue selected from the group consisting of Arg, Lys, Gln, Cys, and Glu.

In the peptide according to the first aspect of the present invention, $X^5$ represents Trp, Ser, Tyr, Val, Leu, Ile, Arg, His, Glu, Asp, Phe, 2-hydroxyglycine, homoserine, norleucine, norvaline, isovaline, 2-aminobutyric acid, or homophenylalanine, or represents Ala having a substituent selected from the group consisting of an alicyclic group, an aromatic hydrocarbon group, an aralkyl group, and a heterocyclic group. For a high myostatin inhibitory activity, it is necessary to substitute Ala at the fifth position from the N-terminal side in the peptide of SEQ ID NO: 1 with the above-described predetermined amino acid.

Examples of the "Ala (alanine) having a substituent selected from the group consisting of an alicyclic group, an aromatic hydrocarbon group, an aralkyl group, and a heterocyclic group" may include 3-cyclopentylalanine, 3-cyclohexylalanine, 3-pyridylalanine, 3-pyrazolylalanine, 3-furanylalanine, 3-thienylalanine, methoxyphenylalanine, 3-naphthylalanine, and the like, but Ala is not limited thereto.

From the viewpoint of the myostatin inhibitory activity, preferably, $X^5$ represents an amino acid residue selected from the group consisting of Trp, Ser, Tyr, Val, Leu, Ile, Arg, His, Glu, Asp, Phe, 2-hydroxyglycine, homoserine, norleucine, norvaline, isovaline, homophenylalanine, 3-cyclopentylalanine, 3-cyclohexylalanine, 3-pyridylalanine, 3-pyrazolylalanine, 3-furanylalanine, 3-thienylalanine, methoxyphenylalanine, and 3-naphthylalanine.

More preferably, $X^5$ represents an amino acid residue selected from the group consisting of Trp, Ser, Tyr, Val, Leu, Ile, Glu, Asp, Phe, 2-hydroxyglycine, homoserine, norleucine, norvaline, isovaline, homophenylalanine, 3-cyclopentylalanine, 3-cyclohexylalanine, and 3-naphthylalanine.

In a still more preferable embodiment, $X^5$ represents an amino acid residue selected from the group consisting of Trp, Ser, Tyr, Val, Leu, Ile, Phe, 2-hydroxyglycine, homoserine, norleucine, norvaline, isovaline, 3-cyclopentylalanine, 3-cyclohexylalanine, and 3-naphthylalanine, provided that, in a case where $X^5$ represents Ser, 2-hydroxyglycine, or homoserine, $X^2$ represents an amino acid residue selected from the group consisting of Tyr, Ser, Thr, Trp, Phe, Leu, Ile, Val, 2-hydroxyglycine, homoserine, homophenylalanine, norleucine, norvaline, isovaline, 3-cyclopentylalanine, 3-cyclohexylalanine, and 3-naphthylalanine. In an embodiment, $X^5$ represents an amino acid residue selected from the group consisting of Trp, Ser, Tyr, Val, Leu, Ile, Phe, 2-hydroxyglycine, homoserine, norleucine, norvaline, isovaline, 3-cyclopentylalanine, 3-cyclohexylalanine, and 3-naphthylalanine, provided that, in a case where $X^5$ represents Ser, 2-hydroxyglycine, or homoserine, $X^2$ represents an amino acid residue selected from the group consisting of Tyr, Ser, Trp, Phe, 2-hydroxyglycine, homoserine, homophenylalanine, 3-cyclohexylalanine, and 3-naphthylalanine. In an embodiment, $X^5$ represents an amino acid residue selected from the group consisting of Trp, Ser, Tyr, Val, Leu, Ile, Phe, 2-hydroxyglycine, homoserine, norleucine, norvaline, isovaline, 3-cyclopentylalanine, 3-cyclohexylalanine, and 3-naphthylalanine, provided that, in a case where $X^5$ represents Ser, 2-hydroxyglycine, or homoserine, $X^2$ represents Tyr.

Particularly preferably, $X^5$ represents an amino acid residue selected from the group consisting of Trp, Ser, Tyr, Leu, His, Phe, and 3-naphthylalanine, provided that, in a case where $X^5$ represents Ser, $X^2$ represents an amino acid residue selected from the group consisting of Tyr, Ser, Thr, Trp, Phe, Leu, Ile, Val, 2-hydroxyglycine, homoserine, homophenylalanine, norleucine, norvaline, isovaline, 3-cyclopentylalanine, 3-cyclohexylalanine, and 3-naphthylalanine. In an embodiment, $X^5$ represents an amino acid residue selected from the group consisting of Trp, Ser, Tyr, Leu, His, Phe, and 3-naphthylalanine, provided that, in a case where $X^5$ represents Ser, $X^2$ represents an amino acid residue selected from the group consisting of Tyr, Ser, Trp, Phe, 2-hydroxyglycine, homoserine, homophenylalanine, 3-cyclohexylalanine, and 3-naphthylalanine. In an embodiment, $X^5$ represents an amino acid residue selected from the group consisting of Trp, Ser, Tyr, Leu, His, Phe, and 3-naphthylalanine, provided that, in a case where $X^5$ represents Ser, $X^2$ represents an amino acid residue selected from the group consisting of Tyr, Ser, Trp, 2-hydroxyglycine, homoserine, 3-cyclohexylalanine, and 3-naphthylalanine.

In an embodiment, $X^5$ represents an amino acid residue selected from the group consisting of Trp, Ser, Tyr, Leu, His, Phe, and 3-naphthylalanine, provided that, in a case where $X^5$ represents Ser, $X^2$ represents Tyr.

In an embodiment of the present invention, the above Formula (1), $X^1$ represents an amino acid residue selected from the group consisting of Trp, Val, Leu, Ile, Phe, His, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, norleucine, norvaline, isovaline, 2-aminobutyric acid, and homophenylalanine, or deletion;

$X^2$ represents an amino acid residue selected from the group consisting of Tyr, Ser, Thr, Trp, Phe, Leu, Ile, Val, Arg, Lys, His, 2-hydroxyglycine, homoserine, homophenylalanine, norleucine, norvaline, isovaline, 3-cyclopentylalanine, 3-cyclohexylalanine, 3-pyridylalanine, 3-pyrazolylalanine, 3-furanylalanine, 3-thienylalanine, methoxyphenylalanine, and 3-naphthylalanine, or deletion; and $X^5$ represents an amino acid residue selected from the group consisting of Trp, Ser, Tyr, Val, Leu, Ile, Glu, Asp, Phe, 2-hydroxyglycine, homoserine, norleucine, norvaline, isovaline, homophenylalanine, 3-cyclopentylalanine, 3-cyclohexylalanine, and 3-naphthylalanine.

Incidentally, in the present embodiment, deletion is preferably only any one of $X^1$ and $X^2$.

In the peptide according to the first aspect of the present invention, amino acids of $X^1$, $X^2$ and $X^5$ are preferably a predetermined combination. More specifically, in an embodiment of the present invention, the amino acid sequence represented by Formula (1) includes an amino acid sequence selected from the group consisting of the following Formula (1-1) to Formula (1-27):

Chem. 6

$$W-Y-X^3-X^4-W-X^6-X^7-X^8-X^9-X^{10}-X^{11}-X^{12}-X^{13}-X^{14}-X^{15}-X^{16} \quad \text{Formula (1-1)}$$

$$Y-W-X^3-X^4-W-X^6-X^7-X^8-X^9-X^{10}-X^{11}-X^{12}-X^{13}-X^{14}-X^{15}-X^{16} \quad \text{Formula (1-2)}$$

$$Y-Y-X^3-X^4-W-X^6-X^7-X^8-X^9-X^{10}-X^{11}-X^{12}-X^{13}-X^{14}-X^{15}-X^{16} \quad \text{Formula (1-3)}$$

$$W-W-X^3-X^4-W-X^6-X^7-X^8-X^9-X^{10}-X^{11}-X^{12}-X^{13}-X^{14}-X^{15}-X^{16} \quad \text{Formula (1-4)}$$

$$X^1-Y-X^3-X^4-W-X^6-X^7-X^8-X^9-X^{10}-X^{11}-X^{12}-X^{13}-X^{14}-X^{15}-X^{16} \quad \text{Formula (1-5)}$$

($X^1$: 3-naphthylalanine)

$$F-Y-X^3-X^4-W-X^6-X^7-X^8-X^9-X^{10}-X^{11}-X^{12}-X^{13}-X^{14}-X^{15}-X^{16} \quad \text{Formula (1-6)}$$

$$L-Y-X^3-X^4-W-X^6-X^7-X^8-X^9-X^{10}-X^{11}-X^{12}-X^{13}-X^{14}-X^{15}-X^{16} \quad \text{Formula (1-7)}$$

$$H-Y-X^3-X^4-W-X^6-X^7-X^8-X^9-X^{10}-X^{11}-X^{12}-X^{13}-X^{14}-X^{15}-X^{16} \quad \text{Formula (1-8)}$$

$$W-F-X^3-X^4-W-X^6-X^7-X^8-X^9-X^{10}-X^{11}-X^{12}-X^{13}-X^{14}-X^{15}-X^{16} \quad \text{Formula (1-9)}$$

$$W-X^2-X^3-X^4-W-X^6-X^7-X^8-X^9-X^{10}-X^{11}-X^{12}-X^{13}-X^{14}-X^{15}-X^{16} \quad \text{Formula (1-10)}$$

($X^2$: 3-naphthylalanine)

$$W-X^2-X^3-X^4-W-X^6-X^7-X^8-X^9-X^{10}-X^{11}-X^{12}-X^{13}-X^{14}-X^{15}-X^{16} \quad \text{Formula (1-11)}$$

($X^2$: 3-cyclohexylalanine)

$$W-L-X^3-X^4-W-X^6-X^7-X^8-X^9-X^{10}-X^{11}-X^{12}-X^{13}-X^{14}-X^{15}-X^{16} \quad \text{Formula (1-12)}$$

$$W-H-X^3-X^4-W-X^6-X^7-X^8-X^9-X^{10}-X^{11}-X^{12}-X^{13}-X^{14}-X^{15}-X^{16} \quad \text{Formula (1-13)}$$

$$W-R-X^3-X^4-W-X^6-X^7-X^8-X^9-X^{10}-X^{11}-X^{12}-X^{13}-X^{14}-X^{15}-X^{16} \quad \text{Formula (1-14)}$$

$$W-S-X^3-X^4-W-X^6-X^7-X^8-X^9-X^{10}-X^{11}-X^{12}-X^{13}-X^{14}-X^{15}-X^{16} \quad \text{Formula (1-15)}$$

$$W-Y-X^3-X^4-X^5-X^6-X^7-X^8-X^9-X^{10}-X^{11}-X^{12}-X^{13}-X^{14}-X^{15}-X^{16} \quad \text{Formula (1-16)}$$

($X^5$: 3-naphthylalanine)

$$W-Y-X^3-X^4-L-X^6-X^7-X^8-X^9-X^{10}-X^{11}-X^{12}-X^{13}-X^{14}-X^{15}-X^{16} \quad \text{Formula (1-16)}$$

$$W-Y-X^3-X^4-S-X^6-X^7-X^8-X^9-X^{10}-X^{11}-X^{12}-X^{13}-X^{14}-X^{15}-X^{16} \quad \text{Formula (1-17)}$$

$$W-Y-X^3-X^4-R-X^6-X^7-X^8-X^9-X^{10}-X^{11}-X^{12}-X^{13}-X^{14}-X^{15}-X^{16} \quad \text{Formula (1-18)}$$

$$W-Y-X^3-X^4-E-X^6-X^7-X^8-X^9-X^{10}-X^{11}-X^{12}-X^{13}-X^{14}-X^{15}-X^{16} \quad \text{Formula (1-19)}$$

$$W-Y-X^3-X^4-F-X^6-X^7-X^8-X^9-X^{10}-X^{11}-X^{12}-X^{13}-X^{14}-X^{15}-X^{16} \quad \text{Formula (1-20)}$$

$$W-Y-X^3-X^4-Y-X^6-X^7-X^8-X^9-X^{10}-X^{11}-X^{12}-X^{13}-X^{14}-X^{15}-X^{16} \quad \text{Formula (1-21)}$$

$$W-Y-X^3-X^4-H-X^6-X^7-X^8-X^9-X^{10}-X^{11}-X^{12}-X^{13}-X^{14}-X^{15}-X^{16} \quad \text{Formula (1-22)}$$

$$Y-Y-X^3-X^4-S-X^6-X^7-X^8-X^9-X^{10}-X^{11}-X^{12}-X^{13}-X^{14}-X^{15}-X^{16} \quad \text{Formula (1-23)}$$

$$W-R-X^3-X^4-S-X^6-X^7-X^8-X^9-X^{10}-X^{11}-X^{12}-X^{13}-X^{14}-X^{15}-X^{16} \quad \text{Formula (1-24)}$$

$$Y-Y-X^3-X^4-X^5-X^6-X^7-X^8-X^9-X^{10}-X^{11}-X^{12}-X^{13}-X^{14}-X^{15}-X^{16} \quad \text{Formula (1-25)}$$

($X^5$: 3-naphthylalanine)

$$X^1-Y-X^3-X^4-W-X^6-X^7-X^8-X^9-X^{10}-X^{11}-X^{12}-X^{13}-X^{14}-X^{15}-X^{16} \quad \text{Formula (1-26)}$$

($X^1$: deletion)

$$Y-X^2-X^3-X^4-W-X^6-X^7-X^8-X^9-X^{10}-X^{11}-X^{12}-X^{13}-X^{14}-X^{15}-X^{16} \quad \text{Formula (1-27)}$$

($X^2$: deletion)

Note that, in the above Formula (1-1) to Formula (1-27), $X^3$, $X^4$, and $X^6$ to $X^{16}$ are the same as in Formula (1), and the descriptions of $X^3$, $X^4$, and $X^6$ to $X^{16}$ in Formula (1) are each independently applied to Formula (1-1) to Formula (1-27).

In a preferable embodiment, the peptide according to the first aspect of the present invention comprises an amino acid sequence selected from the group consisting of amino acid sequences represented by the above Formula (1-1) to Formula (1-17), and Formula (1-19) to Formula (1-27), as the amino acid sequence represented by Formula (1).

In the peptide according to the first aspect of the present invention, $X^7$ and $X^{13}$ each independently represent an amino acid residue selected from the group consisting of Arg, Lys, Pro, Cys, His, (α-methyl)lysine, 2,3-diaminopropionic acid, 2,4-diaminobutanoic acid, and ornithine.

Preferably, in the peptide according to the first aspect of the present invention, $X^7$ and $X^{13}$ each independently represent an amino acid residue selected from the group consisting of Arg, Lys, Pro, Cys, (α-methyl)lysine, and ornithine.

More preferably, in the peptide according to the first aspect of the present invention, $X^7$ and $X^{13}$ represent Arg, Lys, or Pro.

In the peptide according to the first aspect of the present invention, $X^9$ represents an amino acid residue selected from the group consisting of Asn, Pro, Gln, Cys, and 3,4-didehydroproline.

From the viewpoint of the myostatin inhibitory activity, in the peptide according to the first aspect of the present invention, preferably, $X^9$ represents an amino acid residue selected from the group consisting of Asn, Pro, Gln, and Cys.

More preferably, in the peptide according to the first aspect of the present invention, $X^9$ represents an amino acid residue selected from the group consisting of Asn, Gln, and Cys.

In the peptide according to the first aspect of the present invention, $X^{11}$ represents an arbitrary amino acid residue which may have a substituent selected from the group consisting of an alicyclic group, an aromatic hydrocarbon group, an aralkyl group, and a heterocyclic group in a side chain.

From the viewpoint of the myostatin inhibitory activity, $X^{11}$ preferably has a bulky group or a hydrophobic group in a side chain, and more specifically, $X^{11}$ preferably represents an amino acid residue selected from the group consisting of Pro, Tyr, Trp, Thr, Gly, Ala, Met, Phe, Leu, Val, Ile, 3-chloroalanine, 2-aminobutyric acid, norleucine, norvaline, isovaline, 2-aminoisobutyric acid, homophenylalanine, hydroxyproline, 3,4-didehydroproline, homomethionine, aspartate ester, glutamate ester, formyltryptophan, 2-cyclopentylglycine, 2-cyclohexylglycine, 2-phenylglycine, 3-cyclopentylalanine, 3-cyclohexylalanine, 3-pyridylalanine, 3-pyrazolylalanine, 3-furanylalanine, 3-thienylalanine, methoxyphenylalanine, and 3-naphthylalanine.

More preferably, $X^{11}$ represents an amino acid residue selected from the group consisting of Ala, Val, Leu, Ile, Phe, Trp, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, homophenylalanine, 2-aminobutyric acid, 2-aminoisobutyric acid, norleucine, norvaline, and isovaline.

Still more preferably, $X^{11}$ represents an amino acid residue selected from the group consisting of Val, Leu, Ile, Phe, Trp, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, homophenylalanine, norleucine, norvaline, and isovaline, provided that, in a case where X' and $X^5$ represent Trp and $X^2$ represents Tyr, $X^{11}$ represents an amino acid residue selected from the group consisting of Phe, Trp, Tyr, 2-cyclohexylglycine, and norvaline.

Particularly preferably, $X^{11}$ represents Trp. When $X^{11}$ represents Trp, the myostatin inhibitory activity is particularly significantly improved.

In an embodiment of the present invention, in the above Formula (1), $X^1$ represents an amino acid residue selected from the group consisting of Trp, Val, Leu, Ile, Phe, His, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, norleucine, norvaline, isovaline, 2-aminobutyric acid, and homophenylalanine, or deletion;

$X^2$ represents an amino acid residue selected from the group consisting of Tyr, Ser, Trp, Phe, Arg, Lys, His, 2-hydroxyglycine, homoserine, homophenylalanine, 3-cyclohexylalanine, and 3-naphthylalanine, provided that, in a case where $X^5$ represents Ser, 2-hydroxyglycine, or homoserine, $X^2$ represents an amino acid residue selected from the group consisting of Tyr, Ser, Trp, Phe, 2-hydroxyglycine, homoserine, homophenylalanine, 3-cyclohexylalanine, and 3-naphthylalanine, or deletion;

$X^5$ represents an amino acid residue selected from the group consisting of Trp, Ser, Tyr, Val, Leu, Ile, Phe, 2-hydroxyglycine, homoserine, norleucine, norvaline, isovaline, 3-cyclopentylalanine, 3-cyclohexylalanine, and 3-naphthylalanine; and $X^{11}$ represents an amino acid residue selected from the group consisting of Val, Leu, Ile, Phe, Trp, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, homophenylalanine, norleucine, norvaline, and isovaline;

provided that, in a case where X' and $X^5$ represent Trp and $X^2$ represents Tyr, $X^{11}$ represents an amino acid residue selected from the group consisting of Phe, Trp, Tyr, 2-cyclohexylglycine, and norvaline.

Incidentally, in the present embodiment, deletion is preferably only any one of $X^1$ and $X^2$.

In an embodiment of the present invention, in the above Formula (1), $X^1$ represents an amino acid residue selected from the group consisting of Trp, Val, Leu, Ile, Phe, Tyr, 3-naphthylalanine, norleucine, norvaline, and isovaline, or deletion;

$X^2$ represents an amino acid residue selected from the group consisting of Tyr, Ser, Trp, Arg, Lys, His, 2-hydroxyglycine, homoserine, 3-cyclohexylalanine, and 3-naphthylalanine, provided that, in a case where $X^5$ represents Ser, $X^2$ represents an amino acid residue selected from the group consisting of Tyr, Ser, Trp, 2-hydroxyglycine, homoserine, 3-cyclohexylalanine, and 3-naphthylalanine, or deletion;

$X^5$ represents an amino acid residue selected from the group consisting of Trp, Ser, Tyr, Val, Leu, Ile, Phe, 2-hydroxyglycine, homoserine, norleucine, norvaline, isovaline, 3-cyclopentylalanine, 3-cyclohexylalanine, and 3-naphthylalanine; and $X^{11}$ represents an amino acid residue selected from the group consisting of Val, Leu, Ile, Phe, Trp, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, homophenylalanine, norleucine, norvaline, and isovaline;

provided that, in a case where $X^1$ and $X^5$ represent Trp and $X^2$ represents Tyr, $X^{11}$ represents an amino acid residue selected from the group consisting of Phe, Trp, Tyr, 2-cyclohexylglycine, and norvaline.

Incidentally, in the present embodiment, deletion is preferably only any one of $X^1$ and $X^2$.

In the peptide according to the first aspect of the present invention, $X^{12}$ represents an amino acid residue selected from the group consisting of Ser, Pro, Cys, Thr, Tyr, 2-hydroxyglycine, and homoserine.

In the peptide according to the first aspect of the present invention, preferably, $X^{12}$ represents an amino acid residue selected from the group consisting of Ser, Pro, Cys, Thr, 2-hydroxyglycine, and homoserine.

In the peptide according to the first aspect of the present invention, more preferably, $X^{12}$ represents an amino acid residue selected from the group consisting of Ser, Pro, Cys, 2-hydroxyglycine, and homoserine.

In the peptide according to the first aspect of the present invention, still more preferably, $X^{12}$ represents Ser, Pro, or Cys.

In the peptide according to the first aspect of the present invention, $X^{15}$ represents an arbitrary amino acid residue, which may have a substituent selected from the group consisting of an alicyclic group, an aromatic hydrocarbon group, an aralkyl group, and a heterocyclic group in a side chain, or deletion.

From the viewpoint of the myostatin inhibitory activity, in the peptide according to the first aspect of the present invention, $X^{15}$ represents an amino acid residue selected from the group consisting of Arg, Lys, Asp, Asn, Glu, Gln, His, Tyr, Ser, Thr, Gly, Cys, 2,3-diaminopropionic acid, 2,4-diaminobutanoic acid, ornithine, 2-hydroxyglycine, homoserine, hydroxylysine, hydroxyproline, and homocysteine, or deletion.

In the peptide according to the first aspect of the present invention, more preferably, $X^{15}$ represents an amino acid residue selected from the group consisting of Arg, Lys, Asp, Asn, Glu, Gln, His, Ser, Thr, Cys, 2,3-diaminopropionic acid, 2,4-diaminobutanoic acid, ornithine, 2-hydroxyglycine, homoserine, hydroxylysine, and homocysteine.

In the peptide according to the first aspect of the present invention, still more preferably, $X^{15}$ represents an amino acid residue selected from the group consisting of Arg, Lys, His, 2,3-diaminopropionic acid, 2,4-diaminobutanoic acid, and ornithine.

In the peptide according to the first aspect of the present invention, particularly preferably, $X^{15}$ represents Arg.

In a preferable embodiment of the present invention, in the above Formula (1), $X^1$ represents an amino acid residue selected from the group consisting of Trp, Val, Leu, Ile, Phe, His, Tyr, 3-naphthylalanine, norleucine, norvaline, and isovaline, or deletion;

$X^2$ represents an amino acid residue selected from the group consisting of Tyr, Ser, Trp, Phe, Arg, Lys, His, 2-hydroxyglycine, homoserine, homophenylalanine, 3-cyclohexylalanine, and 3-naphthylalanine, provided that, in a case where $X^5$ represents Ser, 2-hydroxyglycine, or homoserine, $X^2$ represents an amino acid residue selected from the group consisting of Tyr, Ser, Trp, Phe, 2-hydroxyglycine, homoserine, homophenylalanine, 3-cyclohexylalanine, and 3-naphthylalanine, or deletion;

$X^3$, $X^6$, $X^8$, $X^{10}$, $X^{14}$ and $X^{16}$ each independently represent an amino acid residue selected from the group consisting of Val, Leu, Ile, Phe, 2-cyclohexylglycine, norleucine, norvaline, and isovaline;

$X^4$ represents an amino acid residue selected from the group consisting of Arg, Lys, Gln, Asp, Glu, Cys, and ornithine;

$X^5$ represents an amino acid residue selected from the group consisting of Trp, Ser, Tyr, Val, Leu, Ile, Phe, 2-hydroxyglycine, homoserine, norleucine, norvaline, isovaline, 3-cyclopentylalanine, 3-cyclohexylalanine, and 3-naphthylalanine;

$X^7$ and $X^{13}$ each independently represent an amino acid residue selected from the group consisting of Arg, Lys, Pro, Cys, (α-methyl)lysine, and ornithine;

$X^9$ represents an amino acid residue selected from the group consisting of Asn, Pro, Gln, Cys, and 3,4-didehydroproline;

$X^{11}$ represents an amino acid residue selected from the group consisting of Val, Leu, Ile, Phe, Trp, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, homophenylalanine, norleucine, norvaline, and isovaline, provided that, in a case where $X^1$ and $X^5$ represent Trp and $X^2$ represents Tyr, $X^{11}$ represents an amino acid residue selected from the group consisting of Phe, Trp, Tyr, 2-cyclohexylglycine, and norvaline;

$X^{12}$ represents an amino acid residue selected from the group consisting of Ser, Pro, Cys, Thr, 2-hydroxyglycine, and homoserine; and $X^{15}$ represents an amino acid residue selected from the group consisting of Arg, Lys, Asp, Asn, Glu, Gln, His, Ser, Thr, Cys, 2,3-diaminopropionic acid, 2,4-diaminobutanoic acid, ornithine, 2-hydroxyglycine, homoserine, hydroxylysine, and homocysteine.

Incidentally, in the present embodiment, deletion is preferably only any one of $X^1$ and $X^2$.

In a particularly preferable embodiment of the present invention, in the above Formula (1), $X^1$ represents an amino acid residue selected from the group consisting of Trp, Leu, Phe, Tyr, and 3-naphthylalanine, or deletion;

$X^2$ represents an amino acid residue selected from the group consisting of Tyr, Ser, Trp, Arg, Lys, His, 3-cyclohexylalanine, and 3-naphthylalanine, provided that, in a case where $X^5$ represents Ser, $X^2$ represents an amino acid residue selected from the group consisting of Tyr, Ser, Trp, 3-cyclohexylalanine, and 3-naphthylalanine, or deletion;

$X^3$ and $X^{10}$ represent an amino acid residue selected from the group consisting of Ile and Phe;

$X^4$ represents an amino acid residue selected from the group consisting of Arg, Lys, Gln, Cys, and Glu;

$X^5$ represents an amino acid residue selected from the group consisting of Trp, Ser, Tyr, Leu, His, Phe, and 3-naphthylalanine;

$X^6$ represents Ile;

$X^7$ and $X^{13}$ represent Arg, Lys, or Pro;

$X^8$ represents an amino acid residue selected from the group consisting of Ile and 2-cyclohexylglycine;

$X^9$ represents an amino acid residue selected from the group consisting of Asn, Gln, and Cys;

$X^{11}$ represents Trp;

$X^{12}$ represents Ser, Pro, or Cys;

$X^{14}$ represents an amino acid residue selected from the group consisting of Leu, Ile, and 2-cyclohexylglycine;

$X^{15}$ represents Arg; and $X^{16}$ represents Leu.

Incidentally, in the present embodiment, deletion is preferably only any one of $X^1$ and $X^2$.

<Peptide According to Second Aspect>

In the peptide according to the second aspect of the present invention satisfies the following (a) or (b) and has the number of amino acid residues of 20 or less:

(a) the peptide comprising any one of amino acid sequences represented by SEQ ID NOs: 2 to 9, SEQ ID NOs: 11 to 38, SEQ ID NOs: 380 to 385, SEQ ID NOs: 573 to 581, and SEQ ID NOs: 583 to 595 described above; or (b) the peptide comprising one amino acid sequence in which one amino acid residue of $X^2$ to $X^4$ and $X^6$ to $X^{16}$ in the amino acid sequences of the above (a) is substituted or deleted and having a myostatin inhibitory activity.

As shown in SEQ ID NOs: 2 to 9, SEQ ID NOs: 11 to 38, SEQ ID NOs: 380 to 385, SEQ ID NOs: 573 to 581, and SEQ ID NOs: 583 to 595 described above, when Ser at the first position and Ala at the fifth position from the N-terminal side in the peptide of SEQ ID NO: 1 are substituted with a predetermined amino acid, a high myostatin inhibitory activity may be obtained.

From the viewpoint of the myostatin inhibitory activity, the peptide according to the second aspect of the present invention preferably satisfies the following (a-1) or (b-1) and has the number of amino acid residues of 20 or less:

(a-1) the amino acid sequence of the peptide satisfying the above (a) being represented by any one of SEQ ID NO: 4, SEQ ID NOs: 6 to 8, SEQ ID NO: 12, SEQ ID NO: 13, SEQ ID NO: 15, SEQ ID NO: 16, SEQ ID NO: 18, SEQ ID NOs: 23 to 29, SEQ ID NOs: 33 to 36, SEQ ID NOs: 380 to 385, SEQ ID NOs: 573 to 581, SEQ ID NO: 583, SEQ ID NO: 584, and SEQ ID NOs: 586 to 594; or (b-1) the peptide comprising one amino acid sequence in which one amino acid residue of $X^2$ to $X^4$, $X^8$, $X^9$, $X^{11}$, and $X^{14}$ in the amino acid sequences of the above (a-1) is substituted or deleted and having a myostatin inhibitory activity.

Incidentally, in the present specification, the expression of the peptide or a salt thereof "has a myostatin inhibitory activity" indicates that, in the reporter assay described in Examples, a relative luciferase activity is 60% or less at a concentration of 1 μM of a test sample (the peptide or a salt thereof). The relative luciferase activity measured by the reporter assay described in Examples is preferably 50% or less, more preferably 40% or less, still more preferably 30% or less, and particularly preferably 25% or less (lower limit: 0%) at a concentration of 1 μM of a test sample. The substitution of the amino acid residue is not particularly limited as long as the peptide has the myostatin inhibitory activity as described above, and for example, the substitution may be substitution with an amino acid residue in which the amino acid after substitution has a "substituent selected from the group consisting of an alicyclic group, an aromatic hydrocarbon group, an aralkyl group, and a heterocyclic group" as described above in a side chain. Preferably, the substitution of amino acid is conservative substitution.

In an embodiment, examples of the amino acid sequence satisfying the above (b) or (b-1) include amino acid sequences selected from the group consisting of the following (b-2) to (b-11):

(b-2) an amino acid sequence in which $X^2$ is substituted with an amino acid residue selected from the group consisting of Tyr, Ser, Thr, Trp, Phe, Ala, Leu, Ile, Val, Arg, Lys, His, 2-hydroxyglycine, homoserine, homophenylalanine, norleucine, norvaline, isovaline, 2-aminobutyric acid, and 2-aminoisobutyric acid, which may have a substituent selected from the group consisting of an alicyclic group, an aromatic hydrocarbon group, an aralkyl group, and a heterocyclic group in a side chain, or represents deletion;

(b-3) an amino acid sequence in which $X^3$, $X^6$, $X^8$, or $X^{10}$ is substituted with an amino acid residue selected from the group consisting of Ala, Val, Leu, Phe, 2-cyclohexylglycine, norleucine, norvaline, isovaline, 2-aminobutyric acid, and 2-aminoisobutyric acid, or represents deletion;

(b-4) an amino acid sequence in which $X^4$ is substituted with an amino acid residue selected from the group consisting of Arg, Lys, Asp, Asn, Glu, Gln, His, Pro, Tyr, Trp, Ser, Thr, Cys, 2,3-diaminopropionic acid, 2,4-diaminobutanoic acid, ornithine, 2-hydroxyglycine, homoserine, hydroxylysine, and hydroxyproline, or represents deletion;

(b-5) an amino acid sequence in which $X^7$ or $X^{13}$ is substituted with an amino acid residue selected from the group consisting of Arg, Lys, Pro, Cys, His, (α-methyl)lysine, 2,3-diaminopropionic acid, 2,4-diaminobutanoic acid, and ornithine, or represents deletion;

(b-6) an amino acid sequence in which $X^9$ is substituted with an amino acid residue selected from the group consisting of Asn, Pro, Gln, Cys, and 3,4-didehydroproline, or represents deletion;

(b-7) an amino acid sequence in which $X^{11}$ is substituted with an amino acid residue selected from the group consisting of Pro, Tyr, Trp, Thr, Gly, Ala, Met, Phe, Leu, Val, Ile, 3-chloroalanine, 2-aminobutyric acid, norleucine, norvaline, isovaline, 2-aminoisobutyric acid, homophenylalanine, hydroxyproline, 3,4-didehydroproline, homomethionine, aspartate ester, glutamate ester, formyltryptophan, 2-cyclopentylglycine, 2-cyclohexylglycine, 2-phenylglycine, 3-cyclopentylalanine, 3-cyclohexylalanine, 3-pyridylalanine, 3-pyrazolylalanine, 3-furanylalanine, 3-thienylalanine, methoxyphenylalanine, and 3-naphthylalanine, or represents deletion;

(b-8) an amino acid sequence in which $X^{12}$ is substituted with an amino acid residue selected from the group consisting of Ser, Pro, Cys, Thr, Tyr, 2-hydroxyglycine, and homoserine, or represents deletion;

(b-9) an amino acid sequence in which $X^{14}$ is substituted with an amino acid residue selected from the group consisting of Ala, Val, Leu, Ile, norleucine, norvaline, isovaline, 2-cyclohexylglycine, 2-aminobutyric acid, and 2-aminoisobutyric acid, or represents deletion;

(b-10) an amino acid sequence in which $X^{15}$ is substituted with an amino acid residue selected from the group consisting of Arg, Pro, Cys, Lys, Asp, Asn, Glu, Gln, His, Tyr, Ser, Thr, Gly, Cys, 2,3-diaminopropionic acid, 2,4-diaminobutanoic acid, ornithine, 2-hydroxyglycine, homoserine, hydroxylysine, hydroxyproline, and homocysteine, or represents deletion; and (b-11) an amino acid sequence in which $X^{16}$ is substituted with an amino acid residue selected from the group consisting of Ala, Val, Ile, norleucine, norvaline, isovaline, 2-aminobutyric acid, and 2-aminoisobutyric acid, or represents deletion.

Preferable examples of the amino acid sequence satisfying the above (b) or (b-1) include amino acid sequences selected from the group consisting of the following (b-12) to (b-23):

(b-12) an amino acid sequence in which $X^8$ is substituted with an amino acid residue selected from the group consisting of Tyr, Ser, Trp, Arg, Lys, His, 3-cyclohexylalanine, and 3-naphthylalanine, provided that, in a case where $X^5$ represents Ser, $X^8$ is substituted with an amino acid residue selected from the group consisting of Tyr, Ser, Trp, 3-cyclohexylalanine, and 3-naphthylalanine;

(b-13) an amino acid sequence in which $X^3$ or $X^{10}$ is substituted with an amino acid residue selected from the group consisting of Val, Leu, Ile, and Phe;

(b-14) an amino acid sequence in which $X^4$ is substituted with an amino acid residue selected from the group consisting of Arg, Lys, Gln, Cys, and Glu;

(b-15) an amino acid sequence in which $X^6$ is substituted with an amino acid residue selected from the group consisting of Val and Leu;

(b-16) an amino acid sequence in which $X^7$ or $X^{13}$ is substituted with an amino acid residue selected from the group consisting of Arg, Lys, Pro, Cys, (α-methyl)lysine, and ornithine;

(b-17) an amino acid sequence in which $X^8$ is substituted with an amino acid residue selected from the group consisting of Val, Leu, Ile, and 2-cyclohexylglycine;

(b-18) an amino acid sequence in which $X^9$ is substituted with an amino acid residue selected from the group consisting of Asn, Gln, and Cys;

(b-19) an amino acid sequence in which $X^{11}$ is substituted with an amino acid residue selected from the group consisting of Val, Leu, Ile, Phe, Trp, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, homophenylalanine, norleucine, norvaline, and isovaline, provided that, in a case where $X^1$ and $X^5$ represent Trp and $X^2$ represents Tyr, $X^{11}$ is substituted with an amino acid residue selected from the group consisting of Phe, Trp, Tyr, 2-cyclohexylglycine, and norvaline;

(b-20) an amino acid sequence in which $X^{22}$ is substituted with an amino acid residue selected from the group consisting of Ser, Pro, Cys, 2-hydroxyglycine, and homoserine;

(b-21) an amino acid sequence in which $X^{24}$ is substituted with an amino acid residue selected from the group consisting of Val, Leu, and Ile;

(b-22) an amino acid sequence in which $X^{25}$ is substituted with an amino acid residue selected from the group consisting of Lys, His, 2,3-diaminopropionic acid, 2,4-diaminobutanoic acid, 2-cyclohexylglycine, and ornithine; and (b-23) an amino acid sequence in which $X^{16}$ is substituted with an amino acid residue selected from the group consisting of Val and Ile.

More preferable examples of the amino acid sequence satisfying the above (b) or (b-1) include amino acid sequences selected from the group consisting of the following amino acid sequences of SEQ ID NOs: 40 to 379, SEQ ID NOs: 386 to 581, and SEQ ID NOs: 583 to 595. Note that, in the following SEQ ID NOs: 40 to 379, SEQ ID NOs: 386 to 581, and SEQ ID NOs: 583 to 595, Cha represents 3-cyclohexylalanine, Nva represents norvaline, Naa represents 3-naphthylalanine, Chg represents 2-cyclohexylglycine, w represents D-tryptophan, s represents D-serine, (α-Me)Lys represents (α-methyl)lysine, and c represents D-cysteine;

```
SEQ ID40:   Y-S-I-E-W-I-K-I-Q-I-I-S-K-L-R-L

SEQ ID41:   Y-R-I-E-W-I-K-I-Q-I-I-S-K-L-R-L

SEQ ID42:   Y-K-I-E-W-I-K-I-Q-I-I-S-K-L-R-L

SEQ ID43:   Y-H-I-E-W-I-K-I-Q-I-I-S-K-L-R-L

SEQ ID44:   Y-X²-I-E-W-I-K-I-Q-I-I-S-K-L-R-L   (X² = Cha)

SEQ ID45:   Y-X²-I-E-W-I-K-I-Q-I-I-S-K-L-R-L   (X² = Naa)

SEQ ID46:   Y-Y-I-R-W-I-K-I-Q-I-I-S-K-L-R-L

SEQ ID47:   Y-Y-I-K-W-I-K-I-Q-I-I-S-K-L-R-L

SEQ ID48:   Y-Y-I-N-W-I-K-I-Q-I-I-S-K-L-R-L

SEQ ID49:   Y-Y-I-Q-W-I-K-I-Q-I-I-S-K-L-R-L

SEQ ID50:   Y-Y-I-D-W-I-K-I-Q-I-I-S-K-L-R-L

SEQ ID51:   Y-Y-I-E-W-I-K-I-N-I-I-S-K-L-R-L

SEQ ID52:   Y-Y-I-E-W-I-K-I-P-I-I-S-K-L-R-L

SEQ ID53:   Y-Y-I-E-W-I-K-I-Q-I-V-S-K-L-R-L

SEQ ID54:   Y-Y-I-E-W-I-K-I-Q-I-L-S-K-L-R-L

SEQ ID55:   Y-Y-I-E-W-I-K-I-Q-I-F-S-K-L-R-L

SEQ ID56:   Y-Y-I-E-W-I-K-I-Q-I-W-S-K-L-R-L

SEQ ID57:   Y-Y-I-E-W-I-K-I-Q-I-Y-S-K-L-R-L

SEQ ID58:   Y-Y-I-E-W-I-K-I-Q-I-X¹¹-S-K-L-R-L   (X¹¹ = Nva)

SEQ ID59:   Y-Y-I-E-W-I-K-I-Q-I-X¹¹-S-K-L-R-L   (X¹¹ = Chg)

SEQ ID60:   Y-Y-I-E-W-I-K-I-Q-I-I-S-K-I-R-L

SEQ ID61:   X¹-S-I-E-W-I-K-I-Q-I-I-S-K-L-R-L   (X¹ = Naa)

SEQ ID62:   X¹-W-I-E-W-I-K-I-Q-I-I-S-K-L-R-L   (X¹ = Naa)
```

-continued

```
SEQ ID63:   X¹-R-I-E-W-I-K-I-Q-I-I-S-K-L-R-L (X¹ = Naa)

SEQ ID64:   X¹-K-I-E-W-I-K-I-Q-I-I-S-K-L-R-L (X¹ = Naa)

SEQ ID65:   X¹-H-I-E-W-I-K-I-Q-I-I-S-K-L-R-L (X¹ = Naa)

SEQ ID66:   X¹-X²-I-E-W-I-K-I-Q-I-I-S-K-L-R-L (X¹ = Naa, X² = Cha)

SEQ ID67:   X¹-X²-I-E-W-I-K-I-Q-I-I-S-K-L-R-L (X¹ = Naa, X² = Naa)

SEQ ID68:   X¹-Y-I-R-W-I-K-I-Q-I-I-S-K-L-R-L (X¹ = Naa)

SEQ ID69:   X¹-Y-I-K-W-I-K-I-Q-I-I-S-K-L-R-L (X¹ = Naa)

SEQ ID70:   X¹-Y-I-N-W-I-K-I-Q-I-I-S-K-L-R-L (X¹ = Naa)

SEQ ID71:   X¹-Y-I-Q-W-I-K-I-Q-I-I-S-K-L-R-L (X¹ = Naa)

SEQ ID72:   X¹-Y-I-D-W-I-K-I-Q-I-I-S-K-L-R-L (X¹ = Naa)

SEQ ID73:   X¹-Y-I-E-W-I-K-I-N-I-I-S-K-L-R-L (X¹ = Naa)

SEQ ID74:   X¹-Y-I-E-W-I-K-I-P-I-I-S-K-L-R-L (X¹ = Naa)

SEQ ID75:   X¹-Y-I-E-W-I-K-I-Q-I-V-S-K-L-R-L (X¹ = Naa)

SEQ ID76:   X¹-Y-I-E-W-I-K-I-Q-I-L-S-K-L-R-L (X¹ = Naa)

SEQ ID77:   X¹-Y-I-E-W-I-K-I-Q-I-F-S-K-L-R-L (X¹ = Naa)

SEQ ID78:   X¹-Y-I-E-W-I-K-I-Q-I-W-S-K-L-R-L (X¹ = Naa)

SEQ ID79:   X¹-Y-I-E-W-I-K-I-Q-I-Y-S-K-L-R-L (X¹ = Naa)

SEQ ID80:   X¹-Y-I-E-W-I-K-I-Q-I-X¹¹-S-K-L-R-L (X¹ = Naa, X¹¹ = Nva)

SEQ ID81:   X¹-Y-I-E-W-I-K-I-Q-I-X¹¹-S-K-L-R-L (X¹ = Naa, X¹¹ = Chg)

SEQ ID82:   X¹-Y-I-E-W-I-K-I-Q-I-I-S-K-I-R-L (X¹ = Naa)

SEQ ID83:   F-S-I-E-W-I-K-I-Q-I-I-S-K-L-R-L

SEQ ID84:   F-W-I-E-W-I-K-I-Q-I-I-S-K-L-R-L

SEQ ID85:   F-R-I-E-W-I-K-I-Q-I-I-S-K-L-R-L

SEQ ID86:   F-K-I-E-W-I-K-I-Q-I-I-S-K-L-R-L

SEQ ID87:   F-H-I-E-W-I-K-I-Q-I-I-S-K-L-R-L

SEQ ID88:   F-X²-I-E-W-I-K-I-Q-I-I-S-K-L-R-L (X² = Cha)

SEQ ID89:   F-X²-I-E-W-I-K-I-Q-I-I-S-K-L-R-L (X² = Naa)

SEQ ID90:   F-Y-I-R-W-I-K-I-Q-I-I-S-K-L-R-L

SEQ ID91:   F-Y-I-K-W-I-K-I-Q-I-I-S-K-L-R-L

SEQ ID92:   F-Y-I-N-W-I-K-I-Q-I-I-S-K-L-R-L

SEQ ID93:   F-Y-I-Q-W-I-K-I-Q-I-I-S-K-L-R-L

SEQ ID94:   F-Y-I-D-W-I-K-I-Q-I-I-S-K-L-R-L

SEQ ID95:   F-Y-I-E-W-I-K-I-N-I-I-S-K-L-R-L

SEQ ID96:   F-Y-I-E-W-I-K-I-P-I-I-S-K-L-R-L

SEQ ID97:   F-Y-I-E-W-I-K-I-Q-I-V-S-K-L-R-L

SEQ ID98:   F-Y-I-E-W-I-K-I-Q-I-L-S-K-L-R-L

SEQ ID99:   F-Y-I-E-W-I-K-I-Q-I-F-S-K-L-R-L

SEQ ID100:  F-Y-I-E-W-I-K-I-Q-I-W-S-K-L-R-L

SEQ ID101:  F-Y-I-E-W-I-K-I-Q-I-Y-S-K-L-R-L
```

-continued

| SEQ ID | Sequence |
|---|---|
| SEQ ID102: | F-Y-I-E-W-I-K-I-Q-I-$X^{11}$-S-K-L-R-L ($X^{11}$ = Nva) |
| SEQ ID103: | F-Y-I-E-W-I-K-I-Q-I-$X^{11}$-S-K-L-R-L ($X^{11}$ = Chg) |
| SEQ ID104: | F-Y-I-E-W-I-K-I-Q-I-I-S-K-I-R-L |
| SEQ ID105: | L-S-I-E-W-I-K-I-Q-I-I-S-K-L-R-L |
| SEQ ID106: | L-W-I-E-W-I-K-I-Q-I-I-S-K-L-R-L |
| SEQ ID107: | L-R-I-E-W-I-K-I-Q-I-I-S-K-L-R-L |
| SEQ ID108: | L-K-I-E-W-I-K-I-Q-I-I-S-K-L-R-L |
| SEQ ID109: | L-H-I-E-W-I-K-I-Q-I-I-S-K-L-R-L |
| SEQ ID110: | L-$X^2$-I-E-W-I-K-I-Q-I-I-S-K-L-R-L ($X^2$ = Cha) |
| SEQ ID111: | L-$X^2$-I-E-W-I-K-I-Q-I-I-S-K-L-R-L ($X^2$ = Naa) |
| SEQ ID112: | L-Y-I-R-W-I-K-I-Q-I-I-S-K-L-R-L |
| SEQ ID113: | L-Y-I-K-W-I-K-I-Q-I-I-S-K-L-R-L |
| SEQ ID114: | L-Y-I-N-W-I-K-I-Q-I-I-S-K-L-R-L |
| SEQ ID115: | L-Y-I-Q-W-I-K-I-Q-I-I-S-K-L-R-L |
| SEQ ID116: | L-Y-I-D-W-I-K-I-Q-I-I-S-K-L-R-L |
| SEQ ID117: | L-Y-I-E-W-I-K-I-N-I-I-S-K-L-R-L |
| SEQ ID118: | L-Y-I-E-W-I-K-I-P-I-I-S-K-L-R-L |
| SEQ ID119: | L-Y-I-E-W-I-K-I-Q-I-V-S-K-L-R-L |
| SEQ ID120: | L-Y-I-E-W-I-K-I-Q-I-L-S-K-L-R-L |
| SEQ ID121: | L-Y-I-E-W-I-K-I-Q-I-F-S-K-L-R-L |
| SEQ ID122: | L-Y-I-E-W-I-K-I-Q-I-W-S-K-L-R-L |
| SEQ ID123: | L-Y-I-E-W-I-K-I-Q-I-Y-S-K-L-R-L |
| SEQ ID124: | L-Y-I-E-W-I-K-I-Q-I-$X^{11}$-S-K-L-R-L ($X^{11}$ = Nva) |
| SEQ ID125: | L-Y-I-E-W-I-K-I-Q-I-$X^{11}$-S-K-L-R-L ($X^{11}$ = Chg) |
| SEQ ID126: | L-Y-I-E-W-I-K-I-Q-I-I-S-K-I-R-L |
| SEQ ID127: | W-K-I-E-W-I-K-I-Q-I-I-S-K-L-R-L |
| SEQ ID128: | W-$X^2$-I-R-W-I-K-I-Q-I-I-S-K-L-R-L ($X^2$ = Naa) |
| SEQ ID129: | W-$X^2$-I-K-W-I-K-I-Q-I-I-S-K-L-R-L ($X^2$ = Naa) |
| SEQ ID130: | W-$X^2$-I-N-W-I-K-I-Q-I-I-S-K-L-R-L ($X^2$ = Naa) |
| SEQ ID131: | W-$X^2$-I-Q-W-I-K-I-Q-I-I-S-K-L-R-L ($X^2$ = Naa) |
| SEQ ID132: | W-$X^2$-I-D-W-I-K-I-Q-I-I-S-K-L-R-L ($X^2$ = Naa) |
| SEQ ID133: | W-$X^2$-I-E-W-I-K-I-N-I-I-S-K-L-R-L ($X^2$ = Naa) |
| SEQ ID134: | W-$X^2$-I-E-W-I-K-I-P-I-I-S-K-L-R-L ($X^2$ = Naa) |
| SEQ ID135: | W-$X^2$-I-E-W-I-K-I-Q-I-V-S-K-L-R-L ($X^2$ = Naa) |
| SEQ ID136: | W-$X^2$-I-E-W-I-K-I-Q-I-L-S-K-L-R-L ($X^2$ = Naa) |
| SEQ ID137: | W-$X^2$-I-E-W-I-K-I-Q-I-F-S-K-L-R-L ($X^2$ = Naa) |
| SEQ ID138: | W-$X^2$-I-E-W-I-K-I-Q-I-W-S-K-L-R-L ($X^2$ = Naa) |
| SEQ ID139: | W-$X^2$-I-E-W-I-K-I-Q-I-Y-S-K-L-R-L ($X^2$ = Naa) |
| SEQ ID140: | W-$X^2$-I-E-W-I-K-I-Q-I-$X^{11}$-S-K-L-R-L ($X^2$ = Naa, $X^{11}$ = Nva) |
| SEQ ID141: | W-$X^2$-I-E-W-I-K-I-Q-I-$X^{11}$-S-K-L-R-L ($X^2$ = Naa, $X^{11}$ = Chg) |

-continued

SEQ ID142: W-$X^2$-I-E-W-I-K-I-Q-I-I-S-K-I-R-L ($X^2$ = Naa)

SEQ ID143: W-$X^2$-I-R-W-I-K-I-Q-I-I-S-K-L-R-L ($X^2$ = Cha)

SEQ ID144: W-$X^2$-I-K-W-I-K-I-Q-I-I-S-K-L-R-L ($X^2$ = Cha)

SEQ ID145: W-$X^2$-I-N-W-I-K-I-Q-I-I-S-K-L-R-L ($X^2$ = Cha)

SEQ ID146: W-$X^2$-I-Q-W-I-K-I-Q-I-I-S-K-L-R-L ($X^2$ = Cha)

SEQ ID147: W-$X^2$-I-D-W-I-K-I-Q-I-I-S-K-L-R-L ($X^2$ = Cha)

SEQ ID148: W-$X^2$-I-E-W-I-K-I-N-I-I-S-K-L-R-L ($X^2$ = Cha)

SEQ ID149: W-$X^2$-I-E-W-I-K-I-P-I-I-S-K-L-R-L ($X^2$ = Cha)

SEQ ID150: W-$X^2$-I-E-W-I-K-I-Q-I-V-S-K-L-R-L ($X^2$ = Cha)

SEQ ID151: W-$X^2$-I-E-W-I-K-I-Q-I-L-S-K-L-R-L ($X^2$ = Cha)

SEQ ID152: W-$X^2$-I-E-W-I-K-I-Q-I-F-S-K-L-R-L ($X^2$ = Cha)

SEQ ID153: W-$X^2$-I-E-W-I-K-I-Q-I-W-S-K-L-R-L ($X^2$ = Cha)

SEQ ID154: W-$X^2$-I-E-W-I-K-I-Q-I-Y-S-K-L-R-L ($X^2$ = Cha)

SEQ ID155: W-$X^2$-I-E-W-I-K-I-Q-I-$X^{11}$-S-K-L-R-L ($X^2$ = Cha, $X^{11}$ = Nva)

SEQ ID156: W-$X^2$-I-E-W-I-K-I-Q-I-$X^{11}$-S-K-L-R-L ($X^2$ = Cha, $X^{11}$ = Chg)

SEQ ID157: W-$X^2$-I-E-W-I-K-I-Q-I-I-S-K-I-R-L ($X^2$ = Cha)

SEQ ID158: W-H-I-R-W-I-K-I-Q-I-I-S-K-L-R-L

SEQ ID159: W-H-I-K-W-I-K-I-Q-I-I-S-K-L-R-L

SEQ ID160: W-H-I-N-W-I-K-I-Q-I-I-S-K-L-R-L

SEQ ID161: W-H-I-Q-W-I-K-I-Q-I-I-S-K-L-R-L

SEQ ID162: W-H-I-D-W-I-K-I-Q-I-I-S-K-L-R-L

SEQ ID163: W-H-I-E-W-I-K-I-N-I-I-S-K-L-R-L

SEQ ID164: W-H-I-E-W-I-K-I-P-I-I-S-K-L-R-L

SEQ ID165: W-H-I-E-W-I-K-I-Q-I-V-S-K-L-R-L

SEQ ID166: W-H-I-E-W-I-K-I-Q-I-L-S-K-L-R-L

SEQ ID167: W-H-I-E-W-I-K-I-Q-I-F-S-K-L-R-L

SEQ ID168: W-H-I-E-W-I-K-I-Q-I-W-S-K-L-R-L

SEQ ID169: W-H-I-E-W-I-K-I-Q-I-Y-S-K-L-R-L

SEQ ID170: W-H-I-E-W-I-K-I-Q-I-$X^{11}$-S-K-L-R-L ($X^{11}$ = Nva)

SEQ ID171: W-H-I-E-W-I-K-I-Q-I-$X^{11}$-S-K-L-R-L ($X^{11}$ = Chg)

SEQ ID172: W-H-I-E-W-I-K-I-Q-I-I-S-K-I-R-L

SEQ ID173: W-R-I-R-W-I-K-I-Q-I-I-S-K-L-R-L

SEQ ID174: W-R-I-K-W-I-K-I-Q-I-I-S-K-L-R-L

SEQ ID175: W-R-I-N-W-I-K-I-Q-I-I-S-K-L-R-L

SEQ ID176: W-R-I-Q-W-I-K-I-Q-I-I-S-K-L-R-L

SEQ ID177: W-R-I-D-W-I-K-I-Q-I-I-S-K-L-R-L

SEQ ID178: W-R-I-E-W-I-K-I-N-I-I-S-K-L-R-L

SEQ ID179: W-R-I-E-W-I-K-I-P-I-I-S-K-L-R-L

SEQ ID180: W-R-I-E-W-I-K-I-Q-I-V-S-K-L-R-L

| | |
|---|---|
| SEQ ID181: | W-R-I-E-W-I-K-I-Q-I-L-S-K-L-R-L |
| SEQ ID182: | W-R-I-E-W-I-K-I-Q-I-F-S-K-L-R-L |
| SEQ ID183: | W-R-I-E-W-I-K-I-Q-I-W-S-K-L-R-L |
| SEQ ID184: | W-R-I-E-W-I-K-I-Q-I-Y-S-K-L-R-L |
| SEQ ID185: | W-R-I-E-W-I-K-I-Q-I-$X^{11}$-S-K-L-R-L ($X^{11}$ = Nva) |
| SEQ ID186: | W-R-I-E-W-I-K-I-Q-I-$X^{11}$-S-K-L-R-L ($X^{11}$ = Chg) |
| SEQ ID187: | W-R-I-E-W-I-K-I-Q-I-I-S-K-I-R-L |
| SEQ ID188: | W-S-I-E-$X^5$-I-K-I-Q-I-I-S-K-L-R-L ($X^5$ = Naa) |
| SEQ ID189: | W-W-I-E-$X^5$-I-K-I-Q-I-I-S-K-L-R-L ($X^5$ = Naa) |
| SEQ ID190: | W-R-I-E-$X^5$-I-K-I-Q-I-I-S-K-L-R-L ($X^5$ = Naa) |
| SEQ ID191: | W-K-I-E-$X^5$-I-K-I-Q-I-I-S-K-L-R-L ($X^5$ = Naa) |
| SEQ ID192: | W-H-I-E-$X^5$-I-K-I-Q-I-I-S-K-L-R-L ($X^5$ = Naa) |
| SEQ ID193: | W-$X^2$-I-E-$X^5$-I-K-I-Q-I-I-S-K-L-R-L ($X^2$ = Cha, $X^5$ = Naa) |
| SEQ ID194: | W-$X^2$-I-E-$X^5$-I-K-I-Q-I-I-S-K-L-R-L ($X^2$ = Naa, $X^5$ = Naa) |
| SEQ ID195: | W-Y-I-R-$X^5$-I-K-I-Q-I-I-S-K-L-R-L ($X^5$ = Naa) |
| SEQ ID196: | W-Y-I-K-$X^5$-I-K-I-Q-I-I-S-K-L-R-L ($X^5$ = Naa) |
| SEQ ID197: | W-Y-I-N-$X^5$-I-K-I-Q-I-I-S-K-L-R-L ($X^5$ = Naa) |
| SEQ ID198: | W-Y-I-Q-$X^5$-I-K-I-Q-I-I-S-K-L-R-L ($X^5$ = Naa) |
| SEQ ID199: | W-Y-I-D-$X^5$-I-K-I-Q-I-I-S-K-L-R-L ($X^5$ = Naa) |
| SEQ ID200: | W-Y-I-E-$X^5$-I-K-I-N-I-I-S-K-L-R-L ($X^5$ = Naa) |
| SEQ ID201: | W-Y-I-E-$X^5$-I-K-I-P-I-I-S-K-L-R-L ($X^5$ = Naa) |
| SEQ ID202: | W-Y-I-E-$X^5$-I-K-I-Q-I-V-S-K-L-R-L ($X^5$ = Naa) |
| SEQ ID203: | W-Y-I-E-$X^5$-I-K-I-Q-I-L-S-K-L-R-L ($X^5$ = Naa) |
| SEQ ID204: | W-Y-I-E-$X^5$-I-K-I-Q-I-F-S-K-L-R-L ($X^5$ = Naa) |
| SEQ ID205: | W-Y-I-E-$X^5$-I-K-I-Q-I-W-S-K-L-R-L ($X^5$ = Naa) |
| SEQ ID206: | W-Y-I-E-$X^5$-I-K-I-Q-I-Y-S-K-L-R-L ($X^5$ = Naa) |
| SEQ ID207: | W-Y-I-E-$X^5$-I-K-I-Q-I-$X^{11}$-S-K-L-R-L ($X^5$ = Naa, $X^{11}$ = Nva) |
| SEQ ID208: | W-Y-I-E-$X^5$-I-K-I-Q-I-$X^{11}$-S-K-L-R-L ($X^5$ = Naa, $X^{11}$ = Chg) |
| SEQ ID209: | W-Y-I-E-$X^5$-I-K-I-Q-I-I-S-K-I-R-L ($X^5$ = Naa) |
| SEQ ID210: | W-S-I-E-F-I-K-I-Q-I-I-S-K-I-R-L |
| SEQ ID211: | W-W-I-E-F-I-K-I-Q-I-I-S-K-I-R-L |
| SEQ ID212: | W-R-I-E-F-I-K-I-Q-I-I-S-K-I-R-L |
| SEQ ID213: | W-K-I-E-F-I-K-I-Q-I-I-S-K-I-R-L |
| SEQ ID214: | W-H-I-E-F-I-K-I-Q-I-I-S-K-I-R-L |
| SEQ ID215: | W-$X^2$-I-E-F-I-K-I-Q-I-I-S-K-I-R-L ($X^2$ = Cha) |
| SEQ ID216: | W-$X^2$-I-E-F-I-K-I-Q-I-I-S-K-I-R-L ($X^2$ = Naa) |
| SEQ ID217: | W-Y-I-R-F-I-K-I-Q-I-I-S-K-I-R-L |
| SEQ ID218: | W-Y-I-K-F-I-K-I-Q-I-I-S-K-I-R-L |
| SEQ ID219: | W-Y-I-N-F-I-K-I-Q-I-I-S-K-I-R-L |
| SEQ ID220: | W-Y-I-Q-F-I-K-I-Q-I-I-S-K-I-R-L |

```
SEQ ID221:   W-Y-I-D-F-I-K-I-Q-I-I-S-K-I-R-L

SEQ ID222:   W-Y-I-E-F-I-K-I-N-I-I-S-K-I-R-L

SEQ ID223:   W-Y-I-E-F-I-K-I-P-I-I-S-K-I-R-L

SEQ ID224:   W-Y-I-E-F-I-K-I-Q-I-V-S-K-I-R-L

SEQ ID225:   W-Y-I-E-F-I-K-I-Q-I-L-S-K-I-R-L

SEQ ID226:   W-Y-I-E-F-I-K-I-Q-I-F-S-K-I-R-L

SEQ ID227:   W-Y-I-E-F-I-K-I-Q-I-W-S-K-I-R-L

SEQ ID228:   W-Y-I-E-F-I-K-I-Q-I-Y-S-K-I-R-L

SEQ ID229:   W-Y-I-E-F-I-K-I-Q-I-$X^{11}$-S-K-I-R-L  ($X^{11}$ = Nva)

SEQ ID230:   W-Y-I-E-F-I-K-I-Q-I-$X^{11}$-S-K-I-R-L  ($X^{11}$ = Chg)

SEQ ID231:   W-Y-I-E-F-I-K-I-Q-I-I-S-K-L-R-L

SEQ ID232:   W-S-I-E-Y-I-K-I-Q-I-I-S-K-I-R-L

SEQ ID233:   W-W-I-E-Y-I-K-I-Q-I-I-S-K-I-R-L

SEQ ID234:   W-R-I-E-Y-I-K-I-Q-I-I-S-K-I-R-L

SEQ ID235:   W-K-I-E-Y-I-K-I-Q-I-I-S-K-I-R-L

SEQ ID236:   W-H-I-E-Y-I-K-I-Q-I-I-S-K-I-R-L

SEQ ID237:   W-$X^{2}$-I-E-Y-I-K-I-Q-I-I-S-K-I-R-L  ($X^{2}$ = Cha)

SEQ ID238:   W-$X^{2}$-I-E-Y-I-K-I-Q-I-I-S-K-I-R-L  ($X^{2}$ = Naa)

SEQ ID239:   W-Y-I-R-Y-I-K-I-Q-I-I-S-K-I-R-L

SEQ ID240:   W-Y-I-K-Y-I-K-I-Q-I-I-S-K-I-R-L

SEQ ID241:   W-Y-I-N-Y-I-K-I-Q-I-I-S-K-I-R-L

SEQ ID242:   W-Y-I-Q-Y-I-K-I-Q-I-I-S-K-I-R-L

SEQ ID243:   W-Y-I-D-Y-I-K-I-Q-I-I-S-K-I-R-L

SEQ ID244:   W-Y-I-E-Y-I-K-I-N-I-I-S-K-I-R-L

SEQ ID245:   W-Y-I-E-Y-I-K-I-P-I-I-S-K-I-R-L

SEQ ID246:   W-Y-I-E-Y-I-K-I-Q-I-V-S-K-I-R-L

SEQ ID247:   W-Y-I-E-Y-I-K-I-Q-I-L-S-K-I-R-L

SEQ ID248:   W-Y-I-E-Y-I-K-I-Q-I-F-S-K-I-R-L

SEQ ID249:   W-Y-I-E-Y-I-K-I-Q-I-W-S-K-I-R-L

SEQ ID250:   W-Y-I-E-Y-I-K-I-Q-I-Y-S-K-I-R-L

SEQ ID251:   W-Y-I-E-Y-I-K-I-Q-I-$X^{11}$-S-K-I-R-L  ($X^{11}$ = Nva)

SEQ ID252:   W-Y-I-E-Y-I-K-I-Q-I-$X^{11}$-S-K-I-R-L  ($X^{11}$ = Chg)

SEQ ID253:   W-Y-I-E-Y-I-K-I-Q-I-I-S-K-L-R-L

SEQ ID254:   W-S-I-E-H-I-K-I-Q-I-I-S-K-I-R-L

SEQ ID255:   W-W-I-E-H-I-K-I-Q-I-I-S-K-I-R-L

SEQ ID256:   W-R-I-E-H-I-K-I-Q-I-I-S-K-I-R-L

SEQ ID257:   W-K-I-E-H-I-K-I-Q-I-I-S-K-I-R-L

SEQ ID258:   W-H-I-E-H-I-K-I-Q-I-I-S-K-I-R-L

SEQ ID259:   W-$X^{2}$-I-E-H-I-K-I-Q-I-I-S-K-I-R-L  ($X^{2}$ = Cha)
```

-continued

| | |
|---|---|
| SEQ ID260: | W-$X^2$-I-E-H-I-K-I-Q-I-I-S-K-I-R-L ($X^2$ = Naa) |
| SEQ ID261: | W-Y-I-R-H-I-K-I-Q-I-I-S-K-I-R-L |
| SEQ ID262: | W-Y-I-K-H-I-K-I-Q-I-I-S-K-I-R-L |
| SEQ ID263: | W-Y-I-N-H-I-K-I-Q-I-I-S-K-I-R-L |
| SEQ ID264: | W-Y-I-Q-H-I-K-I-Q-I-I-S-K-I-R-L |
| SEQ ID265: | W-Y-I-D-H-I-K-I-Q-I-I-S-K-I-R-L |
| SEQ ID266: | W-Y-I-E-H-I-K-I-N-I-I-S-K-I-R-L |
| SEQ ID267: | W-Y-I-E-H-I-K-I-P-I-I-S-K-I-R-L |
| SEQ ID268: | W-Y-I-E-H-I-K-I-Q-I-V-S-K-I-R-L |
| SEQ ID269: | W-Y-I-E-H-I-K-I-Q-I-L-S-K-I-R-L |
| SEQ ID270: | W-Y-I-E-H-I-K-I-Q-I-F-S-K-I-R-L |
| SEQ ID271: | W-Y-I-E-H-I-K-I-Q-I-W-S-K-I-R-L |
| SEQ ID272: | W-Y-I-E-H-I-K-I-Q-I-Y-S-K-I-R-L |
| SEQ ID273: | W-Y-I-E-H-I-K-I-Q-I-$X^{11}$-S-K-I-R-L ($X^{11}$ = Nva) |
| SEQ ID274: | W-Y-I-E-H-I-K-I-Q-I-$X^{11}$-S-K-I-R-L ($X^{11}$ = Chg) |
| SEQ ID275: | W-Y-I-E-H-I-K-I-Q-I-I-S-K-L-R-L |
| SEQ ID276: | W-S-I-E-W-I-K-I-Q-I-$X^{11}$-S-K-L-R-L ($X^{11}$ = Nva) |
| SEQ ID277: | W-W-I-E-W-I-K-I-Q-I-$X^{11}$-S-K-L-R-L ($X^{11}$ = Nva) |
| SEQ ID278: | W-K-I-E-W-I-K-I-Q-I-$X^{11}$-S-K-L-R-L ($X^{11}$ = Nva) |
| SEQ ID279: | W-Y-I-R-W-I-K-I-Q-I-$X^{11}$-S-K-L-R-L ($X^{11}$ = Nva) |
| SEQ ID280: | W-Y-I-K-W-I-K-I-Q-I-$X^{11}$-S-K-L-R-L ($X^{11}$ = Nva) |
| SEQ ID281: | W-Y-I-N-W-I-K-I-Q-I-$X^{11}$-S-K-L-R-L ($X^{11}$ = Nva) |
| SEQ ID282: | W-Y-I-Q-W-I-K-I-Q-I-$X^{11}$-S-K-L-R-L ($X^{11}$ = Nva) |
| SEQ ID283: | W-Y-I-D-W-I-K-I-Q-I-$X^{11}$-S-K-L-R-L ($X^{11}$ = Nva) |
| SEQ ID284: | W-Y-I-E-W-I-K-I-N-I-$X^{11}$-S-K-L-R-L ($X^{11}$ = Nva) |
| SEQ ID285: | W-Y-I-E-W-I-K-I-P-I-$X^{11}$-S-K-L-R-L ($X^{11}$ = Nva) |
| SEQ ID286: | W-Y-I-E-W-I-K-I-Q-I-V-S-K-L-R-L |
| SEQ ID287: | W-Y-I-E-W-I-K-I-Q-I-L-S-K-L-R-L |
| SEQ ID288: | W-Y-I-E-W-I-K-I-Q-I-$X^{11}$-S-K-I-R-L ($X^{11}$ = Nva) |
| SEQ ID289: | W-S-I-E-W-I-K-I-Q-I-$X^{11}$-S-K-L-R-L ($X^{11}$ = Chg) |
| SEQ ID290: | W-W-I-E-W-I-K-I-Q-I-$X^{11}$-S-K-L-R-L ($X^{11}$ = Chg) |
| SEQ ID291: | W-K-I-E-W-I-K-I-Q-I-$X^{11}$-S-K-L-R-L ($X^{11}$ = Chg) |
| SEQ ID292: | W-Y-I-R-W-I-K-I-Q-I-$X^{11}$-S-K-L-R-L ($X^{11}$ = Chg) |
| SEQ ID293: | W-Y-I-K-W-I-K-I-Q-I-$X^{11}$-S-K-L-R-L ($X^{11}$ = Chg) |
| SEQ ID294: | W-Y-I-N-W-I-K-I-Q-I-$X^{11}$-S-K-L-R-L ($X^{11}$ = Chg) |
| SEQ ID295: | W-Y-I-Q-W-I-K-I-Q-I-$X^{11}$-S-K-L-R-L ($X^{11}$ = Chg) |
| SEQ ID296: | W-Y-I-D-W-I-K-I-Q-I-$X^{11}$-S-K-L-R-L ($X^{11}$ = Chg) |
| SEQ ID297: | W-Y-I-E-W-I-K-I-N-I-$X^{11}$-S-K-L-R-L ($X^{11}$ = Chg) |
| SEQ ID298: | W-Y-I-E-W-I-K-I-P-I-$X^{11}$-S-K-L-R-L ($X^{11}$ = Chg) |
| SEQ ID299: | W-Y-I-E-W-I-K-I-Q-I-$X^{11}$-S-K-I-R-L ($X^{11}$ = Chg) |

-continued

```
SEQ ID300:  W-S-I-E-W-I-K-I-Q-I-F-S-K-L-R-L

SEQ ID301:  W-W-I-E-W-I-K-I-Q-I-F-S-K-L-R-L

SEQ ID302:  W-K-I-E-W-I-K-I-Q-I-F-S-K-L-R-L

SEQ ID303:  W-Y-I-R-W-I-K-I-Q-I-F-S-K-L-R-L

SEQ ID304:  W-Y-I-K-W-I-K-I-Q-I-F-S-K-L-R-L

SEQ ID305:  W-Y-I-N-W-I-K-I-Q-I-F-S-K-L-R-L

SEQ ID306:  W-Y-I-Q-W-I-K-I-Q-I-F-S-K-L-R-L

SEQ ID307:  W-Y-I-D-W-I-K-I-Q-I-F-S-K-L-R-L

SEQ ID308:  W-Y-I-E-W-I-K-I-N-I-F-S-K-L-R-L

SEQ ID309:  W-Y-I-E-W-I-K-I-P-I-F-S-K-L-R-L

SEQ ID310:  W-Y-I-E-W-I-K-I-Q-I-F-S-K-I-R-L

SEQ ID311:  W-S-I-E-W-I-K-I-Q-I-W-S-K-L-R-L

SEQ ID312:  W-W-I-E-W-I-K-I-Q-I-W-S-K-L-R-L

SEQ ID313:  W-K-I-E-W-I-K-I-Q-I-W-S-K-L-R-L

SEQ ID314:  W-Y-I-D-W-I-K-I-Q-I-W-S-K-L-R-L

SEQ ID315:  W-Y-I-E-W-I-K-I-N-I-W-S-K-L-R-L

SEQ ID316:  W-Y-I-E-W-I-K-I-Q-I-W-S-K-I-R-L

SEQ ID317:  W-S-I-E-S-I-K-I-Q-I-W-S-K-L-R-L

SEQ ID318:  W-W-I-E-S-I-K-I-Q-I-W-S-K-L-R-L

SEQ ID319:  W-R-I-E-S-I-K-I-Q-I-W-S-K-L-R-L

SEQ ID320:  W-K-I-E-S-I-K-I-Q-I-W-S-K-L-R-L

SEQ ID321:  W-H-I-E-S-I-K-I-Q-I-W-S-K-L-R-L

SEQ ID322:  W-$X^2$-I-E-S-I-K-I-Q-I-W-S-K-L-R-L  ($X^2$ = Cha)

SEQ ID323:  W-$X^2$-I-E-S-I-K-I-Q-I-W-S-K-L-R-L  ($X^2$ = Naa)

SEQ ID324:  W-Y-I-R-S-I-K-I-Q-I-W-S-K-L-R-L

SEQ ID325:  W-Y-I-K-S-I-K-I-Q-I-W-S-K-L-R-L

SEQ ID326:  W-Y-I-N-S-I-K-I-Q-I-W-S-K-L-R-L

SEQ ID327:  W-Y-I-Q-S-I-K-I-Q-I-W-S-K-L-R-L

SEQ ID328:  W-Y-I-D-S-I-K-I-Q-I-W-S-K-L-R-L

SEQ ID329:  W-Y-I-E-S-I-K-I-N-I-W-S-K-L-R-L

SEQ ID330:  W-Y-I-E-S-I-K-I-P-I-W-S-K-L-R-L

SEQ ID331:  W-Y-I-E-S-I-K-I-Q-I-V-S-K-L-R-L

SEQ ID332:  W-Y-I-E-S-I-K-I-Q-I-L-S-K-L-R-L

SEQ ID333:  W-Y-I-E-S-I-K-I-Q-I-F-S-K-L-R-L

SEQ ID334:  W-Y-I-E-S-I-K-I-Q-I-Y-S-K-L-R-L

SEQ ID335:  W-Y-I-E-S-I-K-I-Q-I-$X^{11}$-S-K-L-R-L  ($X^{11}$ = Nva)

SEQ ID336:  W-Y-I-E-S-I-K-I-Q-I-$X^{11}$-S-K-L-R-L  ($X^{11}$ = Chg)

SEQ ID337:  W-Y-I-E-S-I-K-I-Q-I-W-S-K-I-R-L

SEQ ID338:  W-S-I-K-W-I-K-I-Q-I-W-S-K-L-R-L
```

| | |
|---|---|
| SEQ ID339: | W-W-I-K-W-I-K-I-Q-I-W-S-K-L-R-L |
| SEQ ID340: | W-R-I-K-W-I-K-I-Q-I-W-S-K-L-R-L |
| SEQ ID341: | W-K-I-K-W-I-K-I-Q-I-W-S-K-L-R-L |
| SEQ ID342: | W-H-I-K-W-I-K-I-Q-I-W-S-K-L-R-L |
| SEQ ID343: | W-$X^2$-I-K-W-I-K-I-Q-I-W-S-K-L-R-L ($X^2$ = Cha) |
| SEQ ID344: | W-$X^2$-I-K-W-I-K-I-Q-I-W-S-K-L-R-L ($X^2$ = Naa) |
| SEQ ID345: | W-Y-I-K-W-I-K-I-N-I-W-S-K-L-R-L |
| SEQ ID346: | W-Y-I-K-W-I-K-I-P-I-W-S-K-L-R-L |
| SEQ ID347: | W-Y-I-K-W-I-K-I-Q-I-V-S-K-L-R-L |
| SEQ ID348: | W-Y-I-K-W-I-K-I-Q-I-L-S-K-L-R-L |
| SEQ ID349: | W-Y-I-K-W-I-K-I-Q-I-I-S-K-L-R-L |
| SEQ ID350: | W-Y-I-K-W-I-K-I-Q-I-Y-S-K-L-R-L |
| SEQ ID351: | W-Y-I-K-W-I-K-I-Q-I-W-S-K-I-R-L |
| SEQ ID352: | W-S-I-R-W-I-K-I-Q-I-W-S-K-L-R-L |
| SEQ ID353: | W-W-I-R-W-I-K-I-Q-I-W-S-K-L-R-L |
| SEQ ID354: | W-R-I-R-W-I-K-I-Q-I-W-S-K-L-R-L |
| SEQ ID355: | W-K-I-R-W-I-K-I-Q-I-W-S-K-L-R-L |
| SEQ ID356: | W-H-I-R-W-I-K-I-Q-I-W-S-K-L-R-L |
| SEQ ID357: | W-$X^2$-I-R-W-I-K-I-Q-I-W-S-K-L-R-L ($X^2$ = Cha) |
| SEQ ID358: | W-$X^2$-I-R-W-I-K-I-Q-I-W-S-K-L-R-L ($X^2$ = Naa) |
| SEQ ID359: | W-Y-I-R-W-I-K-I-N-I-W-S-K-L-R-L |
| SEQ ID360: | W-Y-I-R-W-I-K-I-P-I-W-S-K-L-R-L |
| SEQ ID361: | W-Y-I-R-W-I-K-I-Q-I-V-S-K-L-R-L |
| SEQ ID362: | W-Y-I-R-W-I-K-I-Q-I-L-S-K-L-R-L |
| SEQ ID363: | W-Y-I-R-W-I-K-I-Q-I-I-S-K-L-R-L |
| SEQ ID364: | W-Y-I-R-W-I-K-I-Q-I-Y-S-K-L-R-L |
| SEQ ID365: | W-Y-I-R-W-I-K-I-Q-I-W-S-K-I-R-L |
| SEQ ID366: | W-S-I-Q-W-I-K-I-Q-I-W-S-K-L-R-L |
| SEQ ID367: | W-W-I-Q-W-I-K-I-Q-I-W-S-K-L-R-L |
| SEQ ID368: | W-R-I-Q-W-I-K-I-Q-I-W-S-K-L-R-L |
| SEQ ID369: | W-K-I-Q-W-I-K-I-Q-I-W-S-K-L-R-L |
| SEQ ID370: | W-H-I-Q-W-I-K-I-Q-I-W-S-K-L-R-L |
| SEQ ID371: | W-$X^2$-I-Q-W-I-K-I-Q-I-W-S-K-L-R-L ($X^2$ = Cha) |
| SEQ ID372: | W-$X^2$-I-Q-W-I-K-I-Q-I-W-S-K-L-R-L ($X^2$ = Naa) |
| SEQ ID373: | W-Y-I-Q-W-I-K-I-N-I-W-S-K-L-R-L |
| SEQ ID374: | W-Y-I-Q-W-I-K-I-P-I-W-S-K-L-R-L |
| SEQ ID375: | W-Y-I-Q-W-I-K-I-Q-I-V-S-K-L-R-L |
| SEQ ID376: | W-Y-I-Q-W-I-K-I-Q-I-L-S-K-L-R-L |
| SEQ ID377: | W-Y-I-Q-W-I-K-I-Q-I-I-S-K-L-R-L |
| SEQ ID378: | W-Y-I-Q-W-I-K-I-Q-I-Y-S-K-L-R-L |

-continued

| | |
|---|---|
| SEQ ID379: | W-Y-I-Q-W-I-K-I-Q-I-W-S-K-I-R-L |
| SEQ ID386: | Y-Y-I-E-W-I-K-I-Q-I-S-K-$X^{14}$-R-L ($X^{14}$ = Chg) |
| SEQ ID387: | Y-Y-F-E-W-I-K-I-Q-I-S-K-L-R-L |
| SEQ ID388: | Y-Y-I-E-W-I-K-$X^8$-Q-I-S-K-L-R-L ($X^8$ = Chg) |
| SEQ ID389: | $X^2$-Y-I-E-W-I-K-I-Q-I-S-K-$X^{14}$-R-L ($X^1$ = Naa, $X^{14}$ = Chg) |
| SEQ ID390: | $X^2$-Y-F-E-W-I-K-I-Q-I-S-K-L-R-L ($X^1$ = Naa) |
| SEQ ID391: | $X^2$-Y-I-E-W-I-K-$X^8$-Q-I-S-K-L-R-L ($X^1$ = Naa, $X^8$ = Chg) |
| SEQ ID392: | F-Y-I-E-W-I-K-I-Q-I-S-K-$X^{14}$-R-L ($X^{14}$ = Chg) |
| SEQ ID393: | F-Y-F-E-W-I-K-I-Q-I-S-K-L-R-L |
| SEQ ID394: | F-Y-I-E-W-I-K-$X^8$-Q-I-S-K-L-R-L ($X^8$ = Chg) |
| SEQ ID395: | L-Y-I-E-W-I-K-I-Q-I-S-K-$X^{14}$-R-L ($X^{14}$ = Chg) |
| SEQ ID396: | L-Y-F-E-W-I-K-I-Q-I-S-K-L-R-L |
| SEQ ID397: | L-Y-I-E-W-I-K-$X^8$-Q-I-S-K-L-R-L ($X^8$ = Chg) |
| SEQ ID398: | W-$X^2$-I-E-W-I-K-I-Q-I-S-K-$X^{14}$-R-L ($X^2$ = Naa, $X^{14}$ = Chg) |
| SEQ ID399: | W-$X^2$-F-E-W-I-K-I-Q-I-S-K-L-R-L ($X^2$ = Naa) |
| SEQ ID400: | W-$X^2$-I-E-W-I-K-$X^8$-QI-S-K-L-R-L ($X^2$ = Naa, $X^8$ = Chg) |
| SEQ ID401: | W-$X^2$-I-E-W-I-K-I-Q-I-S-K-$X^{14}$-R-L ($X^2$ = Cha, $X^{14}$ = Chg) |
| SEQ ID402: | W-$X^2$-F-E-W-I-K-I-Q-I-S-K-L-R-L ($X^2$ = Cha) |
| SEQ ID403: | W-$X^2$-I-E-W-I-K-$X^8$-Q-I-S-K-L-R-L ($X^2$ = Cha, $X^8$ = Chg) |
| SEQ ID404: | W-H-I-E-W-I-K-I-Q-I-S-K-$X^{14}$-R-L ($X^{14}$ = Chg) |
| SEQ ID405: | W-H-F-E-W-I-K-I-Q-I-S-K-L-R-L |
| SEQ ID406: | W-H-I-E-W-I-K-$X^8$-Q-I-S-K-L-R-L ($X^8$ = Chg) |
| SEQ ID407: | W-R-I-E-W-I-K-I-Q-I-S-K-$X^{14}$-R-L ($X^{14}$ = Chg) |
| SEQ ID408: | W-R-F-E-W-I-K-I-Q-I-S-K-L-R-L |
| SEQ ID409: | W-R-I-E-W-I-K-$X^8$-Q-I-S-K-L-R-L ($X^8$ = Chg) |
| SEQ ID410: | W-Y-I-E-$X^5$-I-K-I-Q-I-S-K-$X^{84}$-R-L ($X^5$ = Naa, $X^{14}$ = Chg) |
| SEQ ID411 : | W-Y-F-E-$X^5$-I-K-I-Q-I-S-K-L-R-L ($X^5$ = Naa) |
| SEQ ID412: | W-Y-I-E-$X^5$-I-K-$X^8$-Q-I-S-K-L-R-L ($X^5$ = Naa, $X^8$ = Chg) |
| SEQ ID413: | W-Y-I-E-F-I-K-I-Q-I-S-K-$X^{14}$-R-L ($X^{14}$ = Chg) |
| SEQ ID414: | W-Y-F-E-F-I-K-I-Q-I-S-K-I-R-L |
| SEQ ID415: | W-Y-I-E-F-I-K-$X^8$-Q-I-S-K-I-R-L ($X^8$ = Chg) |
| SEQ ID416: | W-Y-I-E-Y-I-K-I-Q-I-S-K-$X^{14}$-R-L ($X^{14}$ = Chg) |
| SEQ ID417: | W-Y-F-E-Y-I-K-I-Q-I-S-K-I-RL |
| SEQ ID418: | W-Y-I-E-Y-I-K-$X^8$-Q-I-S-K-I-R-L ($X^8$ = Chg) |
| SEQ ID419: | W-Y-I-E-H-I-K-I-Q-I-S-K-$X^{14}$-R-L ($X^{14}$ = Chg) |
| SEQ ID420: | W-Y-F-E-H-I-K-I-Q-I-S-K-I-R-L |
| SEQ ID421: | W-Y-I-E-H-I-K-$X^8$-Q-I-S-K-I-R-L ($X^8$ = Chg) |
| SEQ ID422: | W-Y-I-E-W-I-K-I-Q-I-$X^{11}$-S-K-$X^{14}$-R-L ($X^{11}$ = Nva, $X^{14}$ = Chg) |
| SEQ ID423: | W-Y-F-E-W-I-K-I-Q-I-$X^{11}$-S-K-L-R-L ($X^{11}$ = Nva) |

| | |
|---|---|
| SEQ ID424: | W-Y-I-E-W-I-K-$X^8$-Q-I-$X^{11}$-S-K-L-R-L ($X^8$ = Chg, $X^{11}$ = Nva) |
| SEQ ID425: | W-Y-I-E-W-I-K-I-Q-I-$X^{11}$-S-K-$X^{14}$-R-L ($X^{11}$ = Chg, $X^{14}$ = Chg) |
| SEQ ID426: | W-Y-F-E-W-I-K-I-Q-I-$X^{11}$-S-K-L-R-L ($X^{11}$ = Chg) |
| SEQ ID427: | W-Y-I-E-W-I-K-$X^8$-Q-I-$X^{11}$-S-K-L-R-L ($X^8$ = Chg, $X^{11}$ = Chg) |
| SEQ ID428: | W-Y-I-E-W-I-K-I-Q-I-F-S-K-$X^{14}$-R-L ($X^{14}$ = Chg) |
| SEQ ID429: | W-Y-F-E-W-I-K-I-Q-I-F-S-K-L-R-L |
| SEQ ID430: | W-Y-I-E-W-I-K-$X^8$-Q-I-F-S-K-L-R-L ($X^8$ = Chg) |
| SEQ ID431: | W-Y-I-E-S-I-K-I-Q-I-W-S-K-$X^{14}$-R-L ($X^{14}$ = Chg) |
| SEQ ID432: | W-Y-F-E-S-I-K-I-Q-I-W-S-K-L-R-L |
| SEQ ID433: | W-Y-I-E-S-I-K-$X^8$-Q-I-W-S-K-L-R-L ($X^8$ = Chg) |
| SEQ ID434: | W-S-I-R-W-I-K-$X^8$-Q-I-W-S-K-L-R-L ($X^8$ = Chg) |
| SEQ ID435: | W-W-I-R-W-I-K-$X^8$-Q-I-W-S-K-L-R-L ($X^8$ = Chg) |
| SEQ ID436: | W-R-I-R-W-I-K-$X^8$-Q-I-W-S-K-L-R-L ($X^8$ = Chg) |
| SEQ ID437: | W-K-I-R-W-I-K-$X^8$-Q-I-W-S-K-L-R-L ($X^8$ = Chg) |
| SEQ ID438: | W-H-I-R-W-I-K-$X^8$-Q-I-W-S-K-L-R-L ($X^8$ = Chg) |
| SEQ ID439: | W-$X^2$-I-R-W-I-K-$X^8$-Q-I-W-S-K-L-R-L ($X^2$ = Cha, $X^8$ = Chg) |
| SEQ ID440: | W-$X^2$-I-R-W-I-K-$X^8$-Q-I-W-S-K-L-R-L ($X^2$ = Naa, $X^8$ = Chg) |
| SEQ ID441: | W-Y-I-K-W-I-K-$X^8$-Q-I-W-S-K-L-R-L ($X^8$ = Chg) |
| SEQ ID442: | W-Y-I-N-W-I-K-$X^8$-Q-I-W-S-K-L-R-L ($X^8$ = Chg) |
| SEQ ID443: | W-Y-I-Q-W-I-K-$X^8$-Q-I-W-S-K-L-R-L ($X^8$ = Chg) |
| SEQ ID444: | W-Y-I-D-W-I-K-$X^8$-Q-I-W-S-K-L-R-L ($X^8$ = Chg) |
| SEQ ID445: | W-Y-I-E-W-I-K-$X^8$-Q-I-W-S-K-L-R-L ($X^8$ = Chg) |
| SEQ ID446: | W-Y-I-R-W-I-K-$X^8$-N-I-W-S-K-L-R-L ($X^8$ = Chg) |
| SEQ ID447: | W-Y-I-R-W-I-K-$X^8$-P-I-W-S-K-L-R-L ($X^8$ = Chg) |
| SEQ ID448: | W-Y-I-R-W-I-K-$X^8$-Q-I-V-S-K-L-R-L ($X^8$ = Chg) |
| SEQ ID449: | W-Y-I-R-W-I-K-$X^8$-Q-I-L-S-K-L-R-L ($X^8$ = Chg) |
| SEQ ID450: | W-Y-I-R-W-I-K-$X^8$-Q-I-I-S-K-L-R-L ($X^8$ = Chg) |
| SEQ ID451: | W-Y-I-R-W-I-K-$X^8$-Q-I-F-S-K-L-R-L ($X^8$ = Chg) |
| SEQ ID452: | W-Y-I-R-W-I-K-$X^8$-Q-I-Y-S-K-L-R-L ($X^8$ = Chg) |
| SEQ ID453: | W-Y-I-R-W-I-K-$X^8$-Q-I-$X^{11}$-S-K-L-R-L ($X^8$ = Chg, $X^{11}$ = Nva) |
| SEQ ID454: | W-Y-I-R-W-I-K-$X^8$-Q-I-$X^{11}$-S-K-L-R-L ($X^8$ = Chg, $X^{11}$ = Chg) |
| SEQ ID455: | W-S-I-R-W-I-K-I-Q-I-W-S-K-$X^{14}$-R-L ($X^{14}$ = Chg) |
| SEQ ID456: | W-W-I-R-W-I-K-I-Q-I-W-S-K-$X^{14}$-R-L ($X^{14}$ = Chg) |
| SEQ ID457: | W-R-I-R-W-I-K-I-Q-I-W-S-K-$X^{14}$-R-L ($X^{14}$ = Chg) |
| SEQ ID458: | W-K-I-R-W-I-K-I-Q-I-W-S-K-$X^{14}$-R-L ($X^{14}$ = Chg) |
| SEQ ID459: | W-H-I-R-W-I-K-I-Q-I-W-S-K-$X^{14}$-R-L ($X^{14}$ = Chg) |
| SEQ ID460: | W-$X^2$-I-R-W-I-K-I-Q-I-W-S-K-$X^{14}$-R-L ($X^2$ = Cha, $X^{14}$ = Chg) |
| SEQ ID461: | W-$X^2$-I-R-W-I-K-I-Q-I-W-S-K-$X^{14}$-R-L ($X^2$ = Naa, $X^{14}$ = Chg) |
| SEQ ID462: | W-Y-I-K-W-I-K-I-Q-I-W-S-K-$X^{14}$-R-L ($X^{14}$ = Chg) |
| SEQ ID463: | W-Y-I-N-W-I-K-I-Q-I-W-S-K-$X^{14}$-R-L ($X^{14}$ = Chg) |

SEQ ID464: W-Y-I-Q-W-I-K-I-Q-I-W-S-K-$X^{14}$-R-L ($X^{14}$ = Chg)

SEQ ID465: W-Y-I-D-W-I-K-I-Q-I-W-S-K-$X^{14}$-R-L ($X^{14}$ = Chg)

SEQ ID466: W-Y-I-E-W-I-K-I-Q-I-W-S-K-$X^{14}$-R-L ($X^{14}$ = Chg)

SEQ ID467: W-Y-I-R-W-I-K-I-N-I-W-S-K-$X^{14}$-R-L ($X^{14}$ = Chg)

SEQ ID468: W-Y-I-R-W-I-K-I-P-I-W-S-K-$X^{14}$-R-L ($X^{14}$ = Chg)

SEQ ID469: W-Y-I-R-W-I-K-I-Q-V-W-S-K-$X^{14}$-R-L ($X^{14}$ = Chg)

SEQ ID470: W-Y-I-R-W-I-K-I-Q-L-W-S-K-$X^{14}$-R-L ($X^{14}$ = Chg)

SEQ ID471: W-Y-I-R-W-I-K-I-Q-I-I-S-K-$X^{14}$-R-L ($X^{14}$ = Chg)

SEQ ID472: W-Y-I-R-W-I-K-I-Q-I-F-S-K-$X^{14}$-R-L ($X^{14}$ = Chg)

SEQ ID473: W-Y-I-R-W-I-K-I-Q-I-Y-S-K-$X^{14}$-R-L ($X^{14}$ = Chg)

SEQ ID474: W-Y-I-R-W-I-K-I-Q-I-$X^{11}$-S-K-$X^{14}$-R-L ($X^{11}$ = Nva, $X^{14}$ = Chg)

SEQ ID475: W-Y-I-R-W-I-K-I-Q-I-$X^{11}$-S-K-$X^{14}$-R-L ($X^{11}$ = Chg, $X^{14}$ = Chg)

SEQ ID476: W-S-I-R-W-I-K-$X^{8}$-Q-I-W-S-K-$X^{14}$-R-L ($X^{8}$ = Chg, $X^{14}$ = Chg)

SEQ ID477: W-W-I-R-W-I-K-$X^{8}$-Q-I-W-S-K-$X^{14}$-R-L ($X^{8}$ = Chg, $X^{14}$ = Chg)

SEQ ID478: W-R-I-R-W-I-K-$X^{8}$-Q-I-W-S-K-$X^{14}$-R-L ($X^{8}$ = Chg, $X^{14}$ = Chg)

SEQ ID479: W-K-I-R-W-I-K-$X^{8}$-Q-I-W-S-K-$X^{14}$-R-L ($X^{8}$ = Chg, $X^{14}$ = Chg)

SEQ ID480: W-H-I-R-W-I-K-$X^{8}$-Q-I-W-S-K-$X^{14}$-R-L ($X^{8}$ = Chg, $X^{14}$ = chg)

SEQ ID481: W-$X^{2}$-I-R-W-I-K-$X^{8}$-Q-I-W-S-K-$X^{14}$-R-L ($X^{2}$ = Cha, $X^{8}$ = Chg, $X^{14}$ = Chg)

SEQ ID482: W-$X^{2}$-I-R-W-I-K-$X^{8}$-Q-I-W-S-K-$X^{14}$-R-L ($X^{2}$ = Naa, $X^{8}$ = Chg, $X^{14}$ = Chg)

SEQ ID483: W-Y-I-K-W-I-K-$X^{8}$-Q-I-W-S-K-$X^{14}$-R-L ($X^{8}$ = Chg, $X^{14}$ = Chg)

SEQ ID484: W-Y-I-N-W-I-K-$X^{8}$-Q-I-W-S-K-$X^{14}$-R-L ($X^{8}$ = Chg, $X^{14}$ = Chg)

SEQ ID485: W-Y-I-Q-W-I-K-$X^{8}$-Q-I-W-S-K-$X^{14}$-R-L ($X^{8}$ = Chg, $X^{14}$ = Chg)

SEQ ID486: W-Y-I-D-W-I-K-$X^{8}$-Q-I-W-S-K-$X^{14}$-R-L ($X^{8}$ = Chg, $X^{14}$ = Chg)

SEQ ID487: W-Y-I-E-W-I-K-$X^{8}$-Q-I-W-S-K-$X^{14}$-R-L ($X^{8}$ = Chg, $X^{14}$ = Chg)

SEQ ID488: W-Y-I-R-W-I-K-$X^{8}$-N-I-W-S-K-$X^{14}$-R-L ($X^{8}$ = Chg, $X^{14}$ = Chg)

SEQ ID489: W-Y-I-R-W-I-K-$X^{8}$-P-I-W-S-K-$X^{14}$-R-L ($X^{8}$ = Chg, $X^{14}$ = Chg)

SEQ ID490: W-Y-I-R-W-I-K-$X^{8}$-Q-V-W-S-K-$X^{14}$-R-L ($X^{8}$ = Chg, $X^{14}$ = Chg)

SEQ ID491: W-Y-I-R-W-I-K-$X^{8}$-Q-L-W-S-K-$X^{14}$-R-L ($X^{8}$ = Chg, $X^{14}$ = Chg)

SEQ ID492: W-Y-I-R-W-I-K-$X^{8}$-Q-I-I-S-K-$X^{14}$-R-L ($X^{8}$ = Chg, $X^{14}$ = Chg)

SEQ ID493: W-Y-I-R-W-I-K-$X^{8}$-Q-I-F-S-K-$X^{14}$-R-L ($X^{8}$ = Chg, $X^{14}$ = Chg)

SEQ ID494: W-Y-I-R-W-I-K-$X^{8}$-Q-I-Y-S-K-$X^{14}$-R-L ($X^{8}$ = Chg, $X^{14}$ = Chg)

SEQ ID495: W-Y-I-R-W-I-K-$X^{8}$-Q-I-$X^{11}$-S-K-$X^{14}$-R-L ($X^{8}$ = Chg, $X^{11}$ = Nva, $X^{14}$ = Chg)

SEQ ID496: W-Y-I-R-W-I-K-$X^{8}$-Q-I-$X^{11}$-S-K-$X^{14}$-R-L ($X^{8}$ = Chg, $X^{11}$ = chg, $X^{14}$ = Chg)

SEQ ID497: W-Y-I-R-W-I-K-$X^{8}$-Q-I-W-S-K-I-R-L ($X^{8}$ = Chg)

SEQ ID498: W-Y-F-R-W-I-K-$X^{8}$-Q-I-W-S-K-$X^{14}$-R-L ($X^{8}$ = Chg, $X^{14}$ = Chg)

SEQ ID499: W-S-F-R-W-I-K-I-Q-I-W-S-K-L-R-L

SEQ ID500: W-W-F-R-W-I-K-I-Q-I-W-S-K-L-R-L

SEQ ID501: W-R-F-R-W-I-K-I-Q-I-W-S-K-L-R-L

SEQ ID502: W-K-F-R-W-I-K-I-Q-I-W-S-K-L-R-L

| | |
|---|---|
| SEQ ID503: | W-H-F-R-W-I-K-I-Q-I-W-S-K-L-R-L |
| SEQ ID504: | W-$X^2$-F-R-W-I-K-I-Q-I-W-S-K-L-R-L ($X^2$ = Cha) |
| SEQ ID505: | W-$X^2$-F-R-W-I-K-I-Q-I-W-S-K-L-R-L ($X^2$ = Naa) |
| SEQ ID506: | W-Y-F-K-W-I-K-I-Q-I-W-S-K-L-R-L |
| SEQ ID507: | W-Y-F-N-W-I-K-I-Q-I-W-S-K-L-R-L |
| SEQ ID508: | W-Y-F-Q-W-I-K-I-Q-I-W-S-K-L-R-L |
| SEQ ID509: | W-Y-F-D-W-I-K-I-Q-I-W-S-K-L-R-L |
| SEQ ID510: | W-Y-F-E-W-I-K-I-Q-I-W-S-K-L-R-L |
| SEQ ID511: | W-Y-F-R-W-I-K-I-N-I-W-S-K-L-R-L |
| SEQ ID512: | W-Y-F-R-W-I-K-I-P-I-W-S-K-L-R-L |
| SEQ ID513: | W-Y-F-R-W-I-K-I-Q-V-W-S-K-L-R-L |
| SEQ ID514: | W-Y-F-R-W-I-K-I-Q-L-W-S-K-L-R-L |
| SEQ ID515: | W-Y-F-R-W-I-K-I-Q-I-W-S-K-L-R-L |
| SEQ ID516: | W-Y-F-R-W-I-K-I-Q-F-W-S-K-L-R-L |
| SEQ ID517: | W-Y-F-R-W-I-K-I-Q-Y-W-S-K-L-R-L |
| SEQ ID518: | W-Y-F-R-W-I-K-I-Q-I-$X^{11}$-S-K-L-R-L ($X^{11}$ = Nva) |
| SEQ ID519: | W-Y-F-R-W-I-K-I-Q-I-$X^{11}$-S-K-L-R-L ($X^{11}$ = Chg) |
| SEQ ID520: | W-Y-F-R-W-I-K-I-Q-I-W-S-K-I-R-L |
| SEQ ID521: | W-Y-F-R-W-I-K-I-Q-I-W-S-K-$X^{14}$-R-L ($X^{14}$ = Chg) |
| SEQ ID522: | W-Y-F-R-W-I-K-$X^8$-Q-I-W-S-K-L-R-L ($X^8$ = Chg) |
| SEQ ID523: | W-S-I-R-W-I-K-I-Q-F-W-S-K-L-R-L |
| SEQ ID524: | W-W-I-R-W-I-K-I-Q-F-W-S-K-L-R-L |
| SEQ ID525: | W-R-I-R-W-I-K-I-Q-F-W-S-K-L-R-L |
| SEQ ID526: | W-K-I-R-W-I-K-I-Q-F-W-S-K-L-R-L |
| SEQ ID527: | W-H-I-R-W-I-K-I-Q-F-W-S-K-L-R-L |
| SEQ ID528: | W-$X^2$-I-R-W-I-K-I-Q-F-W-S-K-L-R-L ($X^2$ = Cha) |
| SEQ ID529: | W-$X^2$-I-R-W-I-K-I-Q-F-W-S-K-L-R-L ($X^2$ = Naa) |
| SEQ ID530: | W-Y-I-K-W-I-K-I-Q-F-W-S-K-L-R-L |
| SEQ ID531: | W-Y-I-N-W-I-K-I-Q-F-W-S-K-L-R-L |
| SEQ ID532: | W-Y-I-Q-W-I-K-I-Q-F-W-S-K-L-R-L |
| SEQ ID533: | W-Y-I-D-W-I-K-I-Q-F-W-S-K-L-R-L |
| SEQ ID534: | W-Y-I-E-W-I-K-I-Q-F-W-S-K-L-R-L |
| SEQ ID535: | W-Y-I-R-W-I-K-I-N-F-W-S-K-L-R-L |
| SEQ ID536: | W-Y-I-R-W-I-K-I-P-F-W-S-K-L-R-L |
| SEQ ID537: | W-Y-I-R-W-I-K-I-Q-F-V-S-K-L-R-L |
| SEQ ID538: | W-Y-I-R-W-I-K-I-Q-F-L-S-K-L-R-L |
| SEQ ID539: | W-Y-I-R-W-I-K-I-Q-F-I-S-K-L-R-L |
| SEQ ID540: | W-Y-I-R-W-I-K-I-Q-F-F-S-K-L-R-L |
| SEQ ID541: | W-Y-I-R-W-I-K-I-Q-F-Y-S-K-L-R-L |
| SEQ ID542: | W-Y-I-R-W-I-K-I-Q-F-$X^{11}$-S-K-L-R-L ($X^{11}$ = Nva) |

-continued

SEQ ID543:  W-Y-I-R-W-I-K-I-Q-F-$X^{11}$-S-K-L-R-L   ($X^{11}$ = Chg)

SEQ ID544:  W-Y-I-R-W-I-K-I-Q-F-W-S-K-I-R-L

SEQ ID545:  W-Y-I-R-W-I-K-I-Q-F-W-S-K-$X^{14}$-R-L   ($X^{14}$ = Chg)

SEQ ID546:  W-Y-F-R-W-I-K-I-Q-F-W-S-K-L-R-L

SEQ ID547:  W-Y-I-R-W-I-K-$X^2$-Q-F-W-S-K-L-R-L   ($X^2$ = Chg)

SEQ ID548:  Y-S-I-R-$X^5$-I-K-I-Q-I-W-S-K-L-R-L   ($X^5$ = Naa)

SEQ ID549:  Y-W-I-R-$X^5$-I-K-I-Q-I-W-S-K-L-R-L   ($X^5$ = Naa)

SEQ ID550:  Y-R-I-R-$X^5$-I-K-I-Q-I-W-S-K-L-R-L   ($X^5$ = Naa)

SEQ ID551:  Y-K-I-R-$X^5$-I-K-I-Q-I-W-S-K-L-R-L   ($X^5$ = Naa)

SEQ ID552:  Y-H-I-R-$X^5$-I-K-I-Q-I-W-S-K-L-R-L   ($X^5$ = Naa)

SEQ ID553:  Y-$X^2$-I-R-$X^5$-I-K-I-Q-I-W-S-K-L-R-L   ($X^2$ = Cha, $X^5$ = Naa)

SEQ ID554:  Y-$X^2$-I-R-$X^5$-I-K-I-Q-I-W-S-K-L-R-L   ($X^2$ = Naa, $X^5$ = Naa)

SEQ ID555:  Y-Y-I-K-$X^5$-I-K-I-Q-I-W-S-K-L-R-L   ($X^5$ = Naa )

SEQ ID556:  Y-Y-I-N-$X^5$-I-K-I-Q-I-W-S-K-L-R-L   ($X^5$ = Naa)

SEQ ID557:  Y-Y-I-Q-$X^5$-I-K-I-Q-I-W-S-K-L-R-L   ($X^5$ = Naa)

SEQ ID558:  Y-Y-I-D-$X^5$-I-K-I-Q-I-W-S-K-L-R-L   ($X^5$ = Naa)

SEQ ID559:  Y-Y-I-E-$X^5$-I-K-I-Q-I-W-S-K-L-R-L   ($X^5$ = Naa)

SEQ ID560:  Y-Y-I-R-$X^5$-I-K-I-N-I-W-S-K-L-R-L   ($X^5$ = Naa)

SEQ ID561:  Y-Y-I-R-$X^5$-I-K-I-P-I-W-S-K-L-R-L   ($X^5$ = Naa)

SEQ ID562:  Y-Y-I-R-$X^5$-I-K-I-Q-I-V-S-K-L-R-L   ($X^5$ = Naa)

SEQ ID563:  Y-Y-I-R-$X^5$-I-K-I-Q-I-L-S-K-L-R-L   ($X^5$ = Naa)

SEQ ID564:  Y-Y-I-R-$X^5$-I-K-I-Q-I-I-S-K-L-R-L   ($X^5$ = Naa)

SEQ ID565:  Y-Y-I-R-$X^5$-I-K-I-Q-I-F-S-K-L-R-L   ($X^5$ = Naa)

SEQ ID566:  Y-Y-I-R-$X^5$-I-K-I-Q-I-Y-S-K-L-R-L   ($X^5$ = Naa)

SEQ ID567:  Y-Y-I-R-$X^5$-I-K-I-Q-I-$X^{11}$-S-K-L-R-L   ($X^5$ = Naa, $X^{11}$ = Nva)

SEQ ID568:  Y-Y-I-R-$X^5$-I-K-I-Q-I-$X^{11}$-S-K-L-R-L   ($X^5$ = Naa, $X^{11}$ = Chg)

SEQ ID569:  Y-Y-I-R-$X^5$-I-K-I-Q-I-W-S-K-I-R-L   ($X^5$ = Naa)

SEQ ID570:  Y-Y-I-R-$X^5$-I-K-I-Q-I-W-S-K-$X^{14}$-R-L   ($X^5$ = Naa, $X^{14}$ = Chg)

SEQ ID571:  Y-Y-F-R-$X^5$-I-K-I-Q-I-W-S-K-L-R-L   ($X^5$ = Naa)

SEQ ID572:  Y-Y-I-R-$X^5$-I-K-$X^8$-Q-I-W-S-K-L-R-L   ($X^5$ = Naa, $X^8$ = Chg)

SEQ ID573:  W-Y-I-R-W-I-K-$X^8$-Q-I-W-S-R-$X^{14}$-R-L   ($X^8$ = Chg, $X^{14}$ = Chg)

SEQ ID574:  W-Y-I-R-W-I-R-$X^8$-Q-I-W-S-K-$X^{14}$-R-L   ($X^8$ = Chg, $X^{14}$ = Chg)

SEQ ID575:  W-Y-I-R-W-I-R-$X^8$-Q-I-W-S-R-$X^{14}$-R-L   ($X^8$ = Chg, $X^{14}$ = Chg)

SEQ ID576:  W-Y-I-R-W-I-R-$X^8$-Q-I-W-S-R-$X^{14}$-P-L   ($X^8$ = Chg, $X^{14}$ = Chg)

SEQ ID577:  W-Y-I-R-W-I-R-$X^8$-Q-I-W-P-R-$X^{14}$-R-L   ($X^8$ = Chg, $X^{14}$ = Chg)

SEQ ID578:  W-Y-I-R-W-I-R-$X^8$-P-I-W-S-R-$X^{14}$-R-L   ($X^8$ = Chg, $X^{14}$ = Chg)

SEQ ID579:  W-Y-I-R-W-I-P-$X^8$-Q-I-W-S-R-$X^{14}$-R-L   ($X^8$ = Chg, $X^{14}$ = Chg)

SEQ ID580:  W-Y-I-R-W-I-R-$X^8$-P-I-W-S-R-$X^{14}$-P-L   ($X^8$ = Chg, $X^{14}$ = Chg)

SEQ ID581:  $X^1$-Y-I-R-W-I-R-$X^8$-Q-I-W-S-R-$X^{14}$-P-L   ($X^1$ = deletion, $X^8$ = Chg, $X^{14}$ = Chg)

-continued

| | |
|---|---|
| SEQ ID583: | W-Y-I-R-W-I-X$^7$-X$^8$-Q-I-W-S-K-X$^{14}$-R-L  (X$^7$ = (α-Me)Lys, X$^8$ = Chg, X$^{14}$ = Chg) |
| SEQ ID584: | W-Y-I-R-W-I-K-X$^8$-Q-I-W-S-K-X$^{14}$-R-L  (X$^8$ = Chg, X$^{14}$ = Chg) |
| SEQ ID585: | W-Y-I-C-W-I-C-I-Q-I-W-S-K-L-R-L  (a disulfide bond may be formed between side-chain SH groups of C) |
| SEQ ID586: | W-Y-I-E-W-I-K-I-C-I-W-C-K-L-R-L  (a disulfide bond may be formed between side-chain SH groups of C) |
| SEQ ID587: | W-Y-I-E-W-I-K-I-Q-I-W-C-K-L-C-L  (a disulfide bond may be formed between side-chain SH groups of C) |
| SEQ ID588: | W-Y-I-R-w-I-R-X$^8$-Q-I-W-S-R-X$^{14}$-P-L  (X$^8$ = Chg, X$^{14}$ = Chg, w = D-Trp) |
| SEQ ID589: | W-Y-I-R-w-I-R-X$^8$-Q-I-W-s-R-X$^{14}$-P-L  (X$^8$ = Chg, X$^{14}$ = Chg, w = D-Trp, s = D-Ser) |
| SEQ ID590: | W-Y-I-R-w-I-K-X$^8$-Q-I-W-S-K-X$^{14}$-R-L  (X$^8$ = Chg, X$^{14}$ = Chg, w = D-Trp) |
| SEQ ID591: | W-Y-I-R-w-I-K-X$^8$-Q-I-W-s-K-X$^{14}$-R-L  (X$^8$ = Chg, X$^{14}$ = Chg, w = D-Trp, s = D-Ser) |
| SEQ ID592: | W-Y-I-R-w-I-X$^7$-X$^8$-Q-I-W-S-K-X$^{14}$-R-L  (X$^7$ = (α-Me)Lys, X$^8$ = Chg, X$^{14}$ = Chg, w = D-Trp) |
| SEQ ID593: | W-Y-I-c-W-I-C-I-Q-I-W-S-K-L-R-L  (c = D-Cys, a disulfide bond may be formed between side-chain SH groups of c and C) |
| SEQ ID594: | W-Y-I-E-W-I-K-I-c-I-W-C-K-L-R-L  (c = D-Cys, a disulfide bond may be formed between side-chain SH groups of c and C) |
| SEQ ID595: | W-Y-I-E-W-I-K-I-Q-I-W-c-K-L-C-L  (c = D-Cys, a disulfide bond may be formed between side-chain SH groups of c and C) |

From the viewpoint of the myostatin inhibitory activity, still more preferably, the peptide according to the second aspect of the present invention satisfies the following (a-2), (a-3), (a-4) or (b-24) and has the number of amino acid residues of 20 or less:

(a-2) the amino acid sequence satisfying the above (a) is represented by any one of SEQ ID NO: 29, SEQ ID NO: 33, SEQ ID NOs: 380 to 382, and SEQ ID NO: 385;

(a-3) the amino acid sequence satisfying the above (a) is represented by any one of SEQ ID NO: 29, SEQ ID NOs: 33 to 36, SEQ ID NO: 381, SEQ ID NO: 382, SEQ ID NO: 385, SEQ ID NOs: 573 to 579, SEQ ID NO: 581, and SEQ ID NOs: 588 to 590;

(a-4) the amino acid sequence of the peptide satisfying the above (a) is represented by any one of SEQ ID NOs: 573 to 579, SEQ ID NO: 581, and SEQ ID NOs: 588 to 590; or (b-24) the amino acid sequence satisfying the above (b) is represented by any one of SEQ ID NO: 138, SEQ ID NO: 153, SEQ ID NO: 168, SEQ ID NO: 183, SEQ ID NO: 286, SEQ ID NO: 287, SEQ ID NO: 311 to SEQ ID NO: 337, SEQ ID NO: 431 to SEQ ID NO: 498, SEQ ID NO: 521, SEQ ID NO: 522, and SEQ ID NO: 548 to SEQ ID NO: 572.

Incidentally, the amino acid sequence of SEQ ID NO: 138, SEQ ID NO: 153, SEQ ID NO: 168, SEQ ID NO: 183, SEQ ID NO: 286, SEQ ID NO: 287, SEQ ID NO: 311 to SEQ ID NO: 337, SEQ ID NO: 431 to SEQ ID NO: 498, SEQ ID NO: 521, SEQ ID NO: 522, and SEQ ID NO: 548 to SEQ ID NO: 572 described above is an amino acid sequence in which one amino acid residue of $X^2$ to $X^4$, $X^8$, $X^9$, $X^{11}$, and $X^{14}$ in the amino acid sequence represented by any one of SEQ ID NO: 29, SEQ ID NO: 33, SEQ ID NOs: 380 to 382, and SEQ ID NO: 385 is substituted.

<Method for Producing Peptide>

The peptide according to the present invention can be produced by conventionally known methods including a chemical synthesis method and a recombinant technique. For producing the peptide by chemical synthesis, the peptide can be produced by a method of usually using each amino acid in peptide chemistry, for example, a method described in "The Peptides" vol. 1 [written by Schroder and Luhke, Academic Press, New York, U.S.A. (1966)], "The basis and experiments in peptide syntheses" (written by IZUMIYA Nobuo et al., Maruzen, 1985), or the like, and the peptide can also be produced by any one of a liquid-phase method and a solid-phase method. Further, any method of a column method and a batch method can also be used.

The peptide according to the present invention may also be produced, for example, by a method as described in the following Current Protocols in Molecular Biology, Chapter 16 or a recombinant technique using animal cells, insect cells, microorganisms, or the like. The peptide is generated by cultured cells or microorganisms and then may be purified by a conventionally known method. The purification and isolation method of the peptide is known for an engineer in the field, and can be performed, for example, by a method described in Current Protocols in Molecular Biology, Chapter 16 (written by Ausubel et al., John Wiley and Sons, 2006), or the like.

Examples of a condensation method for forming a peptide bond may include an azide method, an acid halide method, an acid anhydride method, a carbodiimide method, a carbodiimide-additive method, an active ester method, a carbonylimidazole method, an oxidation-reduction method, an enzyme method, a method using Woodward reagent K, HATU reagent, or Bop reagent, and the like. Incidentally, regarding the condensation reaction in the solid-phase method, among the above-described methods, an acid anhydride method, a carbodiimide method, and an active ester method are exemplified as main methods.

Further, when the peptide chain is stretched by the solid-phase method, a C-terminal amino acid is bonded to a support such as a resin that is not soluble to an organic solvent to be used. As such a resin, a resin into which a functional group is introduced in order to bond amino acid to the resin, a resin in which a spacer is inserted between the resin and a functional group, or the like can also be used according to purpose. More specifically, for example, a halomethyl resin such as a chloromethyl resin, an oxymethyl resin, a 4-(oxymethyl)-phenylacetamidemethyl resin, a 4-(oxymethyl)-phenoxymethyl resin, a Rink amide resin, and the like can be exemplified. Incidentally, before performing those condensation reactions, a protection means such as a carboxyl group, an amino group, a hydroxyl group, or an amidino group that is not involved in the condensation reaction can be applied by a generally known means. Further, conversely, a carboxyl group or an amino group that is directly involved in the condensation reaction can also be activated.

As a protective group used for a protection means of a functional group that is not involved in the condensation reaction of each unit, protection can be performed by a protective group usually used in organic chemistry, for example, a protective group described in "Protective Groups in Organic Synthesis (written by Greene, John Wiley & Sons, Inc. (1981)) or the like. More specific examples of a protective group of a carboxyl group may include various generally known protective groups such as methyl ester, ethyl ester, benzyl ester, p-nitrobenzyl ester, t-butyl ester, and cyclohexyl ester. Examples of a protective group of an amino group may include a benzyloxycarbonyl group, a t-butoxycarbonyl group, an isobornyloxycarbonyl group, a 9-fluorenylmethoxycarbonyl group (Fmoc group), and the like.

Examples of activated forms of carboxyl groups include an acid anhydride corresponding to the carboxyl group; azide; and an active ester with pentafluorophenol, 2,4-dinitrophenol, cyanomethyl alcohol, p-nitrophenol, N-hydroxysuccinimide, N-hydroxy-5-norbornene-2,3-dicarboximide, N-hydroxyphthalimide, 1-hydroxybenzotriazole, or the like. Examples of activated forms of amino groups may include amide phosphate corresponding to the amino group, and the like.

The condensation reaction at the time of peptide synthesis is usually performed in a solvent. Examples of the solvent may include chloroform, dichloromethane, ethyl acetate, N,N-dimethylformamide, dimethylsulfoxide, pyridine, dioxane, tetrahydrofuran, N-methylpyrrolidone, water, and methanol, or a mixture thereof. Further, regarding the reaction temperature of the condensation reaction, the condensation reaction can be performed in a range of −30° C. to 50° C. similarly to the usual case.

Further, the types of elimination reaction of the protective group in the production process of the peptide of the present invention can be selected depending on the types of protective group to be used as long as the protective group can be eliminated without influence on a peptide bond. Examples thereof include an acid treatment with hydrogen chloride, hydrogen bromide, anhydrous hydrogen fluoride, methanesulfonic acid, trifluoromethanesulfonic acid, trifluoroacetic acid, a mixture thereof, or the like, an alkaline treatment with sodium hydroxide, potassium hydroxide, hydrazine, diethylamine, piperidine, or the like, a sodium treatment or reduction with palladium carbon in liquid ammonia, and a silylation treatment of trimethylsilyl triflate, trimethylsilyl bromide, or the like. Incidentally, in the protective group elimination reaction by the acid or silylation agent treatment described above, it is preferable to add a cationic scavenger such as anisole, phenol, cresol, thioanisole, or ethanedithiol from the viewpoint of efficiently performing the protective group elimination reaction.

Incidentally, a cutting method from the solid phase of the peptide of the present invention synthesized by the solid-phase method is also performed according to a generally known method. For example, the above-described treatment using an acid or a silylation agent, or the like can be exemplified as the cutting method. Generally Known separation and purification means can be used for the peptide of the present invention produced in this way after a series of reactions described above. For example, the peptide of the present invention can be obtained with a higher purity by extraction, distribution, reprecipitation, recrystallization, solid-phase extraction, column chromatography, or the like.

The obtained peptide can be analyzed by an amino acid automatic analyzer, capillary electrophoresis, reversed-phase high-performance liquid chromatography, mass spectrometry, or the like. Further, peptides may be sorted using an interaction with a myostatin as an index by utilizing various biomolecule interaction analytical methods such as a phage display method, a two-hybrid method, an affinity chromatography, a surface plasmon resonance method, a co-immunoprecipitation method, a protein chip method, conformational analysis, a far-Western blotting method, and a fluorescence quenching method.

The peptide according to the present invention may be isolated or purified. The expression "isolated or purified" means that an operation to remove components other than the target component has been applied. The purity of the isolated or purified peptide according to the present invention is usually 50% or more (for example, 70% or more, 80% or more, 90% or more, 95% or more, 98% or more, 99% or more, or 100%).

<Myostatin Inhibitory Agent, Preventive Agent/Therapeutic Agent, and Preventive Method/Therapeutic Method>

In an embodiment of the present invention, a myostatin inhibitory agent containing the peptide according to the present invention or a prodrug thereof is provided (hereinafter, the "myostatin inhibitory agent containing the peptide according to the present invention or a prodrug thereof" is also simply referred to as the "myostatin inhibitory agent"). When an effective dose of the myostatin inhibitory agent is administered to a subject, effects of maintaining, increasing, enhancing, decreasing, and the like of muscle mass or muscular power can be achieved. The myostatin inhibitory agent may be configured by one or more kinds of the peptide according to the present invention or one or more kinds of prodrug thereof, or a mixture thereof, but in general, the myostatin inhibitory agent is a pharmaceutical composition which contains one or more kinds selected from the peptide according to the present invention and a prodrug thereof, and a pharmaceutically acceptable carrier.

An embodiment of the present invention relates to a method for inhibition of a myostatin, the method including administering an effective dose of the peptide according to the present invention or a prodrug thereof to a patient. Further, an embodiment of the present invention relates to the peptide according to the present invention or a prodrug thereof which is used for inhibition of a myostatin.

In an embodiment of the present invention, a preventive and/or therapeutic agent of amyotrophic disorder, the agent containing the peptide according to the present invention or a prodrug thereof is provided (hereinafter, the "preventive and/or therapeutic agent of amyotrophic disorder, the agent containing the peptide according to the present invention or a prodrug thereof" is also simply referred to as the "preventive/therapeutic agent of amyotrophic disorder"). When an effective dose of the preventive/therapeutic agent of amyotrophic disorder is administered to a patient, therapeutic effects such as decreasing a progression rate of amyotrophic disorder, inhibiting progression, stopping progression, improving, curing, and/or preventing amyotrophic disorder can be achieved. The preventive/therapeutic agent of amyotrophic disorder may be configured by one or more kinds of the peptide according to the present invention or one or more kinds of prodrug thereof, or a mixture thereof, but in general, the preventive/therapeutic agent of amyotrophic disorder is a pharmaceutical composition which contains one or more kinds selected from the peptide according to the present invention and a prodrug thereof, and a pharmaceutically acceptable carrier.

An embodiment of the present invention relates to a method for prevention and/or treatment of amyotrophic disorder, the method including administering an effective dose of the peptide according to the present invention or a prodrug thereof to a patient. Further, an embodiment of the present invention relates to the peptide according to the present invention or a prodrug thereof which is used for prevention and/or treatment of amyotrophic disorder.

The myostatin inhibitory agent, the preventive/therapeutic agent of amyotrophic disorder, and the method for prevention and/or treatment are, generally, also effective for enhancing anterior tibial muscles by local administration for an elderly person having a difficulty for walking. Only by enhancing anterior tibial muscles, ankle dorsiflexion is facilitated, which leads to fall prevention. Further, for example, if continuous local administration can be executed at the time of staying in space, it can contribute to rehabilitation period shortening after repatriation, or the like.

The above-described amyotrophic disorder is not particularly limited, but examples thereof may include myopathy such as muscular dystrophy, distal myopathy, congenital myopathy, inflammatory myopathy such as inclusion body myositis, or mitochondrial myopathy; disuse muscle atrophy; sarcopenia, and the like. More suitably, the preventive/therapeutic agent of amyotrophic disorder is effectively used for muscular dystrophy such as Duchenne muscular dystrophy, Becker muscular dystrophy, Fukuyama congenital muscular dystrophy, merosin-deficient congenital muscular dystrophy, limb girdle muscular dystrophy, facioscapulohumeral muscular dystrophy, Emery-Dreifuss muscular dystrophy, Miyoshi muscular dystrophy, and infantile neuroaxonal muscular dystrophy, and of them, the preventive/therapeutic agent of amyotrophic disorder is particularly effective for Duchenne muscular dystrophy.

The amyotrophic disorder may be also caused from chronic diseases such as amyotrophic lateral sclerosis, chronic obstructive pulmonary disease (COPD), cancer, AIDS, renal failure, and articular rheumatism. Therefore, the preventive/therapeutic agent of amyotrophic disorder and the method for prevention and/or treatment of the present invention can be used for improvement in cachexia with atrophy of muscles. Moreover, when the muscle mass is increases by inhibition of myostatin, bone strength is improved, and osteoporosis and other altered bone disorders can also be reduced.

In the present specification, the "effective dose" in the treatment is an amount that is commensurate with a reasonable profit/risk ratio and is effective for causing any desired treatment effects.

In the present specification, examples of the "subject" and the "patient" include humans and non-human animals including fishes, but preferably, the "subject" and the "patient" are selected from mammals such as humans, dogs, cats, mice, rats, hamsters, guinea pigs, horses (including racehorses), cattle, pigs, rabbits, and sheep, and domestic poultry such as chickens, quails, and turkeys, and are more preferably humans.

The pharmaceutically acceptable carrier is not particularly limited, but examples thereof include diluting agents such as lactose, sucrose, mannitol, starch, corn starch, crystalline cellulose, and light anhydrous silicate; lubricating agents such as silica, talc, calcium stearate, and magnesium stearate; binding agents such as hydroxypropyl cellulose, hydroxypropylmethyl cellulose, carboxymethyl cellulose, sodium carboxymethyl cellulose, methyl cellulose, polyvinyl pyrrolidone, crystalline cellulose, dextrin, and gelatin; antioxidizing agents such as ascorbic acid, sodium sulfite, sodium hydrogen sulfite, and tocopherol; chelating agents such as ethylenediaminetetraacetic acid (EDTA); buffers such as a borate salt, bicarbonate, Tris-HCl, a citric salt, a phosphoric salt, and other organic acids; solvents such as water for injection, saline, ethanol, propanol, ethylene glycol, propylene glycol, macrogol, olive oil, and corn oil; surfactants or moistening agents such as Pluronic (registered trademark), polyethylene glycol, sorbitan fatty acid ester, polysorbate, Triton (registered trademark), lecithin, cholesterol, benzalkonium chloride, benzethonium chloride, and glycerine monostearate; isotonizing agents such as sodium chloride, potassium chloride, glycerine, dextrose, sorbitol, and mannitol; preserving agents such as benzoic acid, salicylic acid, thimerosal, phenethyl alcohol, methylparaben, propylparaben, and chlorhexidine; complexing agents; amino acids; antifungus agents; colorants; flavoring agents and diluents; emulsifying agents; salt formation counter ions such as sodium; delivery vehicles; and diluents; and the like (Remington's Pharmaceutical Sciences, 18th Edition, editorial supervisor: A. R. Gennaro, Mack Publishing Company, 1990).

The content of the peptide or a prodrug thereof according to the present invention in the medical agent may be 0.01 to 100% by weight with respect to the whole medical agent.

Although the dose of the compound of the present invention differs depending on age, symptom, an administration method, or the like, in the case of oral administration, generally, the dose to a human (weight: 60 kg) per day is about 0.1 to 100 mg, preferably about 1.0 to 50 mg, and more preferably about 1.0 to 20 mg. In the case of parenteral administration, although the dose of the compound once differs depending on age, symptom, an administration method, or the like, for example, in the form of an injection, usually, it is suitable that the dose administered to a human (weight: 60 kg) per day is about 0.01 to 30 mg, preferably about 0.1 to 20 mg, and more preferably about 0.1 to 10 mg. Also in the case of animals other than humans, an amount of the compound converted per a weight of 60 kg can be administered.

EMBODIMENTS

Hereinbelow, an embodiment of the present invention is examplified.

[1] A peptide or a pharmaceutically acceptable salt thereof, or a prodrug thereof, the peptide comprising an amino acid sequence represented by a following Formula (1) and having a number of amino acid residues of 20 or less:

[Chem. 7]

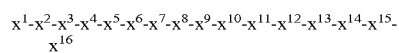

Formula (1)

in the above Formula (1),

X¹ represents an amino acid residue selected from the group consisting of Trp, Gly, Ala, Val, Leu, Ile, Pro, Phe, His, Tyr, norleucine, norvaline, isovaline, 2-aminobutyric acid, 2-aminoisobutyric acid, 3,4-didehydroproline, homophenylalanine, and homomethionine, which may have a substituent selected from the group consisting of an alicyclic group, an aromatic hydrocarbon group, an aralkyl group, and a heterocyclic group in a side chain, or deletion;

X² represents an amino acid residue selected from the group consisting of Tyr, Ser, Thr, Trp, Phe, Ala, Leu, Ile, Val, Arg, Lys, His, 2-hydroxyglycine, homoserine, homophenylalanine, norleucine, norvaline, isovaline, 2-aminobutyric acid, and 2-aminoisobutyric acid, which may have a substituent selected from the group consisting of an alicyclic group, an aromatic hydrocarbon group, an aralkyl group, and a heterocyclic group in a side chain, or deletion;

X³, X⁶, X⁸, X¹⁰, X¹⁴, and X¹⁶ each independently represent an amino acid residue selected from the group consisting of Gly, Ala, Phe, Val, Leu, Ile, Met, norleucine, norvaline, isovaline, 2-aminobutyric acid, 2-aminoisobutyric acid, homophenylalanine, and homomethionine, which may have a substituent selected from the group consisting of an alicyclic group, an aromatic hydrocarbon group, an aralkyl group, and a heterocyclic group in a side chain;

X⁴ represents a hydrophilic amino acid residue or Cys;

X⁵ represents an amino acid residue selected from the group consisting of Trp, Ser, Tyr, Val, Leu, Ile, Arg, His, Glu, Asp, Phe, 2-hydroxyglycine, homoserine, norleucine, norvaline, isovaline, 2-aminobutyric acid, homophenylalanine, and Ala which has a substituent selected from the group consisting of an alicyclic group, an aromatic hydrocarbon group, an aralkyl group, and a heterocyclic group;

X⁷ and X¹³ each independently represent an amino acid residue selected from the group consisting of Arg, Lys, Pro, Cys, His, (α-methyl)lysine, 2,3-diaminopropionic acid, 2,4-diaminobutanoic acid, and ornithine;

X⁹ represents an amino acid residue selected from the group consisting of Asn, Pro, Gln, Cys, and 3,4-didehydroproline;

X¹¹ represents an arbitrary amino acid residue which may have a substituent selected from the group consisting of an alicyclic group, an aromatic hydrocarbon group, an aralkyl group, and a heterocyclic group in a side chain;

X¹² represents an amino acid residue selected from the group consisting of Ser, Pro, Cys, Thr, Tyr, 2-hydroxyglycine, homoserine, and homocysteine; and X¹⁵ represents an arbitrary amino acid residue, which may have a substituent selected from the group consisting of an alicyclic group, an aromatic hydrocarbon group, an aralkyl group, and a heterocyclic group in a side chain, or deletion.

[2] The peptide or the pharmaceutically acceptable salt of the peptide, or the prodrug thereof according to [1], wherein X¹ represents an amino acid residue selected from the group consisting of Trp, Val, Leu, Ile, Phe, His, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, norleucine, norvaline, isovaline, 2-aminobutyric acid, and homophenylalanine, or deletion.

[3] The peptide or the pharmaceutically acceptable salt of the peptide, or the prodrug thereof according to [1] or [2], wherein X³, X⁶, X⁸, X¹⁰, X¹⁴, and X¹⁶ each independently represent an amino acid residue selected from the group consisting of Ala, Val, Leu, Ile, Phe, 2-cyclohexylglycine, norleucine, norvaline, isovaline, 2-aminobutyric acid, and 2-aminoisobutyric acid.

[4] The peptide or the pharmaceutically acceptable salt of the peptide, or the prodrug thereof according to any one of [1] to [3], wherein X¹¹ represents an amino acid residue selected from the group consisting of Ala, Val, Leu, Ile, Phe, Trp, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, homophenylalanine, 2-aminobutyric acid, 2-aminoisobutyric acid, norleucine, norvaline, and isovaline.

[5] The peptide or the pharmaceutically acceptable salt of the peptide, or the prodrug thereof according to any one of [1] to [4], wherein X⁴ represents an amino acid residue selected from the group consisting of Arg, Lys, His, Asn, Gln, Asp, Glu, Cys, 2,3-diaminopropionic acid, 2,4-diaminobutanoic acid, and ornithine.

[6] The peptide or the pharmaceutically acceptable salt of the peptide, or the prodrug thereof according to any one of [1] to [5], wherein X¹⁵ represents an amino acid residue selected from the group consisting of Arg, Pro, Cys, Lys, His, 2,3-diaminopropionic acid, 2,4-diaminobutanoic acid, and ornithine.

[7] The peptide or the pharmaceutically acceptable salt of the peptide, or the prodrug thereof according to any one of [1] to [6], wherein X¹² represents an amino acid residue selected from the group consisting of Ser, Pro, Cys, Thr, 2-hydroxyglycine, and homoserine.

[8] The peptide or the pharmaceutically acceptable salt of the peptide, or the prodrug thereof according to any one of [1] to [7], wherein the peptide comprises an amino acid sequence selected from the group consisting of the following Formula (1-1) to Formula (1-27) as the amino acid sequence represented by Formula (1):

[Chem. 8]

$$W-Y-X^3-X^4-W-X^6-X^7-X^8-X^9-X^{10}-X^{11}-X^{12}-X^{13}-X^{14}-X^{15}-X^{16}$$ Formula (1-1)

$$Y-W-X^3-X^4-W-X^6-X^7-X^8-X^9-X^{10}-X^{11}-X^{12}-X^{13}-X^{14}-X^{15}-X^{16}$$ Formula (1-2)

$$Y-Y-X^3-X^4-W-X^6-X^7-X^8-X^9-X^{10}-X^{11}-X^{12}-X^{13}-X^{14}-X^{15}-X^{16}$$ Formula (1-3)

$$W-W-X^3-X^4-W-X^6-X^7-X^8-X^9-X^{10}-X^{11}-X^{12}-X^{13}-X^{14}-X^{15}-X^{16}$$ Formula (1-4)

$$X^1-Y-X^3-X^4-W-X^6-X^7-X^8-X^9-X^{10}-X^{11}-X^{12}-X^{13}-X^{14}-X^{15}-X^{16}$$ Formula (1-5)

(X¹: 3-naphthylalanine)

$$F-Y-X^3-X^4-W-X^6-X^7-X^8-X^9-X^{10}-X^{11}-X^{12}-X^{13}-X^{14}-X^{15}-X^{16}$$ Formula (1-6)

$$L-Y-X^3-X^4-W-X^6-X^7-X^8-X^9-X^{10}-X^{11}-X^{12}-X^{13}-X^{14}-X^{15}-X^{16} \quad \text{Formula (1-7)}$$

$$H-Y-X^3-X^4-W-X^6-X^7-X^8-X^9-X^{10}-X^{11}-X^{12}-X^{13}-X^{14}-X^{15}-X^{16} \quad \text{Formula (1-8)}$$

$$W-F-X^3-X^4-W-X^6-X^7-X^8-X^9-X^{10}-X^{11}-X^{12}-X^{13}-X^{14}-X^{15}-X^{16} \quad \text{Formula (1-9)}$$

$$W-X^2-X^3-X^4-W-X^6-X^7-X^8-X^9-X^{10}-X^{11}-X^{12}-X^{13}-X^{14}-X^{15}-X^{16} \quad \text{Formula (1-10)}$$

($X^2$: 3-naphthylalanine)

$$W-X^2-X^3-X^4-W-X^6-X^7-X^8-X^9-X^{10}-X^{11}-X^{12}-X^{13}-X^{14}-X^{15}-X^{16} \quad \text{Formula (1-11)}$$

($X^2$: 3-cyclohexylalanine)

$$W-L-X^3-X^4-W-X^6-X^7-X^8-X^9-X^{10}-X^{11}-X^{12}-X^{13}-X^{14}-X^{15}-X^{16} \quad \text{Formula (1-12)}$$

$$W-H-X^3-X^4-W-X^6-X^7-X^8-X^9-X^{10}-X^{11}-X^{12}-X^{13}-X^{14}-X^{15}-X^{16} \quad \text{Formula (1-13)}$$

$$W-R-X^3-X^4-W-X^6-X^7-X^8-X^9-X^{10}-X^{11}-X^{12}-X^{13}-X^{14}-X^{15}-X^{16} \quad \text{Formula (1-14)}$$

$$W-S-X^3-X^4-W-X^6-X^7-X^8-X^9-X^{10}-X^{11}-X^{12}-X^{13}-X^{14}-X^{15}-X^{16} \quad \text{Formula (1-15)}$$

$$W-Y-X^3-X^4-X^5-X^6-X^7-X^8-X^9-X^{10}-X^{11}-X^{12}-X^{13}-X^{14}-X^{15}-X^{16} \quad \text{Formula (1-16)}$$

($X^5$: 3-naphthylalanine)

$$W-Y-X^3-X^4-L-X^6-X^7-X^8-X^9-X^{10}-X^{11}-X^{12}-X^{13}-X^{14}-X^{15}-X^{16} \quad \text{Formula (1-16)}$$

$$W-Y-X^3-X^4-S-X^6-X^7-X^8-X^9-X^{10}-X^{11}-X^{12}-X^{13}-X^{14}-X^{15}-X^{16} \quad \text{Formula (1-17)}$$

$$W-Y-X^3-X^4-R-X^6-X^7-X^8-X^9-X^{10}-X^{11}-X^{12}-X^{13}-X^{14}-X^{15}-X^{16} \quad \text{Formula (1-18)}$$

$$W-Y-X^3-X^4-E-X^6-X^7-X^8-X^9-X^{10}-X^{11}-X^{12}-X^{13}-X^{14}-X^{15}-X^{16} \quad \text{Formula (1-19)}$$

$$W-Y-X^3-X^4-F-X^6-X^7-X^8-X^9-X^{10}-X^{11}-X^{12}-X^{13}-X^{14}-X^{15}-X^{16} \quad \text{Formula (1-20)}$$

$$W-Y-X^3-X^4-Y-X^6-X^7-X^8-X^9-X^{10}-X^{11}-X^{12}-X^{13}-X^{14}-X^{15}-X^{16} \quad \text{Formula (1-21)}$$

$$W-Y-X^3-X^4-H-X^6-X^7-X^8-X^9-X^{10}-X^{11}-X^{12}-X^{13}-X^{14}-X^{15}-X^{16} \quad \text{Formula (1-22)}$$

$$Y-Y-X^3-X^4-S-X^6-X^7-X^8-X^9-X^{10}-X^{11}-X^{12}-X^{13}-X^{14}-X^{15}-X^{16} \quad \text{Formula (1-23)}$$

$$W-R-X^3-X^4-S-X^6-X^7-X^8-X^9-X^{10}-X^{11}-X^{12}-X^{13}-X^{14}-X^{15}-X^{16} \quad \text{Formula (1-24)}$$

$$Y-Y-X^3-X^4-X^5-X^6-X^7-X^8-X^9-X^{10}-X^{11}-X^{12}-X^{13}-X^{14}-X^{15}-X^{16} \quad \text{Formula (1-25)}$$

($X^5$: 3-naphthylalanine)

$$X^1-Y-X^3-X^4-W-X^6-X^7-X^8-X^9-X^{10}-X^{11}-X^{12}-X^{13}-X^{14}-X^{15}-X^{16} \quad \text{Formula (1-26)}$$

($X^1$: deletion)

$$Y-X^2-X^3-X^4-W-X^6-X^7-X^8-X^9-X^{10}-X^{11}-X^{12}-X^{13}-X^{14}-X^{15}-X^{16} \quad \text{Formula (1-27)}$$

($X^2$: deletion)

[9] The peptide or the pharmaceutically acceptable salt of the peptide, or the prodrug thereof according to any one of [1] to [8], wherein $X^5$ represents an amino acid residue selected from the group consisting of Trp, Ser, Tyr, Val, Leu, Ile, Phe, 2-hydroxyglycine, homoserine, norleucine, norvaline, isovaline, 3-cyclopentylalanine, 3-cyclohexylalanine, and 3-naphthylalanine;

provided that, in a case where $X^5$ represents Ser, 2-hydroxyglycine, or homoserine, $X^2$ represents an amino acid residue selected from the group consisting of Tyr, Ser, Thr, Trp, Phe, Leu, Ile, Val, 2-hydroxyglycine, homoserine, homophenylalanine, norleucine, norvaline, isovaline, 3-cyclopentylalanine, 3-cyclohexylalanine, and 3-naphthylalanine.

[10] The peptide or the pharmaceutically acceptable salt of the peptide, or the prodrug thereof according to any one of [1] to [9], wherein $X^2$ represents an amino acid residue selected from the group consisting of Tyr, Ser, Trp, Phe, Arg, Lys, His, 2-hydroxyglycine, homoserine, homophenylalanine, 3-cyclohexylalanine, and 3-naphthylalanine, or deletion.

[11] The peptide or the pharmaceutically acceptable salt of the peptide, or the prodrug thereof according to any one of [1] to [10], wherein $X^{11}$ represents an amino acid residue selected from the group consisting of Val, Leu, Ile, Phe, Trp, Tyr, 2-cyclopentylglycine, 2-cyclohexylglycine, 2-phenylglycine, 3-cyclopentylalanine, 3-cyclohexylalanine, 3-furanylalanine, 3-thienylalanine, methoxyphenylalanine, 3-naphthylalanine, homophenylalanine, norleucine, norvaline, and isovaline;

provided that, in a case where $X^1$ and $X^5$ represent Trp and $X^2$ represents Tyr, $X^{11}$ represents an amino acid residue selected from the group consisting of Phe, Trp, Tyr, 2-cyclohexylglycine, and norvaline.

[12] A peptide or a pharmaceutically acceptable salt of the peptide, or a prodrug thereof, the peptide satisfying the following (a) or (b) and having a number of amino acid residues of 20 or less:

(a) the peptide comprising any one of amino acid sequences represented by the following SEQ ID NOs: 2 to 9, SEQ ID NOs: 11 to 38, SEQ ID NOs: 380 to 385, SEQ ID NOs: 573 to 581, and SEQ ID NOs: 583 to 595; or (b) the peptide comprising one amino acid sequence in which one amino acid residue of $X^2$ to $X^4$ and $X^6$ to $X^{16}$ in the amino acid sequences of the above (a) is substituted or deleted and having a myostatin inhibitory activity.

TABLE 3-1

| | (Position) | | | | | | | | | | | | | | |
|---|---|---|---|---|---|---|---|---|---|---|---|---|---|---|---|
| | $X^1$ | $X^2$ | $X^3$ | $X^4$ | $X^5$ | $X^6$ | $X^7$ | $X^8$ | $X^9$ | $X^{10}$ | $X^{11}$ | $X^{12}$ | $X^{13}$ | $X^{14}$ | $X^{15}$ | $X^{16}$ |
| SEQ ID NO: 2 | W | Y | I | E | W | I | K | I | Q | I | I | S | K | L | R | L |
| SEQ ID NO: 3 | Y | W | I | E | W | I | K | I | Q | I | I | S | K | L | R | L |
| SEQ ID NO: 4 | Y | Y | I | E | W | I | K | I | Q | I | I | S | K | L | R | L |
| SEQ ID NO: 5 | W | W | I | E | W | I | K | I | Q | I | I | S | K | L | R | L |
| SEQ ID NO: 6 | Naa | Y | I | E | W | I | K | I | Q | I | I | S | K | L | R | L |
| SEQ ID NO: 7 | F | Y | I | E | W | I | K | I | Q | I | I | S | K | L | R | L |
| SEQ ID NO: 8 | L | Y | I | E | W | I | K | I | Q | I | I | S | K | L | R | L |
| SEQ ID NO: 9 | H | Y | I | E | W | I | K | I | Q | I | I | S | K | L | R | L |
| SEQ ID NO: 11 | W | F | I | E | W | I | K | I | Q | I | I | S | K | L | R | L |
| SEQ ID NO: 12 | W | Naa | I | E | W | I | K | I | Q | I | I | S | K | L | R | L |
| SEQ ID NO: 13 | W | Cha | I | E | W | I | K | I | Q | I | I | S | K | L | R | L |
| SEQ ID NO: 14 | W | L | I | E | W | I | K | I | Q | I | I | S | K | L | R | L |
| SEQ ID NO: 15 | W | H | I | E | W | I | K | I | Q | I | I | S | K | L | R | L |
| SEQ ID NO: 16 | W | R | I | E | W | I | K | I | Q | I | I | S | K | L | R | L |
| SEQ ID NO: 17 | W | S | I | E | W | I | K | I | Q | I | I | S | K | L | R | L |
| SEQ ID NO: 18 | W | Y | I | E | Naa | I | K | I | Q | I | I | S | K | L | R | L |
| SEQ ID NO: 19 | W | Y | I | E | L | I | K | I | Q | I | I | S | K | L | R | L |
| SEQ ID NO: 20 | W | Y | I | E | S | I | K | I | Q | I | I | S | K | L | R | L |
| SEQ ID NO: 21 | W | Y | I | E | R | I | K | I | Q | I | I | S | K | L | R | L |
| SEQ ID NO: 22 | W | Y | I | E | E | I | K | I | Q | I | I | S | K | L | R | L |
| SEQ ID NO: 23 | W | Y | I | E | F | I | K | I | Q | I | I | S | K | I | R | L |
| SEQ ID NO: 24 | W | Y | I | E | Y | I | K | I | Q | I | I | S | K | I | R | L |
| SEQ ID NO: 25 | W | Y | I | E | H | I | K | I | Q | I | I | S | K | I | R | L |
| SEQ ID NO: 26 | W | Y | I | E | W | I | K | I | Q | I | Nva | S | K | L | R | L |
| SEQ ID NO: 27 | W | Y | I | E | W | I | K | I | Q | I | Chg | S | K | L | R | L |
| SEQ ID NO: 28 | W | Y | I | E | W | I | K | I | Q | I | F | S | K | L | R | L |
| SEQ ID NO: 29 | W | Y | I | E | W | I | K | I | Q | I | W | S | K | L | R | L |
| SEQ ID NO: 30 | W | Y | I | E | W | I | K | I | Q | I | Y | S | K | L | R | L |

TABLE 3-2

| | (Position) | | | | | | | | | | | | | | |
|---|---|---|---|---|---|---|---|---|---|---|---|---|---|---|---|
| | $X^1$ | $X^2$ | $X^3$ | $X^4$ | $X^5$ | $X^6$ | $X^7$ | $X^8$ | $X^9$ | $X^{10}$ | $X^{11}$ | $X^{12}$ | $X^{13}$ | $X^{14}$ | $X^{15}$ | $X^{16}$ |
| SEQ ID NO: 31 | Y | Y | I | E | S | I | K | I | Q | I | I | S | K | L | R | L |
| SEQ ID NO: 32 | W | R | I | E | S | I | K | I | Q | I | I | S | K | L | R | L |
| SEQ ID NO: 33 | W | Y | I | E | S | I | K | I | Q | I | W | S | K | L | R | L |
| SEQ ID NO: 34 | W | Y | I | K | W | I | K | I | Q | I | W | S | K | L | R | L |
| SEQ ID NO: 35 | W | Y | I | R | W | I | K | I | Q | I | W | S | K | L | R | L |
| SEQ ID NO: 36 | W | Y | I | Q | W | I | K | I | Q | I | W | S | K | L | R | L |
| SEQ ID NO: 37 | W | Y | I | N | W | I | K | I | Q | I | W | S | K | L | R | L |
| SEQ ID NO: 38 | W | Y | I | E | W | I | K | I | P | I | W | S | K | L | R | L |
| SEQ ID NO: 380 | W | Y | I | R | W | I | K | Chg | Q | I | W | S | K | L | R | L |
| SEQ ID NO: 381 | W | Y | I | R | W | I | K | I | Q | I | W | S | K | Chg | R | L |
| SEQ ID NO: 382 | W | Y | I | R | W | I | K | Chg | Q | I | W | S | K | Chg | R | L |
| SEQ ID NO: 383 | W | Y | F | R | W | I | K | I | Q | I | W | S | K | L | R | L |
| SEQ ID NO: 384 | W | Y | I | R | W | I | K | I | Q | F | W | S | K | L | R | L |
| SEQ ID NO: 385 | Y | Y | I | R | Naa | I | K | I | Q | I | W | S | K | L | R | L |
| SEQ ID NO: 573 | W | Y | I | R | W | I | K | Chg | Q | I | W | S | R | Chg | R | L |
| SEQ ID NO: 574 | W | Y | I | R | W | I | R | Chg | Q | I | W | S | K | Chg | R | L |
| SEQ ID NO: 575 | W | Y | I | R | W | I | R | Chg | Q | I | W | S | R | Chg | R | L |
| SEQ ID NO: 576 | W | Y | I | R | W | I | R | Chg | Q | I | W | S | R | Chg | P | L |
| SEQ ID NO: 577 | W | Y | I | R | W | I | R | Chg | Q | I | W | P | R | Chg | R | L |
| SEQ ID NO: 578 | W | Y | I | R | W | I | R | Chg | P | I | W | S | R | Chg | R | L |
| SEQ ID NO: 579 | W | Y | I | R | W | I | P | Chg | Q | I | W | S | R | Chg | R | L |
| SEQ ID NO: 580 | W | Y | I | R | W | I | R | Chg | P | I | W | S | R | Chg | P | L |
| SEQ ID NO: 581 | Deletion | Y | I | R | W | I | R | Chg | Q | I | W | S | R | Chg | P | L |
| SEQ ID NO: 583 | W | Y | I | R | W | I | (□-Me)Lys | Chg | Q | I | W | S | K | Chg | R | L |
| SEQ ID NO: 584 | W | Y | I | R | W | I | K | Chg | Q | I | W | S | K | Chg | R | L |
| SEQ ID NO: 585 | W | Y | I | C | W | I | C | I | Q | I | W | S | L | R | L |  |
| SEQ ID NO: 586 | W | Y | I | E | W | I | K | I | C | I | W | C | K | L | R | L |
| SEQ ID NO: 587 | W | Y | I | E | W | I | K | I | Q | I | W | C | K | L | C | L |

TABLE 3-3

| | (Position) | | | | | | | | | | | | | | | |
|---|---|---|---|---|---|---|---|---|---|---|---|---|---|---|---|---|
| | $X^1$ | $X^2$ | $X^3$ | $X^4$ | $X^5$ | $X^6$ | $X^7$ | $X^8$ | $X^9$ | $X^{10}$ | $X^{11}$ | $X^{12}$ | $X^{13}$ | $X^{14}$ | $X^{15}$ | $X^{16}$ |
| SEQ ID NO: 588 | W | Y | I | R | w | I | R | Chg | Q | I | W | S | R | Chg | P | L |
| SEQ ID NO: 589 | W | Y | I | R | w | I | R | Chg | Q | I | W | s | R | Chg | P | L |
| SEQ ID NO: 590 | W | Y | I | R | w | I | K | Chg | Q | I | W | S | K | Chg | R | L |
| SEQ ID NO: 591 | W | Y | I | R | w | I | K | Chg | Q | I | W | s | K | Chg | R | L |
| SEQ ID NO: 592 | W | Y | I | R | w | I | (□-Me)Lys | Chg | Q | I | W | S | K | Chg | R | L |
| SEQ ID NO: 593 | W | Y | I | c | W | I | C | I | Q | I | W | S | K | L | R | L |
| SEQ ID NO: 594 | W | Y | I | E | W | I | K | I | c | I | W | C | K | L | R | L |
| SEQ ID NO: 595 | W | Y | I | E | W | I | K | I | Q | I | W | c | K | L | C | L |

Naa: 3-naphthylalanine
Cha: 3-cyclohexylalanine
Nva: norvaline
Chg: 2-cyclohexylglycine
(□-Me)Lys: (□-methyl)lysine
w and c represent D-Trp and D-Cys, respectively.
SEQ ID NOs: 585 to 587 and SEQ ID NOs: 593 to 595 may represent a cyclic peptide in which a disulfide bond is formed between side-chain SH groups of two Cys's.

[13] The peptide or the pharmaceutically acceptable salt of the peptide, or the prodrug thereof according to [12], wherein the peptide satisfies the following (a-1) or (b-1):

(a-1) the amino acid sequence of the peptide satisfying the above (a) being represented by any one of SEQ ID NO: 4, SEQ ID NOs: 6 to 8, SEQ ID NO: 12, SEQ ID NO: 13, SEQ ID NO: 15, SEQ ID NO: 16, SEQ ID NO: 18, SEQ ID NOs: 23 to 29, SEQ ID NOs: 33 to 36, SEQ ID NOs: 380 to 385, SEQ ID NOs: 573 to 581, SEQ ID NO: 583, SEQ ID NO: 584, and SEQ ID NOs: 586 to 594; or (b-1) the peptide comprising one amino acid sequence in which one amino acid residue of $X^2$ to $X^4$, $X^8$, $X^9$, $X^{11}$, and $X^{14}$ in the amino acid sequences of the above (a-1) is substituted or deleted and having a myostatin inhibitory activity.

[14] A myostatin inhibitory agent comprising the peptide or the pharmaceutically acceptable salt of the peptide, or the prodrug thereof according to any one of [1] to [13].

[15] A preventive and/or therapeutic agent of amyotrophic disorder, the agent comprising the peptide or the pharmaceutically acceptable salt of the peptide, or the prodrug thereof according to any one of [1] to [13].

[16] The preventive and/or therapeutic agent of amyotrophic disorder according to [15], wherein the amyotrophic disorder is muscular dystrophy.

[17] A method for prevention and/or treatment of amyotrophic disorder, the method comprising administering an effective dose of the peptide or the pharmaceutically acceptable salt of the peptide, or the prodrug thereof according to any one of [1] to [13] to a patient.

[18] The method for prevention and/or treatment of amyotrophic disorder according to [17], wherein the amyotrophic disorder is muscular dystrophy.

EXAMPLES

Hereinafter, the effect of the present invention will be described by means of the following Examples and Comparative Examples. Note that the technical scope of the present invention is not limited only to the following Examples.

Synthesis of Peptide

Synthesis Example 1

Peptide comprising an amino acid sequence of SEQ ID NO: 2: synthesis of PDM-27
$R^{111}$-WYIEWIKIQIISKLRL-NH$_2$ (PDM-27)
Note that $R^{111}$ represents a group represented by the following Formula (4).

[Chem. 9]

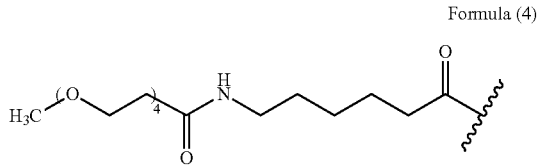

Formula (4)

PDM-27 was synthesized by the following Fmoc solid phase peptide synthesis method.

54 mg (0.020 mmol) of Rink Amide resin (0.37 mmol/g, WATANABE CHEMICAL INDUSTRIES, LTD.) was weighed in a reaction container for Prelude 6-channel peptide synthesizer (Protein Technologies, Inc.) and set to the synthesizer. The following reactions all were performed under a nitrogen atmosphere. A resin was swollen in a dimethylformamide (DMF) solution at room temperature (25° C.) for 30 minutes and reacted in a 20% (v/v) piperidine/DMF solution (2.5 mL) at room temperature (25° C.) for 5 minutes for two cycles to remove a protective group Fmoc (9-fluorenylmethoxycarbonyl) group on the resin. The resin was washed with DMF (2.5 mL) 6 times, and Fmoc-Leu-OH (0.20 mmol, 10 eq.) was reacted in DMF (2 mL) at room temperature (25° C.) for 30 minutes in the presence of 1-hydroxy-7-azabenzotriazole (HOAt, 0.20 mmol, 10 eq.), O-(7-aza-1H-benzotriazole-1-yl)-N,N,N',N'-tetramethyluronium hexafluorophosphate (HATU, 0.20 mmol, 10 eq.), and N,N-diisopropylethylamine (DIEA, 0.20 mmol, 10 eq.) to introduce amino acid onto the resin. Subsequently, in order to condense the amino acid, the Fmoc group on the resin was removed by performing the reaction in a 20% (v/v) piperidine/DMF solution (2.5 mL) for 5 minutes for two cycles. Thereafter, similarly to the case of Fmoc-Leu-OH, Fmoc-Arg(Pbf)-OH (0.20 mmol, 10 eq.), Fmoc-Leu-OH (0.20 mmol, 10 eq.), Fmoc-Lys(Boc)-OH (0.20 mmol, 10 eq.), Fmoc-Ser(tBu)-OH (0.20 mmol, 10 eq.), Fmoc-Ile-OH (0.20 mmol, 10 eq.), Fmoc-Ile-OH (0.20 mmol, 10 eq.), Fmoc-Gln(Trt)-OH (0.20 mmol, 10 eq.), Fmoc-Ile-OH (0.20 mmol, 10 eq.), Fmoc-Lys(Boc)-OH (0.20 mmol, 10 eq.), Fmoc-Ile-OH (0.20 mmol, 10 eq.), Fmoc-Trp(Boc)-OH (0.20 mmol, 10 eq.), Fmoc-Glu(OtBu)-OH (0.20 mmol, 10 eq.), Fmoc-Ile-OH (0.20 mmol, 10 eq.), Fmoc-Tyr(tBu)-OH (0.20 mmol, 10 eq.), Fmoc-Trp(Boc)-OH (0.20 mmol, 10 eq.), and Fmoc-Acp-OH (0.20 mmol, 10 eq.; Acp: aminocaproic acid) were sequentially introduced from the C-terminal side to stretch the peptide chain. The reaction was performed in a 20% (v/v) piperidine/DMF solution (2.5 mL) for 5 minutes for two cycles to remove the N-terminal Fmoc group, m-dPEG (4) Acid (NACALAI TESQUE, INC., 0.20 mmol, 10 eq.) was introduced by the similar condensation method to the Fmoc amino acid, washing was performed with DMF (2.5 mL, 6 times) and methanol (2.5 mL, 5 times), and the resin was dried by nitrogen purge. For the removal of various side chain protective groups and the cleavage from resin, the reaction was performed in 5.0 mL of trifluoroacetic acid (TFA) for 2 hours in the presence of m-cresol (0.125 mL), thioanisole (0.125 mL), and 1,2-ethanedithiol (0.050 mL). The resin was removed by filtration using a funnel equipped with a glass filter, TFA was vacuum-distilled by a rotary evaporator, and 40 mL of diethyl ether was added thereto to precipitate a crudely purified peptide. The crudely purified peptide was dissolved in 1 M acetic acid and purified using high-performance liquid chromatography to obtain a white solid (2.8 mg, yield: 5.1%).

HRMS (ES+) calcd for ($M^{3+}$+3H) 811.4947, found 811.4844.

Synthesis Example 2

Peptide comprising an amino acid sequence of SEQ ID NO: 3: synthesis of PDM-28

$R^{111}$-YWIEWIKIQIISKLRL-$NH_2$ (PDM-28)

Note that $R^{111}$ represents a group represented by the above Formula (4).

PDM-28 was synthesized and purified using 54 mg (0.020 mmol) of Rink Amide resin (0.37 mmol/g, WATANABE CHEMICAL INDUSTRIES, LTD.) by the similar method to Synthesis Example 1 (2.2 mg, yield: 4.0%).

HRMS (ES+) calcd for ($M^{3+}$+3H) 811.4947, found 811.4984.

Synthesis Example 3

Peptide comprising an amino acid sequence of SEQ ID NO: 4: synthesis of PDM-29

$R^{111}$-YYIEWIKIQIISKLRL-$NH_2$ (PDM-29)

Note that $R^{111}$ represents a group represented by the above Formula (4).

PDM-29 was synthesized and purified using 54 mg (0.020 mmol) of Rink Amide resin (0.37 mmol/g, WATANABE CHEMICAL INDUSTRIES, LTD.) by the similar method to Synthesis Example 1 (0.9 mg, yield: 1.6%).

HRMS (ES+) calcd for ($M^{3+}$+3H) 803.8227, found 803.8185.

Synthesis Example 4

Peptide comprising an amino acid sequence of SEQ ID NO: 5: synthesis of PDM-30

$R^{111}$-WWIEWIKIQIISKLRL-$NH_2$ (PDM-30) Note that $R^{111}$ represents a group represented by the above Formula (4).

PDM-30 was synthesized and purified using 54 mg (0.020 mmol) of Rink Amide resin (0.37 mmol/g, WATANABE CHEMICAL INDUSTRIES, LTD.) by the similar method to Synthesis Example 1 (2.1 mg, yield: 3.8%).

HRMS (ES+) calcd for ($M^{3+}$+3H) 819.1667, found 819.1708.

Synthesis Example 5

Peptide comprising an amino acid sequence of SEQ ID NO: 6: synthesis of PDM-31

$R^{111}$-(Naa)-YIEWIKIQIISKLRL-$NH_2$ (PDM-31; Naa: 3-(2-naphthyl)-alanine)

Note that $R^{111}$ represents a group represented by the above Formula (4).

PDM-31 was synthesized and purified using 54 mg (0.020 mmol) of Rink Amide resin (0.37 mmol/g, WATANABE CHEMICAL INDUSTRIES, LTD.) by the similar method to Synthesis Example 1 (2.1 mg, yield: 3.8%).

HRMS (ES+) calcd for ($M^{3+}$+3H) 815.1629, found 815.1537.

Synthesis Example 6

Peptide comprising an amino acid sequence of SEQ ID NO: 7: synthesis of PDM-32

$R^{111}$-FYIEWIKIQIISKLRL-$NH_2$ (PDM-32)

Note that $R^{111}$ represents a group represented by the above Formula (4).

PDM-32 was synthesized and purified using 54 mg (0.020 mmol) of Rink Amide resin (0.37 mmol/g, WATANABE CHEMICAL INDUSTRIES, LTD.) by the similar method to Synthesis Example 1 (2.7 mg, yield: 4.9%).

HRMS (ES+) calcd for ($M^{3+}$+3H) 798.4911, found 798.5083.

Synthesis Example 7

Peptide comprising an amino acid sequence of SEQ ID NO: 8: synthesis of PDM-34

$R^{111}$-LYIEWIKIQIISKLRL-$NH_2$ (PDM-34)

Note that $R^{111}$ represents a group represented by the above Formula (4).

PDM-34 was synthesized and purified using 54 mg (0.020 mmol) of Rink Amide resin (0.37 mmol/g, WATANABE CHEMICAL INDUSTRIES, LTD.) by the similar method to Synthesis Example 1 (3.7 mg, yield: 6.9%).

HRMS (ES+) calcd for ($M^{3+}$+3H) 787.1629, found 787.1746.

Synthesis Example 8

Peptide comprising an amino acid sequence of SEQ ID NO: 9: synthesis of PDM-35

$R^{111}$-HYIEWIKIQIISKLRL-$NH_2$ (PDM-35)

Note that $R^{111}$ represents a group represented by the above Formula (4).

PDM-35 was synthesized and purified using 54 mg (0.020 mmol) of Rink Amide resin (0.37 mmol/g, WATANABE CHEMICAL INDUSTRIES, LTD.) by the similar method to Synthesis Example 1 (10.2 mg, yield: 19%).

HRMS (ES+) calcd for ($M^{3+}$+3H) 795.1546, found 795.1572.

Synthesis Example 9

Peptide comprising an amino acid sequence of SEQ ID NO: 11: synthesis of PDM-37

$R^{111}$-WFIEWIKIQIISKLRL-$NH_2$ (PDM-37)

Note that $R^{111}$ represents a group represented by the above Formula (4).

PDM-37 was synthesized and purified using 54 mg (0.020 mmol) of Rink Amide resin (0.37 mmol/g, WATANABE CHEMICAL INDUSTRIES, LTD.) by the similar method to Synthesis Example 1 (3.3 mg, yield: 6.0%).

HRMS (ES+) calcd for $(M^{3+}+3H)$ 806.1631, found 806.1714.

Synthesis Example 10

Peptide comprising an amino acid sequence of SEQ ID NO: 12: synthesis of PDM-38

$R^{111}$-W-(Naa)-IEWIKIQIISKLRL-$NH_2$ (PDM-38; Naa: 3-(2-naphthyl)-alanine)

Note that $R^{111}$ represents a group represented by the above Formula (4).

PDM-38 was synthesized and purified using 54 mg (0.020 mmol) of Rink Amide resin (0.37 mmol/g, WATANABE CHEMICAL INDUSTRIES, LTD.) by the similar method to Synthesis Example 1 (2.7 mg, yield: 4.8%).

HRMS (ES+) calcd for $(M^{3+}+3H)$ 822.8349, found 822.8392.

Synthesis Example 11

Peptide comprising an amino acid sequence of SEQ ID NO: 13: synthesis of PDM-39

$R^{111}$-W-Cha-IEWIKIQIISKLRL-$NH_2$ (PDM-39; Cha: 3-cyclohexylalanine)

Note that $R^{111}$ represents a group represented by the above Formula (4).

PDM-39 was synthesized and purified using 54 mg (0.020 mmol) of Rink Amide resin (0.37 mmol/g, WATANABE CHEMICAL INDUSTRIES, LTD.) by the similar method to Synthesis Example 1 (5.5 mg, yield: 10%).

HRMS (ES+) calcd for $(M^{3+}+3H)$ 808.1787, found 808.1852.

Synthesis Example 12

Peptide comprising an amino acid sequence of SEQ ID NO: 14: synthesis of PDM-40

$R^{111}$-WLIEWIKIQIISKLRL-$NH_2$ (PDM-40)

Note that $R^{111}$ represents a group represented by the above Formula (4).

PDM-40 was synthesized and purified using 54 mg (0.020 mmol) of Rink Amide resin (0.37 mmol/g, WATANABE CHEMICAL INDUSTRIES, LTD.) by the similar method to Synthesis Example 1 (1.1 mg, yield: 2.0%).

HRMS (ES+) calcd for $(M^{3+}+3H)$ 794.8349, found 794.8349.

Synthesis Example 13

Peptide comprising an amino acid sequence of SEQ ID NO: 15: synthesis of PDM-41

$R^{111}$-WHIEWIKIQIISKLRL-$NH_2$ (PDM-41)

Note that $R^{111}$ represents a group represented by the above Formula (4).

PDM-41 was synthesized and purified using 54 mg (0.020 mmol) of Rink Amide resin (0.37 mmol/g, WATANABE CHEMICAL INDUSTRIES, LTD.) by the similar method to Synthesis Example 1 (6.5 mg, yield: 12%).

HRMS (ES+) calcd for $(M^{3+}+3H)$ 802.8266, found 802.8266.

Synthesis Example 14

Peptide comprising an amino acid sequence of SEQ ID NO: 16: synthesis of PDM-42

$R^{111}$-WRIEWIKIQIISKLRL-$NH_2$ (PDM-42)

Note that $R^{111}$ represents a group represented by the above Formula (4).

PDM-42 was synthesized and purified using 54 mg (0.020 mmol) of Rink Amide resin (0.37 mmol/g, WATANABE CHEMICAL INDUSTRIES, LTD.) by the similar method to Synthesis Example 1 (7.8 mg, yield: 14%).

HRMS (ES+) calcd for $(M^{3+}+3H)$ 809.1740, found 809.1740.

Synthesis Example 15

Peptide comprising an amino acid sequence of SEQ ID NO: 17: synthesis of PDM-43

$R^{111}$-WSIEWIKIQIISKLRL-$NH_2$ (PDM-43)

Note that $R^{111}$ represents a group represented by the above Formula (4).

PDM-43 was synthesized and purified using 54 mg (0.020 mmol) of Rink Amide resin (0.37 mmol/g, WATANABE CHEMICAL INDUSTRIES, LTD.) by the similar method to Synthesis Example 1 (7.0 mg, yield: 13%).

HRMS (ES+) calcd for $(M^{3+}+3H)$ 786.1509, found 786.1509.

Synthesis Example 16

Peptide comprising an amino acid sequence of SEQ ID NO: 18: synthesis of PDM-44

$R^{111}$-WYIE-(Naa)-IKIQIISKLRL-$NH_2$ (PDM-44; Naa: 3-(2-naphthyl)-alanine)

Note that $R^{111}$ represents a group represented by the above Formula (4).

PDM-44 was synthesized and purified using 54 mg (0.020 mmol) of Rink Amide resin (0.37 mmol/g, WATANABE CHEMICAL INDUSTRIES, LTD.) by the similar method to Synthesis Example 1 (7.0 mg, yield: 13%).

HRMS (ES+) calcd for $(M^{3+}+3H)$ 815.1629, found 815.1629.

Synthesis Example 17

Peptide comprising an amino acid sequence of SEQ ID NO: 19: synthesis of PDM-45

$R^{111}$-WYIELIKIQIISKLRL-$NH_2$ (PDM-45)

Note that $R^{111}$ represents a group represented by the above Formula (4).

PDM-45 was synthesized and purified using 54 mg (0.020 mmol) of Rink Amide resin (0.37 mmol/g, WATANABE CHEMICAL INDUSTRIES, LTD.) by the similar method to Synthesis Example 1 (5.6 mg, yield: 10%).

HRMS (ES+) calcd for $(M^{3+}+3H)$ 787.1629, found 787.1585.

Synthesis Example 18

Peptide comprising an amino acid sequence of SEQ ID NO: 20: synthesis of PDM-46

$R^{111}$-WYIESIKIQIISKLRL-$NH_2$ (PDM-46)

Note that $R^{111}$ represents a group represented by the above Formula (4).

PDM-46 was synthesized and purified using 54 mg (0.020 mmol) of Rink Amide resin (0.37 mmol/g, WATANABE CHEMICAL INDUSTRIES, LTD.) by the similar method to Synthesis Example 1 (3.8 mg, yield: 7.1%).

HRMS (ES+) calcd for (M$^{3+}$+3H) 778.4789, found 778.4739.

Synthesis Example 19

Peptide comprising an amino acid sequence of SEQ ID NO: 21: synthesis of PDM-47

R$^{111}$-WYIERIKIQIISKLRL-NH$_2$ (PDM-47)

Note that R$^{111}$ represents a group represented by the above Formula (4).

PDM-47 was synthesized and purified using 54 mg (0.020 mmol) of Rink Amide resin (0.37 mmol/g, WATANABE CHEMICAL INDUSTRIES, LTD.) by the similar method to Synthesis Example 1 (1.4 mg, yield: 2.6%).

HRMS (ES+) calcd for (M$^{3+}$+3H) 801.5020, found 801.5007.

Synthesis Example 20

Peptide comprising an amino acid sequence of SEQ ID NO: 22: synthesis of PDM-48

R$^{111}$-YWIEEIKIQIISKLRL-NH$_2$ (PDM-48)

Note that R$^{111}$ represents a group represented by the above Formula (4).

PDM-48 was synthesized and purified using 54 mg (0.020 mmol) of Rink Amide resin (0.37 mmol/g, WATANABE CHEMICAL INDUSTRIES, LTD.) by the similar method to Synthesis Example 1 (1.6 mg, yield: 3.0%).

HRMS (ES+) calcd for (M$^{3+}$+3H) 792.4825, found 792.4794.

Synthesis Example 21

Peptide comprising an amino acid sequence of SEQ ID NO: 23: synthesis of PDM-49

R$^{111}$-WYIEFIKIQIISKIRL-NH$_2$ (PDM-49)

Note that R$^{111}$ represents a group represented by the above Formula (4).

PDM-49 was synthesized and purified using 54 mg (0.020 mmol) of Rink Amide resin (0.37 mmol/g, WATANABE CHEMICAL INDUSTRIES, LTD.) by the similar method to Synthesis Example 1 (4.3 mg, yield: 7.9%).

HRMS (ES+) calcd for (M$^{3+}$+3H) 798.4911, found 798.4918.

Synthesis Example 22

Peptide comprising an amino acid sequence of SEQ ID NO: 24: synthesis of PDM-50

R$^{111}$-WYIEYIKIQIISKIRL-NH$_2$ (PDM-50)

Note that R$^{111}$ represents a group represented by the above Formula (4).

PDM-50 was synthesized and purified using 54 mg (0.020 mmol) of Rink Amide resin (0.37 mmol/g, WATANABE CHEMICAL INDUSTRIES, LTD.) by the similar method to Synthesis Example 1 (5.8 mg, yield: 11%).

HRMS (ES+) calcd for (M$^{3+}$+3H) 803.8227, found 803.8186.

Synthesis Example 23

Peptide comprising an amino acid sequence of SEQ ID NO: 25: synthesis of PDM-51

R$^{111}$-WYIEHIKIQIISKIRL-NH$_2$ (PDM-51)

Note that R$^{111}$ represents a group represented by the above Formula (4).

PDM-51 was synthesized and purified using 54 mg (0.020 mmol) of Rink Amide resin (0.37 mmol/g, WATANABE CHEMICAL INDUSTRIES, LTD.) by the similar method to Synthesis Example 1 (6.2 mg, yield: 11%).

HRMS (ES+) calcd for (M$^{3+}$+3H) 795.1546, found 795.1539.

Synthesis Example 24

Peptide comprising an amino acid sequence of SEQ ID NO: 26: synthesis of PDM-52

R$^{111}$-WYIEWIKIQI-Nva-SKLRL-NH$_2$ (PDM-52; Nva: norvaline)

Note that R$^{111}$ represents a group represented by the above Formula (4).

PDM-52 was synthesized and purified using 54 mg (0.020 mmol) of Rink Amide resin (0.37 mmol/g, WATANABE CHEMICAL INDUSTRIES, LTD.) by the similar method to Synthesis Example 1 (7.0 mg, yield: 13%).

HRMS (ES+) calcd for (M$^{3+}$+3H) 806.8228, found 806.8233.

Synthesis Example 25

Peptide comprising an amino acid sequence of SEQ ID NO: 27: synthesis of PDM-53

R$^{111}$-WYIEWIKIQI-Chg-SKLRL-NH$_2$ (PDM-53; Chg: 2-cyclohexylglycine)

Note that R$^{111}$ represents a group represented by the above Formula (4).

PDM-53 was synthesized and purified using 54 mg (0.020 mmol) of Rink Amide resin (0.37 mmol/g, WATANABE CHEMICAL INDUSTRIES, LTD.) by the similar method to Synthesis Example 1 (6.5 mg, yield: 12%).

HRMS (ES+) calcd for (M$^{3+}$+3H) 820.1666, found 820.1666.

Synthesis Example 26

Peptide comprising an amino acid sequence of SEQ ID NO: 28: synthesis of PDM-54

R$^{111}$-WYIEWIKIQIFSKLRL-NH$_2$ (PDM-54)

Note that R$^{111}$ represents a group represented by the above Formula (4).

PDM-54 was synthesized and purified using 54 mg (0.020 mmol) of Rink Amide resin (0.37 mmol/g, WATANABE CHEMICAL INDUSTRIES, LTD.) by the similar method to Synthesis Example 1 (8.5 mg, yield: 15%).

HRMS (ES+) calcd for (M$^{3+}$+3H) 822.8228, found 822.8180.

Synthesis Example 27

Peptide comprising an amino acid sequence of SEQ ID NO: 29: synthesis of PDM-55

R$^{111}$-WYIEWIKIQIWSKLRL-NH$_2$ (PDM-55)

Note that R$^{111}$ represents a group represented by the above Formula (4).

PDM-55 was synthesized and purified using 54 mg (0.020 mmol) of Rink Amide resin (0.37 mmol/g, WATANABE CHEMICAL INDUSTRIES, LTD.) by the similar method to Synthesis Example 1 (9.3 mg, yield: 16%).

HRMS (ES+) calcd for (M$^{3+}$+3H) 835.8264, found 835.8290.

Synthesis Example 28

Peptide comprising an amino acid sequence of SEQ ID NO: 30: synthesis of PDM-56

$R^{111}$-WYIEWIKIQIYSKLRL-$NH_2$ (PDM-56)

Note that $R^{111}$ represents a group represented by the above Formula (4).

PDM-56 was synthesized and purified using 54 mg (0.020 mmol) of Rink Amide resin (0.37 mmol/g, WATANABE CHEMICAL INDUSTRIES, LTD.) by the similar method to Synthesis Example 1 (10.5 mg, yield: 19%).

HRMS (ES+) calcd for ($M^{3+}$+3H) 828.1544, found 828.1489.

Synthesis Example 29

Peptide comprising an amino acid sequence of SEQ ID NO: 31: synthesis of PDM-61

$R^{111}$-YYIESIKIQIISKLRL-$NH_2$ (PDM-61)

Note that $R^{111}$ represents a group represented by the above Formula (4).

PDM-61 was synthesized and purified using 54 mg (0.020 mmol) of Rink Amide resin (0.37 mmol/g, WATANABE CHEMICAL INDUSTRIES, LTD.) by the similar method to Synthesis Example 1 (4.7 mg, yield: 8.9%).

HRMS (ES+) calcd for ($M^{3+}$+3H) 770.8069, found 770.8032.

Synthesis Example 30

Peptide comprising an amino acid sequence of SEQ ID NO: 32: synthesis of PDM-62

$R^{111}$-WRIESIKIQIISKLRL-$NH_2$ (PDM-62)

Note that $R^{111}$ represents a group represented by the above Formula (4).

PDM-62 was synthesized and purified using 54 mg (0.020 mmol) of Rink Amide resin (0.37 mmol/g, WATANABE CHEMICAL INDUSTRIES, LTD.) by the similar method to Synthesis Example 1 (12.7 mg, yield: 23%).

HRMS (ES+) calcd for ($M^{3+}$+3H) 776.1582, found 776.1566.

Synthesis Example 31

Peptide comprising an amino acid sequence of SEQ ID NO: 33: synthesis of PDM-63

$R^{111}$-WYIESIKIQIWSKLRL-$NH_2$ (PDM-63)

Note that $R^{111}$ represents a group represented by the above Formula (4).

PDM-63 was synthesized and purified using 54 mg (0.020 mmol) of Rink Amide resin (0.37 mmol/g, WATANABE CHEMICAL INDUSTRIES, LTD.) by the similar method to Synthesis Example 1 (35.9 mg, yield: 65%).

HRMS (ES+) calcd for ($M^{3+}$+3H) 802.8107, found 802.8067.

Synthesis Example 32

Peptide comprising an amino acid sequence of SEQ ID NO: 20: synthesis of nPDM-46

WYIESIKIQIISKLRL-$NH_2$ (nPDM-46)

The N-terminal of the peptide is a hydrogen atom.

nPDM-46 was synthesized as follows. The peptide chain was stretched using 54 mg (0.020 mmol) of Rink Amide resin (0.37 mmol/g, WATANABE CHEMICAL INDUSTRIES, LTD.) by the similar method to Synthesis Example 1 and the N-terminal Fmoc group was removed by a 20% (v/v) piperidine/DMF solution. Thereafter, washing was performed with DMF (2.5 mL, 6 times) and methanol (2.5 mL, 5 times) and then the resin was dried by nitrogen purge. Thereafter, nPDM-46 was purified by the similar method to Synthesis Example 1 through the removal of the side chain protective group and the cleavage from resin (2.7 mg, yield: 5.8%).

HRMS (ES+) calcd for ($M^{3+}$+3H) 668.0791, found 668.0797.

Synthesis Example 33

Peptide comprising an amino acid sequence of SEQ ID NO: 29: synthesis of nPDM-55

WYIEWIKIQIWSKLRL-$NH_2$ (nPDM-55)

The N-terminal of the peptide is a hydrogen atom.

nPDM-55 was synthesized and purified using 54 mg (0.020 mmol) of Rink Amide resin (0.37 mmol/g, WATANABE CHEMICAL INDUSTRIES, LTD.) by the similar method to Synthesis Example 32 (6.3 mg, yield: 13%).

HRMS (ES+) calcd for ($M^{3+}$+3H) 725.4266, found 725.4266.

Synthesis Example 34

Peptide comprising an amino acid sequence of SEQ ID NO: 33: synthesis of nPDM-63

WYIESIKIQIWSKLRL-$NH_2$ (nPDM-63)

The N-terminal of the peptide is a hydrogen atom.

nPDM-63 was synthesized and purified using 54 mg (0.020 mmol) of Rink Amide resin (0.37 mmol/g, WATANABE CHEMICAL INDUSTRIES, LTD.) by the similar method to Synthesis Example 32 (3.6 mg, yield: 7.5%).

HRMS (ES+) calcd for ($M^{3+}$+3H) 692.4109, found 692.4109.

Synthesis Example 35

Peptide comprising an amino acid sequence of SEQ ID NO: 34: synthesis of nPDM-55/E31K WYIKWIKIQIWSKLRL-$NH_2$ (nPDM-55/E31K)

The N-terminal of the peptide is a hydrogen atom.

nPDM-55/E31K was synthesized and purified using 54 mg (0.020 mmol) of Rink Amide resin (0.37 mmol/g, WATANABE CHEMICAL INDUSTRIES, LTD.) by the similar method to Synthesis Example 32 (8.2 mg, yield: 16%).

HRMS (ES+) calcd for ($M^{3+}$+3H) 725.1107, found 725.0985.

Synthesis Example 36

Peptide comprising an amino acid sequence of SEQ ID NO: 35: synthesis of nPDM-55/E31R WYIRWIKIQIWSKLRL-$NH_2$ (nPDM-55/E31R)

The N-terminal of the peptide is a hydrogen atom.

nPDM-55/E31R was synthesized and purified using 54 mg (0.020 mmol) of Rink Amide resin (0.37 mmol/g, WATANABE CHEMICAL INDUSTRIES, LTD.) by the similar method to Synthesis Example 32 (6.2 mg, yield: 12%).

HRMS (ES+) calcd for ($M^{2+}$+2H) 1101.1653, found 1101.1569.

Synthesis Example 37

Peptide comprising an amino acid sequence of SEQ ID NO: 36: synthesis of nPDM-55/E31Q
WYIQWIKIQIWSKLRL-NH$_2$ (nPDM-55/E31Q)
The N-terminal of the peptide is a hydrogen atom.
nPDM-55/E31Q was synthesized and purified using 54 mg (0.020 mmol) of Rink Amide resin (0.37 mmol/g, WATANABE CHEMICAL INDUSTRIES, LTD.) by the similar method to Synthesis Example 32 (4.4 mg, yield: 8.7%).
HRMS (ES+) calcd for (M$^{3+}$+3H) 725.0986, found 725.0933.

Synthesis Example 38

Peptide comprising an amino acid sequence of SEQ ID NO: 37: synthesis of nPDM-55/E31N
WYINWIKIQIWSKLRL-NH$_2$ (nPDM-55/E31N)
The N-terminal of the peptide is a hydrogen atom.
nPDM-55/E31N was synthesized and purified using 54 mg (0.020 mmol) of Rink Amide resin (0.37 mmol/g, WATANABE CHEMICAL INDUSTRIES, LTD.) by the similar method to Synthesis Example 32 (2.6 mg, yield: 5.2%).
HRMS (ES+) calcd for (M$^{2+}$+2H) 1080.1362, found 1080.1362.

Synthesis Example 39

Peptide comprising an amino acid sequence of SEQ ID NO: 38: synthesis of nPDM-55/Q36P
WYIEWIKIPIWSKLRL-NH$_2$ (nPDM-55/Q36P)
The N-terminal of the peptide is a hydrogen atom.
nPDM-55/Q36P was synthesized and purified using 54 mg (0.020 mmol) of Rink Amide resin (0.37 mmol/g, WATANABE CHEMICAL INDUSTRIES, LTD.) by the similar method to Synthesis Example 32 (3.2 mg, yield: 6.4%).
HRMS (ES+) calcd for (M$^{3+}$+3H) 715.0913, found 715.0822.

Synthesis Example 40

Peptide comprising an amino acid sequence of SEQ ID NO: 29: synthesis of succinyl-nPDM-55
HOOC—(CH$_2$)$_2$—CO-WYIEWIKIQIWSKLRL-NH$_2$ (succinyl-nPDM-55)
Succinyl-nPDM-55 was synthesized as follows. The peptide chain was stretched using 54 mg (0.020 mmol) of Rink Amide resin (0.37 mmol/g, WATANABE CHEMICAL INDUSTRIES, LTD.) by the similar method to Synthesis Example 32 and the N-terminal Fmoc group was removed by a 20% (v/v) piperidine/DMF solution. Thereafter, succinic anhydride (KANTO CHEMICAL CO., INC., 0.20 mmol, 10 eq.) was reacted in the presence of DIEA, and washing was performed with DMF (2.5 mL, 6 times) and methanol (2.5 mL, 5 times). Then, the resin was dried by nitrogen purge. Thereafter, succinyl-nPDM-55 was purified by the similar method to Synthesis Example 1 through the removal of the side chain protective group and the cleavage from resin (2.0 mg, yield: 3.8%).
HRMS (ES+) calcd for (M$^{3+}$+3H) 758.7653, found 758.7484.

Synthesis Example 41

Peptide comprising an amino acid sequence of SEQ ID NO: 29: synthesis of orotinyl-nPDM-55
R$^{112}$-WYIEWIKIQIWSKLRL-NH$_2$ (orotinyl-nPDM-55)
Note that R$^{112}$ represents a group represented by the following Formula (5).

[Chem. 10]

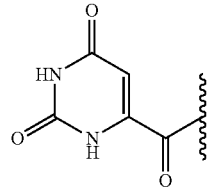

Formula (5)

Orotinyl-nPDM-55 was synthesized as follows. The peptide chain was stretched using 54 mg (0.020 mmol) of Rink Amide resin (0.37 mmol/g, WATANABE CHEMICAL INDUSTRIES, LTD.) by the similar method to Synthesis Example 32 and the N-terminal Fmoc group was removed by a 20% (v/v) piperidine/DMF solution. Thereafter, orotic acid (Tokyo Chemical Industry Co., Ltd., 0.20 mmol, 10 eq.) was introduced by the similar condensation method to Fmoc amino acid and washed with DMF (2.5 mL, 6 times) and methanol (2.5 mL, 5 times). Then, the resin was dried by nitrogen purge. Thereafter, orotinyl-nPDM-55 was purified by the similar method to Synthesis Example 1 through the removal of the side chain protective group and the cleavage from resin (1.8 mg, yield: 3.5%).
HRMS (ES+) calcd for (M$^{3+}$+3H) 771.4288, found 725.4266.

Synthesis Example 42

Peptide comprising an amino acid sequence of SEQ ID NO: 29: synthesis of 3-pyridil-nPDM-55
R$^{113}$-WYIEWIKIQIWSKLRL-NH$_2$ (3-pyridil-nPDM-55)
Note that R$^{113}$ represents a group represented by the following Formula (6).

[Chem. 11]

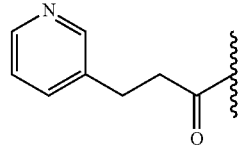

Formula (6)

3-Pyridil-nPDM-55 was synthesized as follows. The peptide chain was stretched using 54 mg (0.020 mmol) of Rink Amide resin (0.37 mmol/g, WATANABE CHEMICAL INDUSTRIES, LTD.) by the similar method to Synthesis Example 32 and the N-terminal Fmoc group was removed by a 20% (v/v) piperidine/DMF solution. Thereafter, 3-pyridinepropionic acid (Tokyo Chemical Industry Co., Ltd., 0.20 mmol, 10 eq.) was introduced by the similar condensation method to Fmoc amino acid and washed with DMF (2.5 mL, 6 times) and methanol (2.5 mL, 5 times). Then, the resin was dried by nitrogen purge. Thereafter, 3-pyridil-nPDM-55 was purified by the similar method to Synthesis Example 1 through the removal of the side chain protective group and the cleavage from resin (3.4 mg, yield: 6.5%).

HRMS (ES+) calcd for ($M^{2+}$+2H) 1147.1546, found 1147.1439.

Synthesis Example 43

Peptide comprising an amino acid sequence of SEQ ID NO: 1 (Comparative Example): synthesis of mMPS(28-43)
SRIEAIKIQILSKLRL-$NH_2$ (mMPS(28-43))

The N-terminal of the peptide is a hydrogen atom. The amino acid sequence of SEQ ID NO: 1 included in mMPS (28-43) corresponds to a partial sequence of myostatin propeptide that is common to a plurality of organism species such as humans and mice.

mMPS(28-43) was synthesized and purified using 54 mg (0.020 mmol) of Rink Amide resin (0.37 mmol/g, WATANABE CHEMICAL INDUSTRIES, LTD.) by the similar method to Synthesis Example 32 (11.5 mg, yield: 25%).

HRMS (ES+) calcd for ($M^{4+}$+4H) 470.8102, found 470.8124.

Synthesis Example 44

Peptide comprising an amino acid sequence of SEQ ID NO: 39 (Comparative Example): synthesis of d-14
WYIEAIKIQILSKLRL-$NH_2$ (d-14)

The N-terminal of the peptide is a hydrogen atom.

d-14 was synthesized and purified using 54 mg (0.020 mmol) of Rink Amide resin (0.37 mmol/g, WATANABE CHEMICAL INDUSTRIES, LTD.) by the similar method to Synthesis Example 32 (9.6 mg, yield: 20%).

HRMS (ES+) calcd for ($M^{3+}$+3H) 993.6173, found 993.6211.

Synthesis Example 45

Peptide comprising an amino acid sequence of SEQ ID NO: 10 (Comparative Example): synthesis of PDM-36
$R^{111}$-SYIEWIKIQIISKLRL-$NH_2$ (PDM-36)

Note that $R^{111}$ represents a group represented by the above Formula (4).

PDM-36 was synthesized and purified using 54 mg (0.020 mmol) of Rink Amide resin (0.37 mmol/g, WATANABE CHEMICAL INDUSTRIES, LTD.) by the similar method to Synthesis Example 1 (1.4 mg, yield: 2.6%).

HRMS (ES+) calcd for ($M^{3+}$+3H) 778.4789, found 778.4884.

Synthesis Example 46

Peptide comprising an amino acid sequence of SEQ ID NO: 380: synthesis of nPDM-64
WYIRWIK-Chg-QIWSKLRL-$NH_2$ (nPDM-64; Chg: 2-cyclohexylglycine)

The N-terminal of the peptide is a hydrogen atom.

nPDM-64 was synthesized and purified using 54 mg (0.020 mmol) of Rink Amide resin (0.37 mmol/g, WATANABE CHEMICAL INDUSTRIES, LTD.) by the similar method to Synthesis Example 32 (2.3 mg, yield: 4.5%).

HRMS (ES+) calcd for ($M^{3+}$+3H) 743.1076, found 743.1024.

Synthesis Example 47

Peptide comprising an amino acid sequence of SEQ ID NO: 381: synthesis of nPDM-65
WYIRWIKIQIWSK-Chg-RL-$NH_2$ (nPDM-65; Chg: 2-cyclohexylglycine)

The N-terminal of the peptide is a hydrogen atom.

nPDM-65 was synthesized and purified using 54 mg (0.020 mmol) of Rink Amide resin (0.37 mmol/g, WATANABE CHEMICAL INDUSTRIES, LTD.) by the similar method to Synthesis Example 32 (2.3 mg, yield: 4.5%).

HRMS (ES+) calcd for ($M^{3+}$+3H) 743.1076, found 743.1217.

Synthesis Example 48

Peptide comprising an amino acid sequence of SEQ ID NO: 382: synthesis of nPDM-66
WYIRWIK-Chg-QIWSK-Chg-RL-$NH_2$ (nPDM-66; Chg: 2-cyclohexylglycine)

The N-terminal of the peptide is a hydrogen atom.

nPDM-66 was synthesized and purified using 54 mg (0.020 mmol) of Rink Amide resin (0.37 mmol/g, WATANABE CHEMICAL INDUSTRIES, LTD.) by the similar method to Synthesis Example 32 (2.3 mg, yield: 4.4%).

HRMS (ES+) calcd for ($M^{3+}$+3H) 751.7899, found 751.7762.

Synthesis Example 49

Peptide comprising an amino acid sequence of SEQ ID NO: 383: synthesis of nPDM-67
WYFRWIKIQIWSKLRL-$NH_2$ (nPDM-67)

The N-terminal of the peptide is a hydrogen atom.

nPDM-67 was synthesized and purified using 54 mg (0.020 mmol) of Rink Amide resin (0.37 mmol/g, WATANABE CHEMICAL INDUSTRIES, LTD.) by the similar method to Synthesis Example 32 (5.4 mg, yield: 10%).

HRMS (ES+) calcd for ($M^{3+}$+3H) 745.7742, found 745.7523.

Synthesis Example 50

Peptide comprising an amino acid sequence of SEQ ID NO: 384: synthesis of nPDM-68
WYIRWIKIQIWSKXRL-$NH_2$ (nPDM-68)

The N-terminal of the peptide is a hydrogen atom.

nPDM-68 was synthesized and purified using 54 mg (0.020 mmol) of Rink Amide resin (0.37 mmol/g, WATANABE CHEMICAL INDUSTRIES, LTD.) by the similar method to Synthesis Example 32 (9.1 mg, yield: 18%).

HRMS (ES+) calcd for ($M^{3+}$+3H) 745.7742, found 745.7604.

Synthesis Example 51

Peptide comprising an amino acid sequence of SEQ ID NO: 385: synthesis of nPDM-69
YYIR-Naa-IKIQIWSKLRL-$NH_2$ (nPDM-69; Naa: 3-(2-naphthyl)-alanine)

The N-terminal of the peptide is a hydrogen atom.

nPDM-69 was synthesized and purified using 54 mg (0.020 mmol) of Rink Amide resin (0.37 mmol/g, WATANABE CHEMICAL INDUSTRIES, LTD.) by the similar method to Synthesis Example 32 (5.2 mg, yield: 10%).

HRMS (ES+) calcd for ($M^{3+}$+3H) 730.4424, found 730.4194.

Synthesis Example 52

Peptide comprising an amino acid sequence of SEQ ID NO: 35: synthesis of A-nPDM-55/E31R AWYIRWIKIQIWSKLRL-NH$_2$ (A-nPDM-55/E31R)

The N-terminal of the peptide is a hydrogen atom.

A-nPDM-55/E31R was synthesized and purified using 54 mg (0.020 mmol) of Rink Amide resin (0.37 mmol/g, WATANABE CHEMICAL INDUSTRIES, LTD.) by the similar method to Synthesis Example 32 (10 mg, yield: 19%).

HRMS (ES+) calcd for ($M^{2+}$+2H) 1101.1653, found 1101.1569.

Synthesis Example 53

Peptide comprising an amino acid sequence of SEQ ID NO: 573: synthesis of nPDM-70

WYIRWIK-Chg-QIWSR-Chg-RL-NH$_2$ (nPDM-70, Chg: 2-cyclohexylglycine)

The N-terminal of the peptide is a hydrogen atom.

nPDM-70 was synthesized and purified using 54 mg (0.020 mmol) of Rink Amide resin (0.37 mmol/g, WATANABE CHEMICAL INDUSTRIES, LTD.) by the similar method to Synthesis Example 32 (1.3 mg, yield: 2.4%).

HRMS (ES+) calcd for ($M^{3+}$+3H) 761.1253, found 761.1242.

Synthesis Example 54

Peptide comprising an amino acid sequence of SEQ ID NO: 574: synthesis of nPDM-71

WYIRWIR-Chg-QIWSK-Chg-RL-NH$_2$ (nPDM-71, Chg: 2-cyclohexylglycine)

The N-terminal of the peptide is a hydrogen atom.

nPDM-71 was synthesized and purified using 54 mg (0.020 mmol) of Rink Amide resin (0.37 mmol/g, WATANABE CHEMICAL INDUSTRIES, LTD.) by the similar method to Synthesis Example 32 (4.7 mg, yield: 8.6%).

HRMS (ES+) calcd for ($M^{3+}$+3H) 761.1253, found 761.1221.

Synthesis Example 55

Peptide comprising an amino acid sequence of SEQ ID NO: 575: synthesis of nPDM-72

WYIRWIR-Chg-QIWSR-Chg-RL-NH$_2$ (nPDM-72, Chg: 2-cyclohexylglycine)

The N-terminal of the peptide is a hydrogen atom.

nPDM-72 was synthesized and purified using 54 mg (0.020 mmol) of Rink Amide resin (0.37 mmol/g, WATANABE CHEMICAL INDUSTRIES, LTD.) by the similar method to Synthesis Example 32 (10 mg, yield: 19%).

HRMS (ES+) calcd for ($M^{3+}$+3H) 770.7940, found 770.4622.

Synthesis Example 56

Peptide comprising an amino acid sequence of SEQ ID NO: 576: synthesis of nPDM-73

WYIRWIR-Chg-QIWSR-Chg-PL-NH$_2$ (nPDM-73, Chg: 2-cyclohexylglycine)

The N-terminal of the peptide is a hydrogen atom.

nPDM-73 was synthesized and purified using 54 mg (0.020 mmol) of Rink Amide resin (0.37 mmol/g, WATANABE CHEMICAL INDUSTRIES, LTD.) by the similar method to Synthesis Example 32 (20 mg, yield: 39%).

HRMS (ES+) calcd for ($M^{3+}$+3H) 750.7779, found 750.7799.

Synthesis Example 57

Peptide comprising an amino acid sequence of SEQ ID NO: 577: synthesis of nPDM-75

WYIRWIR-Chg-QIWPR-Chg-RL-NH$_2$ (nPDM-75, Chg: 2-cyclohexylglycine)

The N-terminal of the peptide is a hydrogen atom.

nPDM-75 was synthesized and purified using 54 mg (0.020 mmol) of Rink Amide resin (0.37 mmol/g, WATANABE CHEMICAL INDUSTRIES, LTD.) by the similar method to Synthesis Example 32 (7.9 mg, yield: 14%).

HRMS (ES+) calcd for ($M^{3+}$+3H) 773.8009, found 773.8043.

Synthesis Example 58

Peptide comprising an amino acid sequence of SEQ ID NO: 578: synthesis of nPDM-76 WYIRWIR-Chg-PIWSR-Chg-RL-NH$_2$ (nPDM-76, Chg: 2-cyclohexylglycine)

The N-terminal of the peptide is a hydrogen atom.

nPDM-76 was synthesized and purified using 54 mg (0.020 mmol) of Rink Amide resin (0.37 mmol/g, WATANABE CHEMICAL INDUSTRIES, LTD.) by the similar method to Synthesis Example 32 (9.6 mg, yield: 17%).

HRMS (ES+) calcd for ($M^{3+}$+3H) 760.1254, found 760.1267.

Synthesis Example 59

Peptide comprising an amino acid sequence of SEQ ID NO: 579: synthesis of nPDM-77

WYIRWIP-Chg-QIWSR-Chg-RL-NH$_2$ (nPDM-77, Chg: 2-cyclohexylglycine)

The N-terminal of the peptide is a hydrogen atom.

nPDM-77 was synthesized and purified using 54 mg (0.020 mmol) of Rink Amide resin (0.37 mmol/g, WATANABE CHEMICAL INDUSTRIES, LTD.) by the similar method to Synthesis Example 32 (5.6 mg, 11%).

HRMS (ES+) calcd for ($M^{3+}$+3H) 750.7779, found 750.7751.

Synthesis Example 60

Peptide comprising an amino acid sequence of SEQ ID NO: 588: synthesis of nPDM-80

WYIRwIR-Chg-QIWSR-Chg-PL-NH$_2$ (nPDM-80, Chg: 2-cyclohexylglycine, w: D-Trp)

The N-terminal of the peptide is a hydrogen atom.

nPDM-80 was synthesized and purified using 54 mg (0.020 mmol) of Rink Amide resin (0.37 mmol/g,

Synthesis Example 61

Peptide comprising an amino acid sequence of SEQ ID NO: 589: synthesis of nPDM-82
WYIRwIR-Chg-QIWsR-Chg-PL-NH$_2$ (nPDM-82, Chg: 2-cyclohexylglycine, w: D-Trp, s: D-Ser)
The N-terminal of the peptide is a hydrogen atom.
nPDM-82 was synthesized and purified using 54 mg (0.020 mmol) of Rink Amide resin (0.37 mmol/g, WATANABE CHEMICAL INDUSTRIES, LTD.) by the similar method to Synthesis Example 32 (15 mg, yield: 30%).
HRMS (ES+) calcd for (M$^{3+}$+3H) 750.7779, found 750.7808.

Synthesis Example 62

Peptide comprising an amino acid sequence of SEQ ID NO: 580: synthesis of nPDM-83
WYIRWIR-Chg-PIWSR-Chg-PL-NH$_2$ (nPDM-83, Chg: 2-cyclohexylglycine)
The N-terminal of the peptide is a hydrogen atom.
nPDM-83 was synthesized and purified using 54 mg (0.020 mmol) of Rink Amide resin (0.37 mmol/g, WATANABE CHEMICAL INDUSTRIES, LTD.) by the similar method to Synthesis Example 32 (18 mg, yield: 36%).
HRMS (ES+) calcd for (M$^{3+}$+3H) 740.4426, found 740.4407.

Synthesis Example 63

Peptide comprising an amino acid sequence of SEQ ID NO: 581: synthesis of 3,3-diphenylpropionyl-nPDM-85
R$^{114}$-YIRWIR-Chg-QIWSR-Chg-PL-NH$_2$ (3,3-diphenylpropionyl-nPDM-85, Chg: 2-cyclohexylglycine)
Note that R$^{114}$ represents a group represented by the following Formula (7).

[Chem. 12]

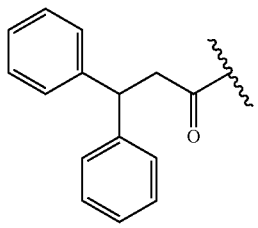

Formula (7)

3,3-Diphenylpropionyl-nPDM-85 was synthesized and purified using 54 mg (0.020 mmol) of Rink Amide resin (0.37 mmol/g, WATANABE CHEMICAL INDUSTRIES, LTD.) by the similar method to Synthesis Example 32 (4.9 mg, yield: 9.4%).
HRMS (ES+) calcd for (M$^{2+}$+2H) 1136.6677, found 1136.6760.

WATANABE CHEMICAL INDUSTRIES, LTD.) by the similar method to Synthesis Example 32 (7.5 mg, yield: 14%).
HRMS (ES+) calcd for (M$^{3+}$+3H) 750.7779, found 750.7756.

Synthesis Example 64

Peptide comprising an amino acid sequence of SEQ ID NO: 590: synthesis of nPDM-86
WYIRwIK-Chg-QIWSK-Chg-RL-NH$_2$ (nPDM-86, Chg: 2-cyclohexylglycine, w: D-Trp)
The N-terminal of the peptide is a hydrogen atom.
nPDM-86 was synthesized and purified using 54 mg (0.020 mmol) of Rink Amide resin (0.37 mmol/g, WATANABE CHEMICAL INDUSTRIES, LTD.) by the similar method to Synthesis Example 32 (4.6 mg, yield: 8.5%).
HRMS (ES+) calcd for (M$^{3+}$+3H) 751.7899, found 751.7857.

Synthesis Example 65

Peptide comprising an amino acid sequence of SEQ ID NO: 591: synthesis of nPDM-88
WYIRwIK-Chg-QIWsK-Chg-RL-NH$_2$ (nPDM-88, Chg: 2-cyclohexylglycine, w: D-Trp, s: D-Ser)
The N-terminal of the peptide is a hydrogen atom.
nPDM-88 was synthesized and purified using 54 mg (0.020 mmol) of Rink Amide resin (0.37 mmol/g, WATANABE CHEMICAL INDUSTRIES, LTD.) by the similar method to Synthesis Example 32 (4.0 mg, yield: 7.4%).
HRMS (ES+) calcd for (M$^{3+}$+3H) 751.7899, found 751.7872.

Synthesis Example 66

Peptide comprising an amino acid sequence of SEQ ID NO: 592: synthesis of nPDM-92
WYIRwI-(α-Me)Lys-Chg-QIWSK-Chg-RL-NH$_2$ (nPDM-92, w: D-Trp, (α-Me)Lys: (α-methyl)lysine, Chg: 2-cyclohexylglycine)
The N-terminal of the peptide is a hydrogen atom.
nPDM-92 was synthesized and purified using 54 mg (0.020 mmol) of Rink Amide resin (0.37 mmol/g, WATANABE CHEMICAL INDUSTRIES, LTD.) by the similar method to Synthesis Example 32 (13 mg, yield: 23%).
MALDI-TOF-MS: calcd for (M$^+$+H) 2267.37, found 2268.06.

Synthesis Example 67

Peptide comprising an amino acid sequence of SEQ ID NO: 588: synthesis of PDM-80
R$^{111}$-WYIRwIR-Chg-QIWSR-Chg-PL-NH$_2$ (PDM-80, w: D-Trp, Chg: 2-cyclohexylglycine)
Note that R$^{111}$ represents a group represented by the above Formula (4).
PDM-80 was synthesized and purified using 54 mg (0.020 mmol) of Rink Amide resin (0.37 mmol/g, WATANABE CHEMICAL INDUSTRIES, LTD.) by the similar method to Synthesis Example 1 (8.8 mg, yield: 15%).
MALDI-TOF-MS: calcd for (M$^+$+H) 2581.52, found 2581.69.

Synthesis Example 68

Peptide comprising an amino acid sequence of SEQ ID NO: 590: synthesis of PDM-86
R$^{111}$-WYIRwIK-Chg-QIWSK-Chg-RL-NH$_2$ (PDM-86, w: D-Trp, Chg: 2-cyclohexylglycine)
Note that R$^{111}$ represents a group represented by the above Formula (4).
PDM-86 was synthesized and purified using 54 mg (0.020 mmol) of Rink Amide resin (0.37 mmol/g, WATANABE CHEMICAL INDUSTRIES, LTD.) by the similar method to Synthesis Example 1 (8.4 mg, yield: 14%).
MALDI-TOF-MS: calcd for (M$^+$+H) 2584.25, found 2584.67.

Synthesis Example 69

Peptide comprising an amino acid sequence of SEQ ID NO: 590: synthesis of PDM-89

$R^{115}$-WYIRwIK-Chg-QIWSK-Chg-RL-NH$_2$ (PDM-89, w: D-Trp, Chg: 2-cyclohexylglycine)

Note that $R^{115}$ represents a group represented by the following Formula (8).

[Chem. 13]

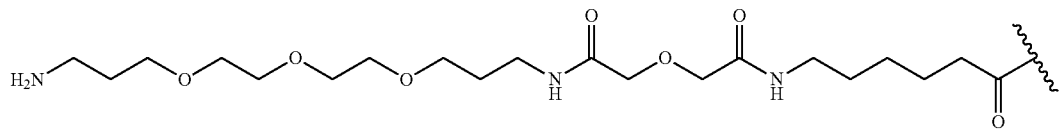

Formula (8)

PDM-89 was synthesized and purified using 54 mg (0.020 mmol) of Rink Amide resin (0.37 mmol/g, WATANABE CHEMICAL INDUSTRIES, LTD.) by the similar method to Synthesis Example 32 (6.2 mg, yield: 9.9%).

MALDI-TOF-MS: calcd for (M$^+$+H) 2684.62, found 2683.39.

Synthesis Example 70

Peptide comprising an amino acid sequence of SEQ ID NO: 590: synthesis of PDM-90

$R^{116}$-WYIRwIK-Chg-QIWSK-Chg-RL-NH$_2$ (PDM-90, w: D-Trp, Chg: 2-cyclohexylglycine)

Note that $R^{116}$ represents a group represented by the following Formula (9).

[Chem. 14]

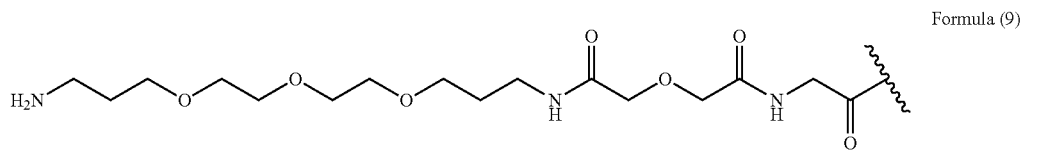

Formula (9)

PDM-90 was synthesized and purified using 54 mg (0.020 mmol) of Rink Amide resin (0.37 mmol/g, WATANABE CHEMICAL INDUSTRIES, LTD.) by the similar method to Synthesis Example 32 (9.5 mg, yield: 15%).

MALDI-TOF-MS: calcd for (M$^+$+H) 2628.55, found 2629.53.

Synthesis Example 71

Peptide comprising an amino acid sequence of SEQ ID NO: 590: synthesis of PDM-91

$R^{117}$-WYIRwIK-Chg-QIWSK-Chg-RL-NH$_2$ (PDM-91, w: D-Trp, Chg: 2-cyclohexylglycine)

Note that $R^{117}$ represents a group represented by the following Formula (10).

[Chem. 15]

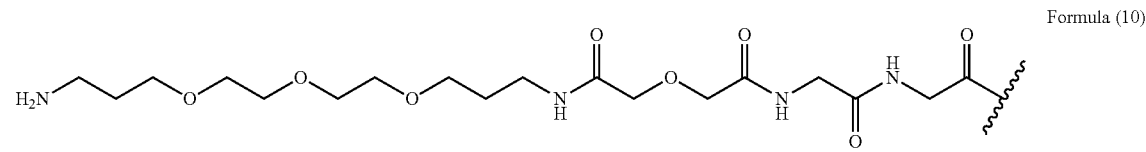

Formula (10)

PDM-91 was synthesized and purified using 54 mg (0.020 mmol) of Rink Amide resin (0.37 mmol/g, WATANABE CHEMICAL INDUSTRIES, LTD.) by the similar method to Synthesis Example 32 (6.8 mg, yield: 11%).

MALDI-TOF-MS: calcd for (M$^+$+H) 2685.58, found 2686.02.

Synthesis Example 72

Peptide comprising an amino acid sequence of SEQ ID NO: 593: synthesis of CR-60

WYIcWICIQIWSKLRL-NH$_2$ (CR-60, c: D-Cys, cyclic peptide in which a disulfide bond is formed between side chain SH groups of c and C)

The N-terminal of the peptide is a hydrogen atom.

CR-60 was obtained as follows. A linear peptide was synthesized and purified using 54 mg (0.020 mmol) of Rink Amide resin (0.37 mmol/g, WATANABE CHEMICAL INDUSTRIES, LTD.) by the similar method to Synthesis Example 32, 3 eq. of methyl 3-nitro-2-pyridinesulfenate was then added to a 25% acetonitrile aqueous solution having the linear peptide with a final concentration of 1 mM dissolved therein, the reaction was performed for 24 hours at room temperature, and the obtained disulfide cyclic peptide was purified with HPLC (1.2 mg, yield: 2.4%).

HRMS (ES+) calcd for (M$^{3+}$+3H) 707.7150, found 707.7081.

Synthesis Example 73

Peptide comprising an amino acid sequence of SEQ ID NO: 594: synthesis of CR-61

WYIEWIKIcIWCKLRL-NH$_2$ (CR-61, c: D-Cys, cyclic peptide in which a disulfide bond is formed between side chain SH groups of c and C)

The N-terminal of the peptide is a hydrogen atom.

CR-61 was synthesized and purified using 54 mg (0.020 mmol) of Rink Amide resin (0.37 mmol/g, WATANABE CHEMICAL INDUSTRIES, LTD.) by the similar method to Synthesis Example 72 (16 mg, yield: 31%).

HRMS (ES+) calcd for (M$^{3+}$+3H) 721.7306, found 721.7327.

Synthesis Example 74

Peptide comprising an amino acid sequence of SEQ ID NO: 595: synthesis of CR-62

WYIEWIKIQIWcKLCL-NH$_2$ (CR-62, c: D-Cys, cyclic peptide in which a disulfide bond is formed between side chain SH groups of c and C)

The N-terminal of the peptide is a hydrogen atom.

CR-62 was synthesized and purified using 54 mg (0.020 mmol) of Rink Amide resin (0.37 mmol/g, WATANABE CHEMICAL INDUSTRIES, LTD.) by the similar method to Synthesis Example 72 (3.3 mg, yield: 7.0%).

HRMS (ES+) calcd for (M$^{3+}$+3H) 712.3831, found 712.3789.

Synthesis Example 75

Peptide comprising an amino acid sequence of SEQ ID NO: 582 (Comparative Example): synthesis of 3d R$^{118}$-RQNTRYSRIEWIKIQIISKLRL-NH$_2$ (3d)

Note that R$^{118}$ represents a group represented by the following Formula (11).

[Chem. 16]

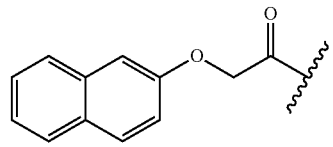

Formula (11)

3d was synthesized and purified using 54 mg (0.020 mmol) of Rink Amide resin (0.37 mmol/g, WATANABE CHEMICAL INDUSTRIES, LTD.) by the similar method to Synthesis Example 32 (21 mg, yield: 29%).

HRMS (ES+) calcd for (M$^{4+}$+4H) 750.1875, found 750.1732.

Evaluation of Myostatin Inhibitory Activity

Test Example 1

The concentration-dependent myostatin inhibitory activity evaluation of PDM-27 synthesized in Synthesis Example 1 was performed by the following reporter assay. The results thereof are shown in FIG. 1. PDM-27 exhibited a significant myostatin inhibitory activity at a concentration of 1 μM or more. Incidentally, in the drawing, "myostatin −" indicates the result of a test section added with dimethylsulfoxide (DMSO) including no myostatin and "myostatin+" indicates the result of a test section including 8 ng/mL of myostatin and including no test sample (peptide). Further, regarding the results of the reporter assay, the results of the test section including 8 ng/mL of myostatin and including no test sample was calculated as myostatin activity 100% (relative luciferase activity 100%) and the calculation results were shown as an average value±a standard deviation of three wells per each test section.

(1) Cell Culturing

Human embryo kidney cell HEK293 cells were cultured in a 5% (v/v) CO$_2$ incubator set to 37° C. using DMEM (NACALAI TESQUE, INC.) including a 10% (v/v) fetal bovine serum (FBS) added with a 1% (v/v) non-essential amino acid (Wako Pure Chemical Corporation).

(2) In Vitro Reporter Assay

HEK293 cells were seeded on a D-Lys-corted 96-well transparent plate (Thermo Fisher Scientific Inc.) in an amount of 2.0×10$^4$ cells (100 μL DMEM+10% (v/v) FBS) per well and were cultured for 24 hours.

100 ng of pGL4.48 [luc2P/SBE/Hygro] (Promega Corporation), and 10 ng of pGL4 [hRluc/TK] (Promega Corporation), and FuGENE HD (Promega Corporation) (final concentration of 41.25 μg/mL) as internal controls were mixed using OPTI-MEM the day after that, and the obtained product was added each in an amount of 8 μL to the culture medium in the well. The cells were cultured at 37° C. for 24 hours, and after the cell culture solution was replaced with serum-free DMEM, the cells were cultured for 8 hours. Incidentally, pGL4.48 [luc2P/SBE/Hygro] includes firefly luciferase reporter gene luc2P under Smad binding region (SBE) control, and when a signaling pathway by the myostatin is activated, intracellular Smad forms a complex, and the complex is bonded to SBE to promote transcription of luc2P.

The peptide as a test sample was suspended as a stock solution using DMSO to become 10 mM and stored at −30° C. Before 1 hour from addition to the culture medium, the peptide and a myostatin (Merck Millipore Corp.) were suspended with serum-free DMEM and left to stand still at room temperature (25° C.) for 20 minutes. Subsequently, a peptide with an arbitrary final concentration (0.3 to μM) and 8 ng/mL of myostatin were added to the culture medium, and then culturing was performed for 4 hours. After culturing for 4 hours, the culture solution was removed by an aspirator and the cells were washed with 1×PBS. Thereafter, Passive Lysis buffer (Promega Corporation) was added in an amount of 50 μL per well to dissolve the cells. The dissolving solution was subjected to centrifugal separation at 4500 rpm for 6 minutes under the condition of 4° C. After 20 μL of supernatant subjected to centrifugal separation was transferred to a white 96-well plate (Costar), 50 μL of Luciferase Assay Reagent (Promega Corporation) was then added, emission was detected by Luminoskan Ascent (Thermo Fisher Scientific Inc.), and a firefly luciferase activity was measured. Further, after 50 μL of Stop & Glo Buffer (Promega Corporation) was added, emission was detected by Luminoskan Ascent, and a *Renilla* luciferase activity was measured to be regarded as an internal control.

Test Example 2

Regarding mMPS(28-43) of Synthesis Example 43 and d-14 of Synthesis Example 44, the myostatin inhibitory activity was evaluated according to the test method of Test Example 1. Regarding mMPS(28-43) and d-14, a high myostatin inhibitory activity was not recognized at a final concentration of 1 μM. In mMPS(28-43), the myostatin inhibitory activity was not recognized even at a final concentration of 10 μM.

Test Example 3

Regarding the peptides prepared in Synthesis Example 2 to Synthesis Example 28, and Synthesis Example 45, the myostatin inhibitory activity of each peptide at a final concentration of 1 μM was evaluated according to the test method of Test Example 1. The results thereof are shown in FIGS. 2 and 3. As shown in FIGS. 2 and 3, the peptides other than PDM-36 (the peptide comprising an amino acid sequence of SEQ ID NO: 10) as Comparative Example exhibited a high inhibitory activity, that is, an inhibitory activity of 40% or more (luciferase activity of 60% or less) at a final concentration of 1 μM.

Test Example 4

Regarding the peptides prepared in Synthesis Example 29 to Synthesis Example 31, the myostatin inhibitory activity of each peptide at a final concentration of 1 μM was evaluated according to the test method of Test Example 1. The results thereof are shown in FIG. 4. As shown in FIG. 4, those peptides exhibited a high inhibitory activity, that is, an inhibitory activity of 40% or more (luciferase activity of 60% or less) at a final concentration of 1 μM.

Test Example 5

Regarding PDM-46 of Synthesis Example 18, PDM-55 of Synthesis Example 27, and PDM-63 of Synthesis Example 31, the myostatin inhibitory activity of each peptide at a final concentration of 0.3 μM was evaluated according to the test method of Test Example 1. The results thereof are shown in FIG. 5. PDM-55 and PDM-63 exhibited a high inhibitory activity, that is, an inhibitory activity of 40% or more (luciferase activity of 60% or less) even at a final concentration of 0.3 μM.

Test Example 6

Regarding the peptides prepared in Synthesis Example 32 to Synthesis Example 34, the myostatin inhibitory activity of each peptide at final concentrations of 1 μM and 0.3 μM was evaluated according to the test method of Test Example 1. The results thereof are shown in FIG. 6. As shown in FIG. 6, those peptides exhibited a high inhibitory activity, that is, an inhibitory activity of 40% or more (luciferase activity of 60% or less) at a final concentration of 1 μM. Further, nPDM-55 of Synthesis Example 33 exhibited a particularly high inhibitory activity, that is, an inhibitory activity of 40% or more (luciferase activity of 60% or less) even at a final concentration of 0.3 μM.

Test Example 7

Regarding the peptides prepared in Synthesis Example 35 to Synthesis Example 42, the myostatin inhibitory activity of each peptide at a final concentration of 0.3 μM was evaluated according to the test method of Test Example 1. The results thereof are shown in FIG. 7. In those peptides, a degradation of the luciferase activity at a final concentration 0.3 μM was recognized, and thus it was estimated that a high inhibitory activity, that is, inhibitory activity of 40% or more (luciferase activity of 60% or less) at a final concentration of 1 μM was exhibited. In particular, nPDM-55/E31K of Synthesis Example 35, nPDM-55/E31R of Synthesis Example 36, and nPDM-55/E31Q of Synthesis Example 37 exhibited a particularly high inhibitory activity, that is, an inhibitory activity 40% or more (luciferase activity 60% or less) even at a final concentration of 0.3 μM.

Test Example 8

Regarding the peptides prepared in Synthesis Example 46 to Synthesis Example 51, the myostatin inhibitory activity of each peptide at final concentrations of 1 μM and 0.3 μM was evaluated according to the test method of Test Example 1. The results thereof are shown in FIG. 8. As shown in FIG. 8, those peptides exhibited a high inhibitory activity, that is, an inhibitory activity of 40% or more (luciferase activity of 60% or less) at a final concentration of 1 μM. Further, nPDM-64 of Synthesis Example 46, nPDM-65 of Synthesis Example 47, nPDM-66 of Synthesis Example 48, and nPDM-69 of Synthesis Example 51 exhibited a particularly high inhibitory activity, that is, an inhibitory activity 40% or more (luciferase activity 60% or less) even at a final concentration of 0.3 μM.

Test Example 9

Regarding the peptides prepared in Synthesis Examples 52 to 59, the myostatin inhibitory activity of each peptide at a final concentration of 0.3 μM was evaluated according to the test method of Test Example 1. The results thereof are shown in FIG. 10. As shown in FIG. 10, those peptides exhibited a particularly high inhibitory activity, that is, an inhibitory activity of 40% or more (luciferase activity of 60% or less) at a final concentration of 0.3 μM. Incidentally, in FIG. 10, "Propeptide" indicates a myostatin propeptide.

Test Example 10

Regarding the peptides prepared in Synthesis Examples 60 to 65, the myostatin inhibitory activity of each peptide at a final concentration of 0.3 µM was evaluated according to the test method of Test Example 1. The results thereof are shown in FIG. 11. As shown in FIG. 11, nPDM-86, nPDM-80, nPDM-82, and nPDM-85 exhibited a particularly high inhibitory activity, that is, an inhibitory activity of 40% or more (luciferase activity of 60% or less) at a final concentration of 0.3 µM. Incidentally, in FIG. 11, "Propeptide" indicates a myostatin propeptide.

Test Example 11

Regarding the peptides prepared in Synthesis Examples 66 to 71, the myostatin inhibitory activity of each peptide at a final concentration of 0.3 µM was evaluated according to the test method of Test Example 1. The results thereof are shown in FIG. 12. As shown in FIG. 12, PDM-80, PDM-86, PDM-89, PDM-90, and PDM-91 exhibited a particularly high inhibitory activity, that is, an inhibitory activity of 40% or more (luciferase activity of 60% or less) at a final concentration of 0.3 µM. Incidentally, in FIG. 12, "Propeptide" indicates a myostatin propeptide.

Test Example 12

Regarding the peptides prepared in Synthesis Examples 72 to 74, the myostatin inhibitory activity of each peptide at a final concentration of 1 µM was evaluated according to the test method of Test Example 1. The results thereof are shown in FIG. 13. As shown in FIG. 13, those peptides exhibited a high inhibitory activity, that is, an inhibitory activity of 40% or more (luciferase activity of 60% or less) at a final concentration of 1 µM.

Test Example 13

Regarding the peptides prepared in Synthesis Examples 64 and 75, the myostatin inhibitory activity in a concentration range of 0.016 to 2 µM was evaluated according to the test method of Test Example 1. The results thereof are shown in FIG. 15. While 3d composed of 22 residues showed the $IC_{50}$ value of 273 nM, nPDM-86 composed of 16 residues showed the $IC_{50}$ value of 131 nM. nPDM-86 whose sequence is shorted than 3d by 6 residues exhibited an approximately two times higher inhibitory activity.

<Influence on Anterior Tibial Muscles of Duchenne Muscular Dystrophy Model Mdx Mice (In Vivo Evaluation)>

Regarding PDM-46 prepared in Synthesis Example 18, evaluation was performed by the following method in order to check the muscle mass increasing effect in vivo.

PDM-46 was dissolved in saline to become 0.75 mM. 40 µL of PDM-46 was intramuscularly administered into the left leg anterior tibial muscles of anesthetized mdx male mice aged 5 weeks (purchased from CLEA Japan, Inc.) (as a control, 40 µL of saline was intramuscularly administered into the right leg anterior tibial muscles). After 2 weeks, the same amount of PDM-46 was administered to the same site again. After further 4 weeks, the mice were subjected to necropsy, the anterior tibial muscles were excised from the both legs, and the weight thereof was measured.

The results thereof are shown in FIG. 9 (FIG. 9(A): individual number 1, FIG. 9(B): individual number 2, the left side in each photograph is the right leg (administered with PDM-46) after the mice were fed for 6 weeks, and the right side is the left leg (administered with saline) after the mice were fed for 6 weeks). PDM-46 caused the muscle mass of anterior tibial muscles of mdx mice to increase by about 13% in terms of weight (average value of three mice) on the basis of the myostatin inhibitory activity thereof.

<Influence on Calf Muscles of Mdx Mice and C57BL/6 Mice (In Vivo Evaluation)>

Evaluation was performed by the following method in order to check the muscle mass increasing effect in vivo of nPDM-55/E31R prepared in Synthesis Example 36.

nPDM-55/E31R was dissolved in saline to become 0.75 mM. 40 µL of nPDM-55/E31R was intramuscularly administered into the calf muscles of both legs of anesthetized mdx mice and C57BL/6 mice aged 5 weeks (all mice were males, purchased from CLEA Japan, Inc.) (40 µL of saline was intramuscularly administered into the calf muscles of both legs of control mice). After 2 weeks, the same amount of nPDM-55/E31R was administered to the same site again. After further 4 weeks, the mice were subjected to necropsy, the calf muscles were excised from the both legs and transverse frozen sections (6 µm) were formed using cryostat. Regarding three sections stained with Hematoxylin-Eosin and randomly selected, cross-sectional areas of muscle fibers (200 fibers) were analyzed by a fluorescence microscope BZX700 (KEYENCE CORPORATION).

The results thereof are shown in FIG. 14. In the mice administered with nPDM-55/E31R, the cross-sectional areas of muscles are increased as compared to the muscle sections of the mice administered with saline. From analysis images of respective mdx and C57BL/6 mice, it became clear that the obtained muscular hypertrophy is not inflammatory but is based on the myostatin inhibitory activity of nPDM-55/E31R.

<Influence on Serum Creatine Kinase Level of Mdx Mice (In Vivo Evaluation)>

Evaluation was performed by the following method in order to check the effect of nPDM-55/E31R prepared in Synthesis Example 36 to a serum creatine kinase (CK) value in mdx mice. Incidentally, 3d prepared in Synthesis Example 75 was used as Comparative Example.

nPDM-55/E31R and 3d were dissolved in saline to become 0.75 mM. 40 µL of nPDM-55/E31R was intramuscularly administered into the calf muscles of both legs of anesthetized mdx mice aged 5 weeks (all mice were males, purchased from CLEA Japan, Inc.). After 2 weeks, the same amount of nPDM-55/E31R was administered to the same site again. Serum samples were collected immediately before administration of nPDM-55/E31R and 3d (day 0, day 14) and further also collected after 4 weeks (day 42). The results obtained by analyzing the CK content in the blood serum are shown in FIG. 16. The CK level of the mice administered with 3d was decreased on day 14, but tended to increase again on day 42. On the other hand, the CK level of the mice administered with nPDM-55/E31R was a clearly lower value on day 14 and day 42 than that on day 0. From those results, it was shown that nPDM-55/E31R has an effect of continually maintaining the CK level in blood to be low as compared to 3d.

The present application is based on Japanese Patent Application No. 2016-158123 filed on Aug. 10, 2016, the entire content of which is incorporated by reference herein.

The invention claimed is:

1. A peptide or a pharmaceutically acceptable salt of the peptide, or a prodrug thereof, the peptide satisfying the following (a) or (b) and having a number of amino acid residues of 20 or less:
   (a) the peptide comprising any one of the amino acid sequences represented by SEQ ID NO: 2 to 9, SEQ ID NO: 11 to 20, SEQ ID NO: 22 to 38, SEQ ID NO: 380 to 385, SEQ ID NO: 573 to 580, and SEQ ID NO: 583 to 595; or
   (b) the peptide comprising one amino acid sequence in which one amino acid residue of $X^2$ to $X^4$ and $X^6$ to $X^{16}$ in the amino acid sequences of the above (a) is substituted or deleted and having a myostatin inhibitory activity
   wherein, SEQ ID NO: 585 to 587 and SEQ ID NO: 593 to 595 may represent a cyclic peptide in which a disulfide bond is formed between side-chain SH groups of two cysteine residues.

2. The peptide or the pharmaceutically acceptable salt of the peptide, or the prodrug thereof according to claim 1, wherein the peptide satisfies the following (a-1) or (b-1):
   (a-1) the amino acid sequence of the peptide satisfying the above (a) being represented by any one of SEQ ID NO: 4, SEQ ID NO: 6 to 8, SEQ ID NO: 12, SEQ ID NO: 13, SEQ ID NO: 15, SEQ ID NO: 16, SEQ ID NO: 18, SEQ ID NO: 23 to 29, SEQ ID NO: 33 to 36, SEQ ID NO: 380 to 385, SEQ ID NO: 573 to 580, SEQ ID NO: 583, SEQ ID NO: 584, and SEQ ID NO: 586 to 594; or
   (b-1) the peptide comprising one amino acid sequence in which one amino acid residue of $X^2$ to $X^4$, $X^8$, $X^9$, $X^{11}$, and $X^{14}$ in the amino acid sequences of the above (a-1) is substituted or deleted and having a myostatin inhibitory activity.

3. A myostatin inhibitory agent comprising the peptide or the pharmaceutically acceptable salt of the peptide, or the prodrug thereof according to claim 1.

4. A method for inhibiting myostatin in a patient, comprising:
   administering an effective dose of the peptide or the pharmaceutically acceptable salt of the peptide, or the prodrug thereof according to claim 1 to the patient.

* * * * *